US008541380B2

(12) United States Patent
Lee et al.

(10) Patent No.: US 8,541,380 B2
(45) Date of Patent: Sep. 24, 2013

(54) C-ARYL GLUCOSIDE SGLT2 INHIBITORS AND PHARMACEUTICAL COMPOSITIONS COMPRISING SAME

(75) Inventors: Jinhwa Lee, Yongin-si (KR); Suk Ho Lee, Yongin-si (KR); Hee Jeong Seo, Yongin-si (KR); Min Ju Kim, Yongin-si (KR); Suk Youn Kang, Yongin-si (KR); Jeongmin Kim, Yongin-si (KR); Sung-Han Lee, Yongin-si (KR); Myung Eun Jung, Yongin-si (KR); Eun Jung Son, Yongin-si (KR); Kwang-Seop Song, Yongin-si (KR); Mi-Soon Kim, Yongin-si (KR)

(73) Assignee: Green Cross Corporation, Yongin-si (KR)

( * ) Notice: Subject to any disclaimer, the term of this patent is extended or adjusted under 35 U.S.C. 154(b) by 0 days.

(21) Appl. No.: 13/379,301

(22) PCT Filed: Jun. 18, 2010

(86) PCT No.: PCT/KR2010/003958
§ 371 (c)(1),
(2), (4) Date: Dec. 19, 2011

(87) PCT Pub. No.: WO2010/147430
PCT Pub. Date: Dec. 23, 2010

(65) Prior Publication Data
US 2012/0101051 A1 Apr. 26, 2012

Related U.S. Application Data

(60) Provisional application No. 61/218,666, filed on Jun. 19, 2009.

(51) Int. Cl.
A01N 43/04 (2006.01)
A61K 31/70 (2006.01)
C07H 1/00 (2006.01)
C07H 5/04 (2006.01)

(52) U.S. Cl.
USPC ................ 514/23; 536/1.11; 536/18.7

(58) Field of Classification Search
None
See application file for complete search history.

(56) References Cited

U.S. PATENT DOCUMENTS 7,683,160 B2 * 3/2010 Eckhardt et al. ........... 536/1.11
2007/0049537 A1 3/2007 Eckhardt et al.
2007/0259821 A1 11/2007 Eckhardt et al.

FOREIGN PATENT DOCUMENTS

WO WO 2006/108842 A1 10/2006
WO WO 2008/055940 A2 5/2008

OTHER PUBLICATIONS

Adachi et al., Metabolism, vol. 49 (8), Aug. 2000, pp. 990-995.*
International Search Report of PCT/KR2010/003958, dated Mar. 21, 2011.

* cited by examiner

*Primary Examiner* — Traviss C McIntosh, III
(74) *Attorney, Agent, or Firm* — Sughrue Mion, PLLC

(57) ABSTRACT

A novel C-aryl glucoside compound, or a pharmaceutically acceptable salt or a prodrug thereof having an inhibitory activity against sodium-dependent glucose cotransporter 2 (SGLT2) being present in the intestine and kidney; and a pharmaceutical composition comprising the same as an active ingredient, which is useful for preventing or treating metabolic disorders, particularly, diabetes, are provided.

16 Claims, 2 Drawing Sheets

C-ARYL GLUCOSIDE SGLT2 INHIBITORS AND PHARMACEUTICAL COMPOSITIONS COMPRISING SAME

CROSS REFERENCE TO RELATED APPLICATION

This application is a National Stage of International Application No. PCT/KR2010/003958 filed Jun. 18, 2010, claiming priority based on U.S. Patent Application No. 61/218,666, filed Jun. 19, 2009, the contents of all of which are incorporated herein by reference in their entirety.

FIELD OF THE INVENTION

The present invention relates to a novel C-aryl glucoside compound having an inhibitory activity against sodium-dependent glucose cotransporter 2 (SGLT2) being present in the intestine and kidney, and a pharmaceutical composition comprising the same as an active ingredient, which is useful for preventing or treating diabetes.

BACKGROUND OF THE INVENTION

Diabetes is caused by multiple factors and is most simply characterized by elevated levels of plasma glucose (hyperglycemia) in the fasting or post glucose-challenge state. Diabetes is a global epidemic affecting more than 240 million people worldwide. The incidence of this disease is growing fast. Each year 3.8 million people die from complications of diabetes, including heart disease, stroke and kidney failure. Metabolic abnormalities in carbohydrate, fat, and protein metabolism contribute to chronic hyperglycemia that leads to microvascular and macrovascular complications. There are two generally recognized forms of diabetes: Type 1 diabetes, or insulin-dependent diabetes mellitus (IDDM), in which insulin is either absent or nearly absent because of autoimmune destruction or dysfunction of insulin-producing β-cells of the pancreas, and Type 2 diabetes, or noninsulin-dependent diabetes mellitus (NIDDM), wherein patients produce some insulin and even exhibit hyperinsulinemia (plasma insulin levels that are the same or even elevated in comparison with non-diabetic subjects), while simultaneously displaying hyperglycemia. Type 2 diabetes is the most prevalent abnormality of glucose homeostasis, accounting for approximately 90-95% of all cases of diabetes. Type 1 diabetes is typically treated with exogenous insulin administered via injection. However, Type 2 diabetes frequently develops insulin resistance, such that the effect of insulin in stimulating glucose and lipid metabolism in the main insulin-sensitive tissues such as muscle, liver and adipose tissues is diminished. Patients who are insulin resistant but not diabetic may have elevated insulin levels that compensate for their insulin resistance, so that serum glucose levels are not elevated. In patients with Type 2 diabetes, the plasma insulin levels, even when they are elevated, are insufficient to overcome the pronounced insulin resistance, resulting in hyperglycemia.

At disease onset, hyperglycemia elicits elevated levels of circulating insulin in most individuals, but they have decreased peripheral glucose utilization and impaired suppression of endogenous glucose production as a result of insulin resistance. Decline of β-cell function tends to be progressive, and can ultimately result in an insulin-dependent state. Type 2 diabetes mellitus is associated with obesity, older age, physical inactivity, certain racial ethnicity populations, a family history of Type 2 diabetes, a history of gestational diabetes, or impaired glucose metabolism (impaired glucose tolerance (IGT), or pre-diabetes).

Diabetes can be treated with a variety of therapeutic agents, including insulin sensitizers, such as PPAR-γ agonists, such as glitazones and glitazars; biguanides; dipeptidyl peptidase-IV (DPP-IV) inhibitors; glucagon-like peptide-1 (GLP-1) agonists; insulin; insulin mimetics; sulfonylureas; meglitinides; and α-glucosidase inhibitors.

Increasing the plasma level of insulin by administration of sulfonylureas or meglitinides, which stimulate the pancreatic β-cells to secret more insulin, or by injection of insulin when sulfonylureas or meglitinides become ineffective, can result in insulin concentrations high enough to stimulate insulin-resistant tissues. However, dangerously low levels of plasma glucose can result, and increasing insulin resistance due to the even higher plasma insulin levels can occur. The biguanides have an unknown mechanism of action but decrease hepatic glucose output and increase insulin sensitivity resulting in some correction of hyperglycemia. Metformin monotherapy is often used for treating Type 2 diabetic patients who are also obese or dyslipidemic. Lack of appropriate response to metformin is often followed by treatment with sulfonylureas, thiazolidinediones, insulin, or α-glucosidase inhibitors. However, the two biguanides, phenformin and metformin, can also induce lactic acidosis and nausea/diarrhea, respectively. α-Glucosidase inhibitors, such as acarbose, work by delaying absorption of glucose in the intestine.

The PPAR-γ agonists, including glitazones, also known as thiazolidinediones (i.e. 5-benzylthiazolidine-2,4-diones) and non-thiazolidinediones, i.e. glitizars, represent another class of compounds with potential for improving many symptoms of Type 2 diabetes. These agents substantially increase insulin sensitivity in muscle, liver and adipose tissue in several animal models of Type 2 diabetes leading to partial or complete correction of the elevated plasma levels of glucose without occurrence of hypoglycemia. PPAR-γ agonism is generally believed to be responsible for the improved insulin sensitization that is observed with the glitazones.

GLP-1 or glucagon-like peptide 1 is one of several incretin compounds that have biologic activity. After release into the blood by the intestine in response to food intake, GLP-1 slows food absorption. This delay in absorption allows the slow insulin response found in Type 2 diabetes to catch up. Improved insulin production also occurs when people take GLP-1 agonists. Both an increase in beta cell mass and improvement of first phase insulin release toward normal have been seen with this drug. Researchers hope that this action may delay progression of Type 2 diabetes or possibly assist in recovery of beta cell activity in early Type 1 diabetes. GLP-1 agonists have multiple sites of action. Giving natural GLP-1 was found to have little benefit because it is broken down by an enzyme called DPP-4 (dipeptidyl peptidose IV) within about 5 minutes. This lead to a search for modified GLP-1 molecules like Byetta, produced by Amylin and Lilly that are not broken down as quickly. Related to the GLP-1 agonists is a second new class of diabetes medications called DPP-4 inhibitors which work by delaying the breakdown of GLP-1, as well as other incretins. Because DPP-4 is involved in the breakdown of several peptides in the body, it will take time to be sure there are no unwanted side effects.

Abnormal glucose homeostasis is also associated both directly and indirectly with obesity, hypertension and alterations in lipid, lipoprotein and apolipoprotein metabolism. Obesity increases the likelihood of insulin resistance, and increases the likelihood that the resulting insulin resistance will increase with increasing body weight. Therefore, therapeutic control of glucose homeostasis, lipid metabolism, obesity and hypertension are critically important in the prevention of and clinical management and treatment of diabetes mellitus.

Despite the availability of a range of agents to treat type 2 diabetes, glucose control remains suboptimal, with less than 50% of patients achieving stated glycemic goals. In addition, current therapies have limited durability and/or are associated with significant side effects such as GI intolerance, hypoglycemia, weight gain, lactic acidosis and edema. Thus, significant unmet medical needs remain. In particular, safer, better tolerated medications which provide increases efficacy and long-term durability are desired.

The obvious need for new approaches to treat patients with uncontrolled T2DM has urged continued exploration of alternative targets in organs involved in maintenance of glucose homeostasis. In T2DM, renal glucose reuptake contributes to elevated plasma glucose levels and the concomitant microvascular complications. Inhibitors of the sodium-dependent glucose cotransporter 2 (SGLT2) prevent renal glucose reabsorption from the glomerular filtrate and provide an insulin-independent way of controlling hyperglycemia.

In healthy individuals, greater than 99% of the plasma glucose that is filtered in the kidney glomerulus is reabsorbed, with less than 1% of the total filtered glucose being excreted in urine. This reabsorption process is mediated by two sodium-dependent glucose cotransporters (SGLTs): SGLT1, a low-capacity, high-affinity transporter expressed in the gut, heart and kidney, and SGLT2, a high-capacity, low-affinity transporter that is expressed mainly in the kidney. It is estimated that 90% of renal glucose reabsorption by SGLT2 dwelling on the surface of the epithelial cells lining the Si segment of the proximal tubule. The remaining 10% is probably mediated by SGLT1 residing on the more distal S3 segment of the proximal tubule. Humans with SGLT1 gene mutations experience glucose-galactose malabsorption, with frequent diarrhea and dehydration when on a glucose diet, confirming that SGLT1 is not the major glucose transporter in the kidney. In contrast, persistent renal glucosuria is the sole reported phenotype of humans with SGLT2 gene mutations [Meng, W.; Washburn, W. N. et al. *J. Med. Chem.* 2008, 51, 1145-1149; Washburn, W. N. *J. Med. Chem.* 2009, 52, 1785-1794].

Selective inhibition of SGLT2 would be desirable, since potentially serious gastrointestinal side effects associated with SGLT1 inhibition would be minimized. Selective inhibition of SGLT2 has been suggested to help the normalization of plasma glucose levels in patients with diabetes by preventing the renal glucose reabsorption process and promoting glucose excretion in urine [Oku, A. et al. *Diabetes* 1999, 48, 1794-1800]. This mode is most likely to be involved in a low risk of hypoglycemia, since there is no interference with the normal counter-regulatory mechanisms for glucose.

The natural product phlorizin is a potent glucosuric agent that was subsequently shown to be a nonselective SGLT inhibitor. However, phlorizin is not a suitable drug candidate since it inhibits SGLT1 and also it has metabolic instability due to its susceptibility to β-glucosidase-mediated cleavage. Researchers at the Tanabe Seiyaku disclosed the identification of selective, potent SGLT2 inhibitors as potential treatments for type 2 diabetes. Subsequently, Kissei disclosed two other series of O-glucoside containing SGLT2 inhibitors. To achieve a significant reduction of hyperglycemia with a concurrent increase of glucosuria, the metabolic instability of the O-glucoside linkage demanded oral administration of their lead compound as the ethyl carbonate prodrug sergliflozin.

Meanwhile, Bristol-Myers Squibb reported discovery of dapagliflozin, as a potent, selective renal sodium-dependent glucose cotransporter 2 (SGLT2) inhibitors for the treatment of type 2 diabetes [Meng, W. et al. *J. Med. Chem.* 2008, 51, 1145-1149]. Dapagliflozin is a metabolically more robust C-aryl glucoside.

Considering the important impact of diabetes on public health and unmet medical needs of current therapy, it is no surprise that SGLT2 inhibitors are currently interesting topics of studies, which were published in the following review articles [Washburn, W. N. *Expert Opin. Ther Patents* 2009, 19(11), 1485-1499; Washburn, W. N. *J. Med. Chem.* 2009, 52, 1785-1794].

SUMMARY OF THE INVENTION

It is a primary object of the present invention to provide a novel C-aryl glucoside compound of formula (I), or a pharmaceutically acceptable salt or a prodrug thereof, which is effective as SGLT2 inhibitor, useful for the prevention or treatment of metabolic disorders, particularly diabetes.

It is another object of the present invention to provide a method for preparing the compound.

It is a further object of the present invention to provide a pharmaceutical composition for preventing or treating metabolic disorders, particularly diabetes comprising said compound as an active ingredient.

In accordance with an aspect of the present invention, there is provided a compound of formula (I), or a pharmaceutically acceptable salt or a prodrug thereof:

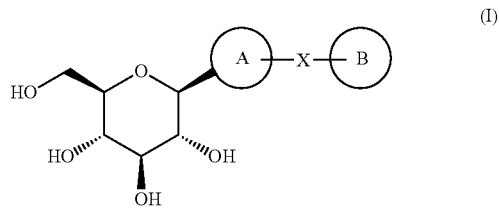

wherein,

Ring A is selected from the group consisting of benzene ring, substituted benzene ring, naphthalene ring and substituted naphthalene ring, Ring B is heteroaryl or substituted heteroaryl, especially including pyridazine, pyridazinone, thiadiazole, triazine, or benzotriazine; and X is —CH$_2$—.

In accordance with another aspect of the present invention, there is provided a method for preparing a compound of formula (Ie) comprising the steps of:

subjecting a compound of formula (II) to a coupling reaction with a hydrazide of formula (III) to obtain an acylhydrazide of formula (IV), or converting the compound of formula (II) to a hydrazide of formula (V) using hydrazine, followed by a coupling reaction of the hydrazide of formula (V) with a carboxylic acid of formula (VI) to obtain an acylhydrazide of formula (IV);

conducting a cyclization of the acylhydrazide of formula (IV) using Lawesson's reagent to obtain a thiadiazole of formula (VII); and carrying out deprotection of the benzyl groups of the thiadiazole of formula (VII), followed by peracylation and hydrolysis of the resulting compound,

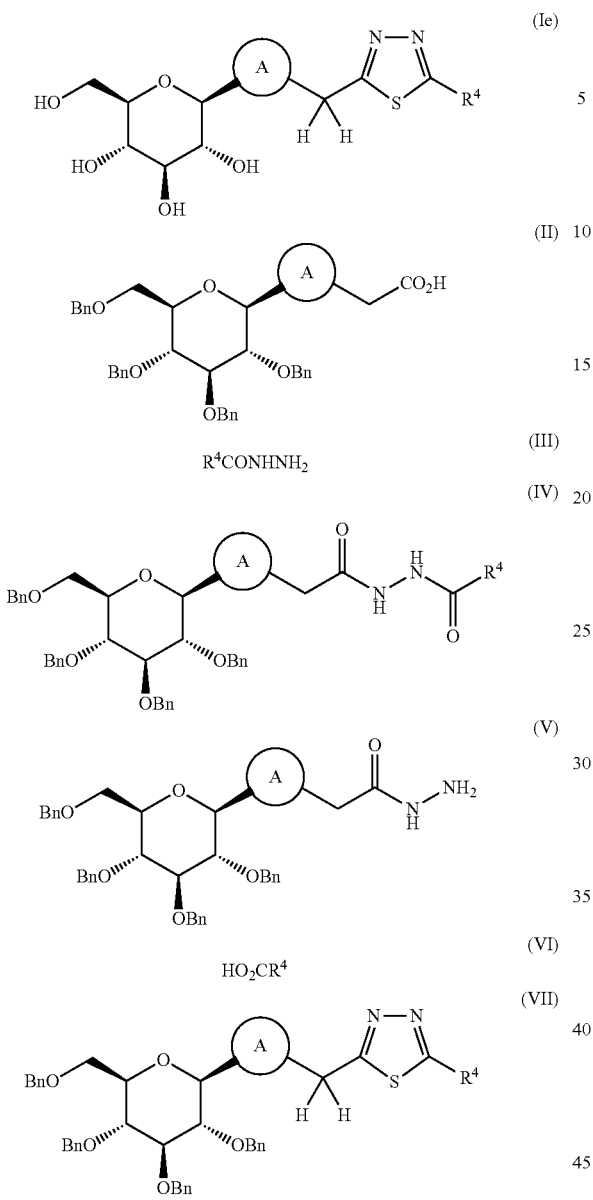

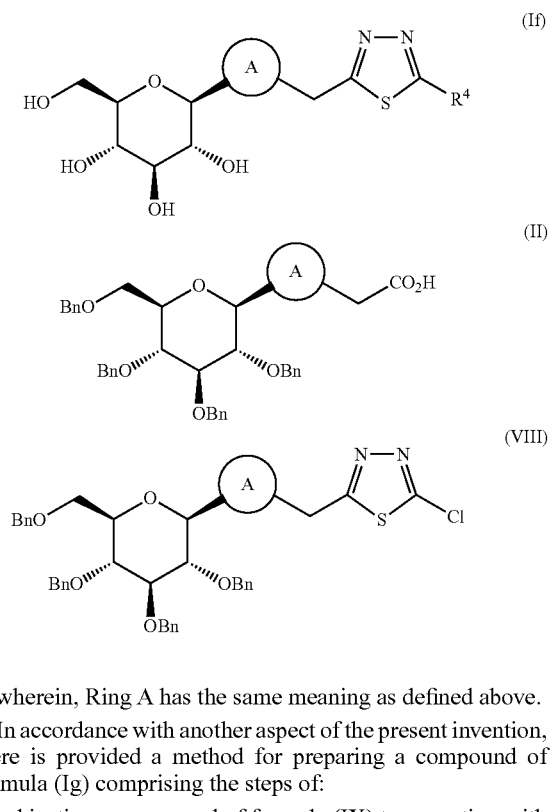

wherein, Ring A has the same meaning as defined above, and $R^4$ is $C_{1-2}$ alkoxy, $C_{1-4}$ alkylthio, $C_{1-7}$ alkyl, substituted $C_{1-7}$ alkyl, $C_{2-7}$ alkenyl, substituted $C_{2-7}$ alkenyl, $C_{2-7}$ alkynyl, substituted $C_{2-7}$ alkynyl, $C_{3-7}$ cycloalkyl, substituted $C_{3-7}$ cycloalkyl, aryl, substituted aryl, heteroaryl, substituted heteroaryl, heterocycloalkyl or substituted heterocycloalkyl.

In accordance with another aspect of the present invention, there is provided a method for preparing a compound of formula (If), comprising the steps of:

subjecting a compound of formula (II) to a coupling reaction and cyclization with thiosemicarbazide using phosphorus(V) oxychloride to obtain an aminothiadiazole;

converting the aminothiadiazole to a thiadiazole of formula (VIII) using sodium nitrite and copper under an acidic condition; and treating the thiadiazole of formula (VIII) with $NaR^4$ (in which $R^4$ has the same meaning as defined above), followed by deprotection of benzyl groups, wherein, Ring A has the same meaning as defined above.

In accordance with another aspect of the present invention, there is provided a method for preparing a compound of formula (Ig) comprising the steps of:

subjecting a compound of formula (IX) to a reaction with 3,6-dichloropyridazine or 3-(methylsulfonyl)-5-phenyl-1,2,4-triazine under a basic condition to obtain an ester of formula (X);

conducting a hydrolyzation and decarboxylation of the ester of formula (X) using lithium hydroxide to obtain a compound of formula (XI); and removing the benzyl groups of the compound of formula (XI),

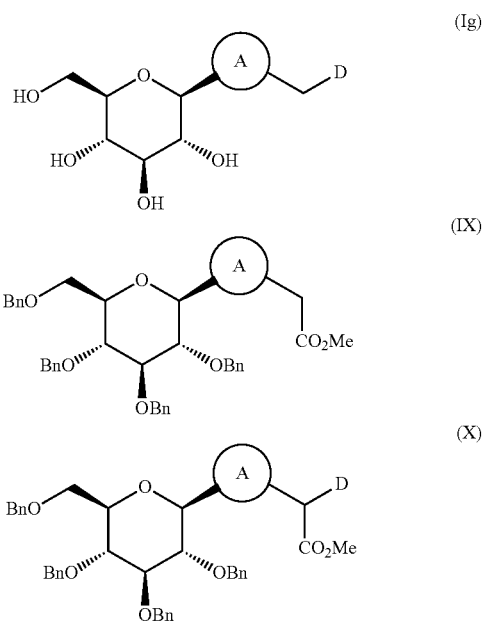

(XI)

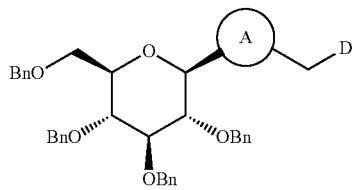

wherein, Ring A has the same meaning as defined above, D is

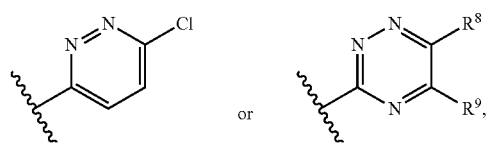

in which $R^8$ is hydrogen, halogen, cyano, amino, mono- or di-($C_{1-4}$ alkyl)amino, $C_{1-8}$ alkoxy, substituted $C_{1-8}$ alkoxy, cycloalkyloxy, heterocyclooxy, $C_{1-4}$ alkylthio, —S-aryl, $C_{1-8}$ alkoxycarbonyl, $C_{1-7}$ alkyl, substituted $C_{1-7}$ alkyl, $C_{2-7}$ alkenyl, substituted $C_{2-7}$ alkenyl, $C_{2-7}$ alkynyl, substituted $C_{2-7}$ alkynyl, $C_{3-7}$ cycloalkyl, substituted $C_{3-7}$ cycloalkyl, $C_{3-7}$ cycloalkenyl, substituted $C_{3-7}$ cycloalkenyl, aryl, substituted aryl, heteroaryl, substituted heteroaryl, heterocyclic, or substituted heterocyclic; and $R^9$ is hydrogen, $C_{1-7}$ alkyl, substituted $C_{1-7}$ alkyl, $C_{2-7}$ alkenyl, substituted $C_{2-7}$ alkenyl, $C_{2-7}$ alkynyl, substituted $C_{2-7}$ alkynyl, $C_{3-7}$ cycloalkyl, substituted $C_{3-7}$ cycloalkyl, aryl, substituted aryl, heteroaryl, substituted heteroaryl, heterocyclic, or substituted heterocyclic.

In accordance with another aspect of the present invention, there is provided a method for preparing a compound of formula (Ih) comprising the steps of:

subjecting a compound of formula (XII) to a reaction with $NaOR^{11}$, NaSMe or $HNR^{12}R^{13}$ ($R^{11}$, $R^{12}$ and $R^{13}$ are each independently H or $C_{1-4}$ alkyl); a Fe(III)-mediated alkylation using Grignard reagent; a Sonogashira reaction with ethynylbenzene; a Palladium(0)-catalyzed cyanation under microwave irradiation; or a Suzuki-Miyaura coupling with boronic acid, to obtain a compound of formula (XIII); and removing the benzyl groups of the compound of formula (XIII), (Ih)

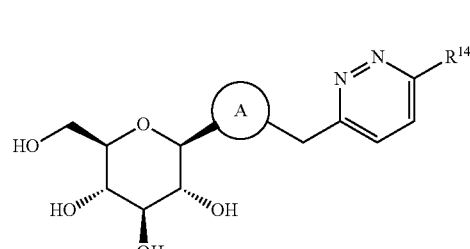

(XII)

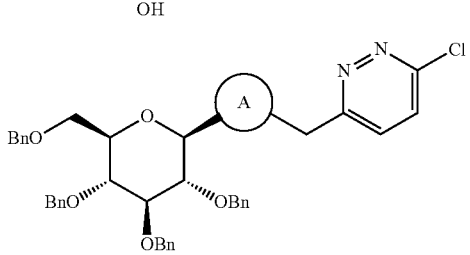

(XIII)

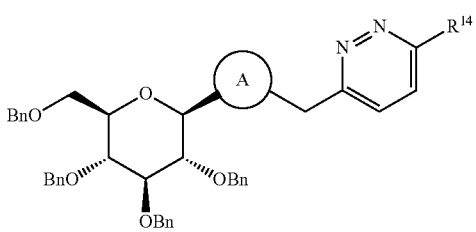

wherein, Ring A has the same meaning as defined above, and $R^{14}$ is $C_{1-4}$ alkyl, $C_{1-4}$ alkoxy, —$SCH_3$, phenylethynyl, cyano, amino or aryl.

In accordance with another aspect of the present invention, there is provided a method for preparing a compound of formula (Ii) comprising the steps of:

subjecting a compound of formula (IX) to a reaction with a chlorobenzotriazine compound to obtain a triazine oxide;

conducting a reduction of the triazine oxide to obtain a compound of formula (XIV);

hydrolyzing the compound of formula (XIV) using metal hydroxide to obtain a compound of formula (XV); and removing benzyl groups of the compound of formula (XV), (Ii)

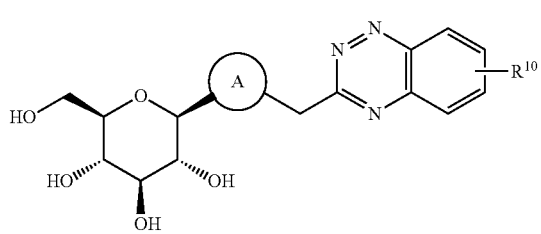

(IX)

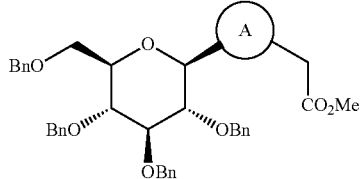

(XIV)

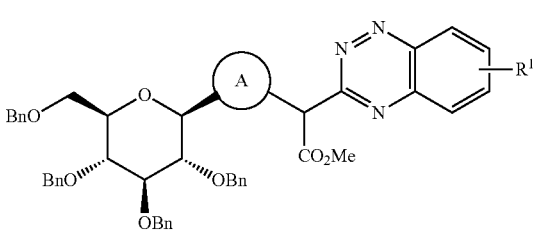

(XV)

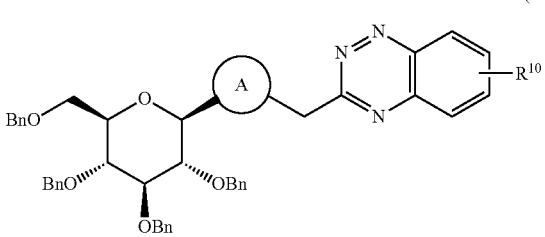

wherein, Ring A has the same meaning as defined above, and $R^{10}$ is hydrogen, halogen, cyano, $C_{1-4}$ alkoxy, substituted $C_{1-4}$ alkoxy, $C_{1-4}$ alkyl, substituted $C_{1-4}$ alkyl, aryl, substituted aryl, heteroaryl, substituted heteroaryl, heterocyclic, or substituted heterocyclic.

In accordance with another aspect of the present invention, there is provided a pharmaceutical composition for preventing or treating a metabolic disorder, which comprises the compound of formula (I), or the pharmaceutically acceptable salt or a prodrug thereof as an active ingredient, and a pharmaceutically acceptable carrier.

In accordance with a further aspect of the present invention, there is provided a method for preventing or treating a metabolic disorder, which comprises administering the compound of formula (I), or the pharmaceutically acceptable salt or a prodrug thereof to the mammal.

In accordance with a still further aspect of the present invention, there is provided a method for inhibiting sodium-dependent glucose cotransporter 2 (SGLT2) in a mammal, which comprises administering the compound of formula (I), or the pharmaceutically acceptable salt or a prodrug thereof to the mammal.

BRIEF DESCRIPTION OF THE DRAWINGS

The above and other objects and features of the present invention will become apparent from the following description of the invention, when taken in conjunction with the accompanying drawings which respectively show.

DETAILED DESCRIPTION OF THE INVENTION

Figure 1A:
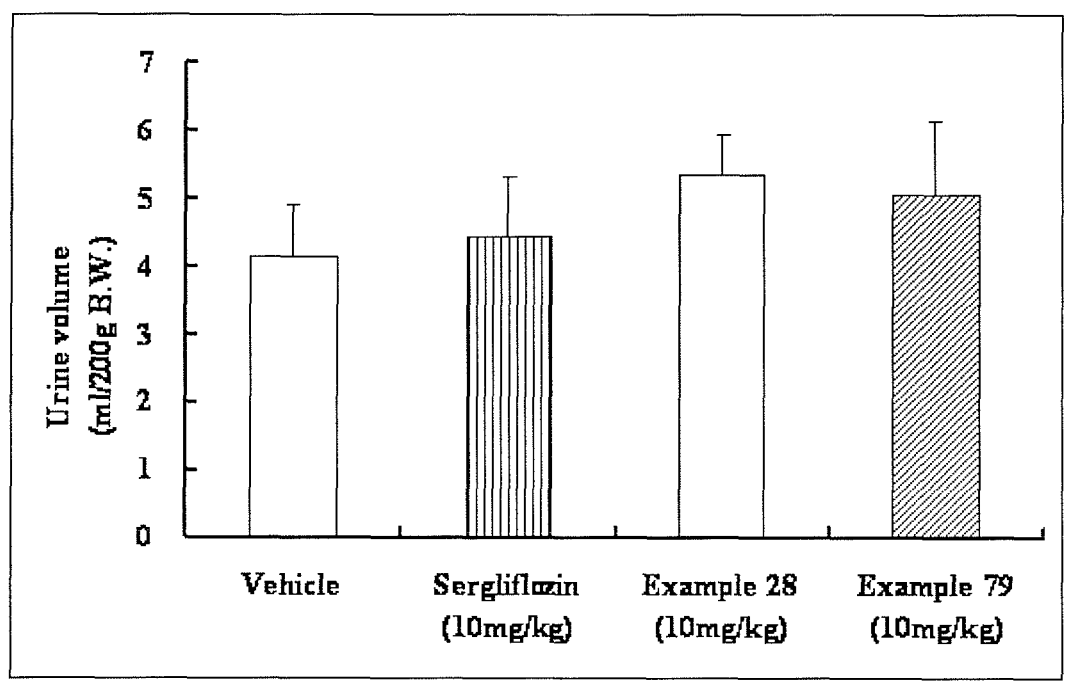
FIG. 1a: a graph showing effect of single oral administration of Sergliflozin, the compound of Example 28 and the compound of Example 79 respectively on urine volume in normal SD rats.

Hereinafter, a detailed description of the present invention is given.

As used herein, the term "alkyl" refers to a straight or branched chain saturated hydrocarbon radical. Examples of "alkyl" as used herein include, but are not limited to, methyl, ethyl, n-propyl, isopropyl, n-butyl, isobutyl, t-butyl, n-pentyl, isopentyl and hexyl.

As used herein, the term "substituted alkyl" refers to a straight or branched chain saturated hydrocarbon radical, which is optionally substituted by one or more substituents selected from the group consisting of $C_{1-3}$ alkyl optionally having one to three fluorine substituents, $C_{2-3}$ alkenyl, $C_{2-3}$ alkynyl, $C_{1-2}$ alkoxy optionally having one to three fluorine substituents, sulfanyl, sulfinyl, sulfonyl, oxo, hydroxy, mercapto, amino, guanidino, carboxy, aminocarbonyl, aryl, aryloxy, heteroaryl, heteroaryloxy, heterocyclic, aminosulfonyl, sulfonylamino, carboxyamide, ureido, nitro, cyano and halogen.

As used herein, the term "alkenyl" refers to a straight or branched chain hydrocarbon radical having at least one carbon-carbon double bond. Examples of "alkenyl" as used herein include, but are not limited to, ethenyl and propenyl.

As used herein, the term "substituted alkenyl" refers to a straight or branched chain hydrocarbon radical having at least one carbon-carbon double bond, which has optional substituents selected from the group consisting of $C_{1-3}$ alkyl optionally having one to three fluorine substituents, amino, aryl, cyano and halogen.

As used herein, the term "alkynyl" refers to a straight or branched chain hydrocarbon radical having at least one carbon-carbon triple bond. Examples of "alkynyl" as used herein include, but are not limited to, acetylenyl and 1-propynyl.

As used herein, the term "substituted alkynyl" refers to a straight or branched chain hydrocarbon radical having at least one carbon-carbon triple bond, optionally having one or more substituents selected from the group consisting of $C_{1-3}$ alkyl optionally having one to three fluorine substituents, amino, aryl and halogen.

As used herein, the term "halogen" refers to fluorine (F), chlorine (Cl), bromine (Br), or iodine (I).

As used herein, the term "carbocycle" refers to a non-aromatic cyclic hydrocarbon radical composed of three to seven carbon atoms. Five- to seven-membered rings may contain a double bond in the ring structure. Exemplary "carbocycle" groups include, but are not limited to, $C_{3-7}$ cycloalkyl such as cyclopropyl, cyclobutyl, cyclopentyl, cyclohexyl or cycloheptyl; and $C_{3-7}$ cycloalkenyl such as cyclopentenyl.

As used herein, the term "substituted carbocycle" refers to a non-aromatic cyclic hydrocarbon radical composed by three to seven carbon atoms, which is optionally substituted with one or more substituents selected from the group consisting of $C_{1-3}$ alkyl optionally having one to three fluorine substituents, $C_{2-3}$ alkenyl, $C_{2-3}$ alkynyl, $C_{1-2}$ alkoxy optionally having one to three fluorine substituents, sulfanyl, sulfinyl, sulfonyl, oxo, hydroxy, mercapto, amino, guanidino, carboxy, aminocarbonyl, aryl, aryloxy, heteroaryl, heterocyclic, aminosulfonyl, sulfonylamino, carboxyamide, nitro, ureido, cyano and halogen.

As used herein, the term "aryl" refers to an optionally substituted benzene ring or refers to a ring system which may result by fusing one or more optional substituents. Exemplary optional substituents include substituted $C_{1-3}$ alkyl, substituted $C_{2-3}$ alkenyl, substituted $C_{2-3}$ alkynyl, heteroaryl, heterocyclic, aryl, alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen, or ureido. Such a ring or ring system may be optionally fused to aryl rings (including benzene rings) optionally having one or more substituents, carbocycle rings or heterocyclic rings. Examples of "aryl" groups include, but are not limited to, phenyl, naphthyl, tetrahydronaphthyl, biphenyl, indanyl, anthracyl or phenanthryl, as well as substituted derivatives thereof.

As used herein, the term "heteroaryl" refers to an optionally substituted monocyclic five to six-membered aromatic ring containing one or more heteroatomic substitutions selected from S, SO, $SO_2$, O, N, or N-oxide, or refers to such an aromatic ring fused to one or more rings such as heteroaryl rings, aryl rings, heterocyclic rings, or carbocycle rings (e.g., a bicyclic or tricyclic ring system), each having optional substituents.

Examples of optional substituents are selected from the group consisting of substituted $C_{1-3}$ alkyl, substituted $C_{2-3}$ alkenyl, substituted $C_{2-3}$ alkynyl, heteroaryl, heterocyclic, aryl, $C_{1-3}$ alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen or ureido. Examples of "heteroaryl" groups used herein include, but are not limited to, benzoimidazolyl, benzothiazolyl, benzoisothiazolyl, benzothiophenyl, benzopyrazinyl, benzotriazolyl, benzo[1,4]dioxanyl, benzofuranyl, 9H-a-carbolinyl, cinnolinyl, furanyl, furo [2,3-b]pyridinyl, imidazolyl, imidazolidinyl, imidazopyridinyl, isoxazolyl, isothiazolyl, isoquinolinyl, indolyl, indazolyl, indolizinyl, naphthyridinyl, oxazolyl, oxothiadiazolyl, oxadiazolyl, phthalazinyl, pyridyl, pyrrolyl, purinyl, pteridinyl, phenazinyl, pyrazolyl, pyridyl, pyrazolopyrimidinyl, pyrrolizinyl, pyridazyl, pyrazinyl, pyrimidyl, 4-oxo-1,2-dihydro-4H-pyrrolo[3,2,1-ij]-quinolin-4-yl, quinoxalinyl, quinazolinyl, quinolinyl, quinolizinyl, thiophenyl, triazolyl, triazinyl, tetrazolopyrimidinyl, triazolopyrimidinyl, tetrazolyl, thiazolyl, thiazolidinyl, and substituted versions thereof.

As used herein, the term "heterocyclic" or "heterocycle" refers to a three to seven-membered ring containing one or more heteroatomic moieties selected from S, SO, $SO_2$, O, N, or N-oxide, optionally substituted with one or more substituents selected from the group which includes substituted $C_{1-3}$ alkyl, substituted $C_{2-3}$ alkenyl, substituted $C_{2-3}$ alkynyl, heteroaryl, heterocyclic, aryl, $C_{1-3}$ alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen, and ureido. Such a ring can be saturated or have one or more degrees of unsaturation. Such a ring may be optionally fused to one or more "heterocyclic" ring(s), aryl ring(s), heteroaryl ring(s), or carbocycle ring(s), each having optional substituents.

Examples of "heterocyclic" moieties include, but are not limited to, 1,4-dioxanyl, 1,3-dioxanyl, pyrrolidinyl, pyrrolidin-2-onyl, piperidinyl, imidazolidine-2,4-dionepiperidinyl, piperazinyl, piperazine-2,5-dionyl, morpholinyl, dihydropyranyl, dihydrocinnolinyl, 2,3-dihydrobenzo[1,4]dioxinyl, 3,4-dihydro-2H-benzo[b][1,4]-dioxepinyl, tetrahydropyranyl, 2,3-dihydrofuranyl, 2,3-dihydrobenzofuranyl, dihydroisoxazolyl, tetrahydrobenzodiazepinyl, tetrahydroquinolinyl, tetrahydrofuranyl, tetrahydronaphthyridinyl, tetrahydropurinyl, tetrahydrothiopyranyl, tetrahydrothiophenyl, tetrahydroquinoxalinyl, tetrahydropyridinyl, tetrahydrocarbolinyl, 4H-benzo[1,3]-dioxinyl, benzo[1,3]dioxonyl, 2,2-difluorobenzo-[1,3]-dioxonyl, 2,3-dihydro-phthalazine-1,4-dionyl, and isoindole-1,3-dionyl.

As used herein, the term "alkoxy" refers to the group —$OR_a$, where $R_a$ is alkyl as defined above. Exemplary alkoxy groups useful in the present invention include, but are not limited to, methoxy, difluoromethoxy, trifluoromethoxy, ethoxy, n-propoxy, isopropoxy, n-butoxy and t-butoxy.

As used herein the term "aralkoxy" refers to the group —$OR_aR_b$, wherein $R_a$ is alkyl and $R_b$ is aryl as defined above.

As used herein the term "aryloxy" refers to the group —$OR_b$, wherein $R_b$ is aryl as defined above.

As used herein, the term "mercapto" refers to the group —SH.

As used herein, the term "sulfanyl" refers to the group —$SR_c$, wherein $R_c$ is substituted alkyl, substituted carbocycle, aryl, heteroaryl or heterocyclic, as defined above.

As used herein, the term "sulfinyl" refers to the group —S—(O)$R_c$, wherein $R_c$ is substituted alkyl, substituted carbocycle, aryl, heteroaryl or heterocyclic, as defined above.

As used herein, the term "sulfonyl" refers to the group —$S(O)_2R_c$, wherein $R_c$ is substituted alkyl, substituted carbocycle, aryl, heteroaryl or heterocyclic, as defined above.

As used herein, the term "oxo" refers to the group =O.

As used herein, the term "carbonyl" refers to the group composed of a carbon atom double-bonded to an oxygen atom, C=O.

As used herein, the term "hydroxy" refers to the group —OH.

As used herein, the term "amino" refers to the group —$NH_2$. The amino group is optionally substituted by substituted alkyl, substituted carbocycle, aryl, heteroaryl or heterocyclic, as defined above.

As used herein, the term "cyano" refers to the group —CN.

As used herein, the term "aminosulfonyl" refers to the group —$S(O)_2NH_2$. The aminosulfonyl group is optionally substituted by substituted alkyl, substituted carbocycle, aryl, heteroaryl or heterocyclic, as defined above.

As used herein, the term "sulfonylamino" refers to the group —$NHS(O)_2R_c$, wherein $R_c$ is substituted alkyl, substituted carbocycle, aryl, heteroaryl or heterocyclic, as defined above.

As used herein, the term "carboxyamide" refers to the group —$NHC(O)R_c$, herein $R_c$ is substituted alkyl, substituted carbocycle, aryl, heteroaryl or heterocyclic, as defined above.

As used herein, the term "carboxy" refers to the group —C(O)OH. The carboxy group is optionally substituted by substituted alkyl, substituted carbocycle, aryl, heteroaryl or heterocyclic, as defined above.

As used herein, the term "aminocarbonyl" or "carbamoyl" refers to the group —C(O)$NH_2$. The aminocarbonyl group is optionally substituted by substituted alkyl, substituted carbocycle, aryl, heteroaryl or heterocyclic, as defined above.

As used herein, the term "ureido" refers to the group —NHC(O)$NHR_d$ wherein $R_d$ is hydrogen, alkyl, carbocycle or aryl as defined above.

As used herein, the term "guanidino" refers to the group —NHC(=NH)$NH_2$.

As used herein, the term "acyl" or "alkanoyl" refers to the group —C(O)$R_e$, wherein $R_e$ is alkyl, carbocycle, or heterocyclic as defined herein.

As used herein, the term "aroyl" refers to the group —C(O)$R_b$, wherein $R_b$ is aryl as defined herein.

As used herein, the term "heteroaroyl" refers to the group —C(O)$R_f$, wherein $R_f$ is heteroaryl as defined herein.

As used herein, the term "acyloxy" refers to the group —OC(O)$R_e$, wherein $R_e$ is alkyl, carbocycle, or heterocyclic as defined herein.

As used herein, the term "aroyloxy" refers to the group —OC(O)$R_b$, wherein $R_b$ is aryl as defined herein.

As used herein, the term "heteroaroyloxy" refers to the group —OC(O)$R_f$, wherein $R_f$ is heteroaryl as defined herein.

It is to be understood that the present invention also includes a pharmaceutically acceptable salt and an addition salt of the inventive compound, such as a hydrochloride, hydrobromide or trifluoroacetate addition salt and sodium, potassium and magnesium salt.

The compounds of the present invention may contain one or more asymmetric carbon atoms and may exist in racemic and optically active forms. All of these compounds and diastereomers are incorporated within the scope of the present invention.

In an aspect of the present invention, there is provided a compound of formula (I), or a pharmaceutically acceptable salt or a prodrug thereof:

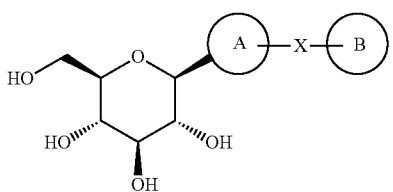

wherein,

Ring A is selected from the group consisting of benzene ring, substituted benzene ring, naphthalene ring and substituted naphthalene ring;

Ring B is heteroaryl or substituted heteroaryl, preferably a ring selected from the group consisting of pyridazine ring, substituted pyridazine ring, pyridazinone ring, substituted pyridazinone ring, thiadiazole ring, substituted thiadiazole ring, triazine ring, substituted triazine ring, benzotriazine ring and substituted benzotriazine ring; and X is —$CH_2$—.

Further, in another aspect of the present invention, preferable examples of the compound of the formula (I) include a compound wherein Ring A is

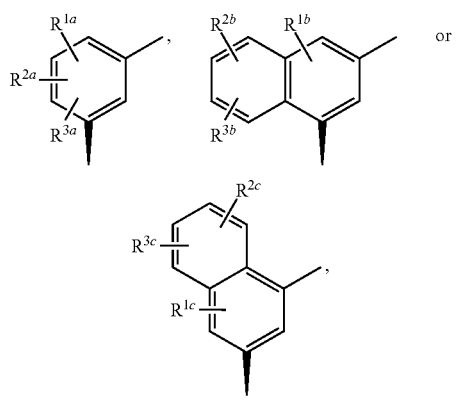

in which $R^{1a}$, $R^{2a}$, $R^{3a}$, $R^{1b}$, $R^{2b}$, $R^{3b}$, $R^{1c}$, $R^{2c}$, and $R^{3c}$ are each independently hydrogen, halogen, hydroxy, $C_{1-4}$ alkyl, substituted $C_{1-4}$ alkyl, $C_{2-4}$ alkenyl, substituted $C_{2-4}$ alkenyl, $C_{2-4}$ alkynyl, substituted $C_{2-4}$ alkynyl, hydroxyl($C_{1-4}$ alkyl), ($C_{1-8}$ alkoxy)($C_{1-4}$ alkyl), $C_{1-8}$ alkoxy, $C_{3-7}$ cycloalkyl, $C_{3-7}$ cycloalkenyl, $C_{3-7}$ cycloalkyloxy, phenyl($C_{1-8}$ alkoxy), cyano, nitro, amino, mono- or di-($C_{1-4}$ alkyl)amino, alkanoylamino, carboxy, ($C_{1-8}$ alkoxy)carbonyl, carbamoyl, mono- or di-($C_{1-4}$ alkyl)carbamoyl, alkanoyl, ($C_{1-4}$ alkyl)sulfonylamino, phenylsulfonylamino, ($C_{1-4}$ alkyl)sulfinyl, ($C_{1-4}$ alkyl)sulfonyl, phenylsulfonyl, aryl, substituted aryl, heteroaryl, substituted heteroaryl heterocycle, or substituted heterocycle, and

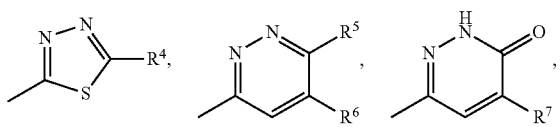

Ring B is

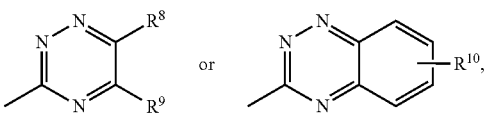

in which $R^4$ is $C_{1-2}$ alkoxy, $C_{1-4}$ alkylthio (e.g., —$SCH_3$, —$SCH_2CH_3$), $C_{1-7}$ alkyl, substituted $C_{1-7}$ alkyl, $C_{2-7}$ alkenyl, substituted $C_{2-7}$ alkenyl, $C_{2-7}$ alkynyl, substituted $C_{2-7}$ alkynyl, $C_{3-7}$ cycloalkyl, substituted $C_{3-7}$ cycloalkyl, aryl, substituted aryl, heteroaryl, substituted heteroaryl, heterocycloalkyl or substituted heterocycloalkyl;

$R^5$ is hydrogen, halogen, cyano, amino, mono- or di-($C_{1-4}$ alkyl)amino, $C_{1-8}$ alkoxy, substituted $C_{1-8}$ alkoxy, cycloalkyloxy, heterocyclooxy, $C_{1-4}$ alkylthio (e.g., —$SCH_3$, —$SCH_2CH_3$), —S-aryl, $C_{1-8}$ alkoxycarbonyl, $C_{1-7}$ alkyl, substituted $C_{1-7}$ alkyl, $C_{2-7}$ alkenyl, substituted $C_{2-7}$ alkenyl, $C_{2-7}$ alkynyl, substituted $C_{2-7}$ alkynyl, $C_{3-7}$ cycloalkyl, substituted $C_{3-7}$ cycloalkyl, $C_{3-7}$ cycloalkenyl, substituted $C_{3-7}$ cycloalkenyl, aryl, substituted aryl, heteroaryl, substituted heteroaryl, heterocycloalkyl, or substituted heterocycloalkyl;

$R^6$ and $R^7$ are each independently hydrogen or methyl;

$R^8$ is hydrogen, halogen, cyano, amino, mono- or di-($C_{1-4}$ alkyl)amino, $C_{1-8}$ alkoxy, substituted $C_{1-8}$ alkoxy, cycloalkyloxy, heterocyclooxy, $C_{1-4}$ alkylthio (e.g., —$SCH_3$, —$SCH_2CH_3$), —S-aryl, $C_{1-8}$ alkoxycarbonyl, $C_{1-7}$ alkyl, substituted $C_{1-7}$ alkyl, $C_{2-7}$ alkenyl, substituted $C_{2-7}$ alkenyl, $C_{2-7}$ alkynyl, substituted $C_{2-7}$ alkynyl, $C_{3-7}$ cycloalkyl, substituted $C_{3-7}$ cycloalkyl, $C_{3-7}$ cycloalkenyl, substituted $C_{3-7}$ cycloalkenyl, aryl, substituted aryl, heteroaryl, substituted heteroaryl, heterocyclic, or substituted heterocyclic;

$R^9$ is hydrogen, $C_{1-7}$ alkyl, substituted $C_{1-7}$ alkyl, $C_{2-7}$ alkenyl, substituted $C_{2-7}$ alkenyl, $C_{2-7}$ alkynyl, substituted $C_{2-7}$ alkynyl, $C_{3-7}$ cycloalkyl, substituted $C_{3-7}$ cycloalkyl, aryl, substituted aryl, heteroaryl, substituted heteroaryl, heterocyclic, or substituted heterocyclic; and $R^{10}$ is hydrogen, halogen, cyano, $C_{1-4}$ alkoxy, substituted $C_{1-4}$ alkoxy, $C_{1-4}$ alkyl, substituted $C_{1-4}$ alkyl, aryl, substituted aryl, heteroaryl, substituted heteroaryl, heterocyclic, or substituted heterocyclic.

One embodiment of the present invention is to provide a compound of formula (Ia), or a pharmaceutically acceptable salt or a prodrug thereof:

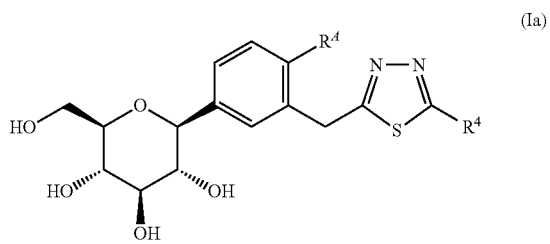

wherein $R^A$ is halogen, $C_{1-4}$ alkyl or $C_{1-4}$ alkoxy; and $R^4$ has the same meaning as defined above.

Another embodiment of the present invention is to provide a compound of formula (Ib), or a pharmaceutically acceptable salt or a prodrug thereof:

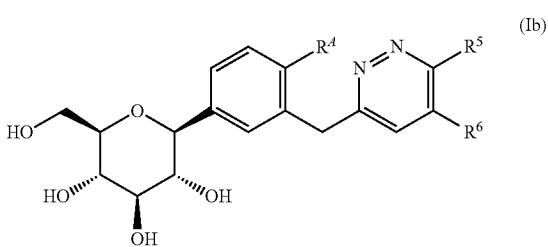

wherein $R^A$ is halogen, $C_{1-4}$ alkyl or $C_{1-4}$ alkoxy; and $R^5$ and $R^6$ have the same meanings as defined above.

Another embodiment of the present invention is to provide a compound of formula (Ic), or a pharmaceutically acceptable salt or a prodrug thereof:

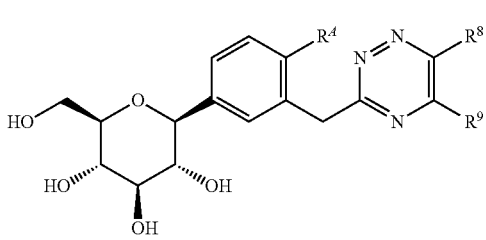

wherein $R^A$ is halogen, $C_{1-4}$ alkyl or $C_{1-4}$ alkoxy; and $R^8$ and $R^9$ have the same meanings as defined above.

Another embodiment of the present invention is to provide a compound of formula (1d), or a pharmaceutically acceptable salt or a prodrug thereof:

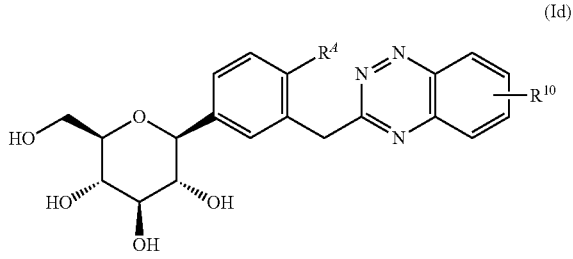

wherein $R^A$ is halogen, $C_{1-4}$ alkyl or $C_{1-4}$ alkoxy; and $R^{10}$ has the same meaning as defined above.

Compounds especially useful in the present invention are selected from the group consisting of:

(2S,3R,4R,5S,6R)-2-(4-Chloro-3-((5-(furan-2-yl)-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-(5-methylfuran-2-yl)-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-(3-methylfuran-2-yl)-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-(furan-3-yl)-1,3,4-thiadiazol-2-yl)methyl)phenyl)-6-(hydroxymethyl)tetrahydro-2H-pyran-3,4,5-triol;

(2S,3R,4R,5S,6R)-2-(4-Chloro-3-((5-(thiophen-2-yl)-1,3,4-thiadiazol-2-yl)methyl)phenyl)-6-(hydroxymethyl)tetrahydro-2H-pyran-3,4,5-triol;

(2S,3R,4R,5S,6R)-2-(3-((5-(Benzo[b]thiophen-2-yl)-1,3,4-thiadiazol-2-yl)methyl)-4-chlorophenyl)-6-(hydroxymethyl)-tetrahydro-2H-pyran-3,4,5-triol;

(2S,3R,4R,5S,6R)-2-(4-chloro-3-((5-(3-methylthiophen-2-yl)-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-(5-chlorothiophen-2-yl)-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-(3-chlorothiophen-2-yl)-1,3,4-thiadiazol-2-yl)methyl)phenyl)-6-(hydroxymethyl)tetrahydro-2H-pyran-3,4,5-triol;

(2S,3R,4R,5S,6R)-2-(4-Chloro-3-((5-(thiophen-3-yl)-1,3,4-thiadiazol-2-yl)methyl)phenyl)-6-(hydroxymethyl)tetrahydro-2H-pyran-3,4,5-triol;

(2S,3R,4R,5S,6R)-2-(4-Chloro-3-((5-(1-methyl-1H-pyrrol-2-yl)-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-(5-methylisoxazol-3-yl)-1,3,4-thiadiazol-2-yl)methyl)phenyl)-6-(hydroxymethyl)tetrahydro-2H-pyran-3,4,5-triol;

(2S,3R,4R,5S,6R)-2-(4-Chloro-3-((5-(thiazol-4-yl)-1,3,4-thiadiazol-2-yl)methyl)phenyl)-6-(hydroxymethyl)tetrahydro-2H-pyran-3,4,5-triol;

(2S,3R,4R,5S,6R)-2-(4-Chloro-3-((5-(2-(pyridin-4-yl)thiazol-5-yl)-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-(pyridin-2-yl)-1,3,4-thiadiazol-2-yl)methyl)phenyl)-6-(hydroxymethyl)tetrahydro-2H-pyran-3,4,5-triol;

(2S,3R,4R,5S,6R)-2-(4-Chloro-3-((5-(6-methylpyridin-3-yl)-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-(quinolin-2-yl)-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-(isoquinolin-3-yl)-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-cyclopentyl-1,3,4-thiadiazol-2-yl)methyl)phenyl)-6-(hydroxymethyl)tetrahydro-2H-pyran-3,4,5-triol;

(3R,4R,5S,6R)-2-(4-Chloro-3-((5-(pyridin-4-yl)-1,3,4-thiadiazol-2-yl)methyl)phenyl)-6-(hydroxymethyl)-tetrahydro-2H-pyran-3,4,5-triol;

(3R,4R,5S,6R)-2-(4-Chloro-3-((5-(pyridin-3-yl)-1,3,4-thiadiazol-2-yl)methyl)phenyl)-6-(hydroxymethyl)-tetrahydro-2H-pyran-3,4,5-triol;

(3R,4R,5S,6R)-2-(4-chloro-3-((5-p-tolyl-1,3,4-thiadiazol-2-yl)methyl)phenyl)-6-(hydroxymethyl)-tetrahydro-2H-pyran-3,4,5-triol;

(3R,4R,5S,6R)-2-(4-Chloro-3-((5-(4-propylphenyl)-1,3,4-thiadiazol-2-yl)methyl)phenyl)-6-(hydroxymethyl)-tetrahydro-2H-pyran-3,4,5-triol;

(3R,4R,5S,6R)-2-(4-Chloro-3-((5-cyclohexyl-1,3,4-thiadiazol-2-yl)methyl)phenyl)-6-(hydroxymethyl)-tetrahydro-2H-pyran-3,4,5-triol;

(3R,4R,5S,6R)-2-(4-Chloro-3-((5-((4-methylcyclohexyl)methyl)-1,3,4-thiadiazol-2-yl)methyl)phenyl)-6-(hydroxymethyl)-tetrahydro-2H-pyran-3,4,5-triol;

(3R,4R,5S,6R)-2-(4-Chloro-3-((5-(2-phenylpropyl)-1,3,4-thiadiazol-2-yl)methyl)phenyl)-6-(hydroxymethyl)-tetrahydro-2H-pyran-3,4,5-triol;

(3R,4R,5S,6R,E)-2-(4-Chloro-3-((5-styryl-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-phenyl-1,3,4-thiadiazol-2-yl)methyl)phenyl)-6-(hydroxymethyl)-tetrahydro-2H-pyran-3,4,5-triol;

(2S,3R,4R,5S,6R)-2-(4-chloro-3-((5-(4-Chlorophenyl)-1,3,4-thiadiazol-2-yl)methyl)phenyl)-6-(hydroxymethyl)-tetrahydro-2H-pyran-3,4,5-triol;

(2S,3R,4R,5S,6R)-2-(3-((5-(Benzofuran-2-yl)-1,3,4-thiadiazol-2-yl)methyl)-4-chlorophenyl)-6-(hydroxymethyl)-tetrahydro-2H-pyran-3,4,5-triol;

(2S,3R,4R,5S,6R)-2-(4-Chloro-3-((5-propyl-1,3,4-thiadiazol-2-yl)methyl)phenyl)-6-(hydroxymethyl)-tetrahydro-2H-pyran-3,4,5-triol;

(2S,3R,4R,5S,6R)-2-(3-((5-Butyl-1,3,4-thiadiazol-2-yl)methyl)-4-chlorophenyl)-6-(hydroxymethyl)-tetrahydro-2H-pyran-3,4,5-triol;

(2S,3R,4R,5S,6R)-2-(4-Chloro-3-((5-pentyl-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-heptyl-1,3,4-thiadiazol-2-yl)methyl)phenyl)-6-(hydroxymethyl)-tetrahydro-2H-pyran-3,4,5-triol;

(2R,3S,4R,5R)-2-(Hydroxymethyl)-6-(3-((5-phenyl-1,3,4-thiadiazol-2-yl)methyl)phenyl)-tetrahydro-2H-pyran-3,4,5-triol;

(2R,3S,4R,5R)-2-(Hydroxymethyl)-6-(3-((5-(pyridin-3-yl)-1,3,4-thiadiazol-2-yl)methyl)phenyl)-tetrahydro-2H-pyran-3,4,5-triol;

(2S,3R,4R,5S,6R)-2-(4-Chloro-3-((5-(5-phenylfuran-2-yl)-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-(trifluoromethyl)-1,3,4-thiadiazol-2-yl)methyl)phenyl)-6-(hydroxymethyl)tetrahydro-2H-pyran-3,4,5-triol;

(2S,3R,4R,5S,6R)-2-(4-Chloro-3-((5-(2,2,2-trifluoroethyl)-1,3,4-thiadiazol-2-yl)methyl)phenyl)-6-(hydroxymethyl)tetrahydro-2H-pyran-3,4,5-triol;

(2S,3R,4R,5S,6R)-2-(4-Chloro-3-((5-(methylthio)-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-methoxy-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-(pyrazin-2-yl)-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-(pyridazin-4-yl)-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-(6-methylpyridin-2-yl)-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-(2-methylpyridin-4-yl)-1,3,4-thiadiazol-2-yl)methyl)phenyl)-6-(hydroxymethyl)-tetrahydro-2H-pyran-3,4,5-triol;

(2S,3R,4R,5S,6R)-2-(3-((6-(1,3,4-Thiadiazol-2-yl)pyridazin-3-yl)methyl)-4-chlorophenyl)-6-(hydroxymethyl)-tetrahydro-2H-pyran-3,4,5-triol;

(2S,3R,4R,5S,6R)-2-(4-Chloro-3-((6-(5-methyloxazol-2-yl)pyridazin-3-yl)methyl)phenyl)-6-(hydroxymethyl)-tetrahydro-2H-pyran-3,4,5-triol;

(2S,3R,4R,5S,6R)-2-(4-Chloro-3-((6-chloropyridazin-3-yl)methyl)phenyl)-6-(hydroxymethyl)-tetrahydro-2H-pyran-3,4,5-triol;

Methyl 6-(2-chloro-5-((2S,3R,4R,5S,6R)-3,4,5-trihydroxy-6-(hydroxymethyl)-tetrahydro-2H-pyran-2-yl)benzyl)pyridazine-3-carboxylate;

(2S,3R,4R,5S,6R)-2-(4-Chloro-3-((6-(phenylethynyl)pyridazin-3-yl)methyl)phenyl)-6-(hydroxymethyl)-tetrahydro-2H-pyran-3,4,5-triol;

(2S,3R,4R,5S,6R)-2-(4-Chloro-3-((6-ethoxypyridazin-3-yl)methyl)phenyl)-6-(hydroxymethyl)-tetrahydro-2H-pyran-3,4,5-triol;

(2S,3R,4R,5S,6R)-2-(4-Chloro-3-((6-propoxypyridazin-3-yl)methyl)phenyl)-6-(hydroxymethyl)-tetrahydro-2H-pyran-3,4,5-triol (2S,3R,4R,5S,6R)-2-(3-((6-Butoxypyridazin-3-yl)methyl)-4-chlorophenyl)-6-(hydroxymethyl)-tetrahydro-2H-pyran-3,4,5-triol;

(2S,3R,4R,5S,6R)-2-(4-Chloro-3-((6-(pentyloxy)pyridazin-3-yl)methyl)phenyl)-6-(hydroxymethyl)-tetrahydro-2H-pyran-3,4,5-triol;

(2S,3R,4R,5S,6R)-2-(4-Chloro-3-((6-(hexyloxy)pyridazin-3-yl)methyl)phenyl)-6-(hydroxymethyl)-tetrahydro-2H-pyran-3,4,5-triol;

(2S,3R,4R,5S,6R)-2-(4-Chloro-3-((6-(octyloxy)pyridazin-3-yl)methyl)phenyl)-6-(hydroxymethyl)-tetrahydro-2H-pyran-3,4,5-triol;

(2S,3R,4R,5S,6R)-2-(4-Chloro-3-((6-isopropoxypyridazin-3-yl)methyl)phenyl)-6-(hydroxymethyl)-tetrahydro-2H-pyran-3,4,5-triol;

(2S,3R,4R,5S,6R)-2-(4-Chloro-3-((6-isobutoxypyridazin-3-yl)methyl)phenyl)-6-(hydroxymethyl)-tetrahydro-2H-pyran-3,4,5-triol;

(2S,3R,4R,5S,6R)-2-(4-Chloro-3-((6-(cyclohexyloxy)pyridazin-3-yl)methyl)phenyl)-6-(hydroxymethyl)-tetrahydro-2H-pyran-3,4,5-triol;

(2S,3R,4R,5S,6R)-2-(4-Chloro-3-((6-(tetrahydro-2H-pyran-4-yloxy)pyridazin-3-yl)methyl)phenyl)-6-(hydroxymethyl)-tetrahydro-2H-pyran-3,4,5-triol;

(2S,3R,4R,5S,6R)-2-(4-chloro-3-((6-phenylpyridazin-3-yl)methyl)phenyl)-6-(hydroxymethyl)-tetrahydro-2H-pyran-3,4,5-triol;

(2S,3R,4R,5S,6R)-2-(4-chloro-3-((6-(furan-2-yl)pyridazin-3-yl)methyl)phenyl)-6-(hydroxymethyl)-tetrahydro-2H-pyran-3,4,5-triol;

(2S,3R,4R,5S,6R)-2-(4-Chloro-3-((6-(furan-3-yl)pyridazin-3-yl)methyl)phenyl)-6-(hydroxymethyl)-tetrahydro-2H-pyran-3,4,5-triol;

(2S,3R,4R,5S,6R)-2-(4-Chloro-3-((6-(pyridin-3-yl)pyridazin-3-yl)methyl)phenyl)-6-(hydroxymethyl)-tetrahydro-2H-pyran-3,4,5-triol;

(2S,3R,4R,5S,6R)-2-(4-Chloro-3-((6-(thiophen-2-yl)pyridazin-3-yl)methyl)phenyl)-6-(hydroxymethyl)-tetrahydro-2H-pyran-3,4,5-triol;

(2S,3R,4R,5S,6R)-2-(4-chloro-3-((6-(thiophen-3-yl)pyridazin-3-yl)methyl)phenyl)-6-(hydroxymethyl)-tetrahydro-2H-pyran-3,4,5-triol;

(2S,3R,4R,5S,6R)-2-(3-((6-(Benzo[d][1,3]dioxol-5-yl)pyridazin-3-yl)methyl)-4-chlorophenyl)-6-(hydroxymethyl)-tetrahydro-2H-pyran-3,4,5-triol;

(2S,3R,4R,5S,6R)-2-(4-Chloro-3-((6-(2,3-dihydrobenzo[b][1,4]dioxin-6-yl)pyridazin-3-yl)methyl)phenyl)-6-(hydroxymethyl)-tetrahydro-2H-pyran-3,4,5-triol;

(2S,3R,4R,5S,6R)-2-(4-Chloro-3-((6-(5-methylthiophen-2-yl)pyridazin-3-yl)methyl)phenyl)-6-(hydroxymethyl)-tetrahydro-2H-pyran-3,4,5-triol;

(2S,3R,4R,5S,6R)-2-(4-Chloro-3-((6-(4-fluorophenyl)pyridazin-3-yl)methyl)phenyl)-6-(hydroxymethyl)-tetrahydro-2H-pyran-3,4,5-triol;

(2S,3R,4R,5S,6R)-2-(4-Chloro-3-((6-(3-methoxyphenyl)pyridazin-3-yl)methyl)phenyl)-6-(hydroxymethyl)-tetrahydro-2H-pyran-3,4,5-triol;

(2S,3R,4R,5S,6R)-2-(4-Chloro-3-((6-ethylpyridazin-3-yl)methyl)phenyl)-6-(hydroxymethyl)-tetrahydro-2H-pyran-3,4,5-triol;

(2S,3R,4R,5S,6R)-2-(4-Chloro-3-((6-methylpyridazin-3-yl)methyl)phenyl)-6-(hydroxymethyl)-tetrahydro-2H-pyran-3,4,5-triol (2S,3R,4R,5S,6R)-2-(4-Chloro-3-((6-propylpyridazin-3-yl)methyl)phenyl)-6-(hydroxymethyl)-tetrahydro-2H-pyran-3,4,5-triol;

(2S,3R,4R,5S,6R)-2-(4-Chloro-3-((6-isopropylpyridazin-3-yl)methyl)phenyl)-6-(hydroxymethyl)-tetrahydro-2H-pyran-3,4,5-triol;

(2S,3R,4R,5S,6R)-2-(3-((6-Butylpyridazin-3-yl)methyl)-4-chlorophenyl)-6-(hydroxymethyl)-tetrahydro-2H-pyran-3,4,5-triol;

(2S,3R,4R,5S,6R)-2-(4-Chloro-3-((6-isobutylpyridazin-3-yl)methyl)phenyl)-6-(hydroxymethyl)-tetrahydro-2H-pyran-3,4,5-triol;

(2S,3R,4R,5S,6R)-2-(4-Chloro-3-((6-pentylpyridazin-3-yl)methyl)phenyl)-6-(hydroxymethyl)-tetrahydro-2H-pyran-3,4,5-triol;

(2S,3R,4R,5S,6R)-2-(4-Chloro-3-((6-(methylthio)pyridazin-3-yl)methyl)phenyl)-6-(hydroxymethyl)-tetrahydro-2H-pyran-3,4,5-triol;

(2S,3R,4R,5S,6R)-2-(4-Chloro-3-((6-(ethylthio)pyridazin-3-yl)methyl)phenyl)-6-(hydroxymethyl)-tetrahydro-2H-pyran-3,4,5-triol;

(2S,3R,4R,5S,6R)-2-(4-Chloro-3-((6-(phenylthio)pyridazin-3-yl)methyl)phenyl)-6-(hydroxymethyl)-tetrahydro-2H-pyran-3,4,5-triol;

(2S,3R,4R,5S,6R)-2-(4-Chloro-3-((5-methyl-6-(methylthio)pyridazin-3-yl)methyl)phenyl)-6-(hydroxymethyl)tetrahydro-2H-pyran-3,4,5-triol;

6-(2-Chloro-5-((2S,3R,4R,5S,6R)-3,4,5-trihydroxy-6-(hydroxymethyl)-tetrahydro-2H-pyran-2-yl)benzyl)-4-methylpyridazin-3(2H)-one;

(2S,3R,4R,5S,6R)-2-(4-Chloro-3-((6-morpholinopyridazin-3-yl)methyl)phenyl)-6-(hydroxymethyl)-tetrahydro-2H-pyran-3,4,5-triol;

(2S,3R,4R,5S,6R)-2-(4-Chloro-3-((6-(phenylamino)pyridazin-3-yl)methyl)phenyl)-6-(hydroxymethyl)-tetrahydro-2H-pyran-3,4,5-triol;

(2S,3R,4R,5S,6R)-2-(4-Chloro-3-((6-(pyrrolidin-1-yl)pyridazin-3-yl)methyl)phenyl)-6-(hydroxymethyl)-tetrahydro-2H-pyran-3,4,5-triol;

(2S,3R,4R,5S,6R)-2-(4-Chloro-3-((7-methylbenzo[e][1,2,4]triazin-3-yl)methyl)phenyl)-6-(hydroxymethyl)tetrahydro-2H-pyran-3,4,5-triol;

(2S,3R,4R,5S,6R)-2-(3-(Benzo[e][1,2,4]triazin-3-ylmethyl)-4-chlorophenyl)-6-(hydroxymethyl)tetrahydro-2H-pyran-3,4,5-triol;

(2S,3R,4R,5S,6R)-2-(3-((1,2,4-triazin-3-yl)methyl)-4-chlorophenyl)-6-(hydroxymethyl)tetrahydro-2H-pyran-3,4,5-triol;

(2S,3R,4R,5S,6R)-2-(4-chloro-3-((5-phenyl-1,2,4-triazin-3-yl)methyl)phenyl)-6-(hydroxymethyl)tetrahydro-2H-pyran-3,4,5-triol;

(2S,3R,4R,5S,6R)-2-(4-Chloro-3-((6-methoxy-1,2,4-triazin-3-yl)methyl)phenyl)-6-(hydroxymethyl)tetrahydro-2H-pyran-3,4,5-triol;

(2S,3R,4R,5S,6R)-2-(3-((5-(Furan-2-yl)-1,3,4-thiadiazol-2-yl)methyl)naphthalene-1-yl)-6-(hydroxymethyl)-tetrahydro-2H-pyran-3,4,5-triol;

(2S,3R,4R,5S,6R)-2-(3-((5-(Furan-2-yl)-1,3,4-thiadiazol-2-yl)methyl)-4-methoxynaphthalen-1-yl)-6-(hydroxymethyl)-tetrahydro-2H-pyran-3,4,5-triol;

(2S,3R,4R,5S,6R)-2-(3-((5-(Furan-2-yl)-1,3,4-thiadiazol-2-yl)methyl)-4-hydroxynaphthalen-1-yl)-6-(hydroxymethyl)-tetrahydro-2H-pyran-3,4,5-triol;

(2S,3R,4R,5S,6R)-2-(4-((5-(Furan-2-yl)-1,3,4-thiadiazol-2-yl)methyl)naphthalen-2-yl)-6-(hydroxymethyl)-tetrahydro-2H-pyran-3,4,5-triol;

(2S,3R,4R,5S,6R)-2-(2,4-Dichloro-5-((5-(furan-2-yl)-1,3,4-thiadiazol-2-yl)methyl)phenyl)-6-(hydroxymethyl)-tetrahydro-2H-pyran-3,4,5-triol; and (2S,3R,4R,5S,6R)-2-(4-Chloro-5-((5-(furan-2-yl)-1,3,4-thiadiazol-2-yl)methyl)-2-methoxyphenyl)-6-(hydroxymethyl)-tetrahydro-2H-pyran-3,4,5-triol.

General Synthetic Sequence

The compounds of the present invention and the preparation thereof will be better understood in connection with the following synthetic schemes, which are merely illustrative of the methods by which the compounds of the invention may be prepared and are not intended to limit the scope of the invention as defined in the appended claims.

Synthesis of the inventive compounds may commence with preparation of the lactone (2). Commercially available perbenzylated gluconolactol (1) is treated with tetrapropylammonium perruthenate (TPAP) in the presence of 4-methylmorpholine N-oxide (NMO) to provide the requisite perbenzylated gluconolactone (2) in high yield as shown in Reaction Scheme 1.

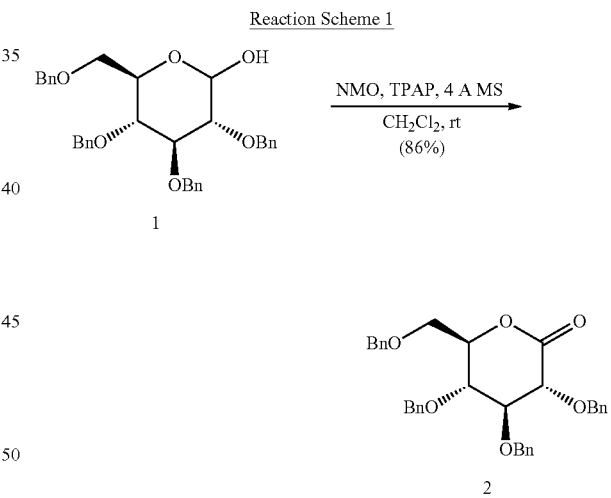

As shown in Reaction Scheme 2, reduction of commercially available 5-bromo-2-chlorobenzoic acid (3) with borane-dimethyl sulfide complex, and subsequent silylation of the corresponding alcohol with triisopropylsilyl chloride (TIPSCl) in the presence of imidazole and 4-(dimethylamino)pyridine (DMAP) may generate bromide (4) in 95% yield for the two steps. Lithium-halogen exchange of bromide (4), followed by addition of the resulting nascent lithiated aromatic to perbenzylated gluconolactone (2), may produce a mixture of the corresponding lactols, which is reduced using triethylsilane and BF$_3$ etherate, followed by desilylation, afford alcohol (5) in 98% yield for the three steps.

Reaction Scheme 2

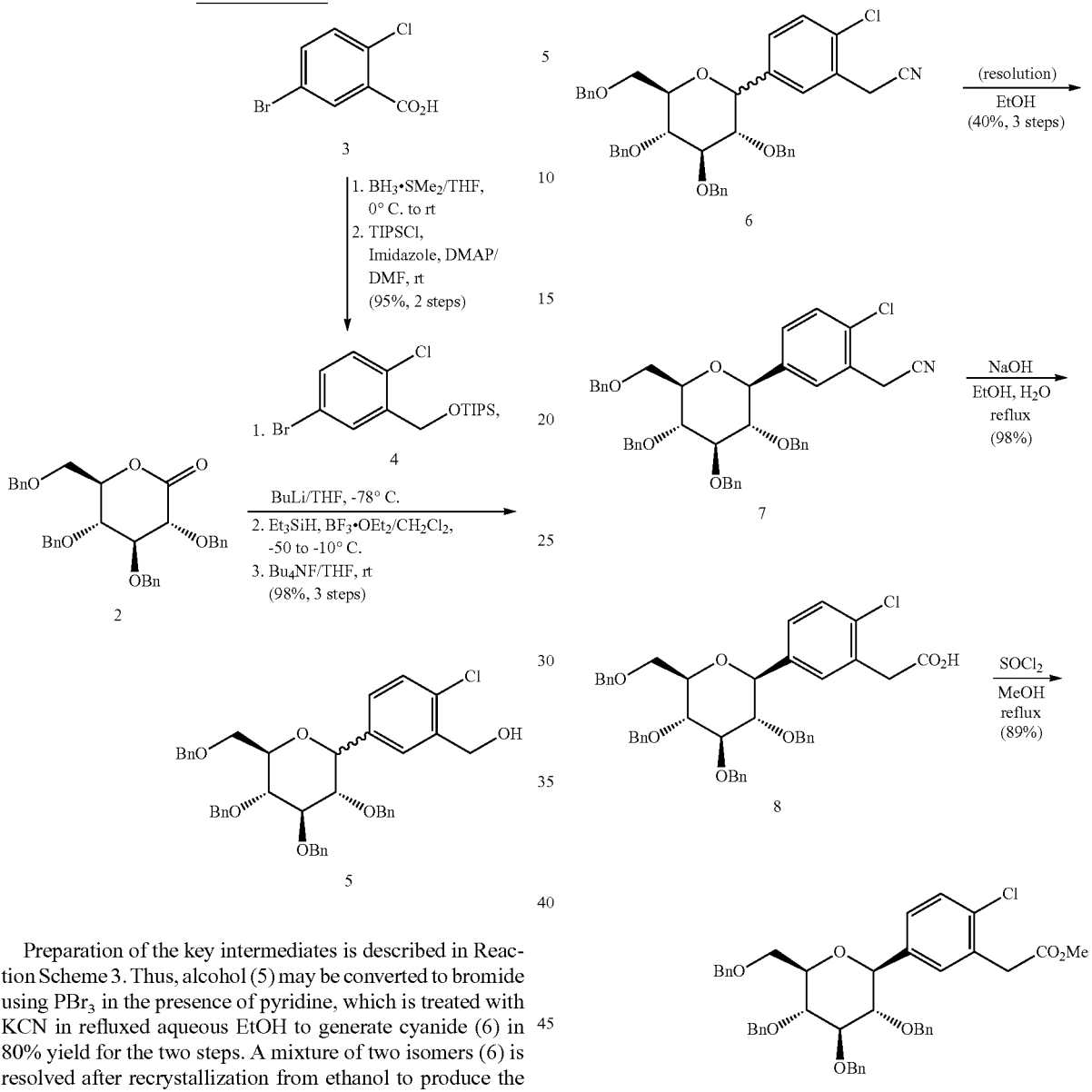

Preparation of the key intermediates is described in Reaction Scheme 3. Thus, alcohol (5) may be converted to bromide using PBr$_3$ in the presence of pyridine, which is treated with KCN in refluxed aqueous EtOH to generate cyanide (6) in 80% yield for the two steps. A mixture of two isomers (6) is resolved after recrystallization from ethanol to produce the required beta-isomer (7) in about 40% yield. Hydrolysis of (7) with sodium hydroxide in aqueous ethanol generates the carboxylic acid (8) in quantitative yield. Treatment of the carboxylic acid (8) with thionyl chloride in refluxed methanol may produce the corresponding methyl ester (9) in 89% yield.

Reaction Scheme 3

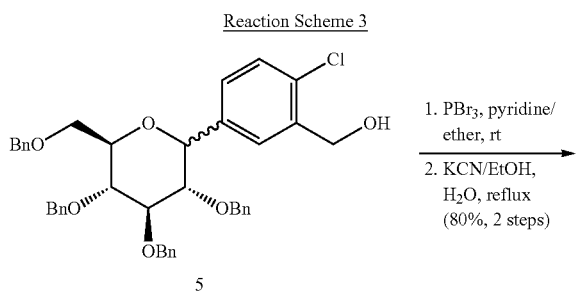

Thiadiazoles at Ring B (formula Ia) may be synthesized as shown in Reaction Scheme 4. Coupling of acid (8) and hydrazide such as furan-2-carbohydrazide (10) using N-(3-dimethylaminopropyl)-N'-ethylcarbodiimide (EDC), 1-hydroxybenzotriazole (HOBt), and 4-methylmorpholine (NMM) in the presence of N,N-dimethylformamide (DMF) yield the corresponding acylhydrazide (11), which is cyclized using Lawesson's reagent to generate thiadiazole (12) in 81% yield for the two steps. Deprotection of the four benzyl groups using trimethylsilyl iodide (TMSI), followed by peracetylation using acetic anhydride and purification by either column chromatography or recrystallization generated the corresponding tetraacetate, which is hydrolyzed with NaOMe in methanol to yield the target compound (13) in 31% yield for the three steps.

Reaction Scheme 4

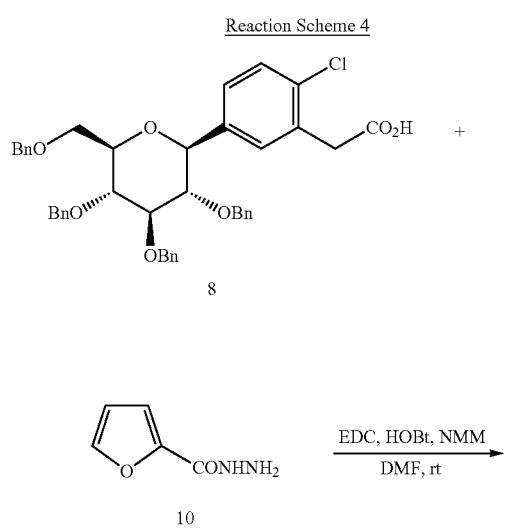

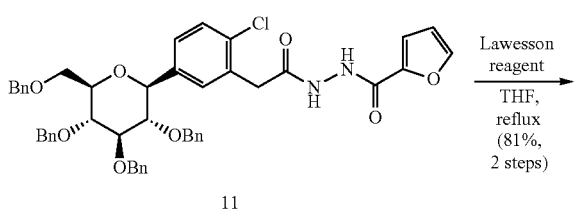

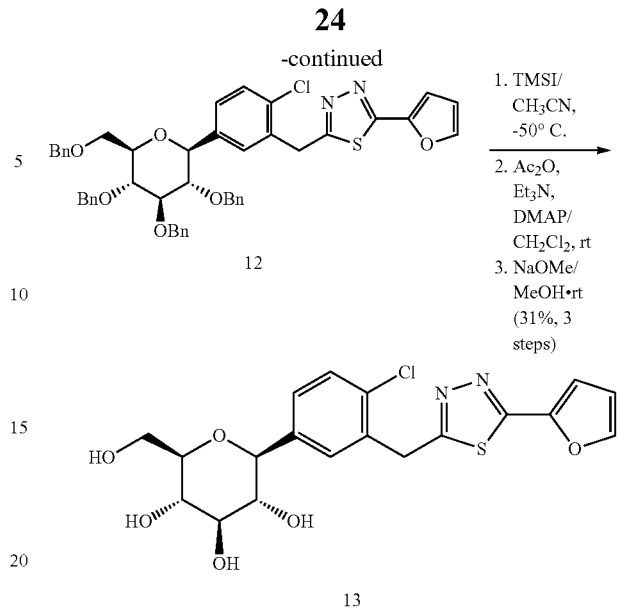

Alternatively, another inventive compound may be prepared as shown in Reaction Scheme 5. Thus, the acid (8) is converted to the hydrazide (14) using hydrazine in the presence of EDC, HOBt and DMF in 95% yield. This hydrazide (14) is coupled to commercially available 5-phenylfuran-2-carboxylic acid (15) under conditions of EDC, HOBt and NMM in DMF to produce the corresponding acylhydrazide. Subsequent cyclization using Lawesson's reagent, followed by deprotection of benzyl groups using trimethylsilyl iodide (TMSI) yield the target compound (16) in 36% yield for the three steps as shown in Reaction Scheme 5.

Reaction Scheme 5

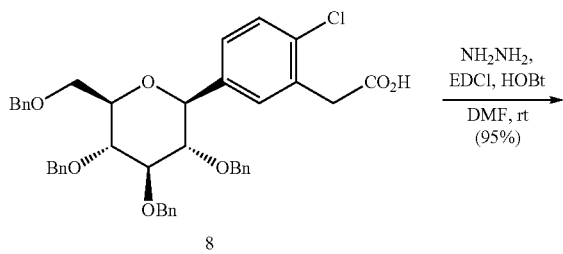

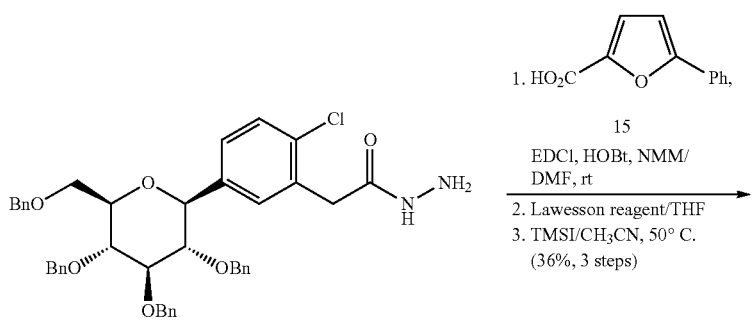

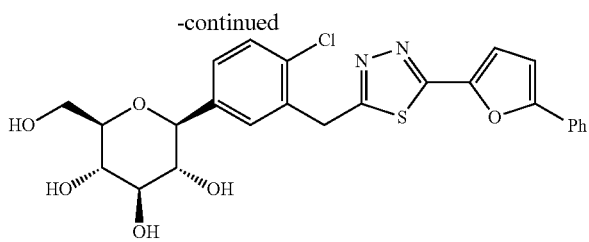

16

Another approach toward thiadiazole compounds are described in Reaction Scheme 6. Thus, acid (8) is coupled and cyclized concomitantly with thiosemicarbazide (17) using phosphorus(V) oxychloride to provide the corresponding aminothiadiazole, which is converted to chlorothiadiazole (18) using sodium nitrite and a catalytic amount of copper in the presence of concentrated HCl and acetic acid in 22% yield. Treatment of chlorothiadiazole (18) with NaSMe and subsequent deprotection of benzyl groups yields the target methylthio-thiadiazole (19) in 25% yield for the two steps.

Reaction Scheme 6

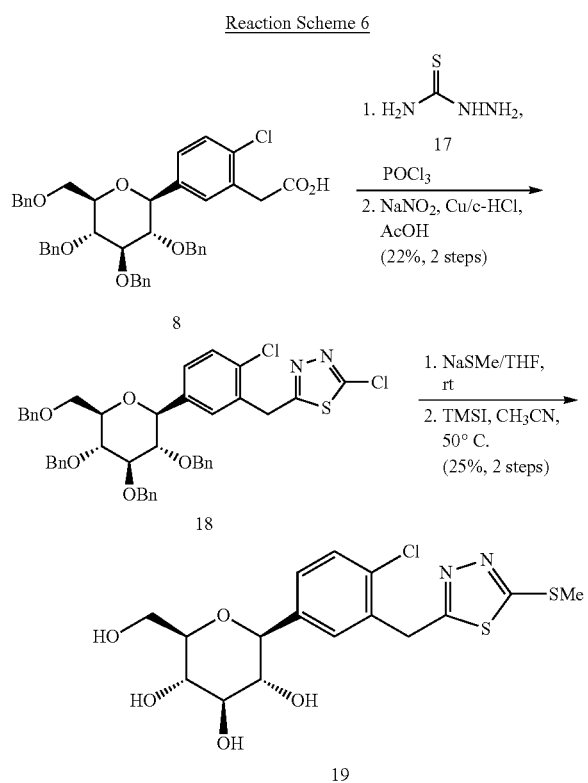

Another approach toward a target compound is illustrated in Reaction Scheme 7. Usual coupling and cyclization with compound (20) as previously described, produce the corresponding acylhydrazide, which is treated with trimethylsilyl trifluoromethanesulfonate (TMSOTf) and acetic anhydride to provide the corresponding tetraacetate. The peracetylated compound is hydrolyzed to yield the target compound (21) in 10% yield for the four steps. This alternative deprotection method is frequently employed, especially in case of unsatisfactory reactions with TMSI.

Reaction Scheme 7

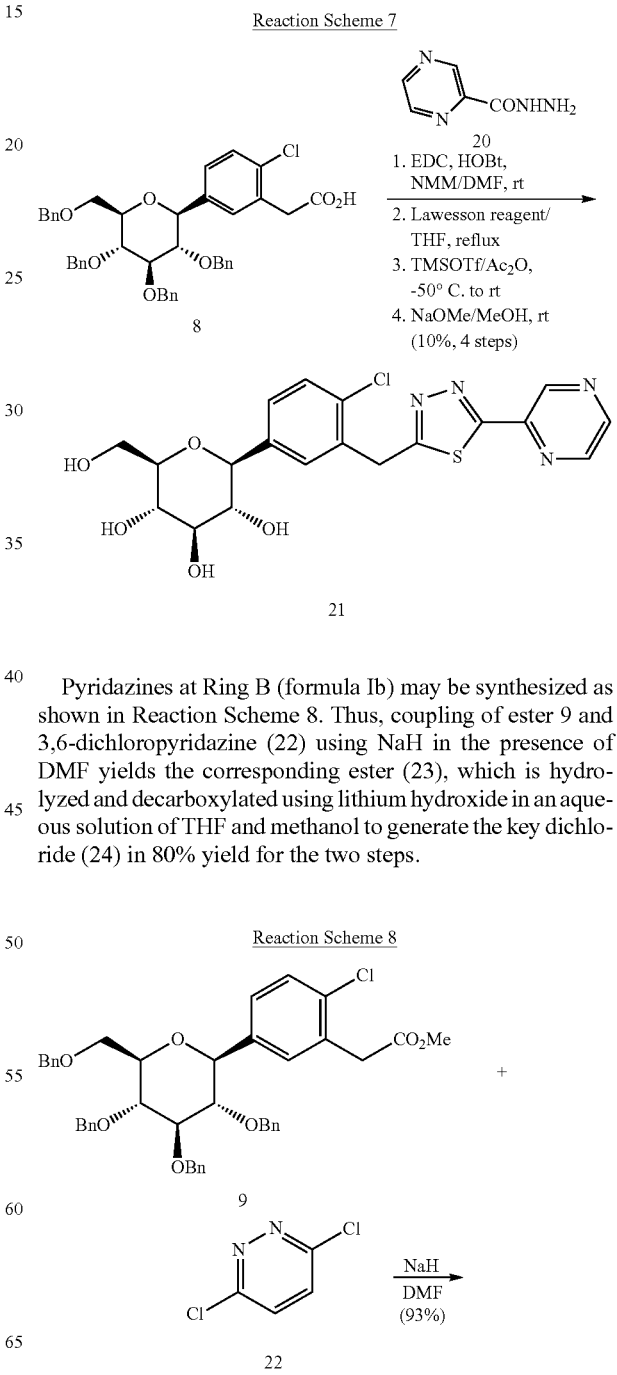

Pyridazines at Ring B (formula Ib) may be synthesized as shown in Reaction Scheme 8. Thus, coupling of ester 9 and 3,6-dichloropyridazine (22) using NaH in the presence of DMF yields the corresponding ester (23), which is hydrolyzed and decarboxylated using lithium hydroxide in an aqueous solution of THF and methanol to generate the key dichloride (24) in 80% yield for the two steps.

Reaction Scheme 8

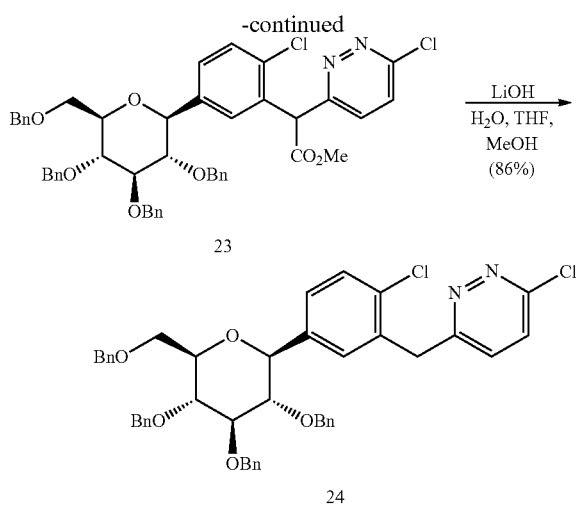

Utilization of the key intermediate dichloride (24) is illustrated in Reaction Scheme 9. Replacement of chloropyridazine with sodium alkoxide provides the corresponding compound (25). Likewise, treatment of the compound (24) with NaSMe yields methylthio-pyridazine (26) in 74% yield uneventfully. Fe(III)-mediated alkylation is conducted on the compound (24) using Grignard reagent such as ethylmagnesium bromide to afford ethylpyridazine (27) in 67% yield. Sonogashira reaction is conducted on the compound (24) with ethynylbenzene (29) to provide the compound (32). Palladium(0)-catalyzed cyanation proceeds smoothly under microwave irradiation to provide the cyanopyridazine (31). Suzuki-Miyaura coupling of the compound (24) with boronic acid such as phenylboronic acid (28) generates phenylpyridazine (30) in 73% yield. Amino group is also introduced smoothly under microwave conditions in approximately 80% yield to produce the compound of structure (33).

Reaction Scheme 9

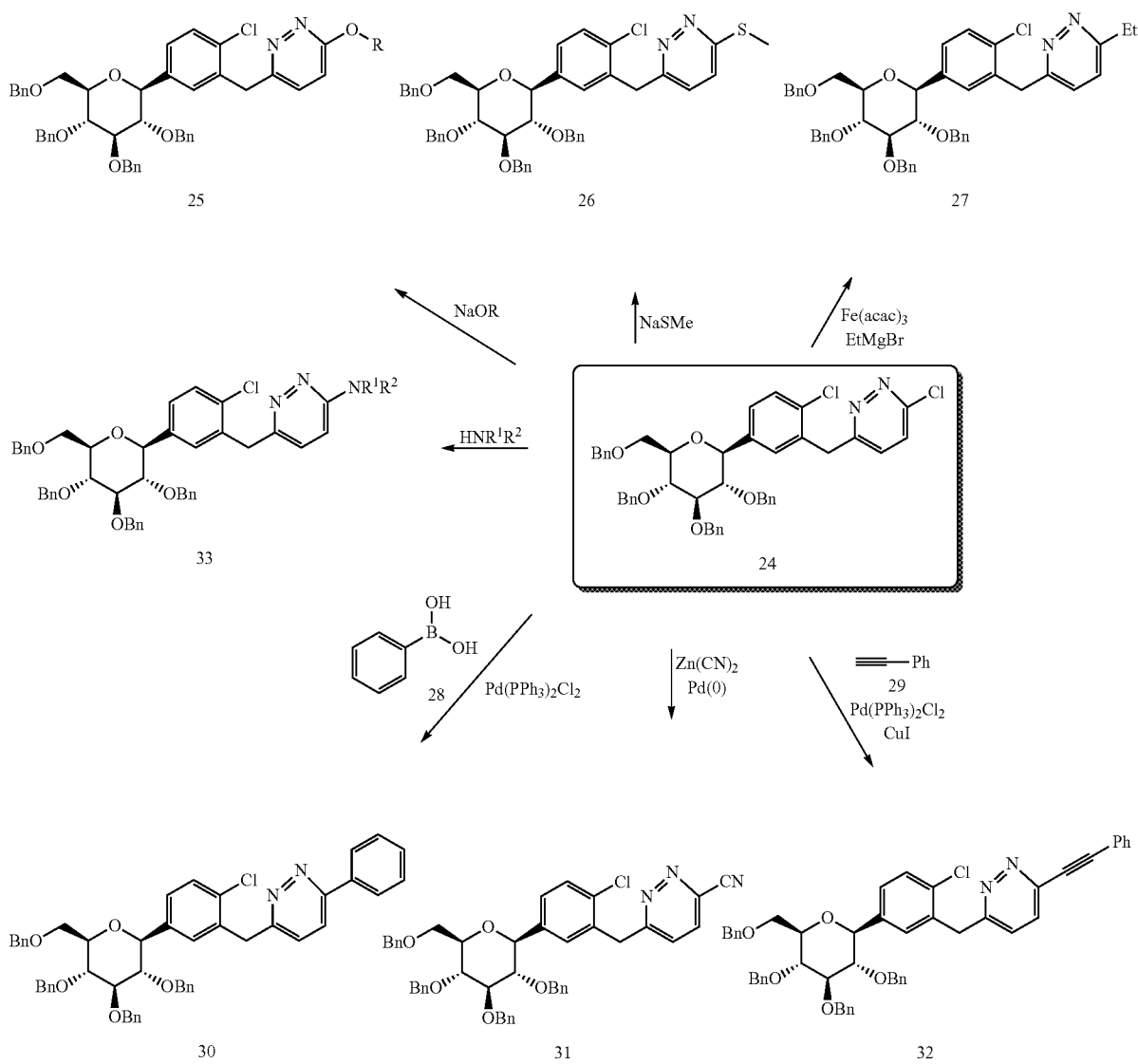

Alternatively, pyridazines at ring B (formula Ib) may be prepared by adopting Lilly's procedure [Hamdouchi, C. et al. *J. Med. Chem.* 2003, 46, 4333-4341] as demonstrated in Reaction Scheme 10. Thus, cyanide (6) is condensed with 3,6-dichloropyridazine (22) under basic conditions. Subsequent oxidation with hydrogen peroxide affords the corresponding ketone (34) in 48% yield for the two steps. Alcohol group is installed as described previously using in situ-generated sodium hexanoate to produce hexyloxypyridazine (36) in 71% yield. After rather extensive experimentation, ketone is reduced successfully to the corresponding benzylpyridazine (38) through the following four steps in overall 34% yield: i. reduction of ketone using sodium borohydride; ii. chlorination of alcohol using thionyl chloride; iii. reduction of chloride using n-Bu$_3$SnH and 2,2'-(azobis)isobutyronitrile (AIBN); and iv. separation of beta-anomer.

Reaction Scheme 10

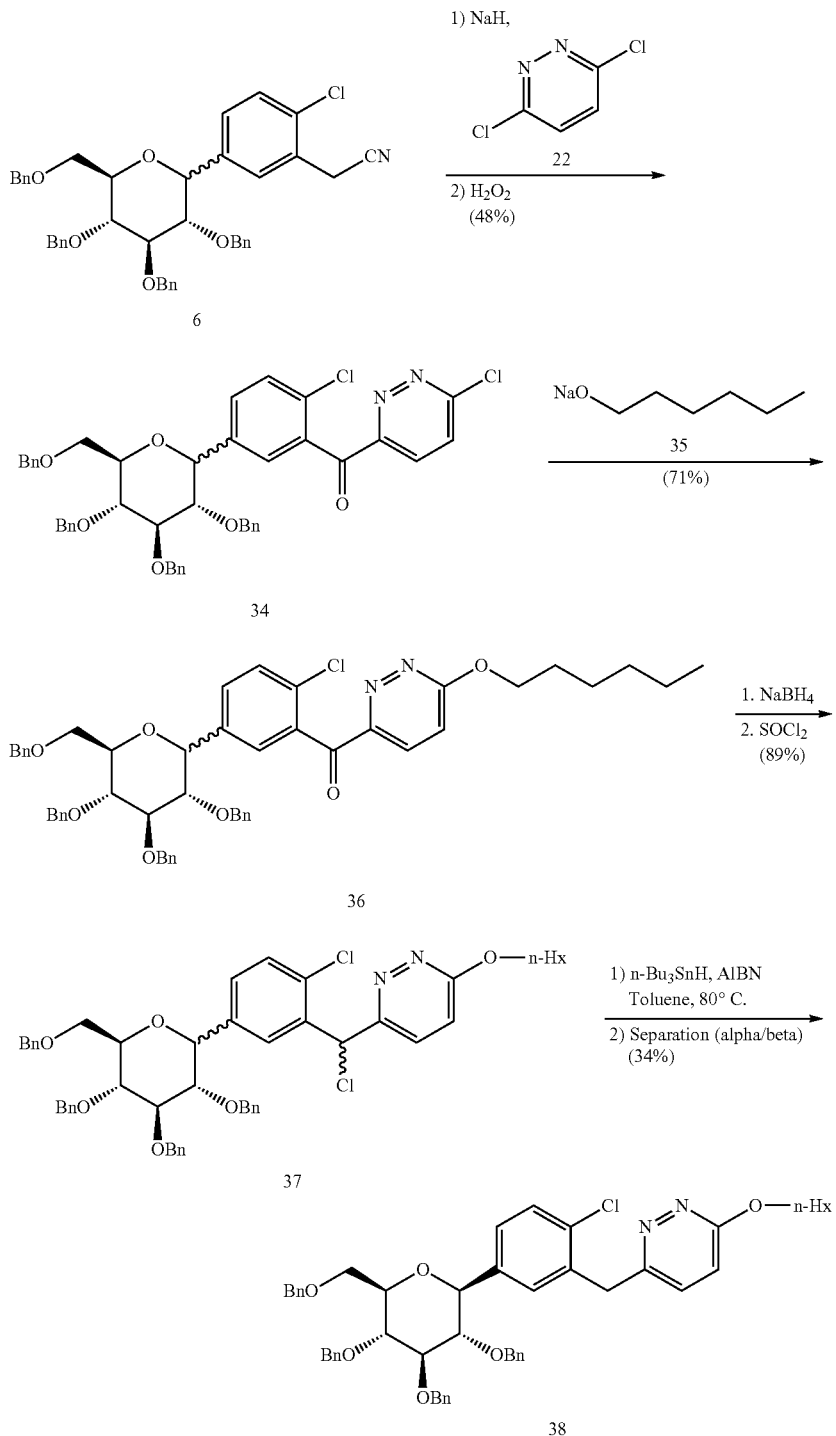

Substituted pyridazines at ring B (formula Ib) may be prepared as shown in Reaction Scheme 11. Thus, cyanide (7) is condensed with 3,6-dichloro-4-methylpyridazine (39) under basic conditions to give rise to the compound (40) in 91% yield. Next, treatment of the compound (40) with HOAc—HCl—H$_2$O (v/v 1:2:1) at 100° C. furnishes a target 4-methylpyridazin-3(2H)-one (41). Subsequently, peracetylation using acetic anhydride in the presence of DMAP and triethylamine, followed by chlorination using phosphorus (III) oxychloride produces the corresponding chloride (42) in 42% yield for the three steps. Finally, treatment of the compound (42) with sodium thiomethoxide generated the target compound (43) in approximately 50% yield.

1,2,4-Triazines at ring B [Formula (Ic)] may be prepared as shown in Reaction Scheme 12. Cyanide (7) is treated with gaseous HCl to yield the corresponding acetimidoyl chloride (44), which is treated with hydrazine to produce the acetimidohydrazide (45) in 71% yield for the two steps. Condensation of the acetimidohydrazide (45) with oxalaldehyde generated the target 1,2,4-triazine (46) in 84% yield.

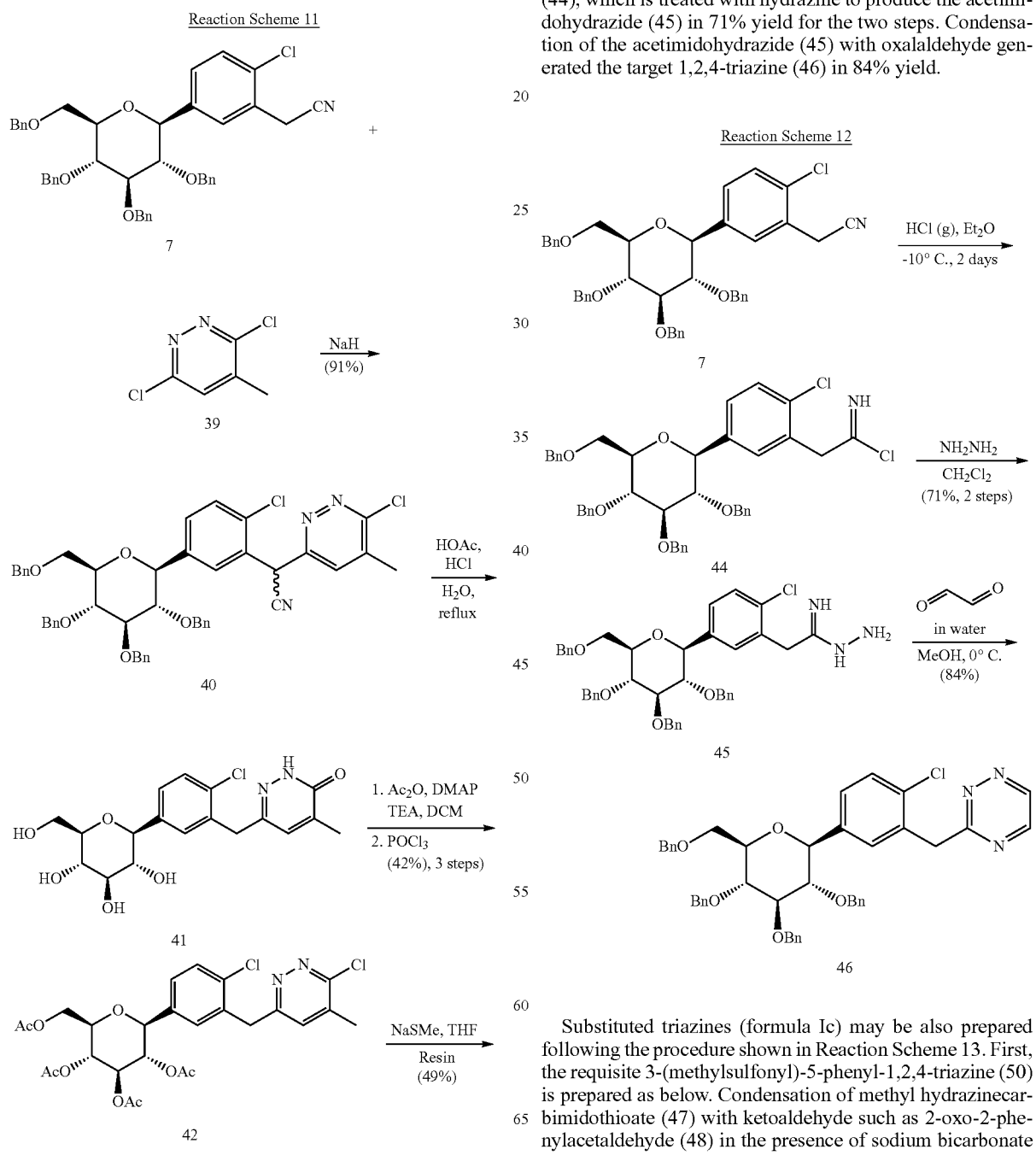

Substituted triazines (formula Ic) may be also prepared following the procedure shown in Reaction Scheme 13. First, the requisite 3-(methylsulfonyl)-5-phenyl-1,2,4-triazine (50) is prepared as below. Condensation of methyl hydrazinecarbimidothioate (47) with ketoaldehyde such as 2-oxo-2-phenylacetaldehyde (48) in the presence of sodium bicarbonate in methanol generates compound (49), which is treated with meta-chloroperoxybenzoic acid (m-CPBA) and CH₂Cl₂ to produce 3-(methylsulfonyl)-5-phenyl-1,2,4-triazine (50). Ester (9) is condensed with 3-(methylsulfonyl)-5-phenyl-1,2,4-triazine (50) under basic conditions to give rise to the compound (51) in 54% yield. Hydrolysis and concomitant decarboxylation result in substituted triazine (52) in 71% yield.

compound (56) with phosphorus(V) oxychloride yield the corresponding chloride (57) in 35% yield for the two steps. Deprotection of benzyl groups is conducted by a sequence of reactions to give rise to 1,2,4-triazine (59): i. peracetylation using TMSOTf and acetic anhydride (yield: 56%); and ii. hydrolysis and concurrent methoxylation using sodium methoxide in methanol (yield: 94%).

Reaction Scheme 13

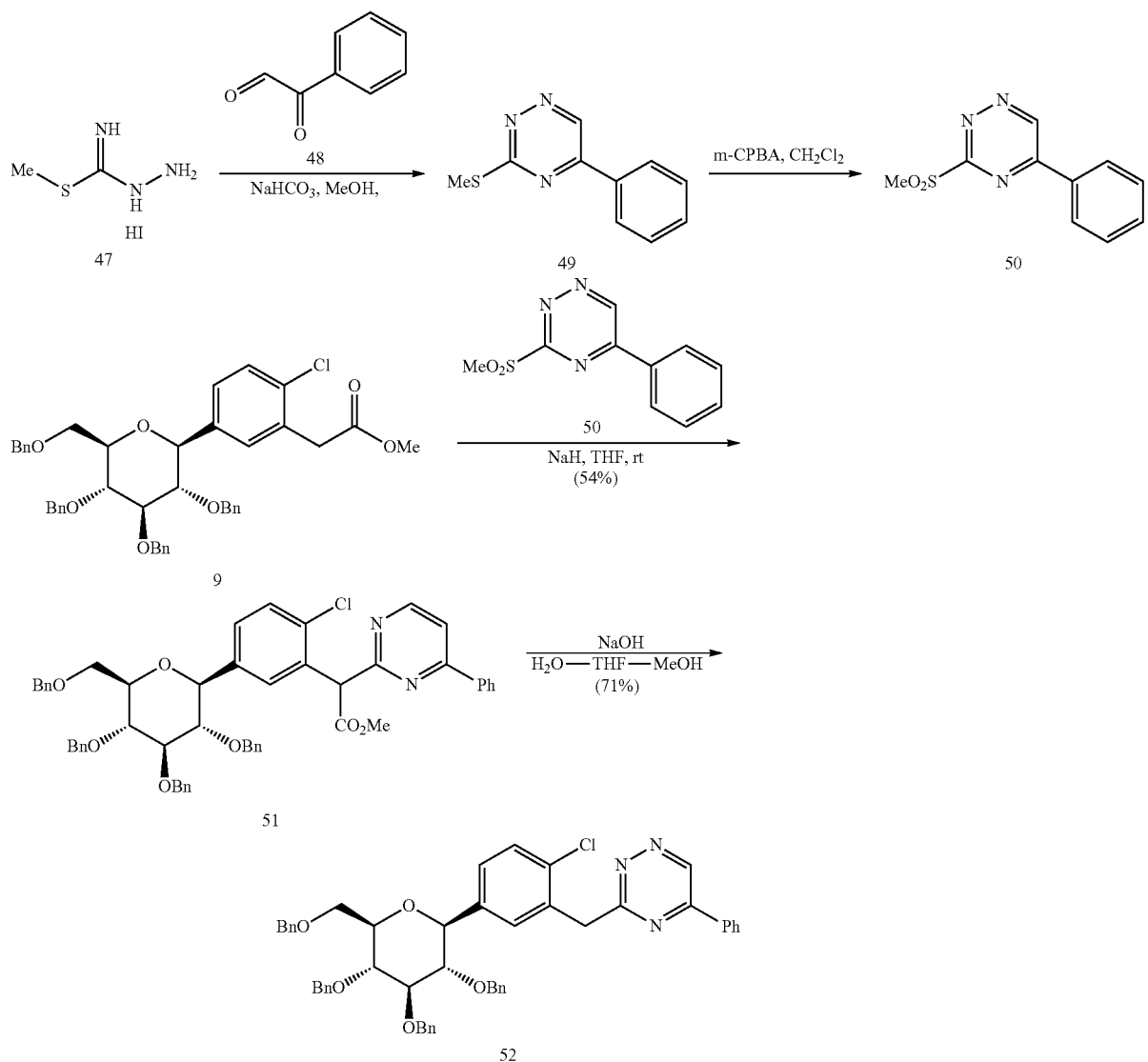

Alternatively, substituted triazines at B ring (formula Ic) may be synthesized as illustrated in Reaction Scheme 14. Thus, acid (8) is coupled with methyl 2-aminoacetate hydrochloride (53) in the presence of 1-ethyl-3-(3'-dimethylaminopropyl) carbodiimide hydrochloride (EDCI), HOBt and NMM to provide the compound (54) in quantitative yield. Condensation of the compound (54) with hydrazine, and subsequent treatment with ammonium acetate in refluxed acetic acid generated dihydrotriazinone (55) in 77% yield. Oxidation of dihydrotriazinone (55) using 2,3-dichloro-5,6-dicyano-1,4-benzoquinone (DDQ), followed by treatment of the Reaction Scheme 14

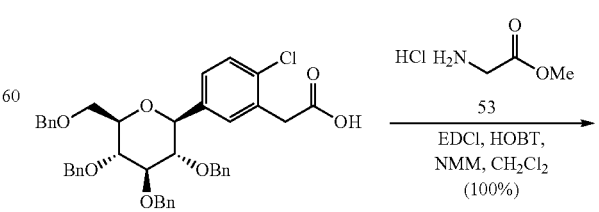

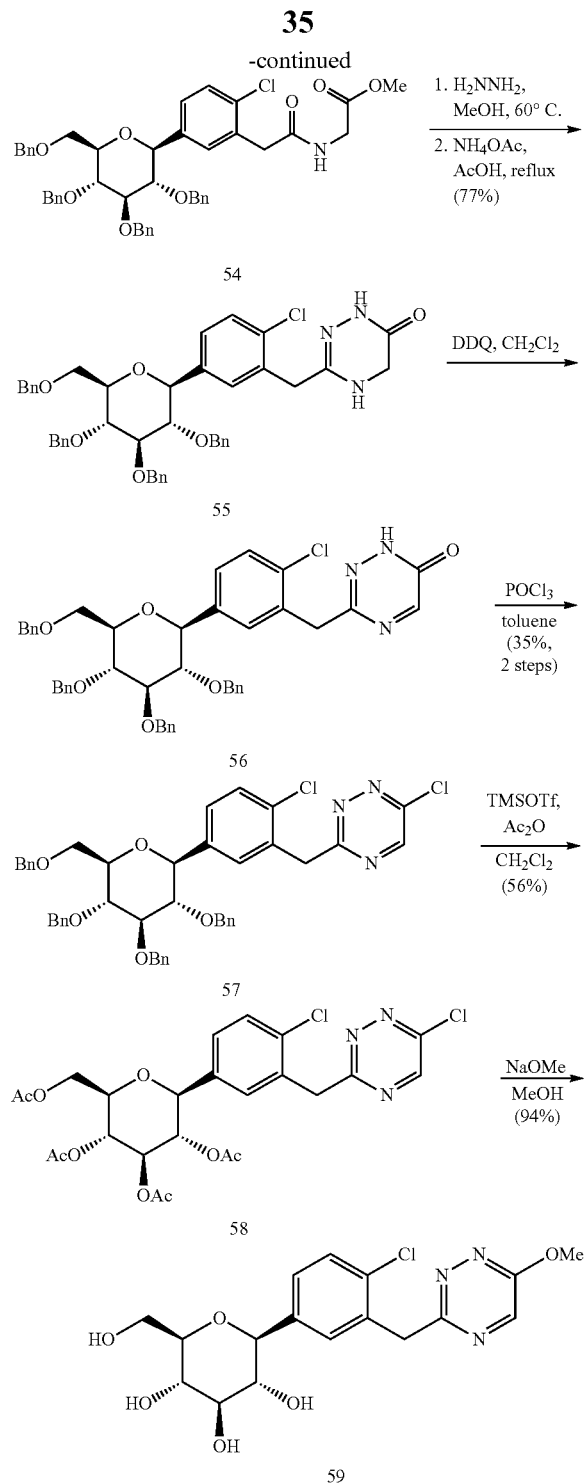

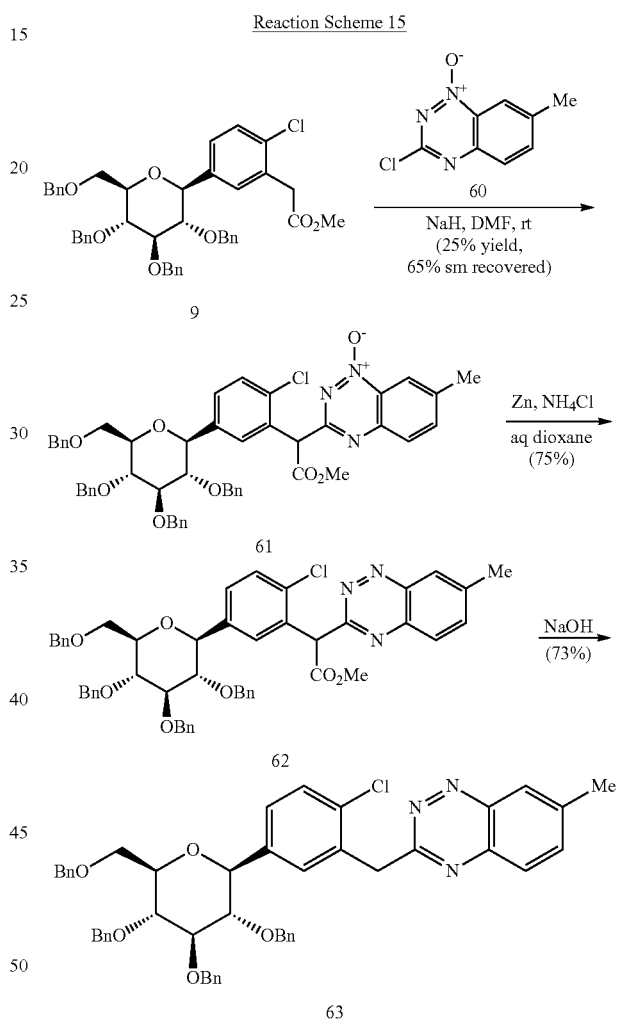

carried out by using a metal such as zinc or Fe. Particularly, when Fe is used, the reduction of triazine oxide is conducted under acidic conditions such as acetic acid (HOAc). When zinc is used, the reduction of triazine oxide is conducted under basic conditions such as ammonium chloride, or under neutral conditions. Also, the reduction of triazine oxide can be carried out by contacting triazine oxide (61) with hydrogen gas in the presence of palladium catalysts supported on carbon.

The hydrolysis of the resulting compound (62) can be conducted by using metal hydroxide such NaOH or LiOH.

Reaction Scheme 15

Preparation of benzotriazine [formula (Id)] may be performed as shown in Reaction Scheme 15. Condensation of ester (9) with chlorobenzotriazine such as 3-chloro-7-methylbenzo[e][1,2,4]triazine 1-oxide (60) undergoes under basic conditions to provide the corresponding triazine oxide (61) in 25% yield, or 65% yield based on recovered starting material. Reduction of triazine oxide (61) using zinc and ammonium chloride in aqueous dioxane, followed by hydrolysis and concurrent decarboxylation of the resulting compound (62), generate the corresponding benzotriazine (63) in 55% yield for the two steps. The reduction of triazine oxide can be In order to accommodate need for SAR optimization of the C-aryl glucosedes, naphthalenes at A ring may be synthesized and evaluated. One isomer of naphthalene may be prepared and evaluated as shown in Reaction Scheme 16. Thus, methyl 4-bromo-2-naphthoate (65a) may be obtained by adopting the procedure shown in the literature [Ashworth, I. W. et al. *Org. Process Res. Dev.* 2003, 7, 74-81] and methyl 4-bromo-1-methoxy-2-naphthoate (65b) may be obtained following the reported procedure [Huang, Y. et al. *J. Med. Chem.* 2001, 44, 1815-1826].

Methyl naphthoate (65a or 65b) may be reduced to the corresponding alcohol by using lithium borohydride in refluxed THF. Subsequently, silylation of the resulting alcohol with triisopropylsilyl chloride (TIPSCl) generates the corresponding 2-naphthalenylmethyl silyl ether (68a or 68b) in high yield.

Lithium-halogen exchange of the 2-naphthalenylmethyl silyl ether (68a or 68b), followed by addition of the resulting nascent lithiated aromatic to gluconolactone (2), produces a mixture of the corresponding lactols, which are reduced using triethylsilane and boron trifluoride etherate. After desilylation of silyl ether to the corresponding alcohol, 2-naphthalenemehanol (69a or 69b) is obtained in high yield following the identical procedure as in Reaction Scheme 2. The reduction of lactol proceeded with high selectivity, thereby giving only β-anomer.

Next, three steps are involved for the preparation of an acid (70a or 70b) in a similar manner as previously described in Reaction Scheme 3 (44-46%, 3 steps): i.e., i. bromination using phosphorus tribromide; ii. cyanation using potassium cyanide; and iii. hydrolysis using hydroxide. Subsequently, usual coupling between acid (70a or 70b) and 2-furoic hydrizide in the presence of EDCI and cyclization using Lawesson's reagent produces thiadiazole ring. Subsequent deprotection of benzyl groups using TMSI yields the target compound (71a and 71b) in moderate yield.

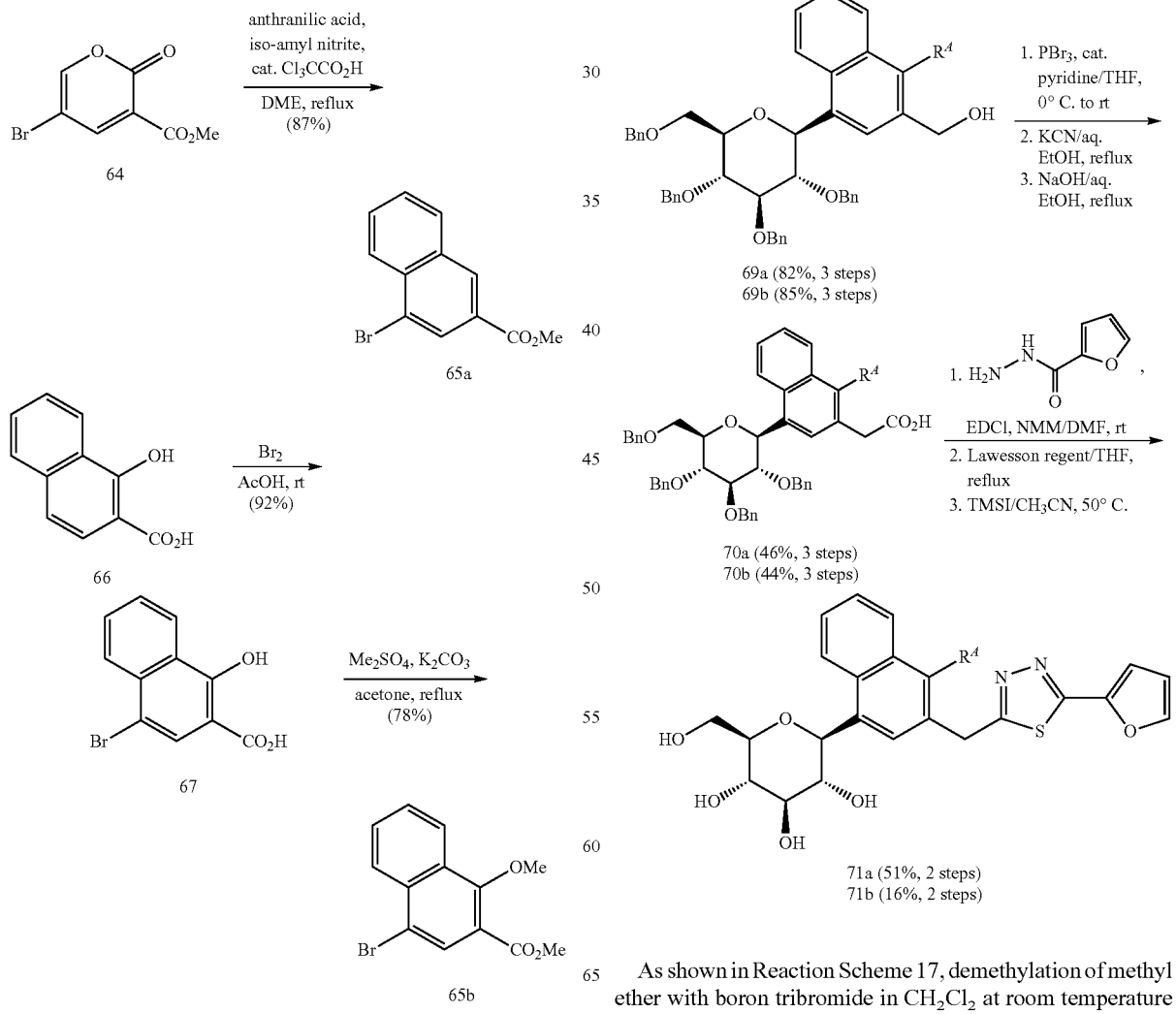
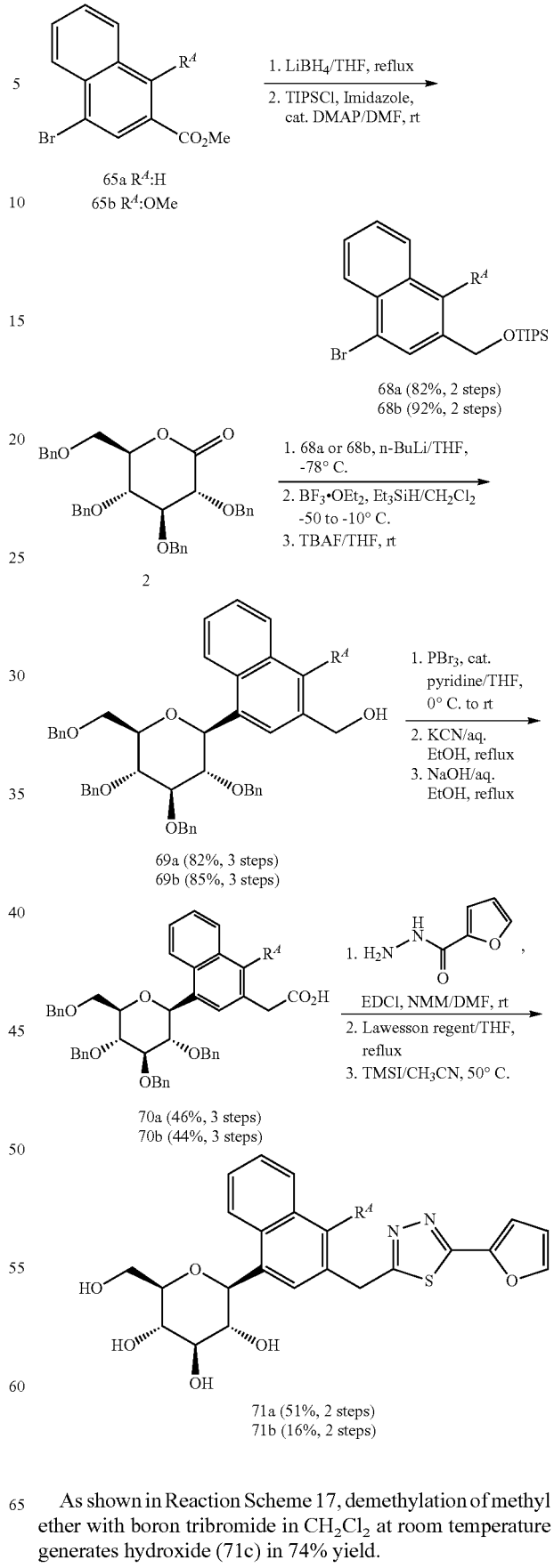

As shown in Reaction Scheme 17, demethylation of methyl ether with boron tribromide in $CH_2Cl_2$ at room temperature generates hydroxide (71c) in 74% yield.

Reaction Scheme 17

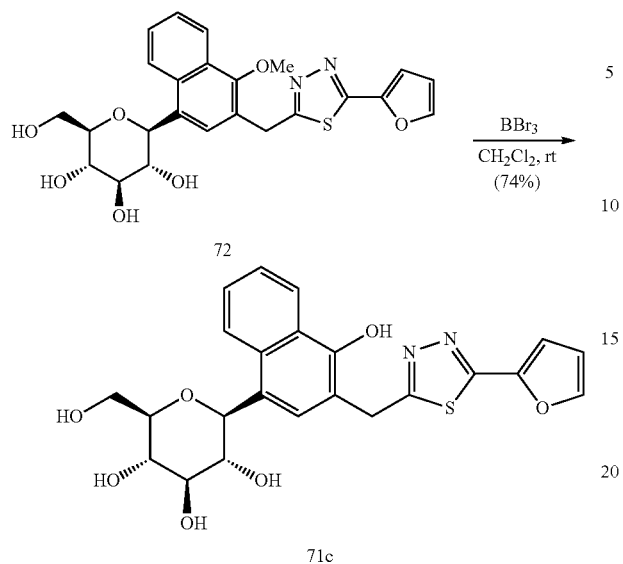

The inventive compounds with different type of naphthalene as ring A may be synthesized and evaluated as shown in Reaction Scheme 18. Thus, 3-bromo-1-naphthoic acid (75) may be obtained from compound (73) by adopting the procedure shown in the literature [Moseley, J. D. et al. *J. Org. Process Res. Dev.* 2003, 7, 58-66].

Reduction of 3-bromo-1-naphthoic acid (75) with borane-dimethyl sulfide complex, and subsequent silylation of the corresponding alcohol with TIPSCl generate the requisite 1-naphtalenylmethyl silyl ether (76) in 96% yield for the two steps.

As in Reaction Scheme 2, lithium-halogen exchange of compound (76), followed by addition of the resulting nascent lithiated aromatic to perbenzylated gluconolactone (2), produces a mixture of the corresponding lactols, which is reduced using triethylsilane and boron trifluoride etherate. Subsequent desilylation using tetrabutylammonium fluoride (TBAF) affords 1-naphthalenemethanol (77) in a reasonable yield for the three steps.

Next, the four steps are involved to give the acid (78) in an analogous manner as previously described in Reaction Scheme 3 (20%, 4 steps): .i.e., i. bromination using phosphorus tribromide; ii. cyanation using potassium cyanide; iii. resolution of beta-anomer by recrystallization; and iv. hydrolysis using sodium hydroxide. After coupling between acid (78) and 2-furoic hydrizide in the presence of EDCI and cyclization using Lawesson's reagent, the target compound (79) is obtained by deprotection of tetrabenzyl groups using TMSI in moderate yield.

Reaction Scheme 18

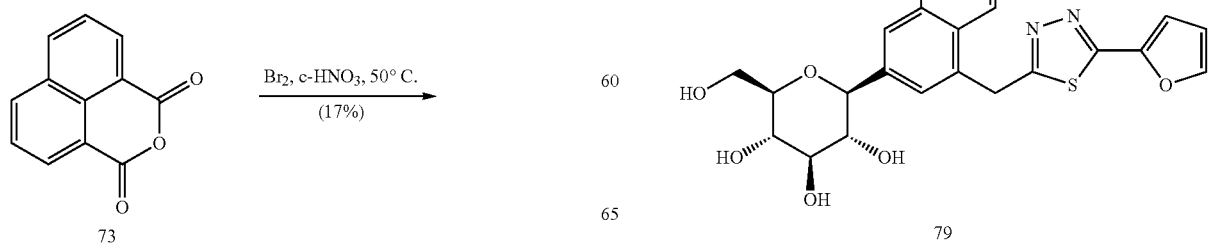

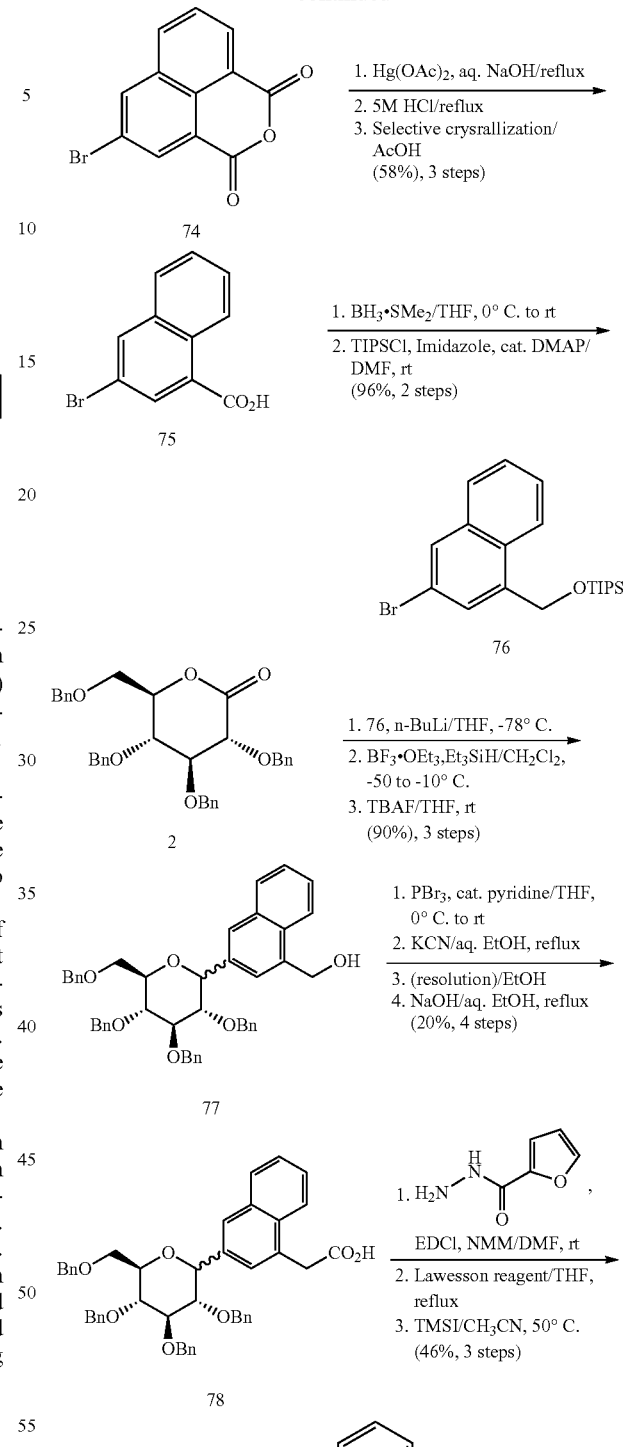

Another variation of Ring A may be accessed by adopting the reported procedure [Rodriguez-Domínguez, J. C. et al. *J. Het. Chem.* 2007, 44, 273-275] as shown in Reaction Scheme 19. Thus, 5-bromo-2,4-dichlorobenzoic acid (81) obtained by Rodríguez-Domínguez's methodology from compound (80) is converted to 2,4-dichlorobenzyl silyl ether (82) via two steps (83%, 2 steps): i. reduction using borane-dimethyl sulfide complex; and ii. silylation using TIPSCl.

As in Reaction Scheme 2, lithium-halogen exchange of compound (82), followed by addition of the resulting nascent lithiated aromatic to gluconolaction (2), produces a mixture of the corresponding lactols, which is reduced using triethylsilane and boron trifluoride etherate. Subsequent desilylation using TBAF affords alcohol (83) in 81% yield for the three steps.

As in Reaction Scheme 3, the installation of the carboxylic acid at the benzylic carbon is carried out using: i. bromination using phosphorus tribromide; ii. cyanation using potassium cyanide; and iii. hydrolysis using sodium hydroxide (65%, 3 steps). Subsequently, usual coupling between acid (84) and 2-furoic hydrizide in the presence of EDCI and cyclization using Lawesson's reagent produce thiadiazole ring. Subsequent deprotection of benzyl groups using TMSI yields the target compound (85) in moderate yield. The small amount of the α-anomer is removed at the final step by preparative reversed-phase HPLC purification.

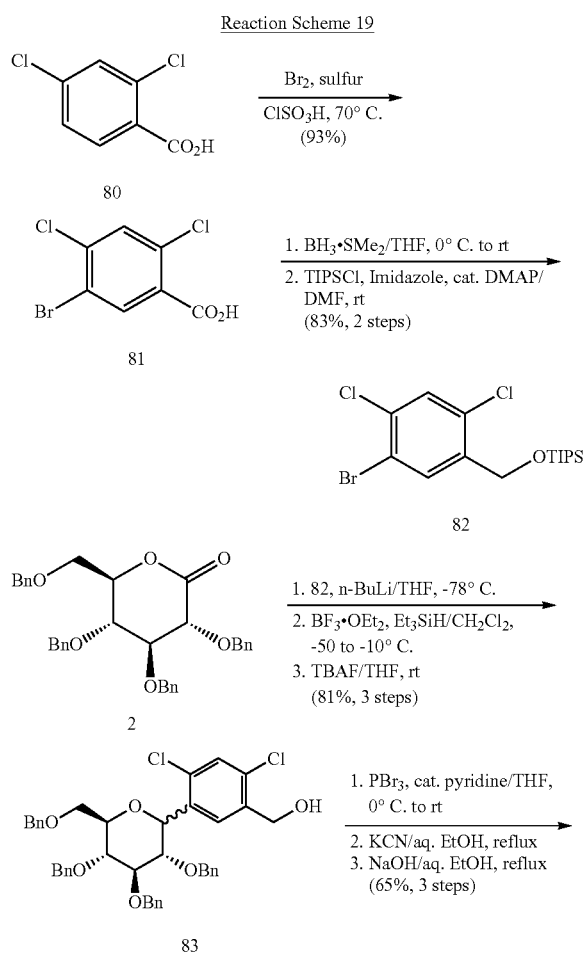

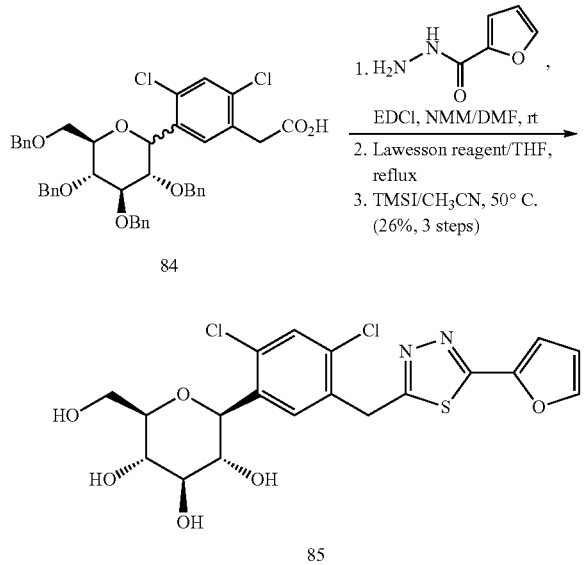

Another variation of Ring A, 2-chloro-4-methoxyphenyl, may be synthesized and evaluated as shown in Reaction Scheme 20. Thus, 2-chloro-4-hydroxybenzonitrile (86) is brominated in the 5-position with N-bromosuccinimide (NBS) and triflic acid in 65% yield. Methylation of phenol (87) is performed with dimethyl sulfate under basic conditions in 76% yield. Subsequent hydrolysis with sodium hydroxide affords the corresponding acid (88) in quantitative yield. Reduction of acid (88) with borane-dimethyl sulfide complex, and subsequent silylation of the corresponding alcohol with TIPSCl in the presence of imidazole and DMAP generates silyl ether (89) in 76% yield for the two steps.

As in Reaction Scheme 2, lithium-halogen exchange of compound (89), followed by addition of the resulting nascent lithiated aromatic to perbenzylated gluconolaction (2), produces a mixture of the corresponding lactols, which is reduced using triethylsilane and boron trifluoride etherate. Subsequent desilylation using TBAF affords alcohol (90) in 59% yield for the three steps.

Next, the four steps involve to give the acid (91) in an analogous manner as previously described in Reaction Scheme 3 (37%, 4 steps): .i.e., i. bromination using phosphorus tribromide; ii. cyanation using potassium cyanide; iii. resolution of beta-isomer by recrystallization; and iv. hydrolysis using sodium hydroxide. After coupling between acid (91) and 2-furoic hydrizide in the presence of EDCI and cyclization using Lawesson's reagent, the target compound (92) is obtained by deprotection of tetrabenzyl groups using TMSI in moderate yield.

Reaction Scheme 20

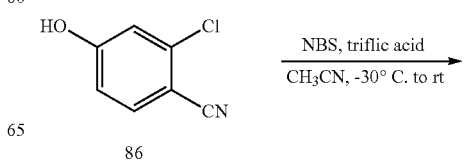

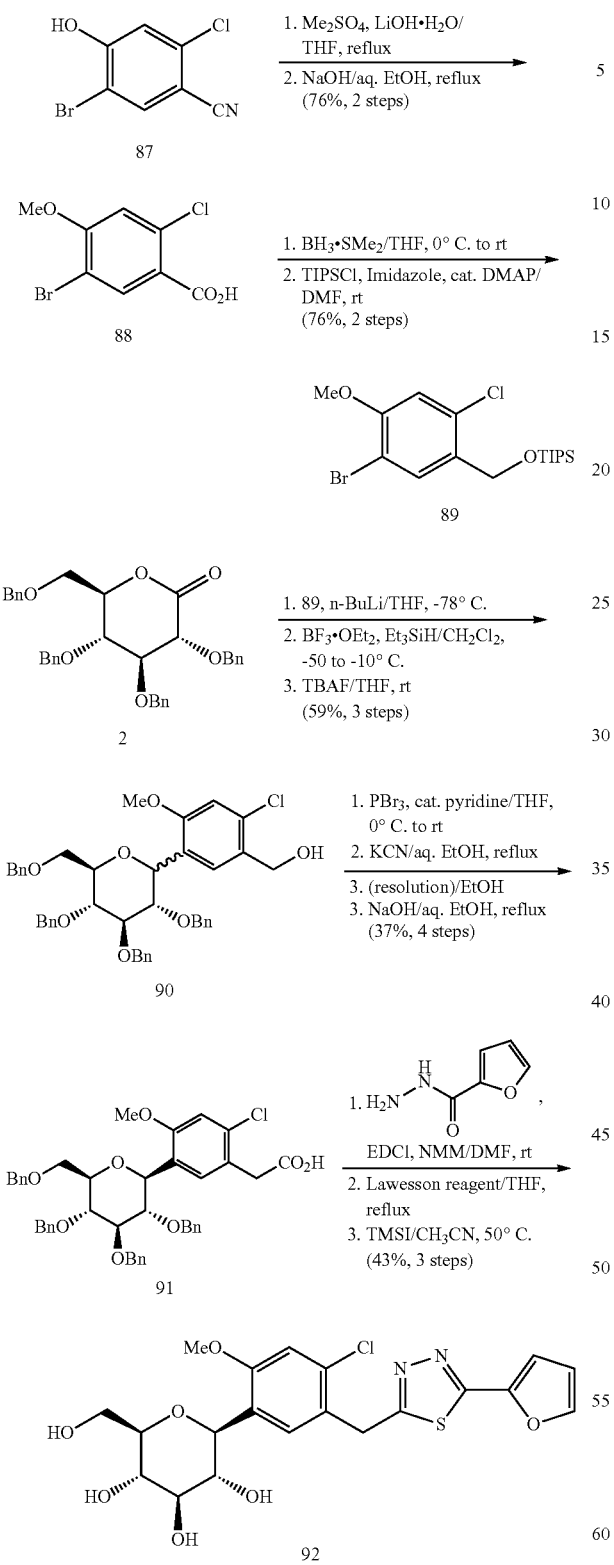

The general procedures for deprotection of benzyl groups which are utilized in this invention are illustrated in Reaction Scheme 21. Thus, the first resort for deprotection is using TMSI in acetonitrile as in Case 1. If the first method fails, use of TMSOTf in combination with acetic anhydride is another option for effective deprotection of benzyl groups up to date as shown in Case 2.

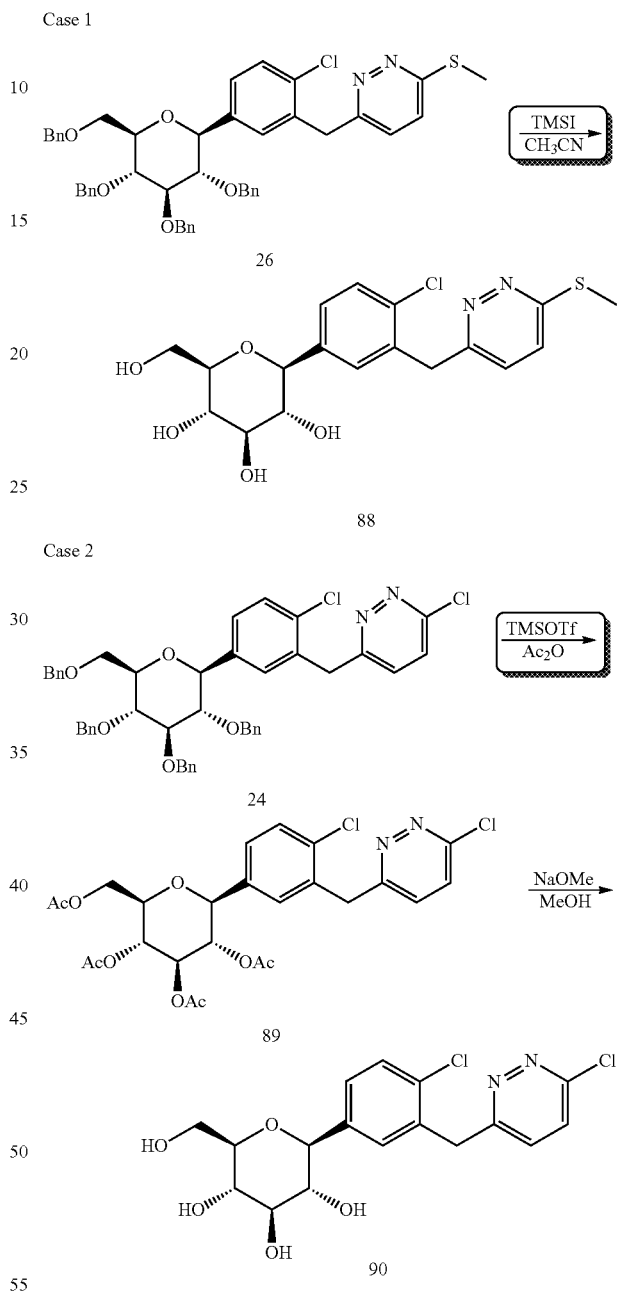

Further, the present invention provides a method for preventing or treating diabetes in a mammal, which comprises administering the compound of formula (I), or the pharmaceutically acceptable salt or a prodrug thereof to the mammal.

Also, the present invention provides a method for inhibiting SGLT2 in a mammal, which comprises administering the compound of formula (I), or the pharmaceutically acceptable salt or a prodrug thereof to the mammal.

The pharmaceutical composition may be administered orally, intramuscularly or subcutaneously. The formulation for oral administration may take various forms such as a syrup, tablet, capsule, cream and lozenge. A syrup formulation will generally contain a suspension or solution of the compound or its salt in a liquid carrier, e.g., ethanol, peanut oil, olive oil, glycerine or water, optionally with a flavoring or coloring agent. When the composition is in the form of a tablet, any one of pharmaceutical carriers routinely used for preparing solid formulations may be used. Examples of such carriers include magnesium stearate, terra alba, talc, gelatin, acacia, stearic acid, starch, lactose and sucrose. When the composition is in the form of a capsule, any of the routine encapsulation procedures may be employed, e.g., using the aforementioned carriers in a hard gelatin capsule shell. When the composition is formulated in the form of a soft gelatin shell capsule, any of the pharmaceutical carrier routinely used for preparing dispersions or suspensions may be prepared using an aqueous gum, cellulose, silicate or oil. The formulation for intramuscular or subcutaneous administration may take a liquid form such as a solution, suspension and emulsion which includes aqueous solvents such as water, physiological saline and Ringer's solution; or lipophilic solvents such as fatty oil, sesame oil, corn oil and synthetic fatty acid ester.

Preferably the composition is formulated in a specific dosage form for a particular patient.

Each dosage unit for oral administration contains suitably from 0.1 mg to 500 mg/Kg, and preferably from 1 mg to 100 mg/Kg of the compound of Formula (I) or its pharmaceutically acceptable salt.

The suitable daily dosage for oral administration is about 0.01 mg/Kg to 40 mg/Kg of the compound of Formula (I) or its pharmaceutically acceptable salt, may be administered 1 to 6 times a day, depending on the patient's condition.

The present invention is further described and illustrated in Examples provided below, which are, however, not intended to limit the scope of the present invention.

EXPERIMENTAL SECTION

As used herein the symbols and conventions used describing the processes, schemes and examples of the present invention are consistent with those used in the contemporary scientific literature, for example, the *Journal of the American Chemical Society* or the *Journal of Biological Chemistry*. Unless otherwise noted, all starting materials were obtained from commercial suppliers and used without further purification.

| | |
|---|---|
| Hz (Hertz) | TLC (thin layer chromatography) |
| T$_r$ (retention time) | RP (reverse phase) |
| MeOH (methanol) | i-PrOH (isopropanol) |
| TFA (trifluoroacetic acid) | TEA (triethylamine) |
| EtOH (ethanol) | THF (tetrahydrofuran) |
| DMSO (dimethylsulfoxide) | EtOAc (ethyl acetate) |
| DCM (dichlromethane) | HOAc (acetic acid) |
| DMF (N,N-dimethylformamide) | Ac (acetyl) |
| CDI (1,1-carbnyldiimidazole) | Bn (benzyl) |
| HOSu (N-hydroxysuccinimide) | NBS (N-Bromosuccinimide) |
| HOBT (1-hydroxybenzotriazole) | |
| Boc (tert-butyloxycarbonyl) | |
| m-CPBA (meta-chloroperbenzoic acid) | |
| FMOC (9-fluorenylmethoxycarbonyl) | |
| DCC (dicyclohexylcarbodiimide) | |
| Cbz (benzyloxycarbonyl) | |
| NMM (N-methyl morpholine) | |
| HOAt (1-hydroxy-7-azabenzotriazole) | |
| TBAF (tetra-n-butylammonium fluoride) | |
| THP (tetrahydro-2H-pyran-2-yl) | |
| DMAP (4-dimethylaminopyridine) | |
| HPLC (high pressure liquid chromatography) | |

-continued

BOP (bis(2-oxo-3-oxazolidinyl)phosphinic chloride);
EDCI (1-ethyl-3-[3-dimethylaminopropyl]carbodiimide hydrochloride)
HBTU (O-Benzotriazole1-yl-N,N,N',N'-tetramethyluronium hexafluoro phosphate)
MTBE (methyl t-butyl ether)

All reactions are conducted under an inert atmosphere at room temperature, unless otherwise noted. n-Butyllithium (Aldrich) was titrated with N-benzylbenzamide as indicator. All reagents were purchased at the highest commercial quality and used without further purification, unless otherwise indicated. All experiment involving moisture- and/or air-sensitive compounds were performed in oven- and/or flame-dried glassware with rubber septa under a positive pressure of nitrogen using standard Schlenck technique. Microwave reaction was conducted with a Biotage Initiator microwave reactor. NMR spectra were obtained on a Varian 400-MR (400 MHz $^1$H, 100 MHz $^{13}$C) spectrometer. NMR spectra were recorded in ppm (δ) relative to tetramethylsilane (δ=0.00) as an internal standard unless stated otherwise and are reported as follows: chemical shift, multiplicity (s=singlet, d=doublet, t=triplet, q=quartet, quint=quintet, sext=sextet, m=multiplet, and br=broad), coupling constant, and integration. $^{13}$C NMR spectra were referenced to the residual chloroform-d$_1$ (δ=77.0) or DMSO-d$_6$ (δ=39.7). Mass spectra were obtained with an Agilent 6110 quadruple LC-MSD (ESI+). High resolution mass spectra were obtained on a Jeol JMS-700 Mstation (10 kV, HFAB). Optical rotations were obtained on a Rudolph Autopol III digital polarimeter. Preparative HPLC purifications were performed on a Gilson purification system. For preparative HPLC, ca. 100 mg of a product was injected in 1 mL of methanol onto a SunFire Prep C18 OBD 5 μm 30×100 mm Column with a 30 min gradient from 5 to 90% acetonitrile in water and a 45 mL/min flow rate. Biotage SP1 and Isolera purification systems were used for normal phase column chromatography with ethyl acetate and hexane. Flash chromatography was performed using E. Merck 230-400 mesh silica gel according to the procedure of Still et al. Reactions were monitored by either thin-layer chromatography (TLC) on 0.25 mm E. Merck silica gel plates (60E-254) using UV light and p-anisaldehyde solution as visualizing agents or HPLC analysis on an Agilent 1200 series system.

The following synthetic schemes are merely illustrative of the methods by which the compounds of the invention may be prepared and are not intended to limit the scope of the invention as defined in the appended claims.

Preparation Example 1

2-(2-Chloro-5-((3S,4R,5R,6R)-3,4,5-tris(benzyloxy)-6-(benzyloxy methyl)-tetrahydro-2H-pyran-2-yl)phenyl)acetonitrile (Intermediate 1)

Step 1: 2,3,4,6-Tetra-O-benzyl-D-glucopyranone (compound 2)

To a solution of 2,3,4,6-tetra-O-benzyl-D-glucopyranose (compound 1, 125 g, 231 mmol) in dichloromethane (1 L) was added 4 Å molecular sieve (40 g) and 4-methylmorpholine N-oxide (41 g, 347 mmol). The solution was stirred for 20 min at room temperature, before adding of tetrapropylammonium perruthenate (2.0 g, 5.6 mmol). After 3 h stirring at ambient temperature, the solution was filtered through a plug of Celite®. The filtrate was washed with saturated sodium thiosulfate, dried over magnesium sulfate, filtered and concentrated in vacuo. The resulting crude residue was purified on a Biotage® purification apparatus (silica gel, 5 to 40% ethyl acetate in hexanes gradient) to yield the title compound (106 g, 198 mmol, 86%) as a colorless oil.

$^1$H NMR (400 MHz, CDCl$_3$) δ 7.39-7.16 (m, 20H), 4.98 (d, J=11.2 Hz, 1H), 4.74-4.44 (m, 8H), 4.12 (d, J=6.4 Hz, 1H), 3.97-3.89 (m, 2H), 3.72 (dd, J=10.8, 2.4 Hz, 1H), 3.67 (dd, J=10.8, 3.2 Hz, 1H).

Step 2: 5-Bromo-2-chlorobenzyl alcohol

To a solution 5-bromo-2-chlorobenzoic acid (compound 3, 100 g, 425 mmol) in tetrahydrofuran (500 mL) at 0° C. was added borane dimethyl sulfide complex (170 mL, 170 mmol). The resulting mixture was stirred with gradual warming to ambient temperature over 15 h, re-cooled to 0° C., and quenched with methanol. The mixture was diluted with water and extracted with ethyl acetate. The organic layer was washed with brine, dried over magnesium sulfate, filtered and evaporated in vacuo to yield the title compound as a white solid, which was used without further purification.

$^1$H NMR (400 MHz, CDCl$_3$) δ 7.67 (d, J=2.4 Hz, 1H), 7.36 (dd, J=8.4, 2.4 Hz, 1H), 7.22 (d, J=8.4 Hz, 1H), 7.76 (d, J=6.4 Hz, 2H), 1.93 (t, J=6.4 Hz, 1H);

[M−H$_2$O]+ 202.

Step 3:
(5-Bromo-2-chlorobenzyloxy)triisopropylsilane
(compound 4)

To a solution of 5-bromo-2-chlorobenzyl alcohol (425 mmol) from Step 2 in N,N-dimethylformamide (400 mL) was added imidazle (58 g, 850 mmol), 4-(dimethylamino)pyridine (2.6 g, 21 mmol), and triisopropylsilyl chloride (136 mL, 638 mmol). The resulting solution was stirred at ambient temperature for 15 h, diluted with a saturated ammonium chloride and extracted with ethyl acetate. The organic layer was washed with water then brine, dried over magnesium sulfate, filtered and concentrated in vacuo. The crude residue was purified on Biotage® purification apparatus (silica gel, 3 to 10% ethyl acetate in hexanes) to yield the title compound (152 g, 403 mmol, 95%) as a colorless oil.

$^1$H NMR (400 MHz, CDCl$_3$) δ 7.77 (d, J=2.4 Hz, 1H), 7.31 (dd, J=8.4, 2.4 Hz, 1H), 7.16 (d, J=8.4 Hz, 1H), 4.83 (s, 2H), 1.25-1.17 (m, 3H), 1.11 (d, J=6.8 Hz, 18H).

Step 4: (3R,4S,5R,6R)-3,4,5-Tris(benzyloxy)-6-(benzyloxymethyl)-2-(4-chloro-3-((triisopropylsilyloxy)methyl)phenyl)-tetrahydro-2H-pyran-2-ol To a solution of (5-Bromo-2-chlorobenzyloxy)triisopropylsilane (compound 4, 97 g, 257 mmol) from Step 3 in tetrahydrofuran (1 L) at −78° C. under an atmosphere of nitrogen was added dropwise n-butyllithium (2.5 M in hexanes, 103 mL, 257 mmol), and the mixture was stirred for 1.5 h at the same temperature. Then a solution of 2,3,4,6-tetra-O-benzyl-D-glucopyranone (compound 2, 106 g, 198 mmol) from Step 1 in tetrahydrofuran (500 mL) was added dropwise, and the mixture was stirred for 3 h at the same temperature. The reaction mixture was quenched by addition of saturated ammonium chloride solution. After complete addition, the solution was gradually raised to room temperature. The organic layer was separated and the aqueous layer was extracted with ethyl acetate. The combined organic layers were washed with brine, dried over magnesium sulfate, filtered and concentrated in vacuo to yield the title compound as a yellow oil which was used without further purification.

Step 5: (2-Chloro-5-((3S,4R,5R,6R)-3,4,5-tris(benzyloxy)-6-(benzyloxymethyl)-tetrahydro-2H-pyran-2-yl)benzyloxy)triisopropylsilane To a stirred −50° C. solution of (3R,4S,5R,6R)-3,4,5-tris(benzyloxy)-6-(benzyloxymethyl)-2-(4-chloro-3-((triisopropylsilyloxy)methyl)phenyl)tetra-hydro-2H-pyran-2-ol (198 mmol) from Step 4 in dichloromethane (500 mL) was added triethylsilane (63 mL, 396 mmol) followed by boron trifluoride diethyl etherate (50 mL, 396 mmol) at a rate such that the reaction temperature was maintained between −40 and −50° C. The solution was allowed to warm to −10° C. over 2 h prior to quenching with saturated potassium carbonate solution. After removal of organic volatiles under reduced pressure, the residue was partitioned between ethyl acetate and water. Following extraction of the aqueous layer with ethyl acetate, the combined organic layers were washed with water prior to drying over magnesium sulfate. Filtration and concentration under reduced pressure yielded the title compound as a yellow oil which was used without further purification.

Step 6: (2-Chloro-5-((3S,4R,5R,6R)-3,4,5-tris(benzyloxy)-6-(benzyloxymethyl)-tetrahydro-2H-pyran-2-yl)phenyl)methanol (compound 5)

To a solution of (2-chloro-5-((3S,4R,5R,6R)-3,4,5-tris(benzyloxy)-6-(benzyloxy-methyl)tetrahydro-2H-pyran-2-yl)benzyloxy)triisopropylsilane (198 mmol) from Step 5 in tetrahydrofuran (500 mL) was added tetrabutylammonium fluoride (1.0 M in tetrahydrofuran, 594 mL, 594 mmol) and the reaction mixture stirred at ambient temperature for 2 h. After removal of organic volatiles under reduced pressure, the residue was partitioned between ethyl acetate and saturated ammonium chloride solution. The organic layer was separated and the aqueous layer was extracted with ethyl acetate. The combined organic layers were washed with brine, dried over magnesium sulfate, filtered and concentrated in vacuo. The crude residue was purified on Biotage® purification apparatus (silica gel, 10 to 60% ethyl acetate in hexanes) to yield the title compound (130 g, 195 mmol, 98%, mixture of α,β-anomer in about 1:2 ratio) as a white solid.

α-anomer: $^1$H NMR (400 MHz, CDCl$_3$) δ 7.78 (s, 1H), 7.63 (dd, J=8.4, 1.6 Hz, 1H), 7.38-7.17 (m, 19H), 7.13-7.10 (m, 2H), 5.15 (d, J=3.6 Hz, 1H), 4.96-4.46 (m, 8H), 4.01-3.95 (m, 2H), 3.83-3.64 (m, 5H), 3.55-3.51 (m, 1H);

β-anomer: $^1$H NMR (400 MHz, CDCl$_3$) δ 7.50 (s, 1H), 7.38-7.17 (m, 20H), 6.94-6.92 (m, 2H), 4.96-4.46 (m, 9H), 4.23 (d, J=9.2 Hz, 1H), 3.86 (d, J=10.4 Hz, 1H), 3.81-3.67 (m, 4H), 3.61-3.59 (m, 1H), 3.44 (t, J=9.2 Hz, 1H);

MNH$_4$+ 682 and MNa+ 687.

Step 7: (2S,3R,4R,5S)-3,4,5-Tris(benzyloxy)-2-(benzyloxymethyl)-6-(3-(bromomethyl)-4-chlorophenyl)-tetrahydro-2H-pyran To a solution of (2-chloro-5-((3S,4R,5R,6R)-3,4,5-tris(benzyloxy)-6-(benzyloxy-methyl) tetrahydro-2H-pyran-2-yl)phenyl)methanol (compound 5, 130 g, 195 mmol) from Step 6 in ether (600 mL) at 0° C. was added pyridine (0.79 mL, 9.8 mmol) and phosphorus tribromide (6.4 mL, 68 mmol). The reaction was allowed to slowly warm to room temperature over 15 h and refluxed 1 h. After cooling to room temperature, the reaction mixture was diluted with ethyl acetate and washed with water then brine. The organic extract was dried over magnesium sulfate, filtered, and evaporated in vacuo to yield the title compound as a yellow oil, which was used without further purification.

MNa+ 749.

Step 8: 2-(2-Chloro-5-((3S,4R,5R,6R)-3,4,5-tris (benzyloxy)-6-(benzyloxymethyl)-tetrahydro-2H-pyran-2-yl)phenyl)acetonitrile (compound 6)

To a solution of (2S,3R,4R,5S)-3,4,5-tris(benzyloxy)-2-(benzyloxymethyl)-6-(3-(bromomethyl)-4-chlorophenyl)-tetrahydro-2H-pyran (195 mmol) from Step 7 in ethanol (260 mL) and water (130 mL) was added potassium cyanide (31.8 g, 488 mmol). The reaction mixture was refluxed overnight. After cooling to room temperature, the mixture was diluted with water and extracted with ethyl acetate. The organic layer was washed with brine, dried over magnesium sulfate, filtered and evaporated in vacuo. Flash chromatography on a Biotage® apparatus (silica gel, 5 to 40% ethyl acetate in hexanes gradient) gave the title compound (105 g, 156 mmol, 80%, mixture of α,β-anomer in about 1:2 ratio) as a colorless oil.

α-anomer: $^1$H NMR (400 MHz, CDCl$_3$) δ 7.83 (d, J=1.6 Hz, 1H), 7.64 (dd, J=8.4, 1.6 Hz, 1H), 7.37-7.19 (m, 19H), 7.13-7.10 (m, 2H), 5.11 (d, J=2.8 Hz, 1H), 4.93-4.46 (m, 8H), 3.96-3.92 (m, 2H), 3.79-3.71 (m, 3H), 3.70-3.62 (m, 2H), 3.55-3.51 (m, 1H);

β-anomer: $^1$H NMR (400 MHz, CDCl$_3$) δ 7.48 (s, 1H), 7.37-7.17 (m, 20H), 6.93-6.91 (m, 2H), 4.93 (s, 2H), 4.86 (d, J=10.8 Hz, 1H), 4.63 (d, J=10.8 Hz, 1H), 4.62 (d, J=12.4 Hz, 1H), 4.56 (d, J=12.4 Hz, 1H), 4.52 (d, J=10.8 Hz, 1H), 4.22 (d, J=9.6 Hz, 1H), 3.93 (d, J=10.8 Hz, 1H), 3.84-3.68 (m, 6H), 3.62-3.58 (m, 1H), 3.43 (t, J=8.8 Hz, 1H);

MNa+ 696.

Preparation Example 2

2-(2-Chloro-5-((2S,3S,4R,5R,6R)-3,4,5-tris(benzyloxy)-6-(benzyloxymethyl)-tetrahydro-2H-pyran-2-yl)phenyl)acetonitrile (compound 7, Intermediate 2)

The preceding Intermediate 1 (compound 6, mixture of α,β-anomer in about 1:2 ratio, 105 g, 156 mmol) was slurried in ethanol (1 L) and heated to reflux with stirring. The reaction mixture was held at reflux for 1 h to ensure that all of solution had homogenized; it was then cooled evenly at 15 t/h to ambient temperature and stirred overnight at this temperature. The resulting solid was isolated by filtration and dried in vacuo to yield the title compound (53 g, 79 mmol, 51%) as a white solid.

$[\alpha]_D^{21}$ −10.6 (c 1.01, chloroform);
$^1$H NMR (400 MHz, CDCl$_3$) δ 7.48 (s, 1H), 7.37-7.17 (m, 20H), 6.93-6.91 (m, 2H), 4.93 (s, 2H), 4.86 (d, J=10.8 Hz, 1H), 4.63 (d, J=10.8 Hz, 1H), 4.62 (d, J=12.4 Hz, 1H), 4.56 (d, J=12.4 Hz, 1H), 4.52 (d, J=10.8 Hz, 1H), 4.22 (d, J=9.6 Hz, 1H), 3.93 (d, J=10.8 Hz, 1H), 3.84-3.68 (m, 6H), 3.62-3.58 (m, 1H), 3.43 (t, J=8.8 Hz, 1H);
$^{13}$C NMR (100 MHz, CDCl$_3$) δ 129.49, 128.86, 128.45, 128.38, 128.26, 128.08, 128.01, 127.87, 127.82, 127.70, 127.68, 127.67, 127.64, 127.61, 139.09, 138.52, 138.23, 138.07, 137.41, 132.97, 129.49, 128.86, 128.45, 128.38, 128.26, 128.08, 128.01, 127.87, 127.82, 127.70, 127.68, 127.67, 127.64, 127.61, 116.57, 86.87, 83.59, 80.47, 79.41, 78.28, 75.67, 75.16, 74.96, 73.47, 69.07, 22.12;
HRMS (FAB, 6 keV) calcd for C$_{42}$H$_{41}$ClNO$_5$ ([M+H]$^+$) 674.2673. found 674.2672;
MNa+ 696.

Preparation Example 3

2-(2-Chloro-5-((2S,3S,4R,5R,6R)-3,4,5-tris(benzyloxy)-6-(benzyloxymethyl)-tetrahydro-2H-pyran-2-yl)phenyl)acetic acid (compound 8, Intermediate 3)

To a solution of intermediate 2 (compound 7, 53 g, 79 mmol) in ethanol (300 mL) was added sodium hydroxide solution (8.0 M, 300 mL, 2.4 mol). The reaction mixture was refluxed overnight. After cooling to room temperature, hydrochloric acid (3.0 M) was added to neutralize the reaction mixture. The mixture was diluted with water and extracted with ethyl acetate. The organic layer was washed with water and brine prior to drying over magnesium sulfate. Filtration and concentration under reduced pressure yielded the title compound (54 g, 78 mmol, 98%) as a white solid.

$[\alpha]_D^{21}$ −4.7 (c 1.10, chloroform);
$^1$H NMR (400 MHz, CDCl$_3$) δ 7.37-7.14 (m, 21H), 6.93-6.90 (m, 2H), 4.94 (d, J=10.8 Hz, 1H), 4.90 (d, J=10.8 Hz, 1H), 4.86 (d, J=11.2 Hz, 1H), 4.63 (d, J=10.8 Hz, 1H), 4.62 (d, J=14.0 Hz, 1H), 4.55 (d, J=12.4 Hz, 1H), 4.43 (d, J=10.4 Hz, 1H), 4.20 (d, J=9.6 Hz, 1H), 3.88 (d, J=10.8 Hz, 1H). 3.81-3.70 (m, 6H), 3.59-3.56 (m, 1H), 3.43 (t, J=8.8 Hz, 1H);
$^{13}$C NMR (100 MHz, DMSO-d$_6$) δ 171.84, 139.10, 138.69, 138.66, 138.17, 133.72, 133.49, 131.99, 129.18, 128.68, 128.66, 128.45, 128.26, 128.19, 128.10, 128.00, 127.92, 127.87, 127.84, 86.25, 83.53, 80.14, 78.77, 78.55, 74.97, 74.51, 74.30, 72.75, 69.39, 39.19;
MNH$_4$+ 710 and MNa+ 715

Preparation Example 4

Methyl 2-(2-chloro-5-((2S,3S,4R,5R,6R)-3,4,5-tris (benzyloxy)-6-(benzyloxymethyl)-tetrahydro-2H-pyran-2-yl)phenyl)acetate (compound 9, Intermediate 4)

To a solution of intermediate 3 (compound 8, 10 g, 14 mmol) in methanol (140 mL) was added thionyl chloride (2.1 mL, 29 mmol). The reaction mixture was refluxed overnight and cooled to room temperature. After removal of organic volatiles under reduced pressure, the residue was partitioned between ethyl acetate and water. The organic layer was separated and the aqueous layer was extracted with ethyl acetate. The combined organic layers were washed with saturated sodium bicarbonate and brine, dried over magnesium sulfate, filtered and concentrated in vacuo. The crude residue was purified on Biotage® purification apparatus (silica gel, 5 to 40% ethyl acetate in hexanes) to yield the title compound (9.1 g, 13 mmol, 89%) as a white solid.

$^1$H NMR (400 MHz, CDCl$_3$) δ 7.36-7.18 (m, 21H), 6.94-6.92 (m, 2H), 4.96 (d, J=11.2 Hz, 1H), 4.90 (d, J=11.2 Hz, 1H), 4.86 (d, J=10.8 Hz, 1H), 4.63 (d, J=11.6 Hz, 2H), 4.55 (d, J=12.0 Hz, 1H), 4.45 (d, J=10.8 Hz, 1H), 4.20 (d, J=9.2 Hz, 1H), 3.90 (d, J=10.8 Hz, 1H), 3.82-3.67 (m, 6H), 3.67 (s, 3H), 3.60-3.57 (m, 1H), 3.47 (t, J=8.8 Hz, 1H);
MNa+ 729

Preparation Example 5

2-(2-Chloro-5-((2S,3S,4R,5R,6R)-3,4,5-tris(benzyloxy)-6-(benzyloxymethyl)-tetrahydro-2H-pyran-2-yl)phenyl)acetohydrazide (compound 14, Intermediate 5)

To a mixture of intermediate 3 (compound 8, 693 mg, 1.0 mmol), EDCI (249 mg, 1.3 mmol), and 1-hydroxybenzotriazole hydrate (233 mg, 1.5 mmol) in N,N-dimethylformamide (10 mL) was added hydrazine monohydrate (2 mL). The resulting mixture was stirred at ambient temperature for 15 h and then poured into water (50 mL). The resulting solid was isolated by filtration and dried in vacuo to yield the title compound (674 mg, 0.95 mmol, 95%) as a white solid.

$^1$H NMR (400 MHz, DMSO-d$_6$) δ 9.17 (s, 1H), 7.39-7.14 (m, 21H), 6.88-6.86 (m, 2H), 4.80 (d, J=11.2 Hz, 1H). 4.77 (d, J=11.2 Hz, 1H), 4.70 (d, J=13.6 Hz, 1H), 4.54 (d, J=10.8 Hz, 1H), 4.51 (d, J=12.4 Hz, 1H), 4.44 (d, J=12.4 Hz, 1H), 4.32 (d, J=10.8 Hz, 1H), 4.26 (d, J=9.6 Hz, 1H), 3.83 (d, J=10.8 Hz, 1H), 3.73 (t, J=8.8 Hz, 1H), 3.66-3.45 (m, 7H);

MH+ 707

Preparation Example 6

3-Chloro-6-(2-chloro-5-((2S,3S,4R,5R,6R)-3,4,5-tris(benzyloxy)-6-(benzyloxymethyl)-tetrahydro-2H-pyran-2-yl)benzyl)pyridazine (compound 24, Intermediate 6)

Step 1: Methyl 2-(2-chloro-5-((2S,3S,4R,5R,6R)-3,4,5-tris(benzyloxy)-6-(benzyloxymethyl)-tetrahydro-2H-pyran-2-yl)phenyl)-2-(6-chloropyridazin-3-yl)acetate (compound 23)

To a solution of intermediate 4 (compound 9, 9.1 g, 13 mmol) in 1V, N-dimethylformamide (80 mL) at 0° C. under an atmosphere of nitrogen was added sodium hydride (60% dispersion in mineral oil, 1.1 g, 28 mmol), and the mixture was stirred for 30 min at the same temperature. Then a solution of 3,6-dichloropyridazine (compound 22, 2.5 g, 17 mmol) in N,N-dimethylformamide (40 mL) was added dropwise, and the mixture was stirred with gradual warming to ambient temperature over 5 h. After re-cooling to 0° C., the reaction mixture was quenched by addition of hydrochloric acid (1.0 M). The mixture was diluted with water and extracted with ethyl acetate. The organic layer was washed with brine, dried over magnesium sulfate, filtered and evaporated in vacuo. The resulting crude residue was purified on a Biotage® purification apparatus (silica gel, 10 to 60% ethyl acetate in hexanes gradient) to yield the title compound (9.9 g, 12 mmol, 93%) as a yellow foam.

MH+ 819.

Step 2: 3-Chloro-6-(2-chloro-5-((2S,3S,4R,5R,6R)-3,4,5-tris(benzyloxy)-6-(benzyloxymethyl)-tetrahydro-2H-pyran-2-yl)benzyl)pyridazine (compound 24)

To a solution of Methyl 2-(2-chloro-5-((2S,3S,4R,5R,6R)-3,4,5-tris(benzyloxy)-6-(benzyloxymethyl)-tetrahydro-2H-pyran-2-yl)phenyl)-2-(6-chloropyridazin-3-yl)acetate (compound 23, 9.9 g, 12 mmol) from Step 1 in terahydrofuran (40 mL) was added methanol (56 mL) and lithium hydroxide solution (0.1 M in water, 180 mL, 180 mmol). The reaction mixture was allowed to stir at room temperature overnight. After cooling to 0° C., hydrochloric acid (1.0 M) was added to neutralize the reaction mixture. The mixture was diluted with water and extracted with ethyl acetate. The organic layer was washed with brine, dried over magnesium sulfate, filtered and concentrated in vacuo. The resulting residue was slurried in methanol (100 mL) and the slurry was stirred at ambient temperature for 2 h. The resulting solid was isolated by filtration and dried in vacuo to yield the title compound (7.8 g, 10 mmol, 86%) as a white solid.

$^1$H NMR (400 MHz, CDCl$_3$) δ 7.41-7.17 (m, 22), 7.04 (d, J=8.8 Hz, 1H), 6.91-6.89 (m, 2H), 4.90 (s, 2H), 4.85 (d, J=10.4 Hz, 1H), 4.61 (d, J=10.8 Hz, 1H), 4.60 (d, J=12.4 Hz, 1H), 4.54 (d, J=12.4 Hz, 1H), 4.49-4.39 (m, 3H), 4.19 (d, J=9.6 Hz, 1H), 3.85 (d, J=10.8 Hz, 1H), 3.81-3.71 (m, 4H), 3.60-3.56 (m, 1H), 3.42 (t, J=8.8 Hz, 1H);

$^{13}$C NMR (100 MHz, CDCl$_3$) δ 160.82, 155.30, 138.85, 138.51, 138.20, 138.06, 137.57, 134.94, 133.76, 130.99, 129.77, 128.42, 128.37, 128.25, 128.22, 127.99, 127.81, 127.70, 127.66, 127.61, 86.72, 83.93, 80.65, 79.37, 78.26, 75.64, 75.12, 74.79, 73.43, 69.05, 39.16;

MH+ 752.

Preparation Example 7

6-(2-Chloro-5-((2S,3S,4R,5R,6R)-3,4,5-tris(benzyloxy)-6-(benzyloxymethyl)-tetrahydro-2H-pyran-2-yl)benzyl)pyridazine-3-carbonitrile (compound 31, Intermediate 7)

Intermediate 6 (compound 24, 4.0 g, 5.3 mmol) was added to a microwave reaction tube containing zinc cyanide (0.93 g, 7.9 mmol) and tetrakis(triphenylphosphine) palladium(0) (1.2 g, 1.1 mmol) in N,N-dimethylformamide (30 mL). The capped reaction tube was placed in a microwave reactor (Biotage® Initiator™) and the mixture was irradiated at 160° C. for 15 min. After dilution with ethyl acetate, the organic layer was subsequently washed with water, 10 wt % potassium carbonate and brine prior to drying over magnesium sulfate. After filtration and concentration under reduced pressure, the residue was purified on a Biotage® purification apparatus (silica gel, 10 to 60% ethyl acetate in hexanes gradient) to yield the title compound (2.0 g, 2.7 mmol, 52%) as a white solid.

$^1$H NMR (400 MHz, CDCl$_3$) δ 7.45-7.15 (m, 24H), 6.90 (d, J=6.4 Hz, 1H), 4.89 (s, 2H), 4.86 (d, J=10.8 Hz, 1H), 4.63-4.48 (m, 6H), 4.20 (d, J=9.6 Hz, 1H), 3.86 (d, J=10.8 Hz, 1H), 3.81-3.71 (m, 4H), 3.61-3.57 (m, 1H), 3.41 (t, J=9.2 Hz, 1H);

MH+ 752.

Example 1

(2S,3R,4R,5S,6R)-2-(4-Chloro-3-((5-(furan-2-yl)-1,3,4-thiadiazol-2-yl)methyl)phenyl)-6-(hydroxymethyl)-tetrahydro-2H-pyran-3,4,5-triol (compound 13)

Step 1: N'-(2-(2-Chloro-5-((2S,3R,4R,5S,6R)-3,4,5-trihydroxy-6-(hydroxymethyl)-tetrahydro-2H-pyran-2-yl)phenyl)acetyl)furan-2-carbohydrazide (compound 14)

To a mixture of Intermediate 3 (compound 8, 500 mg, 0.72 mmol), 2-furoic hydrazide (10, 119 mg, 0.94 mmol), EDCI (207 mg, 1.08 mmol), and 1-hydroxybenzotriazole hydrate (224 mg, 1.44 mmol) in N,N-dimethylformamide (10 mL) was added 4-methylmorpholine (0.24 mL, 2.16 mmol). The resulting mixture was stirred at ambient temperature overnight. After dilution with ethyl acetate, the organic layer was subsequently washed with water, hydrochloric acid (1.0 M), saturated sodium bicarbonate and brine prior to drying over magnesium sulfate. Filtration and removal of the volatiles under reduced pressure yielded titled compound as a glassy off-white amorphous solid, which was used without further purification.

MH+ 801.

Step 2: 2-(2-Chloro-5-((2S,3S,4R,5R,6R)-3,4,5-tris(benzyloxy)-6-(benzyloxymethyl)-tetrahydro-2H-pyran-2-yl)benzyl)-5-(furan-2-yl)-1,3,4-thiadiazole (compound 12)

To a solution of N'-(2-(2-chloro-5-((2S,3R,4R,5S,6R)-3,4,5-trihydroxy-6-(hydroxymethyl)-tetrahydro-2H-pyran-2-yl)phenyl)acetyl)furan-2-carbohydrazide (compound 11, 0.72 mmol) form Step 1 in tetrahydrofuran (15 mL) was added Lawesson reagent (874 mg, 2.16 mmol). The reaction mixture was refluxed overnight. After cooling to room temperature, the reaction mixture was diluted with ethyl acetate and washed with saturated sodium bicarbonate. The organic layer was dried over magnesium sulfate, filtered and concentrated in vacuo. The resulting crude residue was purified on a Biotage® purification apparatus (silica gel, 10 to 60% ethyl acetate in hexanes gradient) to yield the title compound (468 mg, 0.58 mmol, 81%) as a yellow oil.

$^1$H NMR (400 MHz, CDCl$_3$) δ 7.50 (d, J=1.6 Hz, 1H), 7.46 (d, J=1.6 Hz, 1H), 7.39 (d, J=8.0 Hz, 1H), 7.35-7.13 (m, 19H), 7.08 (d, J=3.6 Hz, 1H), 6.90-6.88 (m, 2H), 6.53-6.52 (m, 1H), 4.90 (s, 2H), 4.85 (d, J=10.8 Hz, 1H), 4.63-4.51 (m, 4H), 4.45 (d, J=10.8 Hz, 1H), 4.20 (d, J=9.6 Hz, 1H), 3.88 (d, J=10.8 Hz, 1H), 3.81-3.72 (m, 5H), 3.60-3.57 (m, 1H), 3.43 (t, J=8.8 Hz, 1H);
MH+ 799.

Step 3: (2S,3R,4R,5S,6S)-2-(Acetoxymethyl)-6-(4-chloro-3-((5-(furan-2-yl)-1,3,4-thiadiazol-2-yl)methyl)phenyl)-tetrahydro-2H-pyran-3,4,5-triyl triacetate To a solution of 2-(2-chloro-5-((2S,3S,4R,5R,6R)-3,4,5-tris(benzyloxy)-6-(benzyloxymethyl)-tetrahydro-2H-pyran-2-yl)benzyl)-5-(furan-2-yl)-1,3,4-thiadiazole (compound 12, 468 mg, 0.58 mmol) from Step 2 in acetonitrile (5 mL) was added Iodotrimethylsilane (5 mL). The resulting reaction mixture was heated to 50° C. overnight. After cooling to 0° C., the reaction was quenched with methanol and concentrated in vacuo. Peracetylation was achieved by addition of acetic anhydride (3 mL) and 4-(dimethylamino)pyridine (10 mg, 0.08 mmol) to a solution of this residue in dichloromethane (10 mL) and triethylamine (3 mL). After 2 h stirring at ambient temperature, the reaction was quenched by addition of water, whereupon the resulting mixture was extracted with dichloromethane. The organic layer was washed with hydrochloric acid (1.0 M) and brine prior to drying over magnesium sulfate. After filtration and concentration under reduced pressure, the residue was purified on a Biotage® purification apparatus (silica gel, 10% ethyl acetate in hexanes to neat ethyl acetate gradient) to yield the title compound (187 mg, 0.31 mmol, 53%) as a yellow solid.

$^1$H NMR (400 MHz, CDCl$_3$) δ 7.54 (d, J=2.0 Hz, 1H), 7.42 (d, J=8.4 Hz, 1H), 7.33 (d, J=1.6 Hz, 1H), 7.29 (dd, J=8.4, 2.0 Hz, 1H), 7.13 (d, J=3.6 Hz, 1H), 6.55 (dd, J=3.6, 1.6 Hz, 1H), 5.30 (t, J=9.6 Hz, 1H), 5.20 (t, J=10.0 Hz, 1H), 5.05 (t, J=10.0 Hz, 1H), 4.57 (s, 2H), 4.37 (d, J=9.6 Hz, 1H), 4.28 (dd, J=12.4 Hz, 1H), 4.15 (dd, J=12.4 Hz, 1H), 3.84-3.79 (m, 1H), 3.08 (s, 3H), 2.05 (s, 3H), 1.99 (s, 3H), 1.79 (s, 3H);
MH+ 607.

Step 4: (2S,3R,4R,5S,6R)-2-(4-Chloro-3-((5-(furan-2-yl)-1,3,4-thiadiazol-2-yl)methyl)phenyl)-6-(hydroxymethyl)-tetrahydro-2H-pyran-3,4,5-triol (compound 13)

To a solution of (2S,3R,4R,5S,6S)-2-(acetoxymethyl)-6-(4-chloro-3-((5-(furan-2-yl)-1,3,4-thiadiazol-2-yl)methyl)phenyl)-tetrahydro-2H-pyran-3,4,5-triyl triacetate (187 mg, 0.31 mmol) from Step 3 in methanol (10 mL) was added sodium methoxide (25 wt % in methanol, 1.0 mL). The reaction mixture was stirred at ambient temperature for 2 h. Amberlite® IR120 hydrogen form was then added to neutralize the reaction mixture. The resin was filtered off and the filtrate was concentrated in vacuo. Purification by reverse phase preparative HPLC (Gilson®, SunFire™ Prep, 5 to 50% acetonitrile in water gradient) provided the title compound (78 mg, 0.18 mmol, 58%) as a white solid.

$[α]_D^{21}$ +21.4 (c 0.21, methanol); $^1$H NMR (400 MHz, DMSO-d$_6$) δ 7.93 (d, J=1.6 Hz, 1H), 7.50 (d, J=2.0 Hz, 1H), 7.42 (d, J=8.0 Hz, 1H), 7.30 (dd, J=8.0, 2.0 Hz, 1H), 7.23 (d, J=3.6 Hz, 1H), 6.70 (dd, J=3.6, 1.6 Hz, 1H), 5.00 (br, 2H), 4.88 (d, J=5.6 Hz, 1H), 4.59 (d, J=16 Hz, 1H), 4.53 (d, J=16 Hz, 1H), 4.43 (t, J=5.6 Hz, 1H), 4.01 (d, J=9.6 Hz, 1H), 3.68-3.65 (m, 1H), 3.46-3.40 (m, 1H), 3.26-3.06 (m, 4H);

$^{13}$C NMR (100 MHz, DMSO-d$_6$) δ 167.62, 158.77, 146.61, 144.94, 140.68, 134.60, 132.39, 131.23, 129.35, 129.26, 113.23, 112.67, 81.67, 80.89, 78.71, 75.19, 70.68, 61.75, 33.77;

HRMS (FAB, 6 keV) calcd for C$_{19}$H$_{20}$ClN$_2$O$_6$S ([M+H]$^+$) 439.0731. found 439.0730;
MH+ 439.

Example 2

(2S,3R,4R,5S,6R)-2-(4-Chloro-3-((5-(5-methylfuran-2-yl)-1,3,4-thiadiazol-2-yl)methyl)phenyl)-6-(hydroxymethyl)-tetrahydro-2H-pyran-3,4,5-triol $^1$H NMR (400 MHz, DMSO-d$_6$) δ 7.49 (d, J=2.0 Hz, 1H), 7.42 (d, J=8.4 Hz, 1H), 7.30 (dd, J=8.4, 2.0 Hz, 1H), 7.11 (d, J=3.6 Hz, 1H), 6.32 (d, J=3.6 Hz, 1H), 4.94-4.91 (m, 2H), 4.83 (d, J=5.6 Hz, 1H), 4.56 (d, J=16 Hz, 1H), 4.51 (d, J=16 Hz, 1H), 4.42 (t, J=5.6 Hz, 1H), 4.01 (d, J=9.6 Hz, 1H), 3.70-3.65 (m, 1H), 3.45-3.40 (m, 1H), 3.27-3.04 (m, 4H), 2.32 (s, 3H);
MH+ 453.

Example 3

(2S,3R,4R,5S,6R)-2-(4-Chloro-3-((5-(3-methylfuran-2-yl)-1,3,4-thiadiazol-2-yl)methyl)phenyl)-6-(hydroxymethyl)-tetrahydro-2H-pyran-3,4,5-triol $^1$H NMR (400 MHz, CDCl$_3$) δ 7.80 (d, J=1.2 Hz, 1H), 7.49 (d, J=2.0 Hz, 1H), 7.41 (d, J=8.4 Hz, 1H), 7.30 (dd, J=8.0, 2.0 Hz, 1H), 6.61 (d, J=1.2 Hz, 1H), 4.97-4.80 (m, 2H), 4.83 (d, J=5.2 Hz, 1H), 4.60-4.50 (m, 1H), 4.47-4.39 (m, 1H), 4.01 (d, J=9.6 Hz, 1H), 3.71-3.62 (m, 1H), 3.48-3.37 (m, 1H), 3.33-3.03 (m, 4H), 2.32 (s, 3H);
MH+ 453.

Example 4

(2S,3R,4R,5S,6R)-2-(4-Chloro-3-((5-(furan-3-yl)-1,3,4-thiadiazol-2-yl)methyl)phenyl)-6-(hydroxymethyl)tetrahydro-2H-pyran-3,4,5-triol $^1$H NMR (400 MHz, DMSO-d$_6$) δ 8.44 (dd, J=1.2, 0.4 Hz, 1H), 7.83 (t, J=2.0 Hz, 1H), 7.50 (d, J=1.6 Hz, 1H), 7.42 (d, J=8.4 Hz, 1H), 7.31 (dd, J=8.4, 2.0 Hz, 1H), 6.96 (dd, J=2.0, 0.8 Hz, 1H), 4.96-4.93 (m, 2H), 4.85 (d, J=6.0 Hz, 1H), 4.56 (d, J=16.0 Hz, 1H), 4.51 (d, J=16.0 Hz, 1H), 4.44 (t, J=6.0 Hz, 1H), 4.01 (d, J=9.6 Hz, 1H), 3.70-3.65 (m, 1H), 3.45-3.39 (m, 1H), 3.27-3.04 (m, 4H);
MH+ 439.

Example 5

(2S,3R,4R,5S,6R)-2-(4-Chloro-3-((5-(thiophen-2-yl)-1,3,4-thiadiazol-2-yl)methyl)phenyl)-6-(hydroxymethyl)tetrahydro-2H-pyran-3,4,5-triol $^1$H NMR (400 MHz, DMSO-$d_6$) δ 7.78 (dd, J=4.8, 1.2 Hz, 1H), 7.69 (dd, J=3.6, 1.2 Hz, 1H), 7.51 (d, J=2.4 Hz, 1H), 7.43 (d, J=8.0 Hz, 1H), 7.31 (dd, J=8.0, 2.0 Hz, 1H), 7.16 (dd, J=8.0, 4.0 Hz, 1H), 4.97-4.93 (m, 2H), 4.86 (d, J=6.0 Hz, 1H), 4.57 (d, J=16.0 Hz, 1H), 4.52 (d, J=15.6 Hz, 1H), 4.45 (t, J=5.6 Hz, 1H), 4.02 (d, J=9.2 Hz, 1H), 3.70-3.65 (m, 1H), 3.46-3.39 (m, 1H), 3.27-3.05 (m, 4H);
MH+ 455.

Example 6

(2S,3R,4R,5S,6R)-2-(3-((5-(Benzo[b]thiophen-2-yl)-1,3,4-thiadiazol-2-yl)methyl)-4-chlorophenyl)-6-(hydroxymethyl)-tetrahydro-2H-pyran-3,4,5-triol $^1$H NMR (400 MHz, DMSO-$d_6$) δ 8.11 (s, 1H), 8.02 (d, J=7.2 Hz, 1H), 7.87 (d, J=7.2 Hz, 1H), 7.54 (d, J=2.0 Hz, 1H), 7.47-7.39 (m, 3H), 7.32 (dd, J=8.4, 2.0 Hz, 1H), 4.95 (br, 2H), 4.87 (d, J=5.6 Hz, 1H), 4.62 (d, J=16 Hz, 1H), 4.57 (d, J=16 Hz, 1H), 4.45 (t, J=5.6 Hz, 1H), 4.02 (d, J=9.2 Hz, 1H), 3.70-3.66 (m, 1H), 3.46-3.40 (m, 1H), 3.26-3.06 (m, 4H);
MH+ 505.

Example 7

(2S,3R,4R,5S,6R)-2-(4-chloro-3-((5-(3-methylthiophen-2-yl)-1,3,4-thiadiazol-2-yl)methyl)phenyl)-6-(hydroxymethyl)-tetrahydro-2H-pyran-3,4,5-triol $^1$H NMR (400 MHz, DMSO-$d_6$) δ 7.67 (d, J=5.2 Hz, 1H), 7.50 (d, J=1.6 Hz, 1H), 7.42 (d, J=8.4 Hz, 1H), 7.30 (dd, J=8.4, 1.6 Hz, 1H), 7.06 (d, J=5.2 Hz, 1H), 4.96 (m, 2H), 4.85 (d, J=5.6 Hz, 1H), 4.59 (d, J=16.0 Hz, 1H), 4.55 (d, J=16.0 Hz, 1H), 4.44 (t, J=5.6 Hz, 1H), 4.01 (d, J=9.2 Hz, 1H), 3.69-3.65 (m, 1H), 3.45-3.39 (m, 1H), 3.27-3.04 (m, 4H), 2.37 (s, 3H);
MH+ 469.

Example 8

(2S,3R,4R,5S,6R)-2-(4-Chloro-3-((5-(5-chlorothiophen-2-yl)-1,3,4-thiadiazol-2-yl)methyl)phenyl)-6-(hydroxymethyl)-tetrahydro-2H-pyran-3,4,5-triol $^1$H NMR (400 MHz, DMSO-$d_6$) δ 7.59 (d, J=4.0 Hz, 1H), 7.47 (d, J=2.0 Hz, 1H), 7.39 (d, J=8.4 Hz, 1H), 7.27 (dd, J=8.4 Hz, 2.0 Hz, 1H), 7.19 (d, J=4.0 Hz, 1H), 4.64-4.38 (m, 5H), 3.97 (d, J=9.6 Hz, 1H), 3.64 (d, J=8.0 Hz, 1H), 3.42-3.36 (m, 1H), 3.25-3.10 (m, 5H);
MH+ 489.

Example 9

(2S,3R,4R,5S,6R)-2-(4-Chloro-3-((5-(3-chlorothiophen-2-yl)-1,3,4-thiadiazol-2-yl)methyl)phenyl)-6-(hydroxymethyl)-tetrahydro-2H-pyran-3,4,5-triol $^1$H NMR (400 MHz, DMSO-$d_6$) δ 7.90 (d, J=5.2 Hz, 1H), 7.51 (d, J=2.0 Hz, 1H), 7.43 (d, J=8.4 Hz, 1H), 7.31 (dd, J=8.0, 2.0 Hz, 1H), 7.27 (d, J=5.6 Hz, 1H), 4.92-4.90 (m, 2H), 4.82 (d, J=5.6 Hz, 1H), 4.62 (d, J=16.0 Hz, 1H), 4.58 (d, J=15.6 Hz, 1H), 4.40 (t, J=6.0 Hz, 1H), 4.02 (d, J=9.2 Hz, 1H), 3.70-3.65 (m, 1H), 3.46-3.40 (m, 1H), 3.25-3.05 (m, 4H);
MH+ 489.

Example 10

(2S,3R,4R,5S,6R)-2-(4-Chloro-3-((5-(thiophen-3-yl)-1,3,4-thiadiazol-2-yl)methyl)phenyl)-6-(hydroxymethyl)tetrahydro-2H-pyran-3,4,5-triol $^1$H NMR (400 MHz, DMSO-$d_6$) δ 8.22 (dd, J=2.8, 1.2 Hz, 1H), 7.72-7.69 (m, 1H), 7.58 (dd, J=4.8, 1.2 Hz, 1H), 7.51 (d, J=1.6 Hz, 1H), 7.42 (d, J=8.0 Hz, 1H), 7.31 (dd, J=8.0, 1.6 Hz, 1H), 4.94-4.91 (m, 2H), 4.84 (d, J=6.0 Hz, 1H), 4.57 (d, J=15.6 Hz, 1H), 4.52 (d, J=16.0 Hz, 1H), 4.42 (t, J=6.0 Hz, 1H), 4.01 (d, J=9.6 Hz, 1H), 3.70-3.65 (m, 1H), 3.46-3.40 (m, 1H), 3.25-3.05 (m, 4H);
$^{13}$C NMR (100 MHz, DMSO-$d_6$) δ 166.40, 162.06, 139.16, 133.14, 130.89, 129.85, 129.74, 127.85, 127.68, 127.36, 126.69, 125.08, 80.14, 79.35, 77.19, 73.65, 69.18, 60.24, 32.47;
HRMS (FAB, 6 keV) calcd for $C_{19}H_{20}ClN_2O_5S_2$ ([M+H]$^+$) 455.0502. found 455.0501;
MH+ 455.

Example 11

(2S,3R,4R,5S,6R)-2-(4-Chloro-3-((5-(1-methyl-1H-pyrrol-2-yl)-1,3,4-thiadiazol-2-yl)methyl)phenyl)-6-(hydroxymethyl)-tetrahydro-2H-pyran-3,4,5-triol $^1$H NMR (400 MHz, CDCl$_3$) δ 7.46 (d, J=2.0 Hz, 1H), 7.42 (d, J=8.4 Hz, 1H), 7.30 (dd, J=8.0, 2.0 Hz, 1H), 7.02 (t, J=2.0 Hz, 1H), 6.65-6.60 (m, 1H), 6.13-6.07 (m, 1H), 4.57-4.42 (m, 4H), 4.01 (d, J=9.6 Hz, 1H), 3.80 (s, 3H), 3.67 (dd, J=11.6, 1.6 Hz, 1H), 3.47-3.38 (m, 1H), 3.27-3.05 (m, 6H);
MH+ 452.

Example 12

(2S,3R,4R,5S,6R)-2-(4-Chloro-3-((5-(5-methylisoxazol-3-yl)-1,3,4-thiadiazol-2-yl)methyl)phenyl)-6-(hydroxymethyl)tetrahydro-2H-pyran-3,4,5-triol $^1$H NMR (400 MHz, DMSO-$d_6$) δ 7.52 (d, J=2.0 Hz, 1H), 7.43 (d, J=8.0 Hz, 1H), 7.31 (dd, J=8.0, 1.6 Hz, 1H), 6.87 (s, 1H), 4.93 (t, J=4.8 Hz, 2H), 4.85 (d, J=5.6 Hz, 1H), 4.64 (d, J=16.0 Hz, 1H), 4.59 (d, J=16.0 Hz, 1H), 4.42 (t, J=6.0 Hz, 1H), 4.02 (d, J=9.2 Hz, 1H), 3.69-3.65 (m, 1H), 3.46-3.39 (m, 1H), 3.29-3.05 (m, 4H), 2.48 (s, 3H);
MH+ 454.

Example 13

(2S,3R,4R,5S,6R)-2-(4-Chloro-3-((5-(thiazol-4-yl)-1,3,4-thiadiazol-2-yl)methyl)phenyl)-6-(hydroxymethyl)tetrahydro-2H-pyran-3,4,5-triol $^1$H NMR (400 MHz, DMSO-$d_6$) δ 9.23 (d, J=2.4 Hz, 1H), 8.49 (d, J=2.0 Hz, 1H), 7.51 (d, J=2.0 Hz, 1H), 7.42 (d, J=8.4 Hz, 1H), 7.30 (dd, J=8.0, 2.0 Hz, 1H), 4.93-4.91 (m, 2H), 4.83 (d, J=5.6 Hz, 1H), 4.59 (d, J=15.6 Hz, 1H), 4.54 (d, J=15.6 Hz, 1H), 4.42 (t, J=5.6 Hz, 1H), 4.01 (d, J=9.2 Hz, 1H), 3.69-3.64 (m, 1H), 3.45-3.39 (m, 1H), 3.26-3.05 (m, 4H);
MH+ 456.

Example 14

(2S,3R,4R,5S,6R)-2-(4-Chloro-3-((5-(2-(pyridin-4-yl)thiazol-5-yl)-1,3,4-thiadiazol-2-yl)methyl)phenyl)-6-(hydroxymethyl)-tetrahydro-2H-pyran-3,4,5-triol ¹H NMR (400 MHz, CDCl₃) δ 8.73 (d, J=6.0 Hz, 2H), 8.68 (s, 1H), 7.96 (d, J=4.4 Hz, 2H), 7.54 (d, J=2.0 Hz, 1H), 7.44 (d, J=8.4 Hz, 1H), 7.32 (dd, J=8.0, 1.6 Hz, 1H), 4.67-4.51 (m, 5H), 4.02 (d, J=9.2 Hz, 1H), 3.67 (d, J=10.4 Hz, 1H), 3.49-3.39 (m, 1H), 3.27-3.07 (m, 5H);
MH+ 533.

Example 15

(2S,3R,4R,5S,6R)-2-(4-Chloro-3-((5-(pyridin-2-yl)-1,3,4-thiadiazol-2-yl)methyl)phenyl)-6-(hydroxymethyl)tetrahydro-2H-pyran-3,4,5-triol ¹H NMR (400 MHz, DMSO-d₆) δ 8.62 (dd, J=3.6, 0.8 Hz, 1H), 8.19 (d, J=7.6 Hz, 1H), 7.98 (td, J=7.6, 1.6 Hz, 1H), 7.54-7.50 (m, 2H), 7.43 (d, J=8.4 Hz, 1H), 7.31 (dd, J=8.0, 1.6 Hz, 1H), 4.94-4.91 (m, 2H), 4.84 (d, J=5.6 Hz, 1H), 4.59 (d, J=16.0 Hz, 1H), 4.54 (d, J=16.0 Hz, 1H), 4.42 (t, J=5.6 Hz, 1H), 4.02 (d, J=9.6 Hz, 1H), 3.69-3.65 (m, 1H), 3.44-3.41 (m, 1H), 3.27-3.07 (m, 4H);
MH+ 450.

Example 16

(2S,3R,4R,5S,6R)-2-(4-Chloro-3-((5-(6-methylpyridin-3-yl)-1,3,4-thiadiazol-2-yl)methyl)phenyl)-6-(hydroxymethyl)-tetrahydro-2H-pyran-3,4,5-triol ¹H NMR (400 MHz, CDCl₃) δ 8.92 (d, J=2.0 Hz, 1H), 8.16 (dd, J=8.0 Hz, 2.4 Hz, 1H), 7.52 (d, J=1.6 Hz, 1H), 7.48-7.37 (m, 2H), 7.32 (dd, J=8.4, 2.0 Hz, 1H), 4.99-4.90 (m, 2H), 4.86 (d, J=5.6 Hz, 1H), 4.65-4.53 (m, 2H), 4.43 (t, J=6.0 Hz, 1H), 4.01 (d, J=9.2 Hz, 1H), 3.71-3.63 (m, 1H), 3.47-3.05 (m, 5H), 2.50 (s, 3H);
MH+ 464.

Example 17

(2S,3R,4R,5S,6R)-2-(4-Chloro-3-((5-(quinolin-2-yl)-1,3,4-thiadiazol-2-yl)methyl)phenyl)-6-(hydroxymethyl)tetrahydro-2H-pyran-3,4,5-triol ¹H NMR (400 MHz, DMSO-d₆) δ 8.56 (d, J=8.4 Hz, 1H), 8.31 (d, J=8.8 Hz, 1H), 8.04 (t, J=9.4 Hz, 2H), 7.81 (td, J=8.0 Hz, 1.6 Hz, 1H), 7.67 (td, J=7.2, 1.2 Hz, 1H), 7.56 (d, J=2.0 Hz, 1H), 7.45 (d, J=8.4 Hz, 1H), 7.33 (dd, J=6.4, 2.0 Hz, 1H), 4.99-4.90 (m, 2H), 4.86 (d, J=5.6 Hz, 1H), 4.67-4.55 (m, 2H), 4.43 (t, J=5.6 Hz, 1H), 4.04 (d, J=9.6 Hz, 1H), 3.67 (dd, J=7.6, 3.6 Hz, 1H), 3.49-3.38 (m, 1H), 3.29-3.07 (m, 4H);
MH+ 500.

Example 18

(2S,3R,4R,5S,6R)-2-(4-Chloro-3-((5-(isoquinolin-3-yl)-1,3,4-thiadiazol-2-yl)methyl)phenyl)-6-(hydroxymethyl)-tetrahydro-2H-pyran-3,4,5-triol ¹H NMR (400 MHz, DMSO-d₆) δ 9.36 (s, 1H), 8.72 (s, 1H), 8.18 (d, J=8.8 Hz, 2H), 7.86 (td, J=7.6, 1.2 Hz, 1H), 7.76 (td, J=8.0, 1.2 Hz, 1H), 7.55 (d, J=2.0 Hz, 1H), 7.44 (d, J=8.0 Hz, 1H), 7.32 (dd, J=8.0, 2.0 Hz, 1H), 4.66-4.52 (m, 3H), 4.03 (d, J=9.2 Hz, 1H), 3.68 (d, J=10.8 Hz, 1H), 3.44 (dd, J=11.6, 5.6 Hz, 2H), 3.33-3.05 (m, 6H);
MH+ 500.

Example 19

(2S,3R,4R,5S,6R)-2-(4-Chloro-3-((5-cyclopentyl-1,3,4-thiadiazol-2-yl)methyl)phenyl)-6-(hydroxymethyl)tetrahydro-2H-pyran-3,4,5-triol ¹H NMR (400 MHz, DMSO-d₆) δ 7.45 (d, J=1.6 Hz, 1H), 7.40 (d, J=8.0 Hz, 1H), 7.29 (dd, J=8.4, 2.0 Hz, 1H), 4.96-4.93 (m, 2H), 4.85 (d, J=5.6 Hz, 1H), 4.50-4.41 (m, 3H), 4.00 (d, J=9.2 Hz, 1H), 3.69-3.65 (m, 1H), 3.47-3.40 (m, 2H), 3.26-3.03 (m, 4H), 2.09-2.04 (m, 2H), 1.69-1.57 (m, 6H);
MH+ 441.

Example 20

(3R,4R,5S,6R)-2-(4-Chloro-3-((5-(pyridin-4-yl)-1,3,4-thiadiazol-2-yl)methyl)phenyl)-6-(hydroxymethyl)-tetrahydro-2H-pyran-3,4,5-triol Step 1: 2-(2-Chloro-5-((3S,4R,5R,6R)-3,4,5-tris(benzyloxy)-6-(benzyloxymethyl)-tetrahydro-2H-pyran-2-yl)benzyl)-5-(pyridin-4-yl)-1,3,4-thiadiazole The titled compound was obtained in the same manner as in intermediate 3 and Example 1 (Step 1 and Step 2) from intermediate 1 (compound 6).
MH+ 810.

Step 2: (3R,4R,5S,6R)-2-(4-Chloro-3-((5-(pyridin-4-yl)-1,3,4-thiadiazol-2-yl)methyl)phenyl)-6-(hydroxymethyl)-tetrahydro-2H-pyran-3,4,5-triol To a solution of 2-(2-chloro-5-((3S,4R,5R,6R)-3,4,5-tris(benzyloxy)-6-(benzyloxymethyl)-tetrahydro-2H-pyran-2-yl)benzyl)-5-(pyridin-4-yl)-1,3,4-thiadiazole (2.83 mmol) from Step 1 in acetonitrile (5 mL) was added Iodotrimethylsilane (5 mL). The resulting reaction mixture was heated to 50° C. overnight. After cooling to 0° C., the reaction quenched with methanol and concentrated in vacuo. Purification by reverse phase preparative HPLC (Gilson®, SunFire™ Prep, 5 to 50% acetonitrile in water gradient) provided the title compound (139 mg, 0.31 mmol, 11%, mixture of α,β-anomer) as a yellow solid.
¹H NMR (400 MHz, CD₃OD) δ 8.76 (d, J=6.4 Hz, 2H), 8.12 (d, J=6.4 Hz, 2H), 7.59 (d, J=1.2 Hz, 1H), 7.44-7.39 (m, 2H). 4.68 (s, 2H), 4.14 (d, J=9.6 Hz, 1H), 3.87 (dd, J=12, 2.0 Hz, 1H), 3.70 (dd, J=12, 5.2 Hz, 1H), 3.48-3.38 (m, 3H), 3.34 (s, 1H), 3.26 (d, J=8.8 Hz, 1H);
MH+ 450.

Example 21

(3R,4R,5S,6R)-2-(4-Chloro-3-((5-(pyridin-3-yl)-1,3,4-thiadiazol-2-yl)methyl)phenyl)-6-(hydroxymethyl)-tetrahydro-2H-pyran-3,4,5-triol Mixture of α,β-anomer. ¹H NMR (400 MHz, DMSO-d₆) δ 9.07 (d, J=1.6 Hz, 1H), 8.80 (dd, J=4.8, 1.6 Hz, 1H), 8.30-8.27 (m, 1H), 7.55-7.51 (m, 2H), 7.43 (d, J=8.4 Hz, 1H), 7.32 (dd, J=8.4, 2.0 Hz, 1H), 5.02-4.84 (br, 3H), 4.63 (d, J=16 Hz, 1H), 4.58 (d, J=16 Hz, 1H), 4.41 (br, 1H), 4.02 (d, J=9.6 Hz, 1H), 3.69-3.66 (m, 1H), 3.46-3.41 (m, 1H), 3.23-3.06 (m, 4H);
MH+ 450.

Example 22

(3R,4R,5S,6R)-2-(4-chloro-3-((5-p-tolyl-1,3,4-thiadiazol-2-yl)methyl)phenyl)-6-(hydroxymethyl)-tetrahydro-2H-pyran-3,4,5-triol Mixture of α,β-anomer. $^1$H NMR (400 MHz, CD$_3$OD) δ 7.76 (d, J=8.0 Hz, 2H), 7.56 (d, J=2.0 Hz, 1H), 7.43-7.37 (m, 2H), 7.29 (d, J=8.0 Hz, 2H), 4.58 (s, 2H), 4.14 (d, J=9.6 Hz, 1H), 3.87 (dd, J=12, 2.0 Hz, 1H), 3.70 (dd, J=12, 5.2 Hz, 1H), 3.48-3.38 (m, 3H), 3.26 (d, J=9.2 Hz, 1H), 2.37 (s, 3H); MH+ 463.

Example 23

(3R,4R,5S,6R)-2-(4-Chloro-3-((5-(4-propylphenyl)-1,3,4-thiadiazol-2-yl)methyl)phenyl)-6-(hydroxymethyl)-tetrahydro-2H-pyran-3,4,5-triol Mixture of α,β-anomer. $^1$H NMR (400 MHz, CD$_3$OD) δ 7.79 (d, J=8.0 Hz, 2H), 7.57 (d, J=1.6 Hz, 1H), 7.43-7.37 (m, 2H), 7.30 (d, J=8.0 Hz, 2H), 4.14 (d, J=9.6 Hz, 1H), 3.87 (dd, J=12, 2.0 Hz, 1H), 3.70 (dd, J=12, 5.2 Hz, 1H), 3.48-3.38 (m, 3H), 3.33 (s, 1H), 3.26 (d, J=9.2 Hz, 1H), 2.63 (t, J=7.6 Hz, 2H), 1.65 (sextet, J=7.6 Hz, 2H), 0.93 (t, J=7.6 Hz, 3H); MH+ 491.

Example 24

(3R,4R,5S,6R)-2-(4-Chloro-3-((5-cyclohexyl-1,3,4-thiadiazol-2-yl)methyl)phenyl)-6-(hydroxymethyl)-tetrahydro-2H-pyran-3,4,5-triol Mixture of α,β-anomer. $^1$H NMR (400 MHz, DMSO-d$_6$) δ 7.45 (d, J=2.0 Hz, 1H), 7.39 (d, J=8.4 Hz, 1H), 7.28 (dd, J=8.4, 2.0 Hz, 1H), 5.07-4.89 (br, 3H), 4.48 (d, J=15.6 Hz, 1H), 4.43 (d, J=15.6 Hz, 1H), 4.42 (br, 1H), 3.99 (d, J=9.6 Hz, 1H), 3.69-3.65 (m, 1H), 3.46-3.40 (m, 1H), 3.24-3.00 (m, 5H), 1.99-1.94 (m, 2H), 1.73-1.67 (m, 2H), 1.64-1.59 (m, 1H), 1.46-1.28 (m, 3H), 1.24-1.14 (m, 1H); MH+ 455.

Example 25

(3R,4R,5S,6R)-2-(4-Chloro-3-((5-((4-methylcyclohexyl)methyl-1,3,4-thiadiazol-2-yl)methyl)phenyl)-6-(hydroxymethyl)-tetrahydro-2H-pyran-3,4,5-triol Mixture of α,β-anomer. $^1$H NMR (400 MHz, CD$_3$OD) δ 7.52 (s, 1H), 7.41-7.36 (m, 2H), 4.52 (s, 2H), 4.12 (d, J=9.2 Hz, 1H), 3.86 (dd, J=12, 1.6 Hz, 1H), 3.69 (dd, J=12, 5.2 Hz, 1H), 3.47-3.38 (m, 3H), 3.29 (s, 2H), 3.2 (d, J=8.8 Hz, 1H), 3.03 (d, J=7.2 Hz, 1H), 2.91 (d, J=7.2 Hz, 1H), 1.91-1.87 (m, 1H), 1.70-1.26 (m, 7H), 1.09-0.88 (m, 3H), 0.92 (d, J=7.2 Hz, 1H), 0.85 (d, J=7.2 Hz, 1H); MH+ 483.

Example 26

(3R,4R,5S,6R)-2-(4-Chloro-3-((5-(2-phenylpropyl)-1,3,4-thiadiazol-2-yl)methyl)phenyl)-6-(hydroxymethyl)-tetrahydro-2H-pyran-3,4,5-triol Mixture of α,β-anomer. $^1$H NMR (400 MHz, CD$_3$OD) δ 7.44 (s, 1H), 7.38-7.34 (m, 2H), 7.25-7.13 (m, 5H), 4.48-4.39 (m, 2H), 4.10 (d, J=9.2 Hz, 1H), 3.86 (dd, J=12, 1.6 Hz, 1H), 3.70 (dd, J=12, 5.2 Hz, 1H), 3.47-3.22 (m, 5H), 3.17-3.12 (m, 1H), 1.31 (d, J=6.8 Hz, 3H); MH+ 491.

Example 27

(3R,4R,5S,6R,E)-2-(4-Chloro-3-((5-styryl-1,3,4-thiadiazol-2-yl)methyl)phenyl)-6-(hydroxymethyl)-tetrahydro-2H-pyran-3,4,5-triol Mixture of α,β-anomer. $^1$H NMR (400 MHz, CD$_3$OD) δ 7.60-7.55 (m, 3H), 7.43-7.32 (m, 7H), 4.56 (s, 2H), 4.14 (d, J=9.2 Hz, 1H), 3.87 (dd, J=12, 2 Hz, 1H), 3.70 (dd, J=12, 5.2 Hz, 1H), 3.48-3.33 (m, 3H), 3.26 (d, J=9.6 Hz, 1H); MH+ 475.

Example 28

(2S,3R,4R,5S,6R)-2-(4-Chloro-3-((5-phenyl-1,3,4-thiadiazol-2-yl)methyl)phenyl)-6-(hydroxymethyl)-tetrahydro-2H-pyran-3,4,5-triol Purification by preparative HPLC provided β-anomer. $^1$H NMR (400 MHz, DMSO-d$_6$) δ 7.91-7.88 (m, 2H), 7.53-7.46 (m, 4H), 7.43 (d, J=8.4 Hz, 1H), 7.31 (dd, J=8.4, 2.4 Hz, 1H), 4.99 (br. 2H), 4.89 (d, J=5.6 Hz, 1H), 4.59 (d, J=16 Hz, 1H), 4.54 (d, J=16 Hz, 1H), 4.43 (t, J=5.6 Hz, 1H), 4.01 (d, J=9.2 Hz, 1H), 3.69-3.66 (m, 1H), 3.46-3.40 (m, 1H), 3.26-3.06 (m, 4H);

$^{13}$C NMR (100 MHz, DMSO-d$_6$) β-anomer: δ 168.75, 140.69, 134.65, 132.43, 131.72, 131.31, 129.94, 129.87, 129.38, 129.26, 127.99, 81.70, 80.89, 78.68, 75.18, 70.62, 61.71, 34.08;
MH+ 449.

Example 29

(2S,3R,4R,5S,6R)-2-(4-chloro-3-((5-(4-Chlorophenyl)-1,3,4-thiadiazol-2-yl)methyl)phenyl)-6-(hydroxymethyl)-tetrahydro-2H-pyran-3,4,5-triol Purification by preparative HPLC provided β-anomer. $^1$H NMR (400 MHz, DMSO-d$_6$) δ 7.92 (d, J=8.4 Hz, 2H), 7.56 (d, J=8.4 Hz, 2H), 7.51 (d, J=2.0 Hz, 1H), 7.43 (d, J=8.0 Hz, 1H), 7.31 (dd, J=8.0, 2.0 Hz, 1H), 4.96-4.93 (m, 2H), 4.86 (d, J=5.6 Hz, 1H), 4.60 (d, J=16 Hz, 1H), 4.55 (d, J=16 Hz, 1H), 4.43 (t, J=5.6 Hz, 1H), 4.01 (d, J=9.6 Hz, 1H), 3.68-3.65 (m, 1H), 3.26-3.07 (m, 4H);
MH+ 483.

Example 30

(2S,3R,4R,5S,6R)-2-(3-((5-(Benzofuran-2-yl)-1,3,4-thiadiazol-2-yl)methyl)-4-chlorophenyl)-6-(hydroxymethyl)-tetrahydro-2H-pyran-3,4,5-triol Purification by preparative HPLC provided β-anomer. $^1$H NMR (400 MHz, CD$_3$OD) δ 7.71 (d, J=8.0 Hz, 1H), 7.60-7.52 (m, 3H), 7.44-7.39 (m, 3H), 7.31 (t, J=7.6 Hz, 2H), 4.15 (d, J=9.2 Hz, 1H), 3.87 (dd, J=12, 1.6 Hz, 1H), 3.70 (dd, J=12, 5.2 Hz, 3.48-3.38 (m, 3H), 3.33 (s, 2H);
MH+ 489.

Example 31

(2S,3R,4R,5S,6R)-2-(4-Chloro-3-((5-propyl-1,3,4-thiadiazol-2-yl)methyl)phenyl)-6-(hydroxymethyl)-tetrahydro-2H-pyran-3,4,5-triol Purification by preparative HPLC provided β-anomer. $^1$H NMR (400 MHz, CD$_3$OD) δ 7.51 (d, J=1.6 Hz, 1H), 7.41-7.36 (m, 2H), 4.52 (s, 2H), 4.12 (d, J=9.2 Hz, 1H), 3.86 (dd, J=12, 1.6 Hz, 1H), 3.69 (dd, J=12, 5.2 Hz, 1H), 3.47-3.37 (m, 3H), 3.25 (d, J=8.8 Hz, 1H), 3.01 (t, J=7.6 Hz, 2H), 1.76 (sextet, J=7.6 Hz, 2H), 0.97 (t, J=7.6 Hz, 3H);
MH+ 415.

Example 32

(2S,3R,4R,5S,6R)-2-(3-((5-Butyl-1,3,4-thiadiazol-2-yl)methyl)-4-chlorophenyl)-6-(hydroxymethyl)-tetrahydro-2H-pyran-3,4,5-triol Purification by preparative HPLC provided β-anomer. $^1$H NMR (400 MHz, DMSO-d$_6$) δ 7.45 (d, J=2.0 Hz, 1H), 7.39 (d, J=8.4 Hz, 1H), 7.28 (dd, J=8.4, 2.0 Hz, 1H), 5.04 (br, 2H), 4.87 (d, J=5.6 Hz, 1H), 4.48 (d, J=16 Hz, 1H), 4.43 (d, J=16 Hz, 1H), 4.43 (br, 1H), 3.99 (d, J=9.2 Hz, 1H), 3.68-3.65 (m, 1H), 3.46-3.40 (m, 1H), 3.26-3.04 (m, 4H), 2.97 (t, J=7.6 Hz, 2H), 1.61 (quintet, J=7.6 Hz, 2H), 1.29 (sextet, J=7.6 Hz, 2H), 0.85 (t, J=7.6 Hz, 3H);
MH+ 429.

Example 33

(2S,3R,4R,5S,6R)-2-(4-Chloro-3-((5-pentyl-1,3,4-thiadiazol-2-yl)methyl)phenyl)-6-(hydroxymethyl)-tetrahydro-2H-pyran-3,4,5-triol Purification by preparative HPLC provided β-anomer. $^1$H NMR (400 MHz, DMSO-d$_6$) δ 7.45 (d, J=2.0 Hz, 1H), 7.40 (d, J=8.0 Hz, 1H), 7.28 (dd, J=8.0, 2.0 Hz, 1H), 4.90 (br, 2H), 4.80 (d, 1H), 4.49 (d, J=15.6 Hz, 1H), 4.43 (d, J=15.6 Hz, 1H), 4.39 (t, J=6.0 Hz, 1H), 4.00 (d, J=9.2 Hz, 1H), 3.69-3.65 (m, 1H), 3.45-3.40 (m, 1H), 3.24-3.04 (m, 4H), 2.96 (t, J=7.6 Hz, 2H), 1.67-1.60 (m, 2H), 1.30-1.22 (m, 4H), 0.82 (t, J=7.6 Hz, 3H);
MH+ 443.

Example 34

(2S,3R,4R,5S,6R)-2-(4-Chloro-3-((5-heptyl-1,3,4-thiadiazol-2-yl)methyl)phenyl)-6-(hydroxymethyl)-tetrahydro-2H-pyran-3,4,5-triol Purification by preparative HPLC provided β-anomer. $^1$H NMR (400 MHz, CD$_3$OD) δ 7.52 (d, J=1.6 Hz, 1H), 7.40-7.36 (m, 2H), 4.12 (d, J=9.2 Hz, 1H), 3.86 (dd, J=12, 2.0 Hz, 1H), 3.69 (dd, J=12, 5.2 Hz, 1H), 3.47-3.38 (m, 3H), 3.25 (d, J=8.8 Hz, 1H), 3.03 (t, J=7.6 Hz, 2H), 1.72 (quintet, J=7.6 Hz, 2H), 1.38-1.24 (m, 8H), 0.87 (t, J=7.6 Hz, 3H);
MH+ 471

Example 35

(2R,3S,4R,5R)-2-(Hydroxymethyl)-6-(3-((5-phenyl-1,3,4-thiadiazol-2-yl)methyl)phenyl)-tetrahydro-2H-pyran-3,4,5-triol $^1$H NMR (400 MHz, CD$_3$OD) δ 7.88 (d, J=7.6 Hz, 2H), 7.01-7.45 (m, 4H), 7.37-7.29 (m, 3H), 4.47 (br, 1H), 4.13 (d, J=9.6 Hz, 1H), 3.88-3.85 (m 1H), 3.68 (dd, J=12, 5.2 Hz, 1H), 3.48-3.38 (m, 3H), 3.35-3.30 (m, 2H);
MH+ 415.

Example 36

(2R,3S,4R,5R)-2-(Hydroxymethyl)-6-(3-((5-(pyridin-3-yl)-1,3,4-thiadiazol-2-yl)methyl)phenyl)-tetrahydro-2H-pyran-3,4,5-triol $^1$H NMR (400 MHz, CD$_3$OD) δ 9.05 (s, 1H), 8.65 (d, J=4.8 Hz, 1H), 8.34-8.31 (m, 1H), 7.56 (dd, J=8.0, 5.2 Hz, 1H), 7.46 (s, 1H), 7.37-7.31 (m, 3H), 4.51 (s, 2H), 4.13 (d, J=9.6 Hz, 1H), 3.86 (d, J=11.6 Hz, 1H), 3.68 (dd, J=11.6, 5.2 Hz, 1H), 3.48-3.32 (m, 4H);
MH+ 416.

Example 37

(2S,3R,4R,5S,6R)-2-(4-Chloro-3-((5-(5-phenylfuran-2-yl)-1,3,4-thiadiazol-2-yl)methyl)phenyl)-6-(hydroxymethyl)-tetrahydro-2H-pyran-3,4,5-triol (compound 19)

Step 1: N'-(2-(2-Chloro-5-((2S,3S,4R,5R,6R)-3,4,5-tris(benzyloxy)-6-(benzyloxymethyl)-tetrahydro-2H-pyran-2-yl)phenyl)acetyl)-5-phenylfuran-2-carbohydrazide To a mixture of intermediate 5 (compound 14, 674 mg, 0.95 mmol), 5-phenyl-2-furoic acid (compound 15, 233 mg, 1.24 mmol), EDCI (273 mg, 1.43 mmol), and 1-hydroxybenzotriazole hydrate (295 mg, 1.90 mmol) in 1V, N-dimethylformamide (10 mL) was added 4-methylmorpholine (0.31 mL, 2.85 mmol). The resulting mixture was stirred at ambient temperature overnight. After dilution with ethyl acetate, the organic layer was subsequently washed with water, hydrochloric acid (1.0 M), saturated sodium bicarbonate solution and brine prior to drying over magnesium sulfate. Filtration and removal of the volatiles under reduced pressure yielded titled compound as a glassy yellow amorphous solid, which was used without further purification.
MH+ 877.

Step 2: 2-(2-Chloro-5-((2S,3S,4R,5R,6R)-3,4,5-tris(benzyloxy)-6-(benzyloxymethyl)-tetrahydro-2H-pyran-2-yl)benzyl)-5-(5-phenylfuran-2-yl)-1,3,4-thiadiazole The titled compound was obtained in the same manner as in Example 1 (Step 2).
MH+ 875.

Step 3: (2S,3R,4R,5S,6R)-2-(4-Chloro-3-((5-(5-phenylfuran-2-yl)-1,3,4-thiadiazol-2-yl)methyl)phenyl)-6-(hydroxymethyl)-tetrahydro-2H-pyran-3,4,5-triol (compound 19)

The titled compound (178 mg, 0.35 mmol, 42% from intermediate 5) was obtained in the same manner as in Example 20 (Step 2).
$^1$H NMR (400 MHz, DMSO-d$_6$) δ 7.79-7.77 (m, 2H), 7.52 (d, J=2.0 Hz, 1H), 7.46-7.31 (m, 6H), 7.20 (d, J=3.6 Hz, 1H), 4.95 (dd, J=6.8, 4.8 Hz, 2H), 4.87 (d, J=5.6 Hz, 1H), 4.61 (d, J=16 Hz, 1H), 4.56 (d, J=16 Hz, 1H), 4.50 (t, J=6.0 Hz, 1H). 4.02 (d, J=9.6 Hz, 1H), 3.68-3.62 (m, 1H), 3.43-3.40 (m, 1H), 3.27-3.06 (m, 4H);

$^{13}$C NMR (100 MHz, DMSO-d$_6$) δ 167.63, 158.60, 155.97, 144.51, 143.71, 140.72, 134.63, 132.43, 131.30, 129.52, 129.41, 129.29, 129.14, 124.34, 114.87, 109.08, 81.68, 80.90, 78.73, 75.19, 70.71, 61.78, 33.88;
MH+ 515.

Example 38

(2S,3R,4R,5S,6R)-2-(4-Chloro-3-((5-(trifluoromethyl)-1,3,4-thiadiazol-2-yl)methyl)phenyl)-6-(hydroxymethyl)tetrahydro-2H-pyran-3,4,5-triol $^1$H NMR (400 MHz, DMSO-d$_6$) δ 7.53 (d, J=2.0 Hz, 1H), 7.43 (d, J=8.4 Hz, 1H), 7.33 (dd, J=8.4, 2.4 Hz, 1H), 4.95-4.91 (m, 2H), 4.85 (d, J=5.6 Hz, 1H), 4.71 (d, J=16.4 Hz, 1H), 4.67 (d, J=16.4 Hz, 1H), 4.41 (t, J=6.0 Hz, 1H), 4.01 (d, J=9.2 Hz, 1H), 3.69-3.65 (m, 1H), 3.46-3.40 (m, 1H), 3.25-3.04 (m, 4H);
MH+ 441.

Example 39

(2S,3R,4R,5S,6R)-2-(4-Chloro-3-((5-(2,2,2-trifluoroethyl)-1,3,4-thiadiazol-2-yl)methyl)phenyl)-6-(hydroxymethyl)tetrahydro-2H-pyran-3,4,5-triol $^1$H NMR (400 MHz, DMSO-d$_6$) δ 7.50 (d, J=1.6 Hz, 1H), 7.41 (d, J=8.4 Hz, 1H), 7.29 (dd, J=8.4, 1.6 Hz, 1H), 4.97-4.94 (m, 2H), 4.85 (d, J=6.0 Hz, 1H), 4.56 (d, J=16.0 Hz, 1H), 4.51 (d, J=16.0 Hz, 1H), 4.44 (t, J=6.0 Hz, 1H), 4.33 (q, J=10.8 Hz, 2H), 4.00 (d, J=9.2 Hz, 1H), 3.69-3.63 (m, 1H), 3.45-3.41 (m, 1H), 3.27-3.03 (m, 4H); MH+ 455.

Example 40

(2S,3R,4R,5S,6R)-2-(4-Chloro-3-((5-(methylthio)-1,3,4-thiadiazol-2-yl)methyl)phenyl)-6-(hydroxymethyl)-tetrahydro-2H-pyran-3,4,5-triol (compound 22)

Step 1: 5-(2-Chloro-5-((2S,3S,4R,5R,6R)-3,4,5-tris(benzyloxy)-6-(benzyloxymethyl)-tetrahydro-2H-pyran-2-yl)benzyl)-1,3,4-thiadiazol-2-amine To a solution of intermediate 3 (compound 8, 2.8 g, 4.0 mmol) in 1,4-dioxane (30 mL) was added thiosemicarbazide (compound 17, 0.40 g, 4.4 mmol). The solution is stirred for 1 h at 90° C., before adding of phosphorus oxychloride (0.41 mL, 4.4 mmol). After overnight stirring at 110° C., the reaction was concentrated in vacuo to yield the title compound as a glassy off-white amorphous solid, which was used without further purification.
MH+ 748.

Step 2: 2-Chloro-5-(2-chloro-5-((2S,3S,4R,5R,6R)-3,4,5-tris(benzyloxy)-6-(benzyloxymethyl)-tetrahydro-2H-pyran-2-yl)benzyl)-1,3,4-thiadiazole (compound 18)

To a mixture of 5-(2-chloro-5-((2S,3S,4R,5R,6R)-3,4,5-tris(benzyloxy)-6-(benzyloxymethyl)-tetrahydro-2H-pyran-2-yl)benzyl)-1,3,4-thiadiazol-2-amine (4.0 mmol) from Step 1 and copper (0.04 g, 0.62 mmol) in hydrochloric acid (37%, 6 mL) and acetic acid (30 mL) at 0° C. was slowly added sodium nitrite (2.8 g, 40 mmol) while maintaining an internal reaction temperature below 10° C. After 1 h stirring at 0° C., the resulting mixture was stirred with gradual warming to ambient temperature over 2 h. The mixture was diluted with water and extracted with ethyl acetate. The organic layer was dried over magnesium sulfate, filtered and evaporated in vacuo. Flash chromatography on a Biotage® purification apparatus (silica gel, 10 to 60% ethyl acetate in hexanes) yielded the title compound (0.66 g, 0.86 mmol, 22%) as yellow oil.
MH+ 767.

Step 3: 2-(2-Chloro-5-((2S,3S,4R,5R,6R)-3,4,5-tris(benzyloxy)-6-(benzyloxymethyl)-tetrahydro-2H-pyran-2-yl)benzyl)-5-(methylthio)-1,3,4-thiadiazole To a solution of 2-chloro-5-(2-chloro-5-((2S,3S,4R,5R,6R)-3,4,5-tris(benzyloxy)-6-(benzyloxymethyl)-tetrahydro-2H-pyran-2-yl)benzyl)-1,3,4-thiadiazole (419 mg, 0.55 mmol) from Step 2 in tetrahydrofuran (10 mL) was added sodium methanethiolate (77 mg, 1.1 mmol). The resulting mixture was stirred at ambient temperature overnight. After cooling to 0° C., the reaction was quenched with hydrochloric acid (1.0 M) and diluted with ethyl acetate and water. The organic layer was separated and the aqueous layer was extracted with ethyl acetate. The combined organic layers were washed with brine, dried over magnesium sulfate, filtered and concentrated in vacuo. The residue was purified on Biotage® purification apparatus (silica gel, 10 to 60% ethyl acetate in hexanes) to yield the title compound (331 mg, 0.42 mmol, 77%) as a yellow oil. MH+ 779.

Step 4: (2S,3R,4R,5S,6R)-2-(4-Chloro-3-((5-(methylthio)-1,3,4-thiadiazol-2-yl)methyl)phenyl)-6-(hydroxymethyl)-tetrahydro-2H-pyran-3,4,5-triol (compound 19)

The titled compound (58 mg, 0.14 mmol, 25% from 2-chloro-5-(2-chloro-5-((2S,3S,4R,5R,6R)-3,4,5-tris(benzyloxy)-6-(benzyloxymethyl)-tetrahydro-2H-pyran-2-yl)benzyl)-1,3,4-thiadiazole) was obtained in the same manner as in Example 20 (Step 2).
$^1$H NMR (400 MHz, DMSO-d$_6$) δ 7.45 (d, J=2.0 Hz, 1H), 7.40 (d, J=8.0 Hz, 1H), 7.29 (dd, J=8.0, 2.0 Hz, 1H), 4.49 (d, J=15.6 Hz, 1H), 4.44 (d, J=15.6 z, 1H), 3.99 (d, J=9.6 Hz, 1H), 3.67 (dd, J=12, 2.0 Hz, 1H), 3.42 (dd, J=11.6, 5.6 Hz, 1H), 3.25-3.11 (m, 3H), 3.06 (t, J=9.2 Hz, 1H), 2.67 (s, 3H);
MH+ 419.

Example 41

(2S,3R,4R,5S,6R)-2-(4-Chloro-3-((5-methoxy-1,3,4-thiadiazol-2-yl)methyl)phenyl)-6-(hydroxymethyl)-tetrahydro-2H-pyran-3,4,5-triol Step 1: 2-(2-Chloro-5-((2S,3S,4R,5R,6R)-3,4,5-tris(benzyloxy)-6-(benzyloxymethyl)-tetrahydro-2H-pyran-2-yl)benzyl)-5-(hexyloxy)-1,3,4-thiadiazole The titled compound (372 mg, 0.45 mmol, 25% from 2-chloro-5-(2-chloro-5-((2S,3S,4R,5R,6R)-3,4,5-tris(benzyloxy)-6-(benzyloxymethyl)-tetrahydro-2H-pyran-2-yl)benzyl)-1,3,4-thiadiazole) was obtained in the same manner as in Example 40 (Step 1 to 3).
MH+ 833.

Step 2: (2S,3R,4R,5S,6R)-2-(4-Chloro-3-((5-hydroxy-1,3,4-thiadiazol-2-yl)methyl)phenyl)-6-(hydroxymethyl)-tetrahydro-2H-pyran-3,4,5-triol The titled compound (100 mg, 0.26 mmol, 57%) was obtained in the same manner as in Example 20 (Step 2).
MH+ 389.

Step 3: (2S,3R,4R,5S,6R)-2-(4-Chloro-3-((5-methoxy-1,3,4-thiadiazol-2-yl)methyl)phenyl)-6-(hydroxymethyl)-tetrahydro-2H-pyran-3,4,5-triol To a solution of (2S,3R,4R,5S,6R)-2-(4-chloro-3-((5-hydroxy-1,3,4-thiadiazol-2-yl)methyl)phenyl)-6-(hydroxymethyl)-tetrahydro-2H-pyran-3,4,5-triol (100 mg, 0.26 mmol) from step 2 in dichloromethane (8 mL) and methanol (2 mL) at 0° C. was added (trimethylsilyl)diazomethane (2.0 M in diethyl ether, 0.65 mL, 1.3 mmol). The reaction mixture was stirred with gradual warming to ambient temperature over 1 h and concentrated in vacuo. Purification by reverse phase preparative HPLC (Gilson®, SunFire™ Prep, 5 to 50% acetonitrile in water gradient) provided the title compound (69 mg, 0.17 mmol, 66%) as a yellow solid.

$^1$H NMR (400 MHz, DMSO-d$_6$) δ 7.42-7.39 (m, 2H), 7.29 (dd, J=8.4, 2.0 Hz, 1H), 4.97-4.94 (m, 2H), 4.85 (d, J=5.6 Hz, 1H), 4.44 (t, J=5.6 Hz, 1H), 4.37 (d, J=15.6 Hz, 1H), 4.32 (d, J=15.6 Hz, 1H), 4.01 (d, J=9.2 Hz, 1H), 3.69-3.65 (m, 1H), 3.45-3.40 (m, 1H), 3.27-3.03 (m, 4H), 3.39 (s, 3H);

MH+ 403.

Example 42

(2S,3R,4R,5S,6R)-2-(4-Chloro-3-((5-(pyrazin-2-yl)-1,3,4-thiadiazol-2-yl)methyl)phenyl)-6-(hydroxymethyl)-tetrahydro-2H-pyran-3,4,5-triol (compound 21)

Step 1: 2-(2-Chloro-5-((2S,3S,4R,5R,6R)-3,4,5-tris(benzyloxy)-6-(benzyloxymethyl)-tetrahydro-2H-pyran-2-yl)benzyl)-5-(pyrazin-2-yl)-1,3,4-thiadiazole The titled compound was obtained in the same manner as in Example 1 (Step 1 and Step 2).

MH+ 813.

Step 2: (2S,3R,4R,5S,6R)-2-(4-Chloro-3-((5-(pyrazin-2-yl)-1,3,4-thiadiazol-2-yl)methyl)phenyl)-6-(hydroxymethyl)-tetrahydro-2H-pyran-3,4,5-triol (compound 21)

To a solution of 2-(2-chloro-5-((2S,3S,4R,5R,6R)-3,4,5-tris(benzyloxy)-6-(benzyloxymethyl)-tetrahydro-2H-pyran-2-yl)benzyl)-5-(pyrazin-2-yl)-1,3,4-thiadiazole (680 mg, 0.84 mmol) from Step 1 at −50° C. in acetic anhydride (10 mL) was slowly added a solution of trimethylsilyl trifluoromethanesulfonate (1.5 mL, 8.4 mmol) in acetic anhydride (5 mL). The resulting mixture was stirred with gradual warming to ambient temperature over 15 h, cooled to 0° C., and quenched with saturated sodium bicarbonate. After dilution with ethyl acetate, the organic layer was washed with sodium bicarbonate and brine prior to drying over magnesium sulfate. Filtration and removal of volatiles under reduced pressure yielded peracetylated compound as a brown amorphous solid. Deacetylation was achieved by addition of sodium methoxide (25 wt % in methanol, 1 mL) to a solution of this residue in methanol (10 mL). The reaction mixture was stirred at ambient temperature for 2 h. Amberlite® IR120 hydrogen form was then added to neutralize the reaction mixture. The resin was filtered off and the filtrate was concentrated in vacuo. Purification by reverse phase preparative HPLC (Gilson®, SunFire™ Prep, 5 to 50% acetonitrile in water gradient) provided the title compound (47 mg, 0.10 mmol, 10% from Intermediate 3) as a white solid.

$^1$H NMR (400 MHz, DMSO-d$_6$) δ 9.39 (d, J=1.6 Hz, 1H), 8.78 (d, J=2.4 Hz, 1H), 8.73 (dd, J=2.4, 1.6 Hz, 1H), 7.53 (d, J=1.6 Hz, 1H), 7.43 (d, J=8.4 Hz, 1H), 7.31 (dd, J=8.4, 1.6 Hz, 1H), 4.50 (br, 2H), 4.87 (d, J=5.6 Hz, 1H), 4.64 (d, J=16.4 Hz, 1H), 4.59 (d, J=16.4 Hz, 1H), 4.43 (t, J=5.6 Hz, 1H), 4.02 (d, J=9.2 Hz, 1H), 3.69-3.65 (m, 1H), 3.44-3.41 (m, 1H), 3.26-3.07 (m, 4H);

$^{13}$C NMR (100 MHz, DMSO-d$_6$) δ 171.09, 168.42, 147.00, 145.34, 144.40, 141.88, 140.72, 134.59, 132.40, 131.24, 129.35, 129.32, 81.67, 80.92, 78.71, 75.21, 70.70, 61.76, 34.10;

HRMS (FAB, 6 keV) calcd for $C_{19}H_{20}ClN_4O_5S$ ([M+H]$^+$) 451.0843. found 451.0842;

MH+ 451.

Example 43

(2S,3R,4R,5S,6R)-2-(4-Chloro-3-((5-(pyridazin-4-yl)-1,3,4-thiadiazol-2-yl)methyl)phenyl)-6-(hydroxymethyl)-tetrahydro-2H-pyran-3,4,5-triol $^1$H NMR (400 MHz, DMSO-d$_6$) δ 9.71 (d, J=2.4 Hz, 1H), 9.51 (d, J=5.6 Hz, 1H), 8.15 (dd, J=5.6, 2.4 Hz, 1H), 7.54 (d, J=1.6 Hz, 1H), 7.44 (d, J=8.4 Hz, 1H), 7.32 (dd, J=8.4, 1.6 Hz, 1H), 5.03-4.98 (m, 2H), 4.91 (d, J=5.6 Hz, 1H), 4.68 (d, J=16 Hz, 1H), 4.63 (d, J=16 Hz, 1H), 4.45 (t, J=5.6 Hz, 1H), 4.02 (d, J=9.6 Hz, 1H), 3.69-3.65 (m, 1H), 3.44-3.41 (m, 1H), 3.26-3.06 (m, 4H);

MH+ 451.

Example 44

(2S,3R,4R,5S,6R)-2-(4-Chloro-3-((5-(6-methylpyridin-2-yl)-1,3,4-thiadiazol-2-yl)methyl)phenyl)-6-(hydroxymethyl)-tetrahydro-2H-pyran-3,4,5-triol $^1$H NMR (400 MHz, DMSO-d$_6$) δ 7.99 (d, J=7.6 Hz, 1H), 7.86 (t, J=7.6 Hz, 1H), 7.52 (d, J=1.6 Hz, 1H), 7.43 (d, J=8.4 Hz, 1H), 7.38 (d, J=7.6 Hz, 1H), 7.31 (dd, J=8.4, 1.6 Hz, 1H), 4.96-4.93 (m, 2H), 4.86 (d, J=5.6 Hz, 1H), 4.58 (d, J=15.6 Hz, 1H), 4.53 (d, J=15.6 Hz, 1H), 4.44 (t, J=5.6 Hz, 1H), 4.02 (d, J=9.6 Hz, 1H), 3.69-3.65 (m, 1H), 3.45-3.40 (m, 1H), 3.27-3.05 (m, 4H), 2.47 (s, 3H);

MH+ 464.

Example 45

(2S,3R,4R,5S,6R)-2-(4-Chloro-3-((5-(2-methylpyridin-4-yl)-1,3,4-thiadiazol-2-yl)methyl)phenyl)-6-(hydroxymethyl)-tetrahydro-2H-pyran-3,4,5-triol $^1$H NMR (400 MHz, DMSO-d$_6$) δ 8.56 (d, J=4.8 Hz, 1H), 7.74 (s, 1H), 7.67 (d, J=4.8 Hz, 1H), 7.53 (d, J=1.6 Hz, 1H), 7.44 (d, J=8.0 Hz, 1H), 7.32 (dd, J=8.0, 1.6 Hz, 1H), 4.98-4.94 (m, 2H), 4.87 (d, J=6.0 Hz, 1H), 4.64 (d, J=16 Hz, 1H), 4.53 (d, J=16 Hz, 1H), 4.44 (t, J=5.6 Hz, 1H), 4.01 (d, J=9.2 Hz, 1H), 3.68-3.66 (m, 1H), 3.45-3.39 (m, 1H), 3.27-3.05 (m, 4H), 2.56 (s, 3H);

MH+ 464.

Example 46

(2S,3R,4R,5S,6R)-2-(3-((6-(1,3,4-Thiadiazol-2-yl)pyridazin-3-yl)methyl)-4-chlorophenyl)-6-(hydroxymethyl)-tetrahydro-2H-pyran-3,4,5-triol

Step 1: 6-(2-Chloro-5-((2S,3S,4R,5R,6R)-3,4,5-tris(benzyloxy)-6-(benzyloxymethyl)-tetrahydro-2H-pyran-2-yl)benzyl)pyridazine-3-carboxylic acid To a solution of intermediate 7 (1.0 g, 1.4 mmol) in ethanol (9 mL) was added sodium hydroxide solution (3.0 M, 4.5 mL, 14 mmol). The reaction mixture was refluxed overnight. After cooling to room temperature, hydrochloric acid (1.0 M) was added to neutralize the reaction mixture. The mixture was diluted with water and extracted with ethyl acetate. The organic layer was washed with water and brine prior to drying over magnesium sulfate. Filtration and concentration under reduced pressure yielded the title compound as a white solid, which was used without further purification.
MH+ 771.

Step 2: 6-(2-Chloro-5-((2S,3S,4R,5R,6R)-3,4,5-tris(benzyloxy)-6-(benzyloxymethyl)-tetrahydro-2H-pyran-2-yl)benzyl)-N'-formylpyridazine-3-carbohydrazide To a mixture of 6-(2-chloro-5-((2S,3S,4R,5R,6R)-3,4,5-tris(benzyloxy)-6-(benzyloxymethyl)-tetrahydro-2H-pyran-2-yl)benzyl)pyridazine-3-carboxylic acid (1.4 mmol) from Step 1, formic hydrazide (107 mg, 1.8 mmol), EDCI (394 mg, 2.1 mmol), and 1-hydroxybenzotriazole hydrate (426 mg, 2.7 mmol) in N,N-dimethylformamide (15 mL) was added 4-methylmorpholine (0.45 mL, 4.1 mmol). The resulting mixture was stirred at ambient temperature overnight. After dilution with ethyl acetate, the organic layer was subsequently washed with water, hydrochloric acid (1.0 M), saturated sodium bicarbonate and brine prior to drying over magnesium sulfate. Filtration and removal of the volatiles under reduced pressure yielded titled compound as a glassy off-white amorphous solid, which was used without further purification.
MH+ 813.

Step 3: 2-(6-(2-Chloro-5-((2S,3S,4R,5R,6R)-3,4,5-tris(benzyloxy)-6-(benzyloxymethyl)-tetrahydro-2H-pyran-2-yl)benzyl)pyridazin-3-yl)-1,3,4-thiadiazole To a solution of 6-(2-chloro-5-((2S,3S,4R,5R,6R)-3,4,5-tris(benzyloxy)-6-(benzyloxymethyl)-tetrahydro-2H-pyran-2-yl)benzyl)-N'-formylpyridazine-3-carbohydrazide (1.4 mmol) form Step 2 in tetrahydrofuran (30 mL) was added Lawesson reagent (1.6 g, 4.1 mmol). The reaction mixture was refluxed overnight. After cooling to room temperature, the reaction mixture was diluted with ethyl acetate and washed with saturated sodium bicarbonate. The organic layer was dried over magnesium sulfate, filtered through a plug of silica gel and concentrated in vacuo. The resulting crude residue was used without further purification.
MH+ 811.

Step 4: (2S,3R,4R,5S,6R)-2-(3-((6-(1,3,4-Thiadiazol-2-yl)pyridazin-3-yl)methyl)-4-chlorophenyl)-6-(hydroxymethyl)-tetrahydro-2H-pyran-3,4,5-triol To a solution of 2-(6-(2-chloro-5-((2S,3S,4R,5R,6R)-3,4,5-tris(benzyloxy)-6-(benzyloxymethyl)-tetrahydro-2H-pyran-2-yl)benzyl)pyridazin-3-yl)-1,3,4-thiadiazole (1.4 mmol) from Step 1 at −40° C. in acetic anhydride (10 mL) was slowly added a solution of trimethylsilyl trifluoromethanesulfonate (2.0 mL, 11 mmol) in acetic anhydride (5 mL). The resulting mixture was stirred with gradual warming to ambient temperature over 15 h, cooled to 0° C., and quenched with saturated sodium bicarbonate. After dilution with ethyl acetate, the organic layer was washed with sodium bicarbonate and brine prior to drying over magnesium sulfate. Filtration and removal of volatiles under reduced pressure yielded peracetylated compound as a brown amorphous solid. Deacetylation was achieved by addition of sodium methoxide (25 wt % in methanol, 1 mL) to a solution of this residue in methanol (10 mL). The reaction mixture was stirred at ambient temperature for 2 h. Amberlite® IR120 hydrogen form was then added to neutralize the reaction mixture. The resin was filtered off and the filtrate was concentrated in vacuo. Purification by reverse phase preparative HPLC (Gilson®, SunFire™ Prep, 5 to 50% acetonitrile in water gradient) provided the title compound (43 mg, 0.10 mmol, 7% from Intermediate 7) as a white solid.
$^1$H NMR (400 MHz, DMSO-$d_6$) δ 9.74 (s, 1H), 8.42 (d, J=8.8 Hz, 1H), 7.70 (d, J=8.8 Hz, 1H), 7.46 (d, J=2.0 Hz, 1H), 7.39 (d, J=8.0 Hz, 1H), 7.28 (dd, J=8.0, 2.0 Hz, 1H), 5.00-4.95 (m, 2H), 4.87 (br, 1H), 4.52 (d, J=15.6 Hz, 1H), 4.47 (d, J=15.6 Hz, 1H), 4.45 (br, 1H), 4.00 (d, J=9.6 Hz, 1H), 3.70-3.66 (m, 1H), 4.46-4.40 (m, 1H), 3.26-3.07 (m, 4H);
MH+ 451.

Example 47

(2S,3R,4R,5S,6R)-2-(4-Chloro-3-((6-(5-methyloxazol-2-yl)pyridazin-3-yl)methyl)phenyl)-6-(hydroxymethyl)-tetrahydro-2H-pyran-3,4,5-triol

Step 1: 6-(2-Chloro-5-((2S,3S,4R,5R,6R)-3,4,5-tris(benzyloxy)-6-(benzyloxymethyl)-tetrahydro-2H-pyran-2-yl)benzyl)-N-(2-oxopropyl)pyridazine-3-carboxamide To a mixture of 6-(2-chloro-5-((2S,3S,4R,5R,6R)-3,4,5-tris(benzyloxy)-6-(benzyloxymethyl)-tetrahydro-2H-pyran-2-yl)benzyl)pyridazine-3-carboxylic acid (1.2 mmol), 1-aminopropan-2-one trifluoroacetic acid salt (346 mg, 1.9 mmol), EDCI (472 mg, 2.5 mmol), and 1-hydroxybenzotriazole hydrate (478 mg, 3.1 mmol) in N,N-dimethylformamide (10 mL) was added 4-methylmorpholine (0.68 mL, 6.2 mmol). The resulting mixture was stirred at ambient temperature overnight. After dilution with ethyl acetate, the organic layer was subsequently washed with water, hydrochloric acid (1.0 M), saturated sodium bicarbonate and brine prior to drying over magnesium sulfate. Filtration through a plug of silica gel and removal of the volatiles under reduced pressure yielded titled compound as a brown amorphous solid, which was used without further purification.
MH+ 826.

Step 2: 2-(6-(2-Chloro-5-((2S,3S,4R,5R,6R)-3,4,5-tris(benzyloxy)-6-(benzyloxymethyl)-tetrahydro-2H-pyran-2-yl)benzyl)pyridazin-3-yl)-5-methyloxazole To a solution of 6-(2-chloro-5-((2S,3S,4R,5R,6R)-3,4,5-tris(benzyloxy)-6-(benzyloxymethyl)-tetrahydro-2H-pyran-2-yl)benzyl)-N-(2-oxopropyl)pyridazine-3-carboxamide (1.2 mmol) form Step 1 in tetrahydrofuran (30 mL) was added Burgess reagent (343 mg, 1.4 mmol). The reaction mixture was refluxed overnight. After cooling to room temperature, the reaction mixture was diluted with ethyl acetate and washed with saturated sodium bicarbonate. The organic layer was dried over magnesium sulfate, filtered through a plug of silica gel and concentrated in vacuo. The resulting crude residue was used without further purification.

MH+ 808.

Step 3: (2S,3R,4R,5S,6R)-2-(4-Chloro-3-((6-(5-methyloxazol-2-yl)pyridazin-3-yl)methyl)phenyl)-6-(hydroxymethyl)-tetrahydro-2H-pyran-3,4,5-triol To a solution of 2-(6-(2-chloro-5-((2S,3S,4R,5R,6R)-3,4,5-tris(benzyloxy)-6-(benzyloxymethyl)-tetrahydro-2H-pyran-2-yl)benzyl)pyridazin-3-yl)-5-methyloxazole (1.2 mmol) from Step 2 in acetonitrile (5 mL) was added Iodotrimethylsilane (3 mL). The resulting reaction mixture was heated to 50° C. overnight. After cooling to 0° C., the reaction quenched with methanol and concentrated in vacuo. Purification by reverse phase preparative HPLC (Gilson®, SunFire™ Prep, 5 to 50% acetonitrile in water gradient) provided the title compound (62 mg, 0.14 mmol, 11%) as a yellow solid.

$^1$H NMR (400 MHz, DMSO-d$_6$) δ 8.13 (d, J=8.8 Hz, 1H), 7.56 (d, J=8.8 Hz, 1H), 7.43 (d, J=2.0 Hz, 1H), 7.39 (d, J=8.4 Hz, 1H), 7.28 (dd, J=8.0, 2.0 Hz, 1H), 7.13 (s, 1H), 4.49 (d, J=15.6 Hz, 1H), 4.44 (d, J=15.6 Hz, 1H), 3.99 (d, J=9.2 Hz, 1H), 3.66 (d, J=11.6 Hz, 1H), 3.42 (d, J=11.6 Hz, 1H), 3.25-3.06 (m, 4H), 2.41 (s, 3H);

MH+ 448.

Example 48

(2S,3R,4R,5S,6R)-2-(4-Chloro-3-((6-chloropyridazin-3-yl)methyl)phenyl)-6-(hydroxymethyl)-tetrahydro-2H-pyran-3,4,5-triol (compound 90)

To a solution of Intermediate 6 (compound 24, 152 mg, 0.4 mmol) at −30° C. in acetic anhydride (10 mL) was slowly added a solution of trimethylsilyl trifluoromethanesulfonate (0.73 mL, 4.0 mmol) in acetic anhydride (5 mL). The resulting mixture was stirred with gradual warming to ambient temperature over 15 h, cooled to 0° C., and quenched with saturated sodium bicarbonate. After dilution with ethyl acetate, the organic layer was washed with sodium bicarbonate and brine prior to drying over magnesium sulfate. Filtration and removal of volatiles under reduced pressure yielded peracetylated compound (compound 89) as a brown amorphous solid. Deacetylation was achieved by addition of sodium methoxide (25 wt % in methanol, 1 mL) to a solution of this residue in methanol (10 mL). The reaction mixture was stirred at ambient temperature for 2 h. Amberlite® IR120 hydrogen form was then added to neutralize the reaction mixture. The resin was filtered off and the filtrate was concentrated in vacuo. Purification by reverse phase preparative HPLC (Gilson®, SunFire™ Prep, 5 to 50% acetonitrile in water gradient) provided the title compound (41 mg, 0.10 mmol, 25%) as a white solid.

$^1$H NMR (400 MHz, DMSO-d$_6$) δ 7.80 (d, J=8.8 Hz, 1H), 7.54 (d, J=8.8 Hz, 1H), 7.40 (d, J=2.0 Hz, 1H), 7.37 (d, J=8.4, 1H), 7.27 (dd, J=8.4, 2.0 Hz, 1H), 4.94 (br, 2H), 4.82 (br, 1H), 4.41 (d, J=15.6 Hz, 1H), 4.39 (br, 1H), 4.37 (d, J=15.6 Hz, 1H), 3.99 (d, J=9.2 Hz, 1H), 3.68-3.65 (m, 1H), 3.43-3.40 (m, 1H), 3.26-3.06 (m, 4H);

MH+ 401.

Example 49

Methyl 6-(2-chloro-5-((2S,3R,4R,5S,6R)-3,4,5-trihydroxy-6-(hydroxymethyl)-tetrahydro-2H-pyran-2-yl)benzyl)pyridazine-3-carboxylate The titled compound (52 mg, 0.12 mmol, 19%) was obtained in the same manner as in Example 48 (Step 2) from Intermediate 7.

$^1$H NMR (400 MHz, DMSO-d$_6$) δ 8.11 (d, J=8.8 Hz, 1H), 7.60 (d, J=8.8 Hz, 1H), 7.43 (d, J=2.0 Hz, 1H), 7.38 (d, J=8.4 Hz, 1H), 7.27 (dd, J=8.4, 2.0 Hz, 1H), 4.97-4.94 (m, 2H), 4.85 (d, J=5.6 Hz, 1H), 4.52 (d, J=15.6 Hz, 1H), 4.47 (d, J=15.6 Hz, 1H), 4.44 (t, J=5.6 Hz, 1H), 3.99 (d, J=9.6 Hz, 1H), 3.91 (s, 3H), 3.68-3.65 (m, 1H), 3.46-3.40 (m, 1H), 3.26-3.06 (m, 4H);

MH+ 425.

Example 50

(2S,3R,4R,5S,6R)-2-(4-Chloro-3-((6-(phenylethynyl)pyridazin-3-yl)methyl)phenyl)-6-(hydroxymethyl)-tetrahydro-2H-pyran-3,4,5-triol Step 1: 3-(2-Chloro-5-((2S,3S,4R,5R,6R)-3,4,5-tris(benzyloxy)-6-(benzyloxymethyl)-tetrahydro-2H-pyran-2-yl)benzyl)-6-(phenylethynyl)pyridazine (compound 32)

To a mixture of Intermediate 6 (compound 24, 381 mg, 0.5 mmol), dichlorobis(triphenyl-phosphine)palladium (II) (35 mg, 0.05 mmol) and copper(I) iodide (10 mg, 0.05 mmol) in tetrahydrofuran (10 mL) was added N,N-diisopropylethylamine (0.35 mL, 2.5 mmol) and phenylacethylene (0.07 mL, 0.6 mmol). The resulting mixture was stirred at ambient temperature overnight. After dilution with ethyl acetate, the organic layer was washed with water and brine prior to drying over magnesium sulfate. Filtration through a plug of silica gel and removal of the volatiles under reduced pressure yielded titled compound as a brown solid, which was used without further purification.

MH+ 827.

Step 2: 2S,3R,4R,5S,6R)-2-(4-Chloro-3-((6-(phenylethynyl)pyridazin-3-yl)methyl)phenyl)-6-(hydroxymethyl)-tetrahydro-2H-pyran-3,4,5-triol (compound 32)

To a solution of 3-(2-chloro-5-((2S,3S,4R,5R,6R)-3,4,5-tris(benzyloxy)-6-(benzyloxymethyl)-tetrahydro-2H-pyran-2-yl)benzyl)-6-(phenylethynyl)pyridazine (0.5 mmol) from step 1 at −30° C. in acetic anhydride (10 mL) was slowly added a solution of trimethylsilyl trifluoromethanesulfonate (0.73 mL, 4.0 mmol) in acetic anhydride (5 mL). The resulting mixture was stirred with gradual warming to ambient temperature over 15 h, cooled to 0° C., and quenched with saturated sodium bicarbonate. After dilution with ethyl acetate, the organic layer was washed with sodium bicarbonate and brine prior to drying over magnesium sulfate. Filtration and removal of volatiles under reduced pressure yielded peracetylated compound as a brown amorphous solid. Deacetylation was achieved by addition of sodium methoxide (25 wt % in methanol, 1 mL) to a solution of this residue in methanol (10 mL). The reaction mixture was stirred at ambient temperature for 2 h. Amberlite® IR120 hydrogen form was then added to neutralize the reaction mixture. The resin was filtered off and the filtrate was concentrated in vacuo. Purification by reverse phase preparative HPLC (Gilson®, SunFire™ Prep, 5 to 50% acetonitrile in water gradient) provided the title compound (41 mg, 0.10 mmol, 25%) as a white solid.

$^1$H NMR (400 MHz, DMSO-d$_6$) δ 7.83 (d, J=8.8 Hz, 1H). 7.64-7.62 (m, 2H), 7.49-7.38 (m, 6H), 7.27 (dd, J=8.4, 2 Hz, 1H), 4.95 (br, 2H), 4.84 (br, 1H), 4.46 (d, J=15.6 Hz, 1H), 4.43 (br, 1H), 4.41 (d, J=15.6 Hz, 1H), 4.00 (d, J=9.2 Hz, 1H), 3.68-3.65 (m, 1H), 3.46-3.40 (m, 1H), 3.26-3.07 (m, 4H);

MH+ 467.

Example 51

(2S,3R,4R,5S,6R)-2-(4-Chloro-3-((6-ethoxypyridazin-3-yl)methyl)phenyl)-6-(hydroxymethyl)-tetrahydro-2H-pyran-3,4,5-triol Step 1: 2-(2-Chloro-5-((2S,3S,4R,5R,6R)-3,4,5-tris(benzyloxy)-6-(benzyloxymethyl)-tetrahydro-2H-pyran-2-yl)phenyl)(6-chloropyridazin-3-yl)methanone (compound 33)

Sodium hydride (593 mg; 14.8 mmol; 60% in mineral oil) was added to stirred solution of Intermediate 1 (compound 6, 5.00 g; 7.42 mmol) in 20 mL of N,N-dimethylacetamide (DME) at 0° C. under nitrogen gas. The reaction mixture was stirred for 30 min, and 3,6-dichloropyridazine (compound 22, 1.25 g; 8.16 mmol) was added in one portion. The ice bath was removed, and the reaction mixture was stirred at room temperature for 3.5 h. Cooled to 0° C., H$_2$O$_2$ (2.50 mL) was added to reaction mixture and left stirring additional hour warm-up to room temperature. The reaction solution was washed with 1N HCl solution, 1N NaOH solution and brine. The organic layer was collected, and evaporated under a vacuum. The crude mixture was further purified by flash column chromatography (Biotage SP1™) to obtain 3.10 g (4.00 mmol; 54%) of the title compound as orange oil.

MH+ 775

Step 2: (2-Chloro-5-((2S,3S,4R,5R,6R)-3,4,5-tris(benzyloxy)-6-(benzyloxymethyl)-tetrahydro-2H-pyran-2-yl)phenyl)(6-ethoxypyridazin-3-yl)methanone To a solution of (2-chloro-5-((2S,3S,4R,5R,6R)-3,4,5-tris(benzyloxy)-6-(benzyloxymethyl)-tetrahydro-2H-pyran-2-yl)phenyl)(6-ethoxypyridazin-3-yl)methanone (1.48 g, 2.00 mmol) in THF (20 mL) was added NaOEt (21 wt % in ethanol solution, 0.8 mL; 2.00 mmol) at 0° C., and the mixture was stirred for 2 h at ambient temperature. The reaction was quenched with 1N HCl, extracted with ethyl acetate (3×100 mL). The organic layer was combined and washed with brine (2×100 mL). After drying over MgSO$_4$, the solvents were removed in vacuo and subjected to silica gel column chromatography (eluent: hexane/EtOAc mixture (80/20; v/v)) to obtain 1.37 g (1.83 mmol; 94%) of the title compound as pale yellow oil.

MH+ 785

Step 3: (2-Chloro-5-((2S,3S,4R,5R,6R)-3,4,5-tris(benzyloxy)-6-(benzyloxymethyl)-tetrahydro-2H-pyran-2-yl)phenyl)(6-ethoxypyridazin-3-yl)methanol To a solution of (2-chloro-5-((2S,3S,4R,5R,6R)-3,4,5-tris(benzyloxy)-6-(benzyloxymethyl)-tetrahydro-2H-pyran-2-yl)phenyl)(6-ethoxypyridazin-3-yl)methanone (970 mg; 1.24 mmol) in MeOH (20 mL) was added NaBH$_4$ (93.5 mg; 2.47 mmol) at 0° C., then stirred for 3 h at room temperature. The reaction was quenched with 2N HCl, extracted with ethyl acetate (3×50 mL) and washed with brine. The organic layer was dried over MgSO$_4$ and the solvents were evaporated under a vacuum. The crude mixture was further purified by flash column chromatography (Biotage SP1™) (eluent: hexane/EtOAc mixture (40/60; v/v)) to obtain 907 mg (1.15 mmol; 93%) of the title compound as colorless oil.

MH+ 777

Step 4: 3-(Chloro(2-chloro-5-((3S,4R,5R,6R)-3,4,5-tris(benzyloxy)-6-(benzyloxymethyl)-tetrahydro-2H-pyran-2-yl)phenyl)methyl)-6-ethoxypyridazine To a solution of (2-chloro-5-((3S,4R,5R,6R)-3,4,5-tris(benzyloxy)-6-(benzyloxymethyl)-tetrahydro-2H-pyran-2-yl)phenyl)(6-ethoxypyridazin-3-yl)methanol (598 mg; 0.76 mmol) in toluene (10 mL) was slowly added thionyl chloride (0.18 mL; 1.52 mmol) at 0° C., then stirred for 2 h at room temperature. Toluene was removed on evaporator and residue was extracted with H$_2$O/DCM (2×50 mL). The combined organic layer was dried over MgSO$_4$ and the solvents were evaporated under a vacuum. The crude mixture 589 mg (0.73 mmol; 96%) was used without further purification.

MH+ 805

Step 5: 3-(2-Chloro-5-((3S,4R,5R,6R)-3,4,5-tris(benzyloxy)-6-(benzyloxymethyl)-tetrahydro-2H-pyran-2-yl)benzyl)-6-ethoxypyridazine To a solution of 3-(chloro(2-chloro-5-((3S,4R,5R,6R)-3,4,5-tris(benzyloxy)-6-(benzyloxymethyl)-tetrahydro-2H-pyran-2-yl)phenyl)methyl)-6-ethoxypyridazine (589 mg; 0.73 mmol) in anhydrous toluene (10 mL) was added catalytic amounts of AIBN and tributyltin hydride (0.3 mL; 1.10 mmol) at room temperature under nitrogen gas. The reaction solution was then heated at 80° C. until reaction was completed. The solution was coded to room temperature and toluene was removed on evaporator. The crude α/β mixture was purified by silica gel column chromatography with KF pad (eluent: hexane/EtOAc mixture (60/40; v/v)). The purified α/β mixture was separated by using Gilson prep HPLC system and then obtained α configured product (123 mg; 0.16 mmol) and β configured product (105 mg; 0.14 mmol) as colorless oil.

α configured product:

$^1$H NMR (400 MHz, CDCl$_3$) δ 7.59 (m, 2H), 7.34-7.24 (m, 17H), 7.20-7.18 (m, 2H), 7.10-7.07 (m, 3H), 6.71 (d, J=9.2 Hz, 1H), 5.11 (d, J=4.8 Hz, 1H), 4.85 (d, J=11.2 Hz, 1H), 4.77-4.55 (m, 6H), 4.51-4.38 (m, 4H), 4.33 (d, J=3.6 Hz, 2H), 3.97-3.88 (m, 2H), 3.72-3.56 (m, 3H), 3.47-3.44 (m, 1H), 1.38 (t, J=7.2 Hz, 3H);

MH+ 771.

β configured product:

$^1$H NMR (400 MHz, CDCl$_3$) δ 7.37 (m, 2H), 7.34-7.27 (m, 15H), 7.22-7.16 (m, 5H), 7.05 (d, J=9.2 Hz, 1H), 6.90-6.88 (m, 1H), 6.71 (dd, J=8.8, 4.0 Hz, 1H), 4.90-4.89 (m, 2H), 4.86-4.84 (d, J=10.4 Hz, 1H), 4.62-4.59 (m, 2H), 4.55-4.49 (m, 3H), 4.44-4.29 (m, 4H), 4.17 (d, J=9.6 Hz, 1H), 3.84 (d, J=10.8 Hz, 1H), 3.77-3.71 (m, 3H), 3.59-3.56 (m, 1H), 3.46-3.41 (m, 1H), 1.42 (t, J=7.2 Hz, 3H);

MH+ 771

Step 6: (2S,3R,4R,5S,6S)-2-(acetoxymethyl)-6-(4-chloro-3-((6-ethoxypyridazin-3-yl)methyl)phenyl)-tetrahydro-2H-pyran-3,4,5-triyl triacetate To a solution of 3-(2-chloro-5-((3S,4R,5R,6R)-3,4,5-tris(benzyloxy)-6-(benzyloxymethyl)-tetrahydro-2H-pyran-2-yl)benzyl)-6-ethoxypyridazine (105 mg, 0.14 mmol) in acetonitrile (10 mL) at 0° C. were added iodotrimethyl silane (0.5 mL; 6.72 mmol) dropwise. The reaction was stirred overnight at room temperature and concentrated to dryness to give the crude tetraol, which was used without further purification. To a solution of tetraol in DCM (5 mL) was added TEA (0.19 mL; 1.34 mmol), DMAP (catalytic amount), acetic anhydride (0.13 mL; 1.34 mmol) at 0° C. After stirring overnight at room temperature, the reaction mixture was quenched with water, extracted with ethyl acetate and washed with brine. The organic layers were dried over $MgSO_4$, filtrated and evaporated to dryness to give a residue that was purified by flash column chromatography (Biotage SP1™) (eluent: hexane/EtOAc mixture (60/40; v/v)) to obtain 74 mg (0.13 mmol; 94%) of the title compound as colorless oil.
MH+ 579.

Step 7: (2S,3R,4R,5S,6R)-2-(4-chloro-3-((6-ethoxy-pyridazin-3-yl)methyl)phenyl)-6-(hydroxymethyl)-tetrahydro-2H-pyran-3,4,5-triol To a solution of (2S,3R,4R,5S,6S)-2-(acetoxymethyl)-6-(4-chloro-3-((6-ethoxypyridazin-3-yl)methyl)phenyl)-tetrahydro-2H-pyran-3,4,5-triyl triacetate (74 mg, 0.13 mmol) in MeOH (3 mL) was added NaOMe (0.2 mL), and the mixture was stirred for 1 h at room temperature. The mixture was neutralized with Amberlite IR-120 (H) resin, and filtered, the resin was washed with MeOH, and the combined filtrate and washings were concentrated as pale yellow solid.
$^1$H NMR (400 MHz, $CD_3OD$) δ 7.42-7.39 (m, 2H), 7.35-7.30 (m, 3H), 7.22-7.19 (m, 2H), 4.46 (q, J=7.2 Hz, 2H), 4.33 (s, 2H), 4.10 (d, J=9.2 Hz, 1H), 3.86 (dd, J=12.0, 1.6 Hz, 1H), 3.68 (dd, J=12.0, 5.2 Hz, 1H), 3.47-3.33 (m, 3H), 1.40 (t, J=6.8 Hz, 3H);
MH+ 411.

Example 52

(2S,3R,4R,5S,6R)-2-(4-Chloro-3-((6-propoxypyridazin-3-yl)methyl)phenyl)-6-(hydroxymethyl)-tetrahydro-2H-pyran-3,4,5-triol $^1$H NMR (400 MHz, $CD_3OD$) δ 7.50 (d, J=9.2 Hz, 1H), 7.42 (d, J=1.6 Hz, 1H), 7.40-7.35 (m, 2H), 7.32 (dd, J=8.4, 2.0 Hz, 1H), 7.04 (d, J=9.2 Hz, 1H), 4.36 (t, J=6.8 Hz, 2H), 4.33 (s, 2H), 4.10 (d, J=9.6 Hz, 1H), 3.85 (dd, J=12.4, 2.0 Hz, 1H), 3.68 (dd, J=12.0, 5.2 Hz, 1H), 3.45-3.37 (m, 3H), 1.81 (m, 2H), 1.02 (t, J=7.2 Hz, 3H);
MH+ 425.

Example 53

(2S,3R,4R,5S,6R)-2-(3-((6-Butoxypyridazin-3-yl)methyl)-4-chlorophenyl)-6-(hydroxymethyl)-tetrahydro-2H-pyran-3,4,5-triol $^1$H NMR (400 MHz, $CD_3OD$) δ 7.42 (d, J=1.6 Hz, 1H), 7.41-7.35 (m, 2H), 7.32 (dd, J=8.4, 2.0 Hz, 1H), 7.03 (d, J=9.2 Hz, 1H), 4.41 (t, J=6.8 Hz, 2H), 4.33 (s, 2H), 4.10 (d, J=9.6 Hz, 1H), 3.85 (dd, J=12.4, 2.0 Hz, 1H), 3.68 (dd, J=12.0, 5.2 Hz, 1H), 3.45-3.36 (m, 3H), 1.81-1.74 (m, 2H), 1.51-1.45 (m, 2H), 0.97 (t, J=7.2 Hz, 3H);
MH+ 439.

Example 54

(2S,3R,4R,5S,6R)-2-(4-Chloro-3-((6-(pentyloxy)pyridazin-3-yl)methyl)phenyl)-6-(hydroxymethyl)-tetrahydro-2H-pyran-3,4,5-triol $^1$H NMR (400 MHz, $CD_3OD$) δ 7.42 (d, J=2.0 Hz, 1H), 7.41-7.35 (m, 2H), 7.32 (dd, J=8.0, 1.6 Hz, 1H), 7.04 (d, J=9.2 Hz, 1H), 4.40 (t, J=6.8 Hz, 2H), 4.33 (s, 2H), 4.10 (d, J=9.6 Hz, 1H), 3.85 (dd, J=12.4, 2.4 Hz, 1H), 3.68 (dd, J=12.0, 5.2 Hz, 1H), 3.47-3.37 (m, 3H), 1.83-1.76 (m, 2H), 1.47-1.35 (m, 4H), 0.92 (t, J=6.8 Hz, 3H);
MH+ 453.

Example 55

(2S,3R,4R,5S,6R)-2-(4-Chloro-3-((6-(hexyloxy)pyridazin-3-yl)methyl)phenyl)-6-(hydroxymethyl)-tetrahydro-2H-pyran-3,4,5-triol (37)

$^1$H NMR (400 MHz, $CD_3OD$) δ 7.70 (d, J=9.2 Hz, 1H), 7.50 (m, 1H), 7.44 (d, J=9.2 Hz, 1H), 7.39 (m, 2H), 4.46-4.42 (m, 3H), 4.13 (d, J=9.6 Hz, 1H), 3.86 (dd, J=12.0, 2.0 Hz, 1H), 3.68 (dd, J=11.6, 5.2 Hz, 1H), 3.47-3.37 (m, 3H), 1.86-1.79 (m, 2H), 1.49-1.43 (m, 2H), 1.39-1.28 (m, 4H), 0.90-0.88 (m, 3H);
MH+ 467.

Example 56

(2S,3R,4R,5S,6R)-2-(4-Chloro-3-((6-(octyloxy)pyridazin-3-yl)methyl)phenyl)-6-(hydroxymethyl)-tetrahydro-2H-pyran-3,4,5-triol $^1$H NMR (400 MHz, $CD_3OD$) δ 7.42 (d, J=1.6 Hz, 1H), 7.40-7.35 (m, 2H), 7.32 (dd, J=8.4, 2.0 Hz, 1H), 7.03 (d, J=9.2 Hz, 1H), 4.40 (t, J=6.8 Hz, 2H), 4.33 (s, 2H), 3.85 (dd, J=12.4, 2.0 Hz, 1H), 3.68 (dd, J=11.6, 5.2 Hz, 1H), 3.45-3.37 (m, 3H), 1.82-1.75 (m, 2H), 1.48-1.41 (m, 2H), 1.34-1.29 (m, 8H), 0.90-0.86 (m, 3H);
MH+ 495.

Example 57

(2S,3R,4R,5S,6R)-2-(4-Chloro-3-((6-isopropoxypyridazin-3-yl)methyl)phenyl)-6-(hydroxymethyl)-tetrahydro-2H-pyran-3,4,5-triol $^1$H NMR (400 MHz, $CD_3OD$) δ 7.42 (d, J=1.6 Hz, 1H), 7.39-7.35 (m, 2H), 7.31 (dd, J=8.4, 2.0 Hz, 1H), 6.97 (d, J=9.2 Hz, 1H), 5.41-5.39 (m, 1H), 4.33 (s, 2H), 4.10 (d, J=9.2 Hz, 1H), 3.85 (dd, J=12.0, 2.0 Hz, 1H), 3.68 (dd, J=11.6, 5.2 Hz, 1H), 3.45-3.34 (m, 3H), 1.36 (d, J=6.8 Hz, 6H);
MH+ 439.

Example 58

(2S,3R,4R,5S,6R)-2-(4-Chloro-3-((6-isobutoxypyridazin-3-yl)methyl)phenyl)-6-(hydroxymethyl)-tetrahydro-2H-pyran-3,4,5-triol $^1$H NMR (400 MHz, $CD_3OD$) δ 7.42 (d, J=1.6 Hz, 1H), 7.41-7.35 (m, 2H), 7.32 (dd, J=8.4, 2.0 Hz, 1H), 7.06 (d, J=8.8

Hz, 1H), 4.34 (s, 2H), 4.18 (d, J=6.4 Hz, 2H), 4.10 (d, 9.6 Hz, 1H), 3.85 (dd, J=12.4, 2.0 Hz, 1H), 3.68 (dd, J=12.0, 5.2 Hz, 1H), 3.45-3.37 (m, 3H), 2.12-2.08 (m, 1H), 1.01 (d, J=6.8 Hz, 6H);
MH+ 439.

Example 59

(2S,3R,4R,5S,6R)-2-(4-Chloro-3-((6-(cyclohexyloxy)pyridazin-3-yl)methyl)phenyl)-6-(hydroxymethyl)-tetrahydro-2H-pyran-3,4,5-triol $^1$H NMR (400 MHz, CD$_3$OD) δ 7.50 (d, J=9.2 Hz, 1H), 7.45 (d, J=1.6 Hz, 1H), 7.39-7.33 (m, 2H), 7.14 (d, J=9.2 Hz, 1H), 5.17-5.11 (m, 1H), 4.36 (s, 2H), 4.11 (d, J=9.6 Hz, 1H), 3.86 (d, J=12.0 Hz, 1H), 3.68 (dd, J=11.6, 5.2 Hz, 1H), 3.47-3.41 (m, 1H), 3.40-3.37 (m, 2H), 2.06 (m, 2H), 1.80-1.77 (m, 2H), 1.61-1.52 (m, 3H), 1.48-1.29 (m, 3H); MH+ 465.

Example 60

(2S,3R,4R,5S,6R)-2-(4-Chloro-3-((6-(tetrahydro-2H-pyran-4-yloxy)pyridazin-3-yl)methyl)phenyl)-6-(hydroxymethyl)-tetrahydro-2H-pyran-3,4,5-triol $^1$H NMR (400 MHz, CD$_3$OD) δ 7.43 (d, J=1.6 Hz, 1H), 7.41-7.35 (m, 2H), 7.32 (dd, J=8.4, 2.0 Hz, 1H), 7.05 (d, J=9.2 Hz, 1H), 5.38-5.32 (m, 1H), 4.33 (s, 2H), 4.10 (d, J=9.6 Hz, 1H), 3.96-3.91 (m, 2H), 3.85 (dd, J=12.0, 2.0 Hz, 1H), 3.68 (dd, J=12.0, 5.2 Hz, 1H), 3.62-3.56 (m, 2H), 3.47-3.37 (m, 3H), 3.33 (s, 2H), 2.14-2.08 (m, 2H), 1.82-1.73 (m, 2H); MH+ 467.

Example 61

(2S,3R,4R,5S,6R)-2-(4-chloro-3-((6-phenylpyridazin-3-yl)methyl)phenyl)-6-(hydroxymethyl)-tetrahydro-2H-pyran-3,4,5-triol Step 1: 3-(2-Chloro-5-((2S,3S,4R,5R,6R)-3,4,5-tris(benzyloxy)-6-(benzyloxymethyl)-tetrahydro-2H-pyran-2-yl)benzyl)-6-phenylpyridazine (compound 30)

To a solution of Intermediate 6 (compound 24, 300 mg; 0.39 mmol) in 1.5 mL of 1,2-dimethoxyethane/H$_2$O/ethanol (7:3:2) in microwave sealed tube was phenyl boronic acid (compound 28, 52.8 mg; 0.43 mmol), dichloro bis(triphenylphosphine)palladium (II) (27.6 mg; 0.04 mmol), sodium carbonate (50 mg; 0.47 mmol). The reaction mixture was exposed to microwave irradiation (150° C.) for 15 min. The reaction tube was allowed to reach room temperature before the reaction mixture was diluted in ethyl acetate, and then extracted, washed with brine. The organic layers were dried over MgSO$_4$, filtrated and evaporated to dryness to give a residue that was purified by flash column chromatography (Biotage SP1™) (eluent: hexane/EtOAc mixture (75/25; v/v)) to obtain 231 mg (0.28 mmol; 73%) of the title compound as colorless oil.
$^1$H NMR (400 MHz, CDCl$_3$) δ 8.03 (dd, J=8.0, 1.6 Hz, 2H), 7.57 (d, J=8.4 Hz, 2H), 7.51-7.47 (m, 3H), 7.44-7.39 (m, 2H), 7.34-7.27 (m, 15H), 7.19-7.16 (m, 5H), 4.89 (m, 2H), 4.85 (d, J=10.8 Hz, 1H), 4.66-4.41 (m, 6H), 4.20 (d, J=9.6 Hz, 1H), 3.87 (d, J=10.8 Hz, 1H), 3.80-3.71 (m, 4H), 3.62-3.56 (m, 1H), 3.46-3.42 (m, 1H);
MH+ 803

Step 2: (2S,3R,4R,5S,6R)-2-(4-Chloro-3-((6-phenylpyridazin-3-yl)methyl)phenyl)-6-(hydroxymethyl)-tetrahydro-2H-pyran-3,4,5-triol To a solution of 3-(2-chloro-5-((3S,4R,5R,6R)-3,4,5-tris(benzyloxy)-6-(benzyloxymethyl)-tetrahydro-2H-pyran-2-yl)benzyl)-6-ethoxypyridazine (221 mg, 0.27 mmol) in acetonitrile (5 mL) at 0° C. were added iodotrimethyl silane (2 mL) dropwise. The reaction was stirred overnight at room temperature and concentrated to dryness to give the crude tetraol, which was purified as white solid (55 mg; 45%) by using Gilson prep HPLC system.
$^1$H NMR (400 MHz, CD$_3$OD) δ 8.05-8.02 (m, 3H), 7.56 (d, J=8.8 Hz, 1H), 7.54-7.47 (m, 4H), 7.40-7.34 (m, 2H), 4.46 (q, J=7.2 Hz, 2H), 4.50 (s, 2H), 4.12 (d, J=9.2 Hz, 1H), 3.86 (dd, J=12.0, 1.6 Hz, 1H), 3.68 (dd, J=12.4, 5.6 Hz, 1H), 3.47-3.31 (m, 3H);
MH+ 443.

Example 62

(2S,3R,4R,5S,6R)-2-(4-chloro-3-((6-(furan-2-yl)pyridazin-3-yl)methyl)phenyl)-6-(hydroxymethyl)-tetrahydro-2H-pyran-3,4,5-triol $^1$H NMR (400 MHz, DMSO-d$_6$) δ 7.92-7.88 (m, 2H), 7.47 (d, J=9.2 Hz, 1H), 7.41 (d, J=2.4 Hz, 1H), 7.38 (d, J=8.4 Hz, 1H), 7.28-7.25 (m, 2H), 6.70-6.68 (m, 1H), 4.42 (d, J=15.2 Hz, 1H), 4.37 (d, J=15.2 Hz, 1H), 3.98 (d, J=9.2 Hz, 1H), 3.66 (d, J=11.2 Hz, 1H), 3.41 (dd, J=11.6, 5.6 Hz, 1H), 3.25-3.06 (m, 5H);
MH+ 433.

Example 63

(2S,3R,4R,5S,6R)-2-(4-Chloro-3-((6-(furan-3-yl)pyridazin-3-yl)methyl)phenyl)-6-(hydroxymethyl)-tetrahydro-2H-pyran-3,4,5-triol $^1$H NMR (400 MHz, CD$_3$OD) δ 8.18 (d, J=9.2 Hz, 1H), 7.83 (dd, J=4.0, 1.2 Hz, 1H), 7.66-7.64 (m, 2H), 7.51 (m, 1H), 7.41-7.36 (m, 2H), 7.20-7.18 (m, 1H), 4.49 (s, 2H), 4.13 (d, J=9.2 Hz, 1H), 3.86 (dd, J=12.0, 2.0 Hz, 1H), 3.68 (dd, J=12.0, 1.6 Hz, 1H), 3.48-3.38 (m, 3H), 3.33 (s, 2H);
MH+ 433.

Example 64

(2S,3R,4R,5S,6R)-2-(4-Chloro-3-((6-(pyridin-3-yl)pyridazin-3-yl)methyl)phenyl)-6-(hydroxymethyl)-tetrahydro-2H-pyran-3,4,5-triol $^1$H NMR (400 MHz, CD$_3$OD) δ 9.22 (s, 1H), 8.65 (d, J=4.8 Hz, 1H), 8.50 (d, J=8.0 Hz, 1H), 8.14 (d, J=8.8 Hz, 1H), 7.64-7.58 (m, 2H), 7.52 (m, 1H), 7.40-7.35 (m, 2H), 4.53 (s, 2H), 4.12 (d, J=9.6 Hz, 1H), 3.86 (dd, J=12.0, 1.6 Hz, 1H), 3.68 (dd, J=12.0, 5.2 Hz, 1H), 3.48-3.41 (m, 3H), 3.33 (s, 2H);
MH+ 444.

Example 65

(2S,3R,4R,5S,6R)-2-(4-Chloro-3-((6-(thiophen-2-yl)pyridazin-3-yl)methyl)phenyl)-6-(hydroxymethyl)-tetrahydro-2H-pyran-3,4,5-triol $^1$H NMR (400 MHz, CD$_3$OD) δ 8.18 (d, J=9.2 Hz, 1H), 7.83 (dd, J=4.0, 1.2 Hz, 1H), 7.66-7.64 (m, 2H), 7.51 (m, 1H), 7.41-7.36 (m, 2H), 7.20-7.18 (m, 1H), 4.49 (s, 2H), 4.13 (d, J=9.6 Hz, 1H), 3.86 (dd, J=12.0, 1.6 Hz, 1H), 3.69 (dd, J=12.0, 1.2 Hz, 1H), 3.46-3.38 (m, 3H), 3.33 (s, 2H);

MH+ 449.

Example 66

(2S,3R,4R,5S,6R)-2-(4-chloro-3-((6-(thiophen-3-yl)pyridazin-3-yl)methyl)phenyl)-6-(hydroxymethyl)-tetrahydro-2H-pyran-3,4,5-triol $^1$H NMR (400 MHz, CD$_3$OD) δ 8.33 (s, 1H), 8.05 (d, J=8.4 Hz, 1H), 7.69-7.66 (m, 2H), 7.51 (s, 1H), 7.41-7.36 (m, 2H), 7.08 (m, 1H), 4.46 (s, 2H), 4.12 (d, J=9.2 Hz, 1H), 3.86 (dd, J=12.0, 1.6 Hz, 1H), 3.68 (dd, J=12.0, 5.2 Hz, 1H), 3.45-3.38 (m, 3H), 3.33 (s, 2H);

MH+ 449.

Example 67

(2S,3R,4R,5S,6R)-2-(3-((6-(Benzo[d][1,3]dioxol-5-yl)pyridazin-3-yl)methyl)-4-chlorophenyl)-6-(hydroxymethyl)-tetrahydro-2H-pyran-3,4,5-triol $^1$H NMR (400 MHz, CD$_3$OD) δ 7.96 (d, J=8.8 Hz, 1H), 7.59-7.51 (m, 4H), 7.41-7.35 (m, 2H), 6.95 (d, J=8.0 Hz, 1H), 6.03 (s, 2H), 4.48 (s, 2H), 4.13 (d, J=9.2 Hz, 1H), 3.87 (dd, J=12.4, 2.0 Hz, 1H), 3.70 (dd, J=12.0, 4.8 Hz, 1H), 3.49-3.37 (m, 3H), 3.34 (s, 2H);

MH+ 487.

Example 68

(2S,3R,4R,5S,6R)-2-(4-Chloro-3-((6-(2,3-dihydrobenzo[b][1,4]dioxin-6-yl)pyridazin-3-yl)methyl)phenyl)-6-(hydroxymethyl)-tetrahydro-2H-pyran-3,4,5-triol $^1$H NMR (400 MHz, CD$_3$OD) δ 7.93 (d, J=8.8 Hz, 1H), 7.57 (s, 1H), 7.52-7.48 (m, 3H), 7.39-7.33 (m, 2H), 6.94 (d, J=8.4 Hz, 1H), 4.46 (s, 2H), 4.46 (s, 4H), 4.11 (d, J=9.6 Hz, 1H), 3.86 (dd, J=12.0, 1.6 Hz, 1H), 3.68 (dd, J=12.0, 5.2 Hz, 1H), 3.45-3.37 (m, 3H), 3.33 (s, 2H);

MH+ 501.

Example 69

(2S,3R,4R,5S,6R)-2-(4-Chloro-3-((6-(5-methylthiophen-2-yl)pyridazin-3-yl)methyl)phenyl)-6-(hydroxymethyl)-tetrahydro-2H-pyran-3,4,5-triol $^1$H NMR (400 MHz, CD$_3$OD) δ 7.89 (d, J=8.4 Hz, 1H), 7.53 (s, 1H), 7.47-7.43 (m, 2H), 7.39-7.33 (m, 2H), 6.83 (s, 1H), 4.42 (s, 2H), 4.11 (d, J=9.6 Hz, 1H), 3.86 (dd, J=12.4, 1.6 Hz, 1H), 3.68 (dd, J=12.0, 1.2 Hz, 1H), 3.47-3.37 (m, 3H), 3.33 (s, 2H);

MH+ 463.

Example 70

(2S,3R,4R,5S,6R)-2-(4-Chloro-3-((6-(4-fluorophenyl)pyridazin-3-yl)methyl)phenyl)-6-(hydroxymethyl)-tetrahydro-2H-pyran-3,4,5-triol $^1$H NMR (400 MHz, CD$_3$OD) δ 8.42 (d, J=9.2 Hz, 1H), 8.17-8.12 (m, 2H), 7.91 (d, J=8.8 Hz, 1H), 7.56 (s, 1H), 7.42 (s, 2H), 7.34-7.29 (m, 2H), 4.59 (s, 2H), 3.97 (d, J=9.2 Hz, 1H), 3.86 (dd, J=12.0, 1.6 Hz, 1H), 3.69 (dd, J=12.0, 5.2 Hz, 1H), 3.46-3.34 (m, 3H), 3.34 (s, 2H);

MH+ 461.

Example 71

(2S,3R,4R,5S,6R)-2-(4-Chloro-3-((6-(3-methoxyphenyl)pyridazin-3-yl)methyl)phenyl)-6-(hydroxymethyl)-tetrahydro-2H-pyran-3,4,5-triol $^1$H NMR (400 MHz, CD$_3$OD) δ 8.15 (d, J=8.8 Hz, 1H), 7.67 (d, J=9.2 Hz, 1H), 7.63 (m, 1H), 7.59-7.57 (m, 1H), 7.46-7.36 (m, 3H), 7.10-7.07 (m, 1H), 4.53 (s, 2H), 4.13 (d, J=9.2 Hz, 1H), 3.86 (dd, J=12.0, 2.0 Hz, 1H), 3.86 (s, 3H), 3.68 (dd, J=12.4, 5.6 Hz, 1H), 3.46-3.38 (m, 3H), 3.34 (s, 2H);

MH+ 437.

Example 72

(2S,3R,4R,5S,6R)-2-(4-Chloro-3-((6-ethylpyridazin-3-yl)methyl)phenyl)-6-(hydroxymethyl)-tetrahydro-2H-pyran-3,4,5-triol Step 1: 3-(2-Chloro-5-((2S,3S,4R,5R,6R)-3,4,5-tris(benzyloxy)-6-(benzyloxymethyl)-tetrahydro-2H-pyran-2-yl)benzyl)-6-ethylpyridazine (compound 27)

To a solution of Intermediate 6 (compound 24, 256 mg; 0.34 mmol) in 4.4 mL of N-Methylpyrrolidone/THF (1:10) and iron acetylacetonate (12 mg; 0.034 mmol) was added ethylmagnesium bromide (0.13 mL; 0.40 mmol; 3M solution in ether) dropwise at 0° C. The reaction mixture was stirred for 1 h at room temperature. The reaction mixture was quenched with 1N HCl, extracted with ethyl acetate and washed with brine. The organic layers were dried over MgSO$_4$, filtrated and evaporated to dryness to give a residue that was purified by flash column chromatography (Biotage SP1™) (eluent: hexane/EtOAc mixture (65/35; v/v)) to obtain 171 mg (0.23 mmol; 67%) of the title compound as colorless oil.

MH+ 755.

Step 2: (2S,3R,4R,5S,6R)-2-(4-Chloro-3-((6-ethylpyridazin-3-yl)methyl)phenyl)-6-(hydroxymethyl)-tetrahydro-2H-pyran-3,4,5-triol To a solution of 3-(2-chloro-5-((2S,3S,4R,5R,6R)-3,4,5-tris(benzyloxy)-6-(benzyloxymethyl)-tetrahydro-2H-pyran-2-yl)benzyl)-6-ethylpyridazine (171 mg, 0.23 mmol) in acetonitrile (10 mL) at 0° C. were added iodotrimethyl silane (2 mL) dropwise. The reaction was stirred overnight at room temperature and concentrated to dryness to give the crude tetraol, which was purified as white solid (78.7 mg; 88%) by using Gilson prep HPLC system.

$^1$H NMR (400 MHz, CD$_3$OD) δ 7.50 (d, J=8.4 Hz, 1H), 7.45 (d, J=2.0 Hz, 1H), 7.41 (d, J=8.8 Hz, 1H), 7.38-7.32 (m, 2H), 4.42 (s, 2H), 4.11 (d, J=9.6 Hz, 1H), 3.85 (dd, J=12.4, 2.0 Hz, 1H), 3.68 (dd, J=12.0, 5.2 Hz, 1H), 3.47-3.35 (m, 3H), 3.33 (s, 2H), 2.93 (q, J=8.0 Hz, 2H), 1.31 (t, J=7.6 Hz, 3H);

MH+ 395.

Example 73

(2S,3R,4R,5S,6R)-2-(4-Chloro-3-((6-methylpyridazin-3-yl)methyl)phenyl)-6-(hydroxymethyl)-tetrahydro-2H-pyran-3,4,5-triol $^1$H NMR (400 MHz, CD$_3$OD) δ 7.49-7.45 (m, 2H), 7.40-7.32 (m, 3H), 4.41 (s, 2H), 4.10 (d, J=9.6 Hz, 1H), 3.85 (dd, J=12.4, 2.0 Hz, 1H), 3.67 (dd, J=12.0, 5.2 Hz, 1H), 3.47-3.34 (m, 3H), 2.62 (s, 3H);
MH+ 381.

Example 74

(2S,3R,4R,5S,6R)-2-(4-Chloro-3-((6-propylpyridazin-3-yl)methyl)phenyl)-6-(hydroxymethyl)-tetrahydro-2H-pyran-3,4,5-triol $^1$H NMR (400 MHz, CD$_3$OD) δ 7.71 (d, J=8.8 Hz, 1H), 7.62 (d, J=8.8 Hz, 1H), 7.48 (d, J=1.2 Hz, 1H), 7.39-7.34 (m, 2H), 4.46 (s, 2H), 4.12 (d, J=9.6 Hz, 1H), 3.86 (dd, J=12.0, 2.0 Hz, 1H), 3.68 (dd, J=11.6, 5.2 Hz, 1H), 3.45-3.37 (m, 3H), 2.94 (t, J=7.6 Hz, 2H), 1.82-1.73 (m, 2H), 0.98 (t, J=7.2 Hz, 3H);
MH+ 409.

Example 75

(2S,3R,4R,5S,6R)-2-(4-Chloro-3-((6-isopropylpyridazin-3-yl)methyl)phenyl)-6-(hydroxymethyl)-tetrahydro-2H-pyran-3,4,5-triol $^1$H NMR (400 MHz, DMSO-d$_6$) δ 7.76 (d, J=8.8 Hz, 1H), 7.60 (d, J=8.8 Hz, 1H), 7.41 (d, J=2.0 Hz, 1H), 7.37 (d, J=8.4 Hz, 1H), 7.26 (dd, J=8.4, 2.0 Hz, 1H), 4.41 (d, J=15.6 Hz, 1H), 3.61 (d, J=15.6 Hz, 1H), 3.98 (d, J=9.6 Hz, 1H), 3.66 (dd, J=11.6, 1.2 Hz, 1H), 3.40 (dd, J=11.6, 5.6 Hz, 1H), 3.25-3.17 (m, 3H), 3.13 (s, 2H), 1.25 (d, J=6.8 Hz, 6H);
MH+ 409.

Example 76

(2S,3R,4R,5S,6R)-2-(3-((6-Butylpyridazin-3-yl)methyl)-4-chlorophenyl)-6-(hydroxymethyl)-tetrahydro-2H-pyran-3,4,5-triol $^1$H NMR (400 MHz, DMSO-d$_6$) δ 7.91 (d, J=8.8 Hz, 1H), 7.77 (d, J=8.4 Hz, 1H), 7.42 (d, J=1.6 Hz, 1H), 7.38 (d, J=8.4 Hz, 1H), 7.27 (dd, J=8.0, 1.6 Hz, 1H), 4.45 (d, J=15.6 Hz, 1H), 4.40 (d, J=15.6 Hz, 1H), 3.98 (d, J=9.6 Hz, 1H), 3.66 (dd, J=11.6, 1.2 Hz, 1H), 3.40 (dd, J=11.6, 5.6 Hz, 1H), 3.26-2.99 (m, 3H), 1.67-1.63 (m, 2H), 1.31-1.25 (m, 2H), 1.15 (t, J=7.2 Hz, 2H), 0.86 (t, J=7.6 Hz, 3H);
MH+ 423.

Example 77

(2S,3R,4R,5S,6R)-2-(4-Chloro-3-((6-isobutylpyridazin-3-yl)methyl)phenyl)-6-(hydroxymethyl)-tetrahydro-2H-pyran-3,4,5-triol $^1$H NMR (400 MHz, CD$_3$OD) δ 7.99 (d, J=8.8 Hz, 1H), 7.89 (d, J=8.8 Hz, 1H), 7.51 (s, 1H), 7.39 (s, 2H), 4.51 (s, 2H), 4.13 (d, J=9.2 Hz, 1H), 3.86 (dd, J=12.4, 1.6 Hz, 1H), 3.70 (m, 1H), 3.48-3.38 (m, 3H), 2.81 (d, J=3.2 Hz, 2H), 2.15-2.08 (m, 1H), 0.96 (d, J=6.4 Hz, 6H);
MH+ 423.

Example 78

(2S,3R,4R,5S,6R)-2-(4-Chloro-3-((6-pentylpyridazin-3-yl)methyl)phenyl)-6-(hydroxymethyl)-tetrahydro-2H-pyran-3,4,5-triol $^1$H NMR (400 MHz, DMSO-d$_6$) δ 7.46 (d, J=8.47 Hz, 1H), 7.38-7.32 (m, 3H), 7.24 (dd, J=8.4, 2.0 Hz, 1H), 4.36 (d, J=15.2 Hz, 1H), 4.30 (d, J=15.2 Hz, 1H), 3.97 (d, J=9.6 Hz, 1H), 3.66 (dd, J=11.6, 1.2 Hz, 1H), 3.40 (dd, J=11.6, 5.6 Hz, 1H), 3.43-3.38 (m, 1H), 3.25-3.05 (m, 4H), 2.82 (t, J=7.6 Hz, 2H), 1.67-1.60 (m, 2H), 1.31-1.20 (m, 4H), 0.82 (t, J=6.8 Hz, 3H);
MH+ 437.

Example 79

(2S,3R,4R,5S,6R)-2-(4-Chloro-3-((6-(methylthio)pyridazin-3-yl)methyl)phenyl)-6-(hydroxymethyl)-tetrahydro-2H-pyran-3,4,5-triol (88)

Step 1: 3-(2-Chloro-5-((2S,3S,4R,5R,6R)-3,4,5-tris(benzyloxy)-6-(benzyloxymethyl)-tetrahydro-2H-pyran-2-yl)benzyl)-6-(methylthio)pyridazine (compound 26)

To a solution of Intermediate 6 (compound 24, 200 mg; 0.26 mmol) in THF (5 mL) was added NaSMe (24.5 mg; 0.32 mmol). The reaction mixture was stirred overnight at room temperature. The reaction mixture was quenched with 1N HCl, extracted with ethyl acetate and washed with brine. The organic layers were dried over MgSO$_4$, filtrated and evaporated to dryness to give a residue that was purified by flash column chromatography (Biotage SP1™) (eluent: hexane/EtOAc mixture to obtain 151 mg (0.20 mmol; 74%) of the title compound as colorless oil; MH+ 773.

Step 2: (2S,3R,4R,5S,6R)-2-(4-Chloro-3-((6-(methylthio)pyridazin-3-yl)methyl)phenyl)-6-(hydroxymethyl)-tetrahydro-2H-pyran-3,4,5-triol (compound 88)

To a solution of 3-(2-chloro-5-((2S,3S,4R,5R,6R)-3,4,5-tris(benzyloxy)-6-(benzyloxymethyl)-tetrahydro-2H-pyran-2-yl)benzyl)-6-(methylthio)pyridazine (compound 26, 151 mg, 0.20 mmol) in acetonitrile (10 mL) at 0° C. were added iodotrimethyl silane (2 mL) dropwise. The reaction was stirred overnight at room temperature and concentrated to dryness to give the crude tetraol, which was purified as white solid (60.9 mg; 76%) by using Gilson prep HPLC system.
[α]$_D^{21}$ +13.8 (c 0.32, methanol);
$^1$H NMR (400 MHz, CD$_3$OD) δ 7.46 (m, 1H), 7.44 (m, 1H), 7.38-7.32 (m, 2H), 7.29 (dd, J=8.8, 2.0 Hz, 1H), 4.37 (s, 2H), 4.10 (d, J=9.6 Hz, 1H), 3.85 (dd, J=12.0, 1.6 Hz, 1H), 3.68 (dd, J=11.6, 5.2 Hz, 1H), 3.47-3.37 (m, 3H), 3.32 (s, 2H), 2.62 (s, 3H);
$^{13}$C NMR (100 MHz, DMSO-d$_6$) δ 161.09, 158.36, 140.23, 135.67, 132.60, 131.67, 129.14, 128.48, 126.78, 126.11, 81.67, 81.06, 78.71, 75.13, 70.74, 61.78, 49.05, 13.10;
HRMS (FAB, 6 keV) calcd for C$_{18}$H$_{22}$ClN$_2$O$_5$S ([M+H]$^+$) 413.0938. found 413.0937;
MH+ 413.

Example 80

(2S,3R,4R,5S,6R)-2-(4-Chloro-3-((6-(ethylthio)pyridazin-3-yl)methyl)phenyl)-6-(hydroxymethyl)-tetrahydro-2H-pyran-3,4,5-triol $^1$H NMR (400 MHz, CD$_3$OD) δ 7.45 (m, 1H), 7.43-7.41 (m, 1H), 7.38-7.32 (m, 2H), 7.30-7.27 (m, 1H), 4.36 (s, 2H), 4.10 (d, J=9.2 Hz, 1H), 3.85 (dd, J=12.0, 1.6 Hz, 1H), 3.68 (dd, J=11.6, 5.2 Hz, 1H), 3.45-3.37 (m, 3H), 3.25-3.21 (m, 2H), 1.37 (t, J=7.2 Hz, 3H);
MH+ 427.

Example 81

(2S,3R,4R,5S,6R)-2-(4-Chloro-3-((6-(phenylthio)pyridazin-3-yl)methyl)phenyl)-6-(hydroxymethyl)-tetrahydro-2H-pyran-3,4,5-triol $^1$H NMR (400 MHz, CD$_3$OD) δ 7.59-7.58 (m, 2H), 7.47-7.45 (m, 2H), 7.43-7.28 (m, 4H), 7.10 (d, J=9.2 Hz, 1H), 4.36 (s, 2H), 4.09 (d, J=9.6 Hz, 1H), 3.85 (dd, J=12.0, 1.6 Hz, 1H), 3.66 (dd, J=12.0, 4.8 Hz, 1H), 3.46-3.34 (m, 3H);
MH+ 475.

Example 82

(2S,3R,4R,5S,6R)-2-(4-Chloro-3-((5-methyl-6-(methylthio)pyridazin-3-yl)methyl)phenyl)-6-(hydroxymethyl)tetrahydro-2H-pyran-3,4,5-triol (compound 43)

Step 1: 2-(2-Chloro-5-((2S,3S,4R,5R,6R)-3,4,5-tris(benzyloxy)-6-(benzyloxymethyl)tetrahydro-2H-pyran-2-yl)phenyl)-2-(6-chloro-5-methylpyridazin-3-yl)acetonitrile (compound 40)

Sodium hydride (200 mg; 5.00 mmol; 60% in mineral oil) was added to stirred solution of Intermediate 2 (compound 7, 1.3 g; 1.93 mmol) in 8 mL of N,N-dimethylformamide (DMF) at 0 r under nitrogen gas. The reaction mixture was stirred for 30 min, and 4-methyl-3,6-dichloropyridazine (compound 39, 500 mg; 2.98 mmol) was added in one portion. The ice bath was removed, and the reaction mixture was stirred at room temperature for 1 h. 1N HCl (10 mL) was poured to reaction mixture and extracted with ethyl acetate (3×100 mL). The organic layer was combined and washed with brine (2×100 mL). After drying over MgSO$_4$, the solvents were removed in vacuo and subjected to silica gel column chromatography (eluent: hexane/EtOAc mixture (75/25; v/v)) to obtain the title compound (1.4 g; 91%) as pale orange oil.
MH+ 800.

Step 2: (2S,3R,4R,5S,6S)-2-(Acetoxymethyl)-6-(4-chloro-3-((5-methyl-6-oxo-1,6-dihydropyridazin-3-yl)methyl)phenyl)tetrahydro-2H-pyran-3,4,5-triyl triacetate A mixture of 2-(2-chloro-5-((2S,3S,4R,5R,6R)-3,4,5-tris(benzyloxy)-6-(benzyloxymethyl)tetrahydro-2H-pyran-2-yl)phenyl)-2-(6-chloro-5-methylpyridazin-3-yl)acetonitrile (compound 40, 927 mg; 1.16 mmol), HOAc (6 mL), conc. HCl (12 mL) and H$_2$O (6 mL) were heated at reflux overnight, cooled to room temperature and concentrated in vacuo overnight. Some parts of the crude tetraol was purified by using Gilson prep HPLC system as white solid.
$^1$H NMR (400 MHz, CD$_3$OD) δ 7.38-7.31 (m, 3H), 7.16-7.15 (m, 1H), 4.11-4.09 (m, 1H), 4.06 (s, 2H), 3.88-3.83 (m, 1H), 3.68 (dd, J=12.0, 4.8 Hz, 1H), 3.47-3.34 (m, 3H), 3.33 (s, 2H), 2.15-2.14 (m, 1H), 2.08 (s, 3H);
MH+ 397.

Peracetylation was achieved by addition of Ac$_2$O (1 mL; 11.6 mmol) and DMAP (catalytic amount) to a solution of this crude compound in CH$_2$Cl$_2$ (5 mL) and TEA (1.6 mL; 11.6 mmol). After 5 h, the reaction was quenched with H$_2$O (5 mL) and the reaction mixture was extracted with CH$_2$Cl$_2$ (2×50 mL). The collected organic layer was washed with 1N HCl and brine. After drying over MgSO$_4$, the solvents were evaporated under a vacuum. The crude mixture was further purified by flash column chromatography (Biotage SP1™) (eluent: hexane/EtOAc mixture (40/60; v/v)) to obtain 385 mg (0.68 mmol; 59%) of the title compound as colorless oil.
MH+ 565.

Step 3: (2S,3R,4R,5S,6S)-2-(Acetoxymethyl)-6-(4-chloro-3-((6-chloro-5-methylpyridazin-3-yl)methyl)phenyl)tetrahydro-2H-pyran-3,4,5-triyl triacetate (42)

To a solution of (2S,3R,4R,5S,6S)-2-(Acetoxymethyl)-6-(4-chloro-3-((5-methyl-6-oxo-1,6-dihydropyridazin-3-yl)methyl)phenyl)tetrahydro-2H-pyran-3,4,5-triyl triacetate (385 mg; 0.68 mmol) in toluene (12 mL) was added phosphorous oxychloride (0.3 mL; 3.41 mL) at room temperature. The reaction mixture was heated at 70° C. for 12 hrs, and then evaporated under a vacuum. The crude mixture was extracted with ethyl acetate/H$_2$O, dried over MgSO$_4$, filtered and removed solvents. Purification by flash column chromatography (Biotage SP1™) provided 278 mg (70%) as colorless oil.
MH+ 583.

Step 4: (2S,3R,4R,5S,6R)-2-(4-Chloro-3-((5-methyl-6-(methylthio)pyridazin-3-yl)methyl)phenyl)-6-(hydroxymethyl)tetrahydro-2H-pyran-3,4,5-triol (compound 43)

To a solution of (2S,3R,4R,5S,6S)-2-(acetoxymethyl)-6-(4-chloro-3-((6-chloro-5-methylpyridazin-3-yl)methyl)phenyl)tetrahydro-2H-pyran-3,4,5-triyl triacetate (42, 278 mg, 0.48 mmol) in MeOH (8 mL) was added NaSMe (56 mg; 0.71 mmol), and the mixture was stirred for 1 h at room temperature. The mixture was neutralized with Amberlite IR-120 (H$^+$) resin, and filtered, the resin was washed with MeOH, and the combined filtrate and washings were concentrated. The title compound was obtained 99.5 mg (0.23 mmol; 48%) as a white solid.
$^1$H NMR (400 MHz, CD$_3$OD) δ 7.42 (d, J=1.6 Hz, 1H), 7.38-7.32 (m, 2H), 7.14 (s, 1H), 4.33 (s, 2H), 4.10 (d, J=9.6 Hz, 1H), 3.86 (dd, J=12.4, 2.0 Hz, 1H), 3.68 (dd, J=12.0, 5.2 Hz, 1H), 3.47-3.34 (m, 3H), 3.33 (s, 2H), 2.65 (s, 3H), 2.18 (s, 3H);
MH+ 427.

Example 83

6-(2-Chloro-5-((2S,3R,4R,5S,6R)-3,4,5-trihydroxy-6-(hydroxymethyl)-tetrahydro-2H-pyran-2-yl)benzyl)-4-methylpyridazin-3(2H)-one (compound 41)

$^1$H NMR (400 MHz, CD$_3$OD) δ 7.38-7.31 (m, 3H), 7.16-7.15 (m, 1H), 4.11-4.09 (m, 1H), 4.06 (s, 2H), 3.88-3.83 (m,

1H), 3.68 (dd, J=12.0, 4.8 Hz, 1H), 3.47-3.34 (m, 3H), 3.33 (s, 2H), 2.15-2.14 (m, 1H), 2.08 (s, 3H);
MH+ 397.

Example 84

(2S,3R,4R,5S,6R)-2-(4-Chloro-3-((6-morpholinopyridazin-3-yl)methyl)phenyl)-6-(hydroxymethyl)-tetrahydro-2H-pyran-3,4,5-triol Step 1: 4-(6-(2-Chloro-5-((2S,3S,4R,5R,6R)-3,4,5-tris(benzyloxy)-6-(benzyloxymethyl)-tetrahydro-2H-pyran-2-yl)benzyl)pyridazin-3-yl)morpholine Intermediate 6 (300 mg, 0.394 mmol) was added to a microwave reaction tube containing morpholine (1 mL) in 1,4-dioxane (3 mL). The capped reaction tube was placed in a microwave reactor, and the mixture was irradiated at 175° C. for 90 min. The reaction mixture was diluted with EtOAc (25 mL) and washed with aq. 50% NaCl solution (50 mL). The organic layer was dried over anhydrous $MgSO_4$, filtered, and concentrated in vacuo. Purification by silica gel column chromatography (eluent: hexane/EtOAc=1/1) provided 317 mg (99%) of desired product.
$^1$H NMR (400 MHz, $CDCl_3$) δ 7.37-7.35 (m, 3H), 7.34-7.23 (m, 13H), 7.24-7.16 (m, 5H), 6.95 (d, J=9.2 Hz, 1H), 6.92-6.86 (m, 2H), 6.62 (d, J=9.6 Hz, 1H), 4.92-4.82 (m, 3H), 4.64-4.51 (m, 3H), 4.43-4.26 (m, 3H), 4.17 (d, J=9.6 Hz, 1H), 3.86-3.70 (m, 10H), 3.58-3.51 (m, 5H);
MH+ 812.

Step 2: (2S,3R,4R,5S,6R)-2-(4-Chloro-3-((6-morpholinopyridazin-3-yl)methyl)phenyl)-6-(hydroxymethyl)-tetrahydro-2H-pyran-3,4,5-triol To a solution of 4-(6-(2-chloro-5-((2S,3S,4R,5R,6R)-3,4,5-tris(benzyloxy)-6-(benzyloxymethyl)-tetrahydro-2H-pyran-2-yl)benzyl)pyridazin-3-yl)morpholine (250 mg, 0.308 mmol) from Step 1 in acetonitrile (10 mL) at 0° C. was added iodotrimethylsilane (3 mL) dropwise. The reaction mixture was stirred overnight at 55° C., cooled to room temperature, concentrated to dryness to give the crude tetraol, which was purified as solid (139 mg, 95%) by using Gilson prep HPLC system.
$^1$H NMR (400 MHz, $CD_3OD$) δ 7.94 (d, J=9.6 Hz, 1H), 7.75 (d, J=10.0 Hz, 1H), 7.68 (d, J=2.4 Hz, 1H), 7.45-7.35 (m, 2H), 3.87-3.76 (m, 5H), 3.74-3.65 (m, 4H), 3.55-3.38 (m, 4H), 3.45-3.26 (m, 4H);
MH+ 452.

Example 85

(2S,3R,4R,5S,6R)-2-(4-Chloro-3-((6-(phenylamino)pyridazin-3-yl)methyl)phenyl)-6-(hydroxymethyl)-tetrahydro-2H-pyran-3,4,5-triol $^1$H NMR (400 MHz, $CD_3OD$) δ 7.63-7.51 (m, 2H), 7.42 (d, J=1.2 Hz, 1H), 7.36-7.25 (m, 6H), 7.10 (d, J=9.2 Hz, 1H), 7.03-6.96 (m, 1H), 4.93-4.82 (m, 4H), 4.28 (s, 2H), 4.10 (d, J=9.2 Hz, 1H), 3.86 (dd, J=12.0, 2.0 Hz, 1H), 3.67 (dd, J=12.0, 1.2 Hz, 1H), 3.48-3.25 (m, 5H); MH+ 458.

Example 86

(2S,3R,4R,5S,6R)-2-(4-Chloro-3-((6-(pyrrolidin-1-yl)pyridazin-3-yl)methyl)phenyl)-6-(hydroxymethyl)-tetrahydro-2H-pyran-3,4,5-triol $^1$H NMR (400 MHz, $CD_3OD$) δ 7.39-7.28 (m, 3H), 7.18 (d, J=9.2 Hz, 1H), 6.85 (d, J=9.6 Hz, 1H), 4.99-4.83 (m, 4H), 4.25 (s, 2H), 4.08 (d, J=9.2 Hz, 1H), 3.89-3.82 (m, 1H), 3.70-3.63 (m, 1H), 3.48-3.13 (m, 8H), 2.07-2.01 (m, 4H);
MH+ 436.

Example 87

(2S,3R,4R,5S,6R)-2-(4-Chloro-3-((7-methylbenzo[e][1,2,4]triazin-3-yl)methyl)phenyl)-6-(hydroxymethyl)tetrahydro-2H-pyran-3,4,5-triol Step 1: 3-(1-(2-Chloro-5-((2S,3S,4R,5R,6R)-3,4,5-tris(benzyloxy)-6-(benzyloxymethyl)tetrahydro-2H-pyran-2-yl)phenyl)-2-methoxy-2-oxoethyl)-7-methylbenzo[e][1,2,4]-triazine 1-oxide (compound 61)

Added to a solution of intermediate 4 (compound 9, 1.0 g, 1.42 mmol) and 3-chloro-7-methylbenzo[e][1,2,4]triazine 1-oxide (compound 60, 0.6 g, 3.0 mmol) dissolved in THF (20 ml), was NaH (60 mg, 60% in mineral oil, 1.5 mmol) in one portion at 0° C. The reaction mixture was stirred at room temperature for 6 hrs, and then quenched with saturated $NH_4Cl$ solution. The organic layer was collected, and evaporated under a vacuum. The crude mixture was further purified by silica gel (Hx/EtOAc=1/1), to obtain 0.31 g (0.36 mmol, 25%) of the title compound as yellow solid with recovered starting material (750 mg, 75%).

Step 2: Methyl 2-(2-Chloro-5-((2S,3S,4R,5R,6R)-3,4,5-tris(benzyloxy)-6-(benzyloxymethyl)tetrahydro-2H-pyran-2-yl)phenyl)-2-(7-methylbenzo[e][1,2,4]triazin-3-yl)acetate (compound 62)

3-(1-(2-Chloro-5-((2S,3S,4R,5R,6R)-3,4,5-tris(benzyloxy)-6-(benzyloxymethyl)tetrahydro-2H-pyran-2-yl)phenyl)-2-methoxy-2-oxoethyl)-7-methylbenzo[e][1,2,4]triazine 1-oxide (compound 61, 310 mg, 0.36 mmol) was treated with Zn (500 mg, 7.6 mmol) and ammonium chloride (500 mg, 9.34 mmol) in aqueous dioxane at room temperature for 1 day. The reaction mixture was diluted and work-up with EtOAc. After evaporating the volatile solvent under reduced pressure, the residue was purified with silica gel column (Hx/EtOAc=⅓) to afford title compound (228 mg, 75% yield) as white solid.
$^1$H NMR (400 MHz, $CDCl_3$) δ 7.39-7.36 (m, 2H), 7.35-7.26 (m, 12H), 7.20-7.17 (m, 5H), 7.01-7.04 (m, 2H), 6.90-6.88 (m, 2H), 6.73-6.71 (m, 2H), 4.89-4.87 (d, J=1.2 Hz, 2H), 4.86-4.84 (m, 2H), 4.63-4.51 (m, 4H), 4.44-4.30 (m, 4H), 4.19-4.16 (d, J=9.6 Hz, 1H), 4.10 (s, 3H), 3.86-3.71 (m, 5H), 3.58-3.55 (m, 1H), 3.43-3.41 (t, J=9.2 Hz, 1H), 2.34 (s, 3H).

Step 3: 3-(2-Chloro-5-((2S,3S,4R,5R,6R)-3,4,5-tris(benzyloxy)-6-(benzyloxymethyl)tetrahydro-2H-pyran-2-yl)benzyl)-7-methylbenzo[e][1,2,4]triazine (compound 63)

Sodium hydroxide (40 mg, 0.81 mmol) was added to methyl 2-(2-chloro-5-((2S,3S,4R,5R,6R)-3,4,5-tris(benzyloxy)-6-(benzyloxymethyl)tetrahydro-2H-pyran-2-yl)phenyl)-2-(7-methylbenzo[e][1,2,4]triazin-3-yl)acetate (compound 62, 228 mg, 0.27 mmol) in the mixture of THF, MeOH and water (9/1/1 ratio) at room temperature, and then the mixture was stirred at 70° C. for a 1 day until starting material was disappeared. After reaction complete, the solution was work-up with $CH_2Cl_2$. After evaporating the volatile solvent, silica gel column chromatography (Hx/EtOAc=⅓) gave the desired compound (115 mg, 73% yield) as light yellow oil.

¹H NMR (400 MHz, CDCl₃) δ 7.47-7.40 (m, 3H), 7.39-7.26 (m, 12H), 7.21-7.17 (m, 4H), 7.04 (d, J=9.1 Hz, 1H), 6.88 (dd, J=7.2, 1.6 Hz, 1H), 6.72 (d, J=9.1 Hz, 1H), 4.89 (s, 2H), 4.74 (d, J=10.4 Hz, 2H), 4.61 (d, J=10.8 Hz, 1H), 4.55 (dd, J=12.0, 2.4 Hz, 2H), 4.39 (d, J=12.0 Hz, 1H), 4.37-4.30 (m, 2H), 4.17 (d, J=9.6 Hz, 1H), 3.86-3.71 (m, 5H), 3.58-3.55 (m, 1H), 3.43 (t, J=9.2 Hz, 1H), 2.63 (s, 3H).

Step 4: (2S,3R,4R,5S,6R)-2-(4-Chloro-3-((7-methylbenzo[e][1,2,4]triazin-3-yl)methyl)phenyl)-6-(hydroxymethyl)tetrahydro-2H-pyran-3,4,5-triol 3-(2-Chloro-5-((2S,3S,4R,5R,6R)-3,4,5-tris(benzyloxy)-6-(benzyloxymethyl)tetrahydro-2H-pyran-2-yl)benzyl)-7-methylbenzo[e][1,2,4]triazine (115 mg, 0.15 mmol) in acetonitrile (10 ml) reacted with TMSI (146 mg, 0.73 mmol) at 0° C. The reaction mixture was stirred at room temperature for 1 day. After quenching the reaction with methanol, solvent was evaporated under reduced pressure. The residue was purified with silica gel (10% MeOH in CH₂Cl₂) to afford title compound (33 mg, 52% yield) as a light yellow solid.

¹H NMR (400 MHz, CDCl₃) δ 7.49-7.46 (m, 2H), 7.42-7.31 (m, 3H), 7.05 (d, J=8.8 Hz, 1H), 4.33 (s. 2H), 4.10 (d, J=9.6 Hz, 1H), 3.88-3.84 (m, 1H), 3.68 (dd, J=12.1, 9.9 Hz, 1H), 3.48-3.26 (m, 6H), 2.43 (s, 3H);

MH+ 432.

The following compound of Examples 88 was obtained by using corresponding starting materials and repeating the procedure of Example 87.

Example 88

(2S,3R,4R,5S,6R)-2-(3-(Benzo[e][1,2,4]triazin-3-ylmethyl)-4-chlorophenyl)-6-(hydroxymethyl)tetrahydro-2H-pyran-3,4,5-triol ¹H NMR (400 MHz, CDCl₃) δ 7.51-7.45 (m, 3H), 7.42-7.32 (m, 3H), 7.05 (d, J=8.8 Hz, 1H), 4.32 (s. 2H), 4.11 (d, J=9.6 Hz, 1H), 3.87-3.85 (m, 1H), 3.67 (dd, J=12.1, 9.8 Hz, 1H), 3.47-3.25 (m, 6H), 2.44 (s, 3H);

MH+ 418.

Example 89

(2S,3R,4R,5S,6R)-2-(3-((1,2,4-triazin-3-yl)methyl)-4-chlorophenyl)-6-(hydroxymethyl)tetrahydro-2H-pyran-3,4,5-triol Step 1: 2-(2-Chloro-5-((2S,3S,4R,5R,6R)-3,4,5-tris(benzyloxy)-6-(benzyloxymethyl)tetrahydro-2H-pyran-2-yl)phenyl)acetimidohydrazide (compound 45)

To a solution of intermediate 2 (compound 7, 1 g, 1.5 mmol) in diethyl ether (30 ml) was bubbled HCl gas at 0° C. for 10 min, and allowed to cool down to −10° C. and keep temperature at refrigerate for 2 days. The white solid was appeared and collected to produce 2-(2-chloro-5-((2S,3S,4R,5R,6R)-3,4,5-tris(benzyloxy)-6-(benzyloxymethyl)tetrahydro-2H-pyran-2-yl)phenyl)acetimidoyl chloride (compound 44) hydrogen chloride as white solid. The resulting compound (500 mg, 0.75 mmol) was dissolved in CH₂Cl₂, anhydrous hydrazine (1 ml) was added to the solution at 0° C. After string the reaction mixture for 1 hr, the solution was evaporated. Normal work-up was accomplished to produce title compound (crude 1 g). The title compound was used to the next step without further purification.

MH+ 706.

Step 2: 3-(2-Chloro-5-((2S,3S,4R,5R,6R)-3,4,5-tris(benzyloxy)-6-(benzyloxymethyl)tetrahydro-2H-pyran-2-yl)benzyl)-1,2,4-triazine (compound 46)

2-(2-Chloro-5-((2S,3S,4R,5R,6R)-3,4,5-tris(benzyloxy)-6-(benzyloxymethyl)tetrahydro-2H-pyran-2-yl)phenyl)acetimidohydrazide (compound 45, crude 1 g from step 1) in EtOH (30 ml) reacted with glyoxal (5 ml, 30% in water) at 0° C., and allowed to warm up at room temperature. After the reaction mixture was stirred for 3 hours, it was evaporated under reduced pressure to remove volatile compounds. The residue was purified with silica gel (Hx/EtOAc=⅓) to provided title compound (324 mg, 60% overall yield form intermediate 2).

¹H NMR (400 MHz, CDCl₃) δ 9.30 (d, J=7.2 Hz, 1H), 8.71 (d, J=7.2 Hz, 1H), 7.51-7.45 (m, 3H), 7.41-7.30 (m, 11H), 7.25-7.21 (m, 4H), 7.04 (d, J=8.1 Hz, 1H), 6.91 (dd, J=7.6, 2.2 Hz, 1H), 4.91 (s, 2H), 4.64 (d, J=9.7 Hz, 2H), 4.59 (d, J=9.9 Hz, 1H), 4.51-4.38 (m, 4H), 4.33-4.25 (m, 2H), 4.15 (d, J=9.6 Hz, 1H), 4.11 (s, 2H), 3.88-3.70 (m, 5H), 3.59-3.54 (m, 1H).

Step 3: (2S,3R,4R,5S,6R)-2-(3-((1,2,4-Triazin-3-yl)methyl)-4-chlorophenyl)-6-(hydroxymethyl)tetrahydro-2H-pyran-3,4,5-triol With similar method described in Step 4 of Example 87, 3-(2-chloro-5-((2S,3S,4R,5R,6R)-3,4,5-tris(benzyloxy)-6-(benzyloxymethyl)tetrahydro-2H-pyran-2-yl)benzyl)-1,2,4-triazine (324 mg, 0.44 mmol) was converted to title compound (41 mg, 25%) as light yellow solid.

¹H NMR (400 MHz, CDCl₃) δ 9.25 (d, J=7.1 Hz, 1H), 8.71 (d, J=7.1 Hz, 1H), 7.49-7.20 (m, 3H), 4.19 (s. 2H), 4.10 (d, J=9.5 Hz, 1H), 3.99-3.91 (m, 1H), 3.51-3.25 (m, 7H);

MH+ 368.

Example 90

(2S,3R,4R,5S,6R)-2-(4-Chloro-3-((5-phenyl-1,2,4-triazin-3-yl)methyl)phenyl)-6-(hydroxymethyl)tetrahydro-2H-pyran-3,4,5-triol Step 1: Methyl 2-(2-chloro-5-((2S,3S,4R,5R,6R)-3,4,5-tris(benzyloxy)-6-(benzyloxymethyl)tetrahydro-2H-pyran-2-yl)phenyl)-2-(5-phenyl-1,2,4-triazin-3-yl)acetate (compound 61)

The intermediate 4 (compound 9, 360 mg, 0.51 mmol) and 3-(methylsulfonyl)-5-phenyl-1,2,4-triazine (compound 50, 235 mg, 1.0 mmol) in THF (20 ml) were treated with NaH (34 mg, 60% in mineral oil, 3 mmol) at 0° C., and then allowed to warm up to room temperature. The reaction mixture was stirred at room temperature for 1 day, and it was quenched with saturated NH₄Cl solution. Normal work-up and column chromatography (Hexane/EtOAc=1/5) provided title compound (250 mg, 54% yield) as light yellow oil.

Step 2: 3-(2-Chloro-5-((2S,3S,4R,5R,6R)-3,4,5-tris(benzyloxy)-6-(benzyloxymethyl)tetrahydro-2H-pyran-2-yl)benzyl)-5-phenyl-1,2,4-triazine (compound 52)

The title compound was prepared with same method described in step 3 of Example 87.

¹H NMR (400 MHz, CDCl₃) δ 8.94 (s, 1H), 7.53-7.49 (m, 2H), 7.43-7.39 (m, 13H), 7.33-7.29 (m, 7H), 7.04-6.92 (m,

2H), 4.75 (s, 2H), 4.62-4.58 (m, 2H), 4.53-4.39 (m, 4H), 4.31-4.29 (m, 2H), 4.18 (d, J=9.6 Hz, 1H), 4.19 (s, 2H), 3.86-3.80 (m, 4H), 3.71 (dt, J=9.7, 2.4 Hz, 1H).

Step 3: (2S,3R,4R,5S,6R)-2-(4-Chloro-3-((5-phenyl-1,2,4-triazin-3-yl)methyl)phenyl)-6-(hydroxymethyl) tetrahydro-2H-pyran-3,4,5-triol With similar method described in step 4 of Example 87, 3-(2-chloro-5-((2S,3S,4R,5R,6R)-3,4,5-tris(benzyloxy)-6-(benzyloxymethyl)tetrahydro-2H-pyran-2-yl)benzyl)-5-phenyl-1,2,4-triazine (166 mg, 0.21 mmol) was converted to title compound (21 mg, 22%) as light yellow solid.
$^1$H NMR (400 MHz, CDCl$_3$) δ 8.87 (s, 1H), 7.42-7.37 (m, 5H), 7.33-7.29 (m, 3H), 4.75 (d, J=9.6 Hz, 1H), 4.19 (s, 2H), 3.84-3.79 (m, 4H), 3.65 (m, 1H), 3.61-3.58 (m, 1H);
MH+ 444.

Example 91

(2S,3R,4R,5S,6R)-2-(4-Chloro-3-((6-methoxy-1,2,4-triazin-3-yl)methyl)phenyl)-6-(hydroxymethyl)tetrahydro-2H-pyran-3,4,5-triol (compound 59)

Step 1: Methyl 2-(2-(2-Chloro-5-((2S,3S,4R,5R,6R)-3,4,5-tris(benzyloxy)-6-(benzyloxymethyl)tetrahydro-2H-pyran-2-yl)phenyl)acetamido)acetate (compound 54)

After dissolving intermediate 3 (compound 8, 1 g, 1.44 mmol) and glycine methyl ester hydrogen chloride (272 mg, 2.17 mmol) in CH$_2$Cl$_2$, EDCI (553 mg, 2.88 mmol), HOBT (234 mg, 1.83 mmol) and NMM (0.6 ml, 5.8 mmol) were added to the mixture at room temperature. The resulting solution was stirred at room temperature for 1 day, quenched with 1N HCl solution. The organic solution was extract with CH$_2$Cl$_2$ and dried with MgSO$_4$. With reduced pressure, the volatile material was removed to produce title compound (1.1 g, quantatively) as beige solid and used without further purification.
MH+ 764.

Step 2: 3-(2-Chloro-5-((2S,3S,4R,5R,6R)-3,4,5-tris (benzyloxy)-6-(benzyloxymethyl)tetrahydro-2H-pyran-2-yl)benzyl)-4,5-dihydro-1,2,4-triazin-6(1H)-one (compound 55)

To a solution of methyl 2-(2-(2-chloro-5-((2S,3S,4R,5R,6R)-3,4,5-tris(benzyloxy)-6-(benzyloxymethyl)tetrahydro-2H-pyran-2-yl)phenyl)acetamido)acetate (compound 54, 1.1 g, 1.44 mmol) in MeOH (20 ml) was added hydrazine anhydrous (2 ml) at room temperature. Then, the reaction temperature was raised to 60° C., and maintained for overnight. After reaction complete, the solution was evaporated in vacuo, and the residue was dissolved in acetic acid (10 ml) with ammonium acetate (1 g). The reaction solution was refluxed for 1 day. The resulting solution was cooled to room temperature, and then evaporated under reduced pressure. The residue was purified with column chromatography (Hx/EtOAc=1/1) to afford to title compound (826 mg, 77% overall yield) as white solid.
$^1$H NMR (400 MHz, CDCl$_3$) δ 7.50-7.45 (m, 3H), 7.39-7.26 (m, 12H), 7.24-7.17 (m, 4H), 7.06 (d, J=9.1 Hz, 1H), 6.91-6.88 (m, 1H), 6.80-6.75 (m, 1H), 4.89 (s, 2H), 4.54-4.45 (m, 5H), 4.39 (d, J=9.4 Hz, 1H), 4.37-4.32 (m, 2H), 4.15-4.13 (m, 1H), 3.76-3.60 (m, 5H), 3.55-3.48 (m, 1H), 3.16 (s, 2H);
MH+ 747.

Step 3: 6-Chloro-3-(2-chloro-5-((2S,3S,4R,5R,6R)-3,4,5-tris(benzyloxy)-6-(benzyloxymethyl)tetrahydro-2H-pyran-2-yl)benzyl)-1,2,4-triazine (compound 57)

The 3-(2-chloro-5-((2S,3S,4R,5R,6R)-3,4,5-tris(benzyloxy)-6-(benzyloxymethyl)tetrahydro-2H-pyran-2-yl)benzyl)-4,5-dihydro-1,2,4-triazin-6(1H)-one (compound 55, 826 mg, 1.11 mmol) in a mixture of CH$_2$Cl$_2$ (20 ml) and water (2 ml) treated with DDQ (504 mg, 2.22 mmol) at 0° C. After 3 hours, Et$_2$O and water were added to the reaction mixture. Normal work-up with CH$_2$Cl$_2$ and drying with MgSO$_4$ generated crude title compound. Without further purification, it was reacted with POCl$_3$ (2 ml) in toluene (20 ml) under refluxed condition. After reaction complete, the resulting solution was poured into iced water (50 ml). After work-up with CH$_2$Cl$_2$, organic layer was evaporated under reduced pressure. The residue was purified with use of column chromatography (Hexane/EtOAc=½) to provide title compound (296 mg, 35% overall yield) as yellow oil.
$^1$H NMR (400 MHz, CDCl$_3$) δ 9.10 (s, 1H), 7.49-7.45 (m, 3H), 7.39-7.26 (m, 12H), 7.24-7.17 (m, 4H), 7.07 (d, J=9.2 Hz, 1H), 6.92-6.88 (m, 1H), 6.80-6.75 (m, 1H), 4.92 (s, 2H), 4.54-4.54 (m, 5H), 4.39-4.35 (m, 1H), 4.35-4.32 (m, 2H), 4.15-4.13 (dd, J=9.2, 3.3 Hz, 1H), 3.76-3.65 (m, 5H), 3.55-3.51 (m, 1H).

Step 4: (2S,3R,4R,5S,6S)-2-(Acetoxymethyl)-6-(4-chloro-3-((6-chloro-1,2,4-triazin-3-yl)methyl)phenyl)tetrahydro-2H-pyran-3,4,5-triyl triacetate (58)

To a solution of 6-chloro-3-(2-chloro-5-((2S,3S,4R,5R,6R)-3,4,5-tris(benzyloxy)-6-(benzyloxymethyl)tetrahydro-2H-pyran-2-yl)benzyl)-1,2,4-triazine (compound 57, 148 mg, 0.19 mmol) in CH$_2$Cl$_2$ (20 ml) was added dropwise TMSOTf (430 mg, 1.95 mmol) and acetic anhydride (2 ml) at 0° C. And then it was allowed to warm up to room temperature, and stirred 1 day. After reaction complete, the resulting solution was quenched with saturated NH$_4$Cl solution. Organic layer was collected with CH$_2$Cl$_2$ and the solution was evaporated under reduced pressure. The residue was purified with normal phase preparative HPLC system to afford title compound (62 mg, 56%) as light yellow oil.
$^1$H NMR (400 MHz, CDCl$_3$) δ 9.01 (s, 1H), 7.39-7.26 (m, 2H), 7.24-7.17 (m, 1H), 4.81 (s, 2H), 4.77 (d, J=9.7 Hz, 1H), 4.70 (d, J=9.6 Hz, 1H), 4.61 (dd, J=9.6, 2.4 Hz, 2H), 4.43 (d, J=10.0 Hz, 1H), 4.11 (s, 2H), 2.44 (s, 3H), 2.20 (s, 3H), 2.18 (s, 3H), 2.01 (s, 3H).

Step 4: (2S,3R,4R,5S,6R)-2-(4-Chloro-3-((6-methoxy-1,2,4-triazin-3-yl)methyl)phenyl)-6-(hydroxymethyl)tetrahydro-2H-pyran-3,4,5-triol (compound 59)

To a solution of (2S,3R,4R,5S,6S)-2-(acetoxymethyl)-6-(4-chloro-3-((6-chloro-1,2,4-triazin-3-yl)methyl)phenyl)tetrahydro-2H-pyran-3,4,5-triyl triacetate (compound 58, 62 mg, 0.11 mmol) in MeOH (10 ml) was treated with NaOMe (0.5 ml, 25% wt in MeOH). The reaction mixture was stirred at room temperature for 1 day. After reaction complete, the Amberlite® regin (IR120H+) was added to the solution and stirred 30 min. The resin was filter off, and the filtrate was evaporated in vacuo. The residue was purified with column chromatography (10% MeOH in CH$_2$Cl$_2$) to afford title compound (41 mg, 94%) as light yellow solid.

¹H NMR (400 MHz, CDCl₃) δ 8.97 (s, 1H), 7.31-7.21 (m, 3H), 4.87 (d, J=9.2 Hz, 1H), 4.21 (s, 2H), 4.07 (s, 3H), 3.76-3.69 (m, 4H), 3.68-3.66 (m, 1H), 3.55-3.51 (m, 1H); MH+ 398.

Example 92

(2S,3R,4R,5S,6R)-2-(3-((5-(Furan-2-yl)-1,3,4-thiadiazol-2-yl)methyl)naphthalene-1-yl)-6-(hydroxymethyl)-tetrahydro-2H-pyran-3,4,5-triol (compound 71a)

Step 1: Methyl 4-bromo-2-naphthoate (compound 65)

A solution of isoamyl nitrite (26.5 mL, 202 mmol) in DME (80 mL) and a solution of anthranilic acid (27.7 g, 202 mmol) in DME (80 mL) were both added in separate streams at matching rate over 30 min to a refluxing solution of bromo coumalate (compound 64, 15.7 g, 67.3 mmol) in DME (80 mL) in the presence of trichloroacetic acid (1.1 g, 6.7 mmol). The reaction mixture was heated under reflux for further 1.5 h after the end of addition. The mixture was cooled to ambient temperature and then diluted with toluene. The toluene solution was washed with aq. NaOH (2.0; N), 5% aq. sodium bisulfite, water, hydrochloric acid (2.0; N), and water prior to drying over anhydrous MgSO₄. Filtration and removal of the volatiles under reduced pressure left the crude product which was purified by column chromatography (5-30% EtOAc/hexanes) to yield the title compound (15.5 g, 87%) as a pale brown solid.

¹H NMR (400 MHz, CDCl₃) δ 8.57 (s, 1H), 8.37 (d, J=1.6 Hz, 1H), 8.27 (d, J=8.8 Hz, 1H), 7.95 (d, J=8.8 Hz, 1H), 7.71 (td, J=8.0, 1.6 Hz, 1H), 7.61 (td, J=8.0, 1.6 Hz, 1H), 3.99 (s, 3H);
MH+ 265.

Step 2: ((4-Bromonaphthalen-2-yl)methoxy)triisopropylsilane (compound 68a)

To a solution of methyl 4-bromo-2-naphthoate (compound 65a, 15.3 g, 60.8 mmol) in THF (120 mL) was added lithium borohydride (2.0 M in THF, 91.0 mL, 182 mmol). The reaction mixture was refluxed overnight. After cooling to 0° C., the reaction was quenched by addition of saturated ammonium chloride. The mixture was diluted with water and extracted with EtOAc. The organic layer was washed with brine, dried over anhydrous MgSO₄, filtered and evaporated in vacuo to yield a white solid, which was carried on to the next step without further purification.

To a solution of the (4-bromonaphthalen-2-yl)methanol in DMF (100 mL) was added imidazole (7.6 g, 112 mmol), DMAP (0.68 g, 5.6 mmol), and TIPSCl (18 mL, 84 mmol). The resulting solution was stirred at room temperature for 12 h, diluted with a saturated ammonium chloride and extracted with EtOAc. The organic layer was washed with water then brine, dried over anhydrous MgSO₄, filtered and concentrated in vacuo. The crude residue was purified by column chromatography (3-10% EtOAc/hexanes) to yield the title compound (19.6 g, 82%) as colorless oil.

¹H NMR (400 MHz, CDCl₃) δ 8.20 (d, J=8.0 Hz, 1H), 7.82-7.77 (m, 3H), 7.57-7.49 (m, 2H), 4.96 (s, 2H), 1.25-1.17 (m, 3H), 1.12 (d, J=6.8 Hz, 18H).

Step 3: 4-((2S,3S,4R,5R,6R)-3,4,5-Tris(benzyloxy)-6-(benzyloxy-methyl)-tetrahydro-2H-pyran-2-yl)naphthalen-2-yl)methanol (compound 69a)

To a solution of ((4-bromonaphthalen-2-yl)methoxy)triisopropylsilane (compound 68a, 18.0 g, 45.6 mmol) in THF (200 mL) at −78° C. under an atmosphere of nitrogen was added dropwise n-butyllithium (2.5 M in hexanes, 18.2 mL, 45.6 mmol), and the mixture was stirred for 1.5 h at the same temperature. Then a solution of 2,3,4,6-tetra-O-benzyl-D-glucopyranose (compound 2, 20.5 g, 38.0 mmol) in THF (100 mL) was added dropwise, and the mixture was stirred for 3 h at the same temperature. The reaction mixture was quenched by addition of saturated ammonium chloride and gradually raised to room temperature. The organic layer was separated and the aqueous layer was extracted with EtOAc. The combined organic layers were washed with brine, dried over anhydrous MgSO₄, filtered and concentrated in vacuo to yield a yellow oil, which was carried on to the next step without further purification.

To a stirred −50° C. solution of (3R,4S,5R,6R)-3,4,5-tris(benzyloxy)-6-(benzyloxymethyl)-2-(3-(hydroxymethyl)naphthalen-1-yl)-tetrahydro-2H-pyran-2-ol in dichloromethane (150 mL) was added Et₃SiH (12 mL, 76 mmol) followed by BF₃ diethyl etherate (9.5 mL, 76 mmol) at a rate such that the reaction temperature was maintained between −40 and −50° C. The solution was allowed to warm to −10° C. over 2 h prior to quenching with saturated potassium carbonate. After removal of organic volatiles under reduced pressure, the residue was partitioned between EtOAc and water. Following extraction of the aqueous layer with EtOAc, the combined organic layers were washed with water prior to drying over anhydrous MgSO₄. Filtration and concentration under reduced pressure yielded a yellow oil, which was carried on to the next step without further purification.

To a solution of triisopropyl((4-((2S,3S,4R,5R,6R)-3,4,5-tris(benzyloxy)-6-(benzyloxymethyl)-tetrahydro-2H-pyran-2-yl)naphthalen-2-yl)methoxy)silane in THF (100 mL) was added TBAF (1.0 M in THF, 114 mL, 114 mmol) and the reaction mixture stirred at ambient temperature for 2 h. After removal of organic volatiles under reduced pressure, the residue was partitioned between EtOAc and saturated ammonium chloride. The organic layer was separated and the aqueous layer was extracted with EtOAc. The combined organic layers were washed with brine, dried over anhydrous MgSO₄, filtered and concentrated in vacuo. The crude residue was purified on column chromatography (10-60% EtOAc/hexanes) to yield the title compound (21.2 g, 82%, β-anomer) as a white solid.

¹H NMR (400 MHz, CDCl₃) δ 8.38 (d, J=4.8 Hz, 1H), 7.88-7.81 (m, 3H), 7.62 (s, 1H), 7.51-7.39 (m, 3H), 7.36-7.24 (m, 13H), 7.11-6.99 (m, 3H), 6.49 (d, J=7.2 Hz, 2H), 4.99-4.82 (m, 7H), 4.71-4.54 (m, 3H), 4.18 (d, J=10.4 Hz, 1H), 3.98-3.69 (m, 6H), 3.41 (d, J=10.4 Hz, 1H);
MNH₄+698.

Step 4: 2-(4-((2S,3S,4R,5R,6R)-3,4,5-Tris(benzyloxy)-6-(benzyloxy-methyl)-tetrahydro-2H-pyran-2-yl)naphthalen-2-yl)acetic acid (compound 70a)

To a solution of 4-((2S,3S,4R,5R,6R)-3,4,5-tris(benzyloxy)-6-(benzyloxy-methyl)-tetrahydro-2H-pyran-2-yl)naphthalen-2-yl)methanol (compound 69a, 23.4 g, 34.3 mmol) in THF (120 mL) at 0° C. was added pyridine (0.14 mL, 1.7 mmol) and PBr₃ (1.45 mL, 15.4 mmol). The reaction was allowed to slowly warm to room temperature over 1 h and stirred for 1 h. The reaction mixture was diluted with EtOAc and washed with water then brine. The organic extract was dried over anhydrous MgSO₄, filtered, and evaporated in vacuo to yield a yellow solid, which was carried on to the next step without further purification.

To a solution of the (2S,3R,4R,5S,6S)-3,4,5-tris(benzyloxy)-2-(benzyloxymethyl)-6-(3-(bromomethyl)naphthalen- 1-yl)-tetrahydro-2H-pyran in EtOH (80 mL) and water (40 mL) was added potassium cyanide (4.24 g, 65.1 mmol). The reaction mixture was refluxed overnight. After cooling to room temperature, the mixture was diluted with water and extracted with EtOAc. The organic layer was washed with brine, dried over anhydrous MgSO$_4$, filtered and evaporated in vacuo. The crude residue was purified by column chromatography to yield 2-(4-((2S,3S,4R,5R,6R)-3,4,5-tris(benzyloxy)-6-(benzyloxy-methyl)-tetrahydro-2H-pyran-2-yl)naphthalen-2-yl)acetonitrile (10.9 g, 46%) as a white solid.

$^1$H NMR (400 MHz, DMSO-d$_6$) δ 8.35 (d, J=8.4 Hz, 1H), 7.96 (d, J=7.6 Hz, 1H), 7.89 (s, 1H), 7.61 (s, 1H), 7.56-7.46 (m, 2H), 7.31-7.19 (m, 15H), 7.05 (t, J=7.6 Hz, 1H), 6.96 (t, J=7.6 Hz, 2H), 6.43 (d, 2H), 5.12 (d, J=9.2 Hz, 1H), 4.83 (d, J=11.2 Hz, 1H), 4.80 (d, J=11.2 Hz, 1H), 4.78 (d, J=11.2 Hz, 1H), 4.60 (d, J=11.2 Hz, 1H), 4.53 (d, J=12.0 Hz, 1H), 4.47 (d, J=12.0 Hz, 1H), 4.20 (s, 2H), 4.13 (d, J=10.4 Hz, 1H), 3.90 (t, J=8.8 Hz, 1H), 3.83-3.68 (m, 5H), 3.43 (d, J=10.4 Hz, 1H); MNa+ 712.

To a solution of 2-(4-((2S,3S,4R,5R,6R)-3,4,5-tris(benzyloxy)-6-(benzyloxy-methyl)-tetrahydro-2H-pyran-2-yl)naphthalen-2-yl)acetonitrile (10.9 g, 15.8 mmol) in EtOH (60 mL) was added aq. NaOH solution (10 M, 35 mL, 350 mmol). The reaction mixture was refluxed overnight. After cooling to room temperature, hydrochloric acid (3.0 N) was added to neutralize the reaction mixture. The mixture was diluted with water and extracted with EtOAc. The organic layer was washed with water and brine prior to drying over anhydrous MgSO$_4$. Filtration and concentration under reduced pressure yielded the title compound (11.2 g, quantitative) as a white solid.

$^1$H NMR (400 MHz, CDCl$_3$) δ 8.37 (d, J=8.4 Hz, 1H), 7.83 (d, J=8.0 Hz, 1H), 7.74 (s, 1H), 7.58 (s, 1H), 7.49-7.38 (m, 2H), 7.36-7.23 (m, 15H), 7.05 (t, J=7.6 Hz, 1H), 6.98 (t, J=7.6 Hz, 2H), 6.50 (d, J=7.2 Hz, 2H), 4.97-4.89 (m, 4H), 4.70 (d, J=10.8 Hz, 1H), 4.65 (d, J=12.0 Hz, 1H), 4.54 (d, J=12.0 Hz, 1H), 4.12 (d, J=10.0 Hz, 1H), 3.98-3.85 (m, 4H), 3.80-3.74 (m, 3H), 3.70-3.67 (m, 1H), 3.42 (d, J=10.0 Hz, 1H)), MNa+ 731.

Step 5: (2S,3R,4R,5S,6R)-2-(3-((5-(Turan-2-yl)-1,3,4-thiadiazol-2-yl)methyl)naphthalen-1-yl)-6-(hydroxymethyl)-tetrahydro-2H-pyran-3,4,5-triol (compound 71a)

To a mixture of 2-(4-((2S,3S,4R,5R,6R)-3,4,5-Tris(benzyloxy)-6-(benzyloxy-methyl)-tetrahydro-2H-pyran-2-yl)naphthalen-2-yl)acetic acid (compound 70a, 709 mg, 1.00 mmol), 2-furoic hydrazide (164 mg, 1.30 mmol), EDCI (288 mg, 1.50 mmol), and HOBt hydrate (311 mg, 2.00 mmol) in DMF (10 mL) was added NMM (0.33 mL, 3.00 mmol). The resulting mixture was stirred at ambient temperature overnight. After dilution with EtOAc, the organic layer was subsequently washed with water, hydrochloric acid (1.0 N), saturated sodium bicarbonate, and brine prior to drying over anhydrous MgSO$_4$. Filtration and removal of the volatiles under reduced pressure yielded a glassy yellow amorphous solid, which was carried on to the next step without further purification.

To a solution of N'-(2-(4-((2S,3S,4R,5R,6R)-3,4,5-tris (benzyloxy)-6-(benzyloxymethyl)-tetrahydro-2H-pyran-2-yl)naphthalen-2-yl)acetyl)furan-2-carbohydrazide in THF (20 mL) was added Lawesson reagent (1.2 g, 3.0 mmol). The reaction was refluxed overnight. After cooling to room temperature, the reaction mixture was diluted with EtOAc and washed with saturated sodium bicarbonate. The organic layer was dried over anhydrous MgSO$_4$, filtered through a plug of silica gel and concentrated in vacuo. The resulting crude residue was carried on to the next step without further purification.

To a solution of 2-(furan-2-yl)-5-((4-((2S,3S,4R,5R,6R)-3,4,5-tris(benzyloxy)-6-(benzyloxymethyl)-tetrahydro-2H-pyran-2-yl)naphthalen-2-yl)methyl)-1,3,4-thiadiazole in acetonitrile (5 mL) was added TMSI (5 mL). The resulting reaction mixture was heated to 50° C. overnight. After cooling to 0° C., the reaction quenched with methanol and concentrated in vacuo. The resulting crude residue was purified by reverse phase preparative HPLC to yield the title compound (232 mg, 51%) as a white solid.

$^1$H NMR (400 MHz, DMSO-d$_6$) δ 8.22-8.19 (m, 1H), 7.92 (d, J=1.6 Hz, 1H), 7.87-7.84 (m, 1H), 7.80 (s, 1H), 7.56 (d, J=1.6 Hz, 1H), 7.48-7.44 (m, 2H), 7.22 (d, J=2.8 Hz, 1H), 6.70 (dd, J=3.6, 2.0 Hz, 1H), 4.96 (d, J=3.6 Hz, 1H), 4.95 (d, J=3.2 Hz, 1H), 4.76-4.73 (m 2H), 4.63 (s, 2H), 4.38 (t, J=5.6 Hz, 1H), 3.70-3.66 (m, 1H), 3.56-3.50 (m, 1H), 3.48-3.41 (m, 1H), 3.40-3.34 (m, 2H), 3.27-3.23 (m, 1H); MH+ 455.

Example 93

(2S,3R,4R,5S,6R)-2-(3-((5-(Furan-2-yl)-1,3,4-thiadiazol-2-yl)methyl)-4-methoxynaphthalen-1-yl)-6-(hydroxymethyl)-tetrahydro-2H-pyran-3,4,5-triol (compound 71b)

Step 1: 4-Bromo-1-hydroxy-2-naphthoic acid (compound 67)

Bromine (6.1 mL, 120 mmol) was added to a solution of 1-hydroxy-2-naphthoic acid (compound 66, 18.9 g, 100 mmol) in glacial acetic acid (250 mL). The mixture was stirred at room temperature overnight. The resulting solid was filtered and dried in vacuo to yield the title compound (24.6 g, 92%) as a white solid.

$^1$H NMR (400 MHz, DMSO-d$_6$) δ 8.31 (d, J=8.4 Hz, 1H), 8.04 (d, J=8.4 Hz, 1H), 7.96 (s, 1H), 7.82 (t, J=7.2 Hz, 1H), 7.67 (t, J=7.2 Hz, 1H); MH+ 267.

Step 2: Methyl 4-bromo-1-methoxy-2-naphthoate (compound 65b)

A mixture of 4-bromo-1-hydroxy-2-naphthoic acid (compound 67, 24.7 g, 92.2 mmol), dimethyl sulfate (21.8 mL, 231 mmol), and K$_2$CO$_3$ (31.9 g, 231 mmol) in acetone (200 mL) was refluxed overnight. The solid was filtered, and the filtrate was condensed to give a solid residue, which was recrystallized from EtOAc/hexanes to afford the title compound (21.4 g, 78%) as a white solid.

$^1$H NMR (400 MHz, DMSO-d$_6$) δ 8.27 (d, J=8.4 Hz, 1H), 8.14 (d, J=8.4 Hz, 1H), 8.07 (s, 1H), 7.86-7.82 (m, 1H), 7.77-7.72 (m, 1H), 3.96 (s, 3H), 3.89 (s, 3H); MH+ 295.

Step 3: ((4-Bromo-1-methoxynaphthalen-2-yl)methoxy)-triisopropylsilane (compound 68b)

With similar method described in Step 2 of Example 92, methyl 4-bromo-1-methoxy-2-naphthoate (compound 65b, 16.2 g, 54.8 mmol) was converted to title compound (21.3 g, 92%) as a colorless oil.

$^1$H NMR (400 MHz, CDCl$_3$) δ 8.21-8.19 (m, 1H), 8.10-8.08 (m, 1H), 8.01 (s, 1H), 7.59-7.53 (m, 2H), 5.03 (s, 2H), 3.92 (s, 3H), 1.27-1.18 (m, 3H), 1.12 (d, J=6.8 Hz, 18H).

Step 4: (1-Methoxy-4-((2S,3S,4R,5R,6R)-3,4,5-tris (benzyloxy)-6-(benzyloxymethyl)-tetrahydro-2H-pyran-2-yl)naphthalen-2-yl)methanol (compound 69b)

With similar method described in Step 3 of Example 92, ((4-bromo-1-methoxynaphthalen-2-yl)methoxy)-triisopropylsilane (compound 68b, 21.3 g, 50.3 mmol) and 2,3,4,6-tetra-O-benzyl-D-glucopyranose (compound 2, 22.6 g, 41.9 mmol) were converted to title compound (25.3 g, 85%) as a white solid.

$^1$H NMR (400 MHz, CDCl$_3$) δ 8.40 (d, J=8.4 Hz, 1H), 8.17 (d, J=8.4 Hz, 1H), 7.64 (s, 1H), 7.55-7.23 (m, 17H), 7.09-6.99 (m, 3H), 6.52 (d, J=7.2 Hz, 2H), 4.99-4.86 (m, 7H), 4.71-4.53 (m, 3H), 4.22 (d, J=10.0 Hz, 1H), 3.97 (s, 3H), 3.95-3.68 (m, 6H), 3.47 (d, J=10.0 Hz, 1H);
MNa+ 733.

Step 5: 2-(1-Methoxy-4-((2S,3S,4R,5R,6R)-3,4,5-tris(benzyloxy)-6-(benzyloxymethyl)-tetrahydro-2H-pyran-2-yl)naphthalen-2-yl)acetic acid (compound 70b)

With similar method described in Step 4 of Example 92, (1-methoxy-4-((2S,3S,4R,5R,6R)-3,4,5-tris(benzyloxy)-6-(benzyloxymethyl)-tetrahydro-2H-pyran-2-yl)naphthalen-2-yl)methanol (compound 69b, 25.3 g, 35.5 mmol) was converted to title compound (11.5 g, 44%) as a white solid.

$^1$H NMR (400 MHz, DMSO-d$_6$) δ 12.39 (br, 1H), 8.35 (d, J=8.4 Hz, 1H), 8.06 (d, J=8.0 Hz, 1H), 7.57-7.53 (m 2H), 7.45 (t, J=7.45 Hz, 1H), 7.31-7.15 (m, 15H), 7.04 (t, J=7.6 Hz, 1H), 6.97 (t, J=7.6 Hz, 2H), 6.48 (d, J=7.6 Hz, 2H), 5.01 (br, 1H), 4.83 (d, J=11.2 Hz, 1H), 4.79 (d, J=11.2 Hz, 1H), 4.77 (d, J=10.8 Hz, 1H), 4.59 (d, J=10.8 Hz, 1H), 4.51 (d, J=12.0 Hz, 1H), 4.45 (d, J=12.0 Hz, 1H), 4.11 (d, J=10.4 Hz, 1H), 3.79 (s, 3H), 3.89-3.67 (m, 8H), 3.52 (d, J=10.4 Hz, 1H);
MNa+ 761.

Step 6: (2S,3R,4R,5S,6R)-2-(3-((5-(Furan-2-yl)-1,3,4-thiadiazol-2-yl)methyl)-4-methoxynaphthalen-1-yl)-6-(hydroxymethyl)-tetrahydro-2H-pyran-3,4,5-triol (compound 71b)

With similar method described in Step 5 of Example 91, 2-(1-methoxy-4-((2S,3S,4R,5R,6R)-3,4,5-tris(benzyloxy)-6-(benzyloxymethyl)-tetrahydro-2H-pyran-2-yl)naphthalen-2-yl)acetic acid (compound 70b, 1.00 g, 1.35 mmol) was converted to title compound (78 mg, 16%) as a yellow solid.

$^1$H NMR (400 MHz, DMSO-d$_6$) δ 8.24 (d, J=8.0 Hz, 1H), 8.05 (dd, J=7.6, 2.4 Hz, 1H), 7.91 (d, J=2.4 Hz, 1H), 7.55-7.51 (m, 3H), 7.21 (d, J=3.6 Hz, 1H), 6.69 (dd, J=3.6, 2.0 Hz, 1H), 4.99-4.97 (m, 2H), 4.79 (d, J=5.6 Hz, 1H), 4.70 (d, J=9.6 Hz, 1H), 4.63 (d, J=12.0 Hz, 1H), 4.60 (d, J=12.0 Hz, 1H), 4.37 (t, J=5.6 Hz, 1H), 3.87 (s, 3H), 3.70-3.65 (m, 1H), 3.57-3.50 (m, 1H), 3.48-3.40 (m, 1H), 3.40-3.33 (m, 2H), 3.27-3.23 (m, 1H);
MH+ 485.

Example 94

(2S,3R,4R,5S,6R)-2-(3-((5-(Furan-2-yl)-1,3,4-thiadiazol-2-yl)methyl)-4-hydroxynaphthalen-1-yl)-6-(hydroxymethyl)-tetrahydro-2H-pyran-3,4,5-triol (compound 71c)

To a solution (2S,3R,4R,5S,6R)-2-(3-((5-(Furan-2-yl)-1,3-thiadiazol-2-yl)methyl)-4-methoxynaphthalen-1-yl)-6-(hydroxymethyl)-tetrahydro-2H-pyran-3,4,5-triol (compound 71b, 50 mg, 0.10 mmol) in CH$_2$Cl$_2$ (5 mL) at 0° C. was added boron tribromide (1.0 M in CH$_2$Cl$_2$, 0.52 mL, 0.52 mmol). The resulting mixture was stirred with gradual warming to ambient temperature over 2 h and re-cooled to 0° C. The mixture was quenched with MeOH and concentrated in vacuo. The resulting crude residue was purified by reverse phase preparative HPLC to yield the title compound (36 mg, 74%) as a white solid.

$^1$H NMR (400 MHz, DMSO-d$_6$) δ 9.71 (s, 1H), 8.24-8.21 (m, 1H), 8.15-8.13 (m, 1H), 7.89 (d, J=1.2 Hz, 1H), 7.47-7.40 (m, 3H), 7.18 (d, J=3.6 Hz, 1H), 6.67 (dd, J=3.6, 2.0 Hz, 1H), 4.92 (br, 1H), 4.69 (br, 1H), 4.63 (d, J=10.0 Hz, 1H), 4.59 (d, J=15.6 Hz, 1H), 4.55 (d, J=15.6 Hz, 1H), 4.36 (br, 1H), 3.66 (d, J=10.4 Hz, 1H), 3.54 (t, J=8.8 Hz, 1H), 3.43 (t, J=5.6 Hz, 1H), 3.40-3.21 (m, 4H);
MH+ 471.

Example 95

(2S,3R,4R,5S,6R)-2-(4-((5-(Furan-2-yl)-1,3,4-thiadiazol-2-yl)methyl)naphthalen-2-yl)-6-(hydroxymethyl)-tetrahydro-2H-pyran-3,4,5-triol (compound 79)

Step 1: 3-Bromo-1,8-naphthalic anhydride (compound 74)

1,8-Naphthalic anhydride (compound 73, 100 g, 505 mmol) was slurried in c-nitric acid (70%, 2.0 L) and heated to 50° C. Bromine (19.4 mL, 379 mmol) was added evenly over 10 min, and the resulting solution was held at 50° C. for 4 h before cooling to 0° C. The resulting solid was isolated by filtration and dried in vacuo to yield the title compound (23.8 g, 17%) as a white solid.

$^1$H NMR (400 MHz, DMSO-d$_6$) δ 8.85 (s, 1H), 8.53 (d, J=7.6 Hz, 1H), 8.48 (d, J=7.6 Hz, 2H), 7.95 (t, J=7.8 Hz, 1H);
$^{13}$C NMR (100 MHz, DMSO-d$_6$) δ 160.12, 159.57, 136.73, 134.31, 133.88, 132.65, 132.61, 128.68, 128.32, 121.33, 120.07, 119.38;
MH+ 277.

Step 2: 3-Bromo-1-naphthoic acid (compound 75)

To a mixture of 3-bromo-1,8-naphthalic anhydride (compound 74, 22.8 g, 82.4 mmol) and sodium hydroxide (13.2 g, 330 mmol) in water (500 mL) was added a solution of mercury(II) oxide (23.2 g, 107 mmol) in water (70 mL) and glacial acetic acid (24 mL). The reaction mixture was heated at reflux for 4 days and then cooled to room temperature. The resulting solid was filtered and dried in vacuo.

The organo-Hg intermediates were slurrified in hydrochloric acid (5.0 N, 650 mL) and the reaction mixture heated to reflux for a further 4 h and then cooled to ambient temperature. The resulting solid was filtered and dried in vacuo.

The crude 3-bromo-1-naphthoic acid was recrystallized from glacial acetic acid with hot filtration to remove some insoluble material to afford the title compound (12.0 g, 58%) as a white solid.

$^1$H NMR (400 MHz, DMSO-d$_6$) δ 13.46 (br, 1H), 8.75 (d, J=8.4 Hz, 1H), 8.43 (d, J=2.0 Hz, 1H), 8.11 (d, J=2.0 Hz, 1H), 7.98 (d, J=7.6 Hz, 1H), 7.67-7.58 (m, 2H); $^{13}$C NMR (100 MHz, DMSO-d$_6$) δ 167.25, 134.78, 134.37, 131.96, 130.05, 129.13, 128.08, 127.88, 127.36, 125.58, 117.57;
MH+ 251.

Step 3: ((3-Bromonaphthalen-1-yl)methoxy)triisopropylsilane (compound 76)

To a solution of 3-bromo-1-naphthoic acid (compound 75, 11.9 g, 47.4 mmol) in THF (95 mL) at 0° C. was added borane dimethyl sufide complex (19.0 mL, 190 mmol). The resulting mixture was stirred with gradual warming to ambient temperature over 12 h, re-cooled to 0° C., and quenched with MeOH and then water. The mixture was extracted with EtOAc. The organic layer was washed with brine, dried over anhydrous $MgSO_4$, filtered and evaporated in vacuo to yield a white solid, which was carried on to the next step without further purification.

To a solution of (3-bromonaphthalen-1-yl)methanol in DMF (100 mL) was added imidazole (6.4 g, 93 mmol), DMAP (0.57 g, 4.7 mmol), and TIPSCl (15 mL, 70 mmol). The resulting solution was stirred at room temperature for 12 h, diluted with a saturated ammonium chloride and extracted with EtOAc. The organic layer was washed with water then brine, dried over anhydrous $MgSO_4$, filtered and concentrated in vacuo. The crude residue was purified by column chromatography (3-10% EtOAc/hexanes) to yield the title compound (17.9 g, 96%) as a colorless oil.

$^1$H NMR (400 MHz, $CDCl_3$) δ 7.92 (s, 1H), 7.89-7.86 (m, 1H), 7.78-7.76 (m, 2H), 7.52-7.49 (m, 2H), 5.27 (s, 2H), 1.29-1.20 (m, 3H), 1.14 (d, J=6.8 Hz, 18H).

Step 4: (3-((3S,4R,5R,6R)-3,4,5-Tris(benzyloxy)-6-(benzyloxymethyl)-tetrahydro-2H-pyran-2-yl)naphthalen-1-yl)methanol (compound 77)

With similar method described in Step 3 of Example 92, ((3-bromonaphthalen-1-yl)methoxy)triisopropylsilane (compound 76, 18.0 g, 45.6 mmol) and 2,3,4,6-tetra-O-benzyl-D-glucopyranose (2, 20.5 g, 38.0 mmol) were converted to title compound (23.3 g, 90%, ca. 2:1 mixture of anomers (13:0) as a white solid.

$^1$H NMR (400 MHz, $CDCl_3$) β-anomer: δ 7.89-7.81 (m, 3H), 7.57-7.51 (m, 3H), 7.38-7.20 (m, 15H), 7.14-7.10 (m, 1H), 7.04 (t, J=7.6 Hz, 2H), 6.78 (d, J=6.8 Hz, 1H), 5.10-4.40 (m, 10H), 3.90-3.72 (m, 5H), 3.68-3.65 (m, 1H), 3.58 (t, J=8.8 Hz, 1H);

α-anomer: δ 8.26 (s, 1H), 8.15-8.08 (m, 3H), 7.86-7.81 (m, 2H), 7.38-7.20 (m, 18H), 5.32 (d, J=4.4 Hz, 1H), 5.10-4.40 (m, 10H), 4.18-4.06 (m, 2H), 3.90-3.72 (m, 3H), 3.68-3.65 (m, 1H);

MNa+ 703.

Step 5: 2-(3-((2S,3S,4R,5R,6R)-3,4,5-Tris(benzyloxy)-6-(benzyloxy-methyl)-tetrahydro-2H-pyran-2-yl)naphthalen-1-yl)acetic acid (compound 78)

Except for resolution of 2-(3-((2S,3S,4R,5R,6R)-3,4,5-tris(benzyloxy)-6-(benzyloxy-methyl)-tetrahydro-2H-pyran-2-yl)naphthalen-1-yl)acetonitrile by recrystallization from ethanol, the procedure described in Step 4 of Example 92 was applied to (3-((3S,4R,5R,6R)-3,4,5-tris(benzyloxy)-6-(benzyloxymethyl)-tetrahydro-2H-pyran-2-yl)naphthalen-1-yl)methanol (compound 62, 23.4 g, 34.3 mmol) providing the title compound (4.86 g, 20%) as a white solid.

$^1$H NMR (400 MHz, DMSO-$d_6$) δ 12.38 (br, 1H), 7.94-7.90 (m, 2H), 7.85 (s, 7.85), 7.54-7.51 (m, 3H), 7.30-7.23 (m, 13H), 7.19-7.16 (m, 2H), 7.09-7.05 (m, 1H), 7.01 (t, J=7.2 Hz, 2H), 6.73 (d, J=7.2 Hz, 2H), 4.83 (d, J=11.2 Hz, 1H), 4.79 (d, J=11.2 Hz, 1H), 4.75 (d, J=10.8 Hz, 1H), 4.57 (d, J=11.2 Hz, 1H), 4.53 (d, J=12.0 Hz, 1H), 4.47 (d, J=12.0 Hz, 1H), 4.43 (d, J=9.6 Hz, 1H), 4.26 (d, J=10.8 Hz, 1H), 4.03 (s, 2H), 3.79 (t, J=8.8 Hz, 1H), 3.72-3.58 (m, 6H);

MNa+ 731.

Step 6: (2S,3R,4R,5S,6R)-2-(4-((5-(furan-2-yl)-1,3,4-thiadiazol-2-yl)methyl)naphthalen-2-yl)-6-(hydroxymethyl)-tetrahydro-2H-pyran-3,4,5-triol (compound 79)

With similar method described in Step 5 of Example 92, 2-(3-((2S,3S,4R,5R,6R)-3,4,5-Tris(benzyloxy)-6-(benzyloxy-methyl)-tetrahydro-2H-pyran-2-yl)naphthalen-1-yl) acetic acid (compound 78, 709 mg, 1.00 mmol) was converted to title compound (209 mg, 46%) as pale yellow solid.

$^1$H NMR (400 MHz, DMSO-$d_6$) δ 8.22-8.19 (m, 1H), 7.92 (d, J=1.6 Hz, 1H), 7.87-7.84 (m, 1H), 7.80 (s, 1H), 7.56 (d, J=1.6 Hz, 1H), 7.48-7.44 (m, 2H), 7.22 (d, J=2.8 Hz, 1H), 6.70 (dd, J=3.6, 2.0 Hz, 1H), 4.96 (d, J=3.6 Hz, 1H), 4.95 (d, J=3.2 Hz, 1H), 4.76-4.73 (m 2H), 4.63 (s, 2H), 4.38 (t, J=5.6 Hz, 1H), 3.70-3.66 (m, 1H), 3.56-3.50 (m, 1H), 3.48-3.41 (m, 1H), 3.40-3.34 (m, 2H), 3.27-3.23 (m, 1H);

MH+ 455.

Example 96

(2S,3R,4R,5S,6R)-2-(2,4-Dichloro-5-((5-(furan-2-yl)-1,3,4-thiadiazol-2-yl)methyl)phenyl)-6-(hydroxymethyl)-tetrahydro-2H-pyran-3,4,5-triol (compound 85)

Step 1: 5-Bromo-2,4-dichlorobenzoic acid (compound 81)

To a solution of 2,4-dichlorobenzoic acid (compound 80, 25.0 g, 131 mmol) in chlorosulfonic acid (100 mL) was added bromine (3.4 mL, 65 mmol) and sulfur (0.20 g, 6.6 mmol). The reaction mixture was stirred at 70° C. overnight and then cooled to ambient temperature. The reaction mixture was poured into iced water. The resulting solid was isolated by filtration and dried in vacuo to yield title compound (32.9 g, 93%) as pale brown solid.

$^1$H NMR (400 MHz, $CDCl_3$) δ 8.30 (s, 1H), 7.63 (s, 1H); MH+ 269.

Step 2: (5-Bromo-2,4-dichlorobenzyloxy)triisopropylsilane (compound 82)

With similar method described in Step 3 of Example 95, 5-bromo-2,4-dichlorobenzoic acid (compound 81, 32.9 g, 122 mmol) was converted to title compound (41.7 g, 83%) as a colorless oil.

$^1$H NMR (400 MHz, $CDCl_3$) δ 7.48 (s, 1H), 7.44 (s, 1H), 4.85 (s, 2H), 1.25-1.17 (m, 3H), 1.11 (d, J=6.8 Hz, 18H).

Step 3: (2,4-Dichloro-5-((3S,4R,5R,6R)-3,4,5-tris(benzyloxy)-6-(benzyloxymethyl)-tetrahydro-2H-pyran-2-yl)phenyl)methanol (compound 83)

With similar method described in Step 3 of Example 92, (5-bromo-2,4-dichlorobenzyloxy)triisopropylsilane (compound 82, 41.7 g, 101 mmol) and 2,3,4,6-tetra-O-benzyl-D-glucopyranose (compound 2, 45.4 g, 84.0 mmol) were converted to title compound (47.6 g, 81%, ca. 8:1 mixture of anomers (13:0) as a white solid.

¹H NMR (400 MHz, CDCl₃) δ 7.51 (s, 1H), 7.37-7.14 (m, 19H), 6.98-6.90 (m, 2H), 4.96-4.46 (m, 9H), 4.15-4.09 (m, 3H), 3.87 (t, J=8.8 Hz, 1H), 3.78-3.70 (m, 3H), 3.63-3.57 (m, 2H);
MNa+ 721.

Step 4: 2-(2,4-Dichloro-5-((3S,4R,5R,6R)-3,4,5-Tris (benzyloxy)-6-(benzyloxymethyl)-tetrahydro-2H-pyran-2-yl)phenyl)acetic acid (compound 84)

With similar method described in Step 4 of Example 92, (compound 2,4-dichloro-5-((3S,4R,5R,6R)-3,4,5-tris(benzyloxy)-6-(benzyloxymethyl)-tetrahydro-2H-pyran-2-yl) phenyl)methanol (compound 83, 47.6 g, 68.0 mmol) was converted to title compound (32.2 g, 65%, ca. 8:1 mixture of anomers (β:α)) as a white solid.
¹H NMR (400 MHz, CDCl₃) δ 7.39 (s, 1H), 7.37 (s, 1H), 7.33-7.25 (m, 13H), 7.19-7.12 (m, 5H), 6.95-6.93 (m, 2H), 4.94 (d, J=10.8 Hz, 1H), 4.89 (d, J=10.8 Hz, 1H), 4.86 (d, J=10.8 Hz, 1H), 4.74 (d, J=9.6 Hz, 1H), 4.62 (d, J=10.8 Hz, 1H), 4.60 (d, J=12.0 z, 1H), 4.52 (d, J=12.0 Hz, 1H), 4.45 (d, J=10.8 Hz, 1H), 4.04 (d, J=10.8 Hz, 1H), 3.84 (t, J=8.8 Hz, 1H), 3.78-3.69 (m, 5H), 3.61-3.54 (m, 2H);
MNa+ 749.

Step 5: (2S,3R,4R,5S,6R)-2-(2,4-Dichloro-5-((5-(furan-2-yl)-1,3,4-thiadiazol-2-yl)methyl)phenyl)-6-(hydroxymethyl)-tetrahydro-2H-pyran-3,4,5-triol (compound 85)

With similar method described in Step 5 of Example 92, 2-(2,4-dichloro-5-((3S,4R,5R,6R)-3,4,5-Tris(benzyloxy)-6-(benzyloxymethyl)-tetrahydro-2H-pyran-2-yl)phenyl)acetic acid (compound 84, 1.00 g, 1.38 mmol) was converted to title compound (170 mg, 26%) as a white solid. The small amount of the α-anomer was removed by reverse phase preparative HPLC.
¹H NMR (400 MHz, DMSO-d₆) δ 7.89 (d, J=2.0 Hz, 1H), 7.67 (s, 1H), 7.57 (s, 1H), 7.20 (d, J=3.6 Hz, 1H), 6.67 (dd, J=3.6, 2.0 Hz, 1H), 5.00-4.87 (m, 3H), 4.55 (s, 2H), 4.43-4.38 (m, 2H), 3.64 (dd, J=12.0, 4.0 Hz, 1H), 3.39 (quint, J=5.6 Hz, 1H), 3.30-3.12 (m, 4H);
¹³C NMR (100 MHz, DMSO-d₆) δ 167.11, 158.80, 146.65, 144.92, 137.77, 134.41, 134.14, 133.40, 132.43, 129.73, 113.24, 112.67, 82.19, 78.66, 77.32, 74.77, 70.64, 61.65, 33.33;
MH+ 473.

Example 97

(2S,3R,4R,5S,6R)-2-(4-Chloro-5-((5-(furan-2-yl)-1, 3,4-thiadiazol-2-yl)methyl)-2-methoxyphenyl)-6-(hydroxymethyl)-tetrahydro-2H-pyran-3,4,5-triol (compound 86)

Step 1: 5-Bromo-2-chloro-4-hydroxybenzonitrile (compound 87)

To a solution of 2-chloro-4-hydroxybenzonitrile (compound 86, 10.0 g, 65.1 mmol) in acetonitrile (200 mL) was added triflic acid (10.0 mL, 71.6 mmol) and NBS (16.2 g, 91.2 mmol) at −30° C. The solution was allowed to warm up to room temperature and stirred overnight prior to quenching with saturated sodium bisulfite. The mixture was diluted with water and extracted with EtOAc. The organic layer was dried over anhydrous MgSO₄, filtered and concentrated in vacuo. The crude residue was purified by column chromatography (5-40% EtOAc/hexanes) to yield title compound (9.80 g, 65%) as a white solid.
¹H NMR (400 MHz, CD₃OD) δ 7.91 (s, 1H), 7.03 (s, 1H); MH+ 232.

Step 2: 5-Bromo-2-chloro-4-methoxybenzoic acid (compound 88)

A mixture of 5-bromo-2-chloro-4-hyroxybenzonitrile (compound 87, 38.1 g, 164 mmol), dimethyl sulfate (20.1 mL, 213 mmol), and lithium hydroxide monohydrate (8.93 g, 213 mmol) in THF (500 mL) was refluxed overnight. The mixture was cooled to ambient temperature and then diluted with EtOAc. The EtOAc solution was washed with water and brine prior to drying over anhydrous MgSO₄. Filtration and removal of the voletiles under reduced pressure left the crude product which was purified by column chromatography (5-40% EtOAC/hexanes) to yield 5-bromo-2-chloro-4-methoxybenzonitrile (30.7 g, 76%) as a white solid.
¹H NMR (400 MHz, CDCl₃) δ 7.81 (s, 1H), 6.99 (s, 1H), 3.97 (s, 3H);
MH+ 246.
A mixture of 5-bromo-2-chloro-4-methoxybenzonitrile (30.7 g, 124 mmol) and NaOH (127 g, 3.11 mol) in EtOH (500 mL) and water (250 mL) was refluxed overnight. After cooling to room temperature, EtOH was removed under reduced pressure. The mixture was diluted with water and neutralized with hydrochloric acid (3.0 N). The resulting solid was filtered and dried in vacuo to give title compound (32.9 g, quantitative) as a white solid.
¹H NMR (400 MHz, CDCl₃) δ 8.12 (s, 1H), 6.94 (s, 1H), 3.95 (s, 3H);
MH+ 265.

Step 3: (5-Bromo-2-chloro-4-methoxybenzyloxy) triisopropylsilane (compound 89)

With similar method described in Step 3 of Example 95, 5-bromo-2-chloro-4-methoxybenzoic acid (compound 88, 23.3 g, 87.8 mmol) was converted to title compound (27.2 g, 76%) as a colorless oil.
¹H NMR (400 MHz, CDCl₃) δ 7.79 (s, 1H), 6.84 (s, 1H), 4.72 (s, 2H), 3.88 (s, 3H), 1.25-1.17 (m, 3H), 1.11 (d, J=6.8 Hz, 18H).

Step 4: (2-Chloro-4-methoxy-5-((3S,4R,5R,6R)-3,4, 5-tris(benzyloxy)-6-(benzyloxymethyl)-tetrahydro-2H-pyran-2-yl)phenyl)methanol (compound 90)

With similar method described in Step 3 of Example 92, (5-bromo-2-chloro-4-methoxybenzyloxy)triisopropylsilane (compound 89, 27.2 g, 66.7 mmol) and 2,3,4,6-tetra-O-benzyl-D-glucopyranose (compound 2, 30.0 g, 55.6 mmol) were converted to title compound (22.6 g, 59%, ca. 8:1 mixture of anomers (13:0) as a white solid.
¹H NMR (400 MHz, CDCl₃) δ 7.45 (s, 1H), 7.34-7.13 (m, 19H), 6.88-6.85 (m, 2H), 4.97-4.49 (m, 9H), 4.38-4.10 (m, 2H) 4.04 (d, J=10.8 Hz, 1H), 3.83 (t, J=8.4 Hz, 1H), 3.78-3.71 (m, 3H), 3.76 (s, 3H), 3.65-3.58 (m, 2H);
MNa+ 717.

Step 5: 2-(2-Chloro-4-methoxy-5-((2S,3S,4R,5R, 6R)-3,4,5-tris(benzyloxy)-6-(benzyloxymethyl)-tetrahydro-2H-pyran-2-yl)phenyl)acetic acid (compound 91)

Except for resolution of 2-(2-chloro-4-methoxy-5-((2S, 3S,4R,5R,6R)-3,4,5-tris(benzyloxy)-6-(benzyloxymethyl)- tetrahydro-2H-pyran-2-yl)phenyl)acetonitrile by recrystallization from ethanol, the procedure described in Step 4 of Example 92 was applied to (2-chloro-4-methoxy-5-((3S,4R,5R,6R)-3,4,5-tris(benzyloxy)-6-(benzyloxymethyl)-tetrahydro-2H-pyran-2-yl)phenyl)methanol (compound 90, 22.6 g, 32.5 mmol) providing the title compound (8.66 g, 37%) as a white solid.

$^1$H NMR (400 MHz, CDCl$_3$) δ 7.34-7.19 (m, 14H), 7.17-7.10 (m, 5H), 6.88-6.85 (m, 2H), 6.79 (s, 1H), 4.94 (d, J=11.2 Hz, 1H), 4.87 (d, J=11.2 Hz, 1H), 4.82 (d, J=11.2 Hz, 1H), 4.70 (br, 1H), 4.55-4.52 (m, 2H), 4.46 (d, J=10.8 Hz, 1H), 4.41 (d, J=10.8 Hz, 1H), 3.98 (d, J=11.2 Hz, 1H), 3.79 (d, J=8.8 Hz, 1H), 3.74 (d, J=10.0 Hz, 1H), 3.71-3.61 (m, 5H), 3.63 (s, 3H), 3.54-3.52 (m, 1H);

MNa+ 745.

Step 6: (2S,3R,4R,5S,6R)-2-(4-Chloro-5-((5-(furan-2-yl)-1,3,4-thiadiazol-2-yl)methyl)-2-methoxyphenyl)-6-(hydroxymethyl)-tetrahydro-2H-pyran-3,4,5-triol (compound 92)

With similar method described in Step 5 of Example 92, 2-(2-chloro-4-methoxy-5-((2S,3S,4R,5R,6R)-3,4,5-tris(benzyloxy)-6-(benzyloxymethyl)-tetrahydro-2H-pyran-2-yl)phenyl)acetic acid (compound 91, 1.00 g, 1.38 mmol) was converted to title compound (277 mg, 43%) as a white solid.

$^1$H NMR (400 MHz, DMSO-d$_6$) δ 7.56 (s, 1H), 7.48 (s, 1H), 6.98 (d, J=3.2 Hz, 1H), 3.79 (s, 1H), 6.46-6.45 (m, 1H), 5.44 (br, 1H), 5.20 (br, 1H), 4.72-4.67 (m, 2H), 4.19 (d, J=15.6 Hz, 1H), 4.13 (d, J=15.6 Hz, 1H), 4.02 (br, 1H), 3.89-3.70 (m, 4H), 3.69 (s, 3H), 3.46 (d, J=9.2 Hz, 1H), 2.09 (s, 1H);

MH+ 469.

Experimental Example 1

Cloning and Cell Line Construction for Human SGLT2

Human SGLT2 (hSGLT2) gene was amplified by PCR from cDNA-Human Adult Normal Tissue Kidney (Invitrogen, Carlsbad, Calif.). The hSGLT2 sequence was cloned into pcDNA3.1(+) for mammalian expression and were stably transfected into Chinese hamster ovary (CHO) cells. SGLT2-expressing clones were selected based on resistance to G418 antibiotic (Geneticin®, Invitrogen, Carlsbad, Calif.) and activity in the $^{14}$C-α-methyl-D-glucopyranoside ($^{14}$C-AMG) uptake assay.

Experimental Example 2

Inhibitory Effects on Human SGLT2 Activities

For sodium-dependent glucose transport assay, cells expressing hSGLT2 were seeded into a 96-well culture plate at a density of $5 \times 10^4$ cells/well in RPMI medium 1640 containing 10% fetal bovine serum. The cells were used 1 day after plating. They were incubated in pretreatment buffer (10 mM HEPES, 5 mM Tris, 140 mM choline chloride, 2 mM KCl, 1 mM CaCl$_2$, and 1 mM MgCl$_2$, pH 7.4) at 37° C. for 10 min. They were then incubated in uptake buffer (10 mM HEPES, 5 mM Tris, 140 mM NaCl, 2 mM KCl, 1 mM CaCl$_2$, 1 mM MgCl$_2$, and 1 mM $^{14}$C-nonlabeled AMG pH 7.4) containing $^{14}$C-labeled (8 uM) and inhibitor or dimethyl sulfoxide (DMSO) vehicle at 37° C. for 2 h. Cells were washed twice with washing buffer (pretreatment buffer containing 10 mM AMG at room temperature) and then the radioactivity was measured using a liquid scintillation counter. IC$_{50}$ was determined by nonlinear regression analysis using GraphPad PRISM [Kenji Katsuno, et al (2007), Sergliflozin, a Novel Selective Inhibitor of Low-Affinity Sodium Glucose Cotransporter (SGLT2), Validates the Critical Role of SGLT2 in Renal Glucose Reabsorption and Modulates Plasma Glucose Level., *J Pharmacol Exp Ther.*, 320: 323-330., Songping Han, et al (2008), Dapagliflozin, a selective SGLT2 inhibitor, improves glucose homeostasis in normal and diabetic rats., *Diabetes*, 57:1723-9.]

TABLE 1

| Exam. No. | Structure | Name | IC$_{50}$ (nM) |
|---|---|---|---|
| 1 | 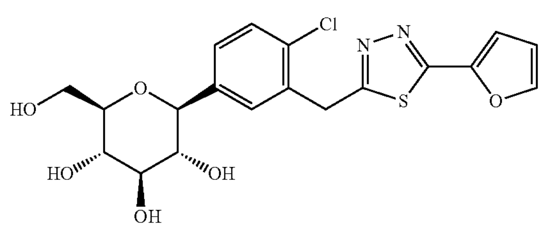 | (2S,3R,4R,5S,6R)-2-(4-Chloro-3-((5-(furan-2-yl)-1,3,4-thiadiazol-2-yl)methyl)phenyl)-6-(hydroxymethyl)-tetrahydro-2H-pyran-3,4,5-triol | 7.03 |
| 2 | | (2S,3R,4R,5S,6R)-2-(4-Chloro-3-((5-(5-methylfuran-2-yl)-1,3,4-thiadiazol-2-yl)methyl)phenyl)-6-(hydroxymethyl)-tetrahydro-2H-pyran-3,4,5-triol | 58.3 | hSGLT2 Inhibitory Activity

TABLE 1-continued hSGLT2 Inhibitory Activity

| Exam. No. | Structure | Name | IC$_{50}$ (nM) |
|---|---|---|---|
| 3 | 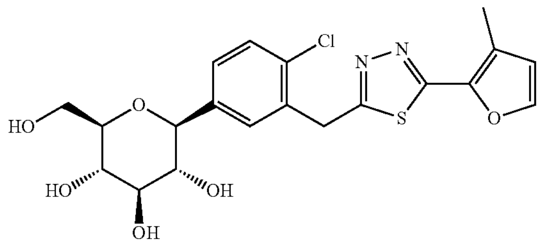 [SMILES: Cc1ccoc1-c1nnc(Cc2cc([C@@H]3O[C@H](CO)[C@@H](O)[C@H](O)[C@H]3O)ccc2Cl)s1] | (2S,3R,4R,5S,6R)-2-(4-Chloro-3-((5-(3-methylfuran-2-yl)-1,3,4-thiadiazol-2-yl)methyl)phenyl)-6-(hydroxymethyl)-tetrahydro-2H-pyran-3,4,5-triol | 106 |
| 4 | 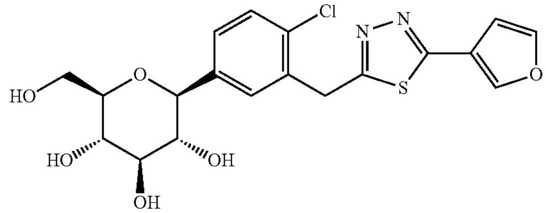 [SMILES: OC[C@H]1O[C@@H](c2ccc(Cl)c(Cc3nnc(-c4ccoc4)s3)c2)[C@H](O)[C@@H](O)[C@@H]1O] | (2S,3R,4R,5S,6R)-2-(4-Chloro-3-((5-(furan-3-yl)-1,3,4-thiadiazol-2-yl)methyl)phenyl)-6-(hydroxymethyl)tetrahydro-2H-pyran-3,4,5-triol | 17.7 |
| 5 | 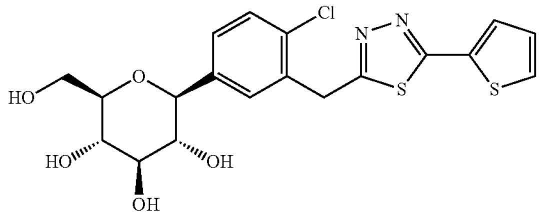 [SMILES: OC[C@H]1O[C@@H](c2ccc(Cl)c(Cc3nnc(-c4cccs4)s3)c2)[C@H](O)[C@@H](O)[C@@H]1O] | (2S,3R,4R,5S,6R)-2-(4-Chloro-3-((5-(thiophen-2-yl)-1,3,4-thiadiazol-2-yl)methyl)phenyl)-6-(hydroxymethyl)tetrahydro-2H-pyran-3,4,5-triol | 14.4 |
| 6 | 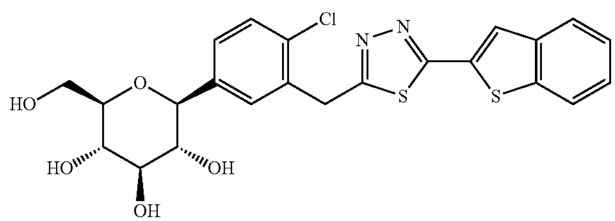 [SMILES: OC[C@H]1O[C@@H](c2ccc(Cl)c(Cc3nnc(-c4cc5ccccc5s4)s3)c2)[C@H](O)[C@@H](O)[C@@H]1O] | (2S,3R,4R,5S,6R)-2-(3-((5-(Benzo[b]thiophen-2-yl)-1,3,4-thiadiazol-2-yl)methyl)-4-chlorophenyl)-6-(hydroxymethyl)-tetrahydro-2H-pyran-3,4,5-triol | 44.5 |
| 7 | 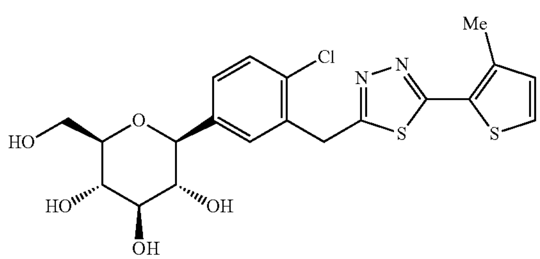 [SMILES: Cc1ccsc1-c1nnc(Cc2cc([C@@H]3O[C@H](CO)[C@@H](O)[C@H](O)[C@H]3O)ccc2Cl)s1] | (2S,3R,4R,5S,6R)-2-(4-chloro-3-((5-(3-methylthiophen-2-yl)-1,3,4-thiadiazol-2-yl)methyl)phenyl)-6-(hydroxymethyl)-tetrahydro-2H-pyran-3,4,5-triol | 762 |
| 8 | 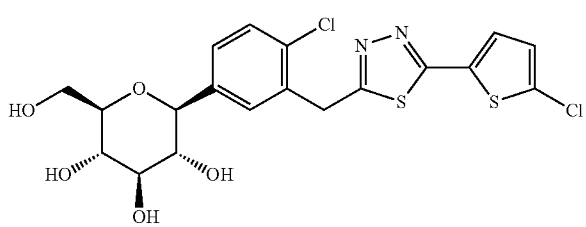 [SMILES: OC[C@H]1O[C@@H](c2ccc(Cl)c(Cc3nnc(-c4ccc(Cl)s4)s3)c2)[C@H](O)[C@@H](O)[C@@H]1O] | (2S,3R,4R,5S,6R)-2-(4-Chloro-3-((5-(5-chlorothiophen-2-yl)-1,3,4-thiadiazol-2-yl)methyl)phenyl)-6-(hydroxymethyl)-tetrahydro-2H-pyran-3,4,5-triol | 18.2 |

TABLE 1-continued hSGLT2 Inhibitory Activity

| Exam. No. | Structure | Name | IC$_{50}$ (nM) |
|---|---|---|---|
| 9 | 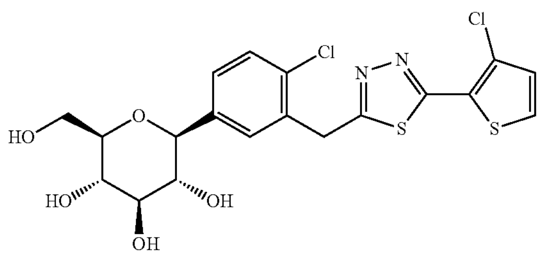 [SMILES: OC[C@H]1O[C@@H](c2ccc(Cl)c(Cc3nnc(-c4sccc4Cl)s3)c2)[C@H](O)[C@@H](O)[C@@H]1O] | (2S,3R,4R,5S,6R)-2-(4-Chloro-3-((5-(3-chlorothiophen-2-yl)-1,3,4-thiadiazol-2-yl)methyl)phenyl)-6-(hydroxymethyl)tetrahydro-2H-pyran-3,4,5-triol | 712 |
| 10 | 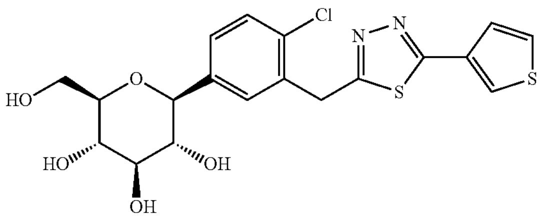 | (2S,3R,4R,5S,6R)-2-(4-Chloro-3-((5-(thiophen-3-yl)-1,3,4-thiadiazol-2-yl)methyl)phenyl)-6-(hydroxymethyl)tetrahydro-2H-pyran-3,4,5-triol | 3.51 |
| 11 | 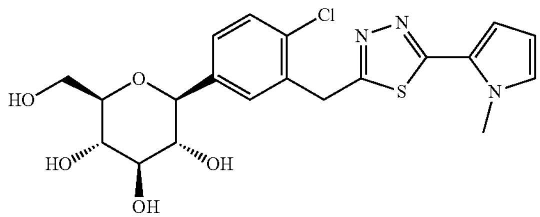 [SMILES: Cn1cccc1-c1nnc(Cc2cc([C@@H]3O[C@H](CO)[C@@H](O)[C@H](O)[C@H]3O)ccc2Cl)s1] | (2S,3R,4R,5S,6R)-2-(4-Chloro-3-((5-(1-methyl-1H-pyrrol-2-yl)-1,3,4-thiadiazol-2-yl)methyl)phenyl)-6-(hydroxymethyl)-tetrahydro-2H-pyran-3,4,5-triol | 119 |
| 12 | 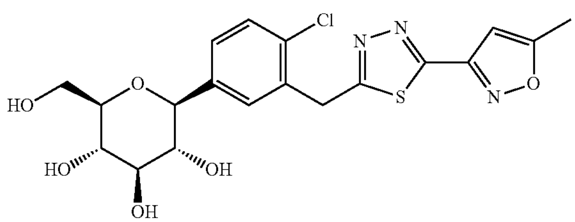 [SMILES: Cc1cc(-c2nnc(Cc3cc([C@@H]4O[C@H](CO)[C@@H](O)[C@H](O)[C@H]4O)ccc3Cl)s2)no1] | (2S,3R,4R,5S,6R)-2-(4-Chloro-3-((5-(5-methylisoxazol-3-yl)-1,3,4-thiadiazol-2-yl)methyl)phenyl)-6-(hydroxymethyl)tetrahydro-2H-pyran-3,4,5-triol | 257 |
| 13 | 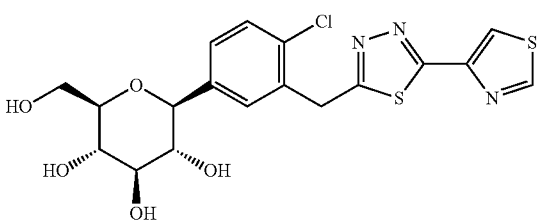 [SMILES: OC[C@H]1O[C@@H](c2ccc(Cl)c(Cc3nnc(-c4cscn4)s3)c2)[C@H](O)[C@@H](O)[C@@H]1O] | (2S,3R,4R,5S,6R)-2-(4-Chloro-3-((5-(thiazol-4-yl)-1,3,4-thiadiazol-2-yl)methyl)phenyl)-6-(hydroxymethyl)tetrahydro-2H-pyran-3,4,5-triol | 21.8 |
| 14 | 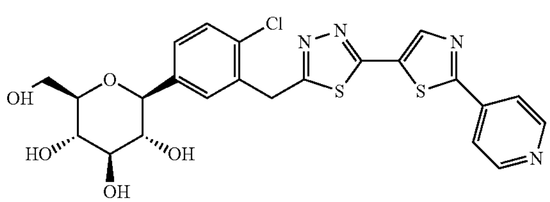 [SMILES: OC[C@H]1O[C@@H](c2ccc(Cl)c(Cc3nnc(-c4cnc(-c5ccncc5)s4)s3)c2)[C@H](O)[C@@H](O)[C@@H]1O] | (2S,3R,4R,5S,6R)-2-(4-Chloro-3-((5-(2-(pyridin-4-yl)thiazol-5-yl)-1,3,4-thiadiazol-2-yl)methyl)phenyl)-6-(hydroxymethyl)-tetrahydro-2H-pyran-3,4,5-triol | 72.6 |

TABLE 1-continued hSGLT2 Inhibitory Activity

| Exam. No. | Structure | Name | IC$_{50}$ (nM) |
|---|---|---|---|
| 15 | 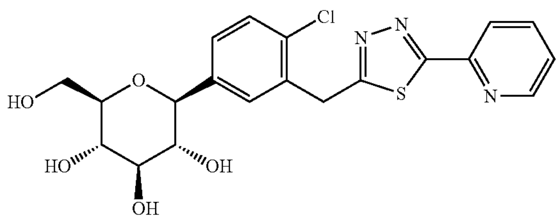 [SMILES: OC[C@H]1O[C@@H](c2ccc(Cl)c(Cc3nnc(-c4ccccn4)s3)c2)[C@H](O)[C@@H](O)[C@@H]1O] | (2S,3R,4R,5S,6R)-2-(4-Chloro-3-((5-(pyridin-2-yl)-1,3,4-thiadiazol-2-yl)methyl)phenyl)-6-(hydroxymethyl)tetrahydro-2H-pyran-3,4,5-triol | 30.3 |
| 16 | 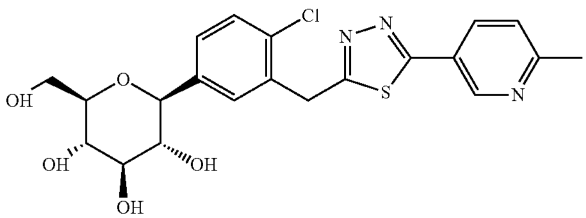 [SMILES: Cc1ccc(-c2nnc(Cc3cc([C@@H]4O[C@H](CO)[C@@H](O)[C@H](O)[C@H]4O)ccc3Cl)s2)cn1] | (2S,3R,4R,5S,6R)-2-(4-Chloro-3-((5-(6-methylpyridin-3-yl)-1,3,4-thiadiazol-2-yl)methyl)phenyl)-6-(hydroxymethyl)-tetrahydro-2H-pyran-3,4,5-triol | 97.4 |
| 17 | 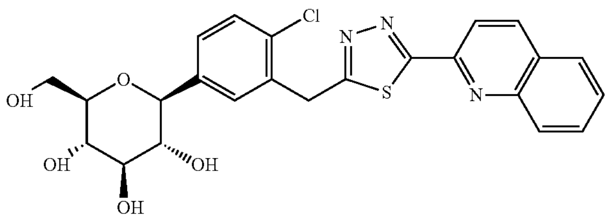 [SMILES: OC[C@H]1O[C@@H](c2ccc(Cl)c(Cc3nnc(-c4ccc5ccccc5n4)s3)c2)[C@H](O)[C@@H](O)[C@@H]1O] | (2S,3R,4R,5S,6R)-2-(4-Chloro-3-((5-(quinolin-2-yl)-1,3,4-thiadiazol-2-yl)methyl)phenyl)-6-(hydroxymethyl)-tetrahydro-2H-pyran-3,4,5-triol | 562 |
| 18 | 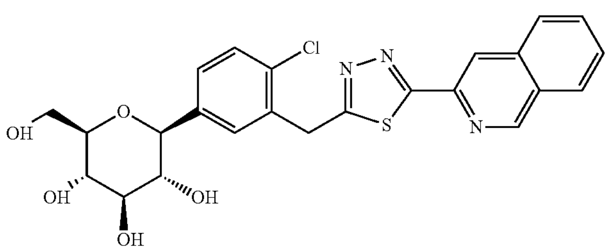 [SMILES: OC[C@H]1O[C@@H](c2ccc(Cl)c(Cc3nnc(-c4cc5ccccc5cn4)s3)c2)[C@H](O)[C@@H](O)[C@@H]1O] | (2S,3R,4R,5S,6R)-2-(4-Chloro-3-((5-(isoquinolin-3-yl)-1,3,4-thiadiazol-2-yl)methyl)phenyl)-6-(hydroxymethyl)-tetrahydro-2H-pyran-3,4,5-triol | 81.6 |
| 19 | 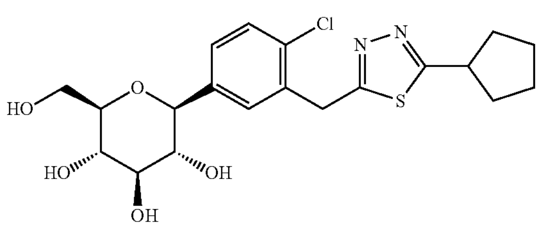 [SMILES: OC[C@H]1O[C@@H](c2ccc(Cl)c(Cc3nnc(C4CCCC4)s3)c2)[C@H](O)[C@@H](O)[C@@H]1O] | (2S,3R,4R,5S,6R)-2-(4-Chloro-3-((5-cyclopentyl-1,3,4-thiadiazol-2-yl)methyl)phenyl)-6-(hydroxymethyl)tetrahydro-2H-pyran-3,4,5-triol | 445 |
| 20 | 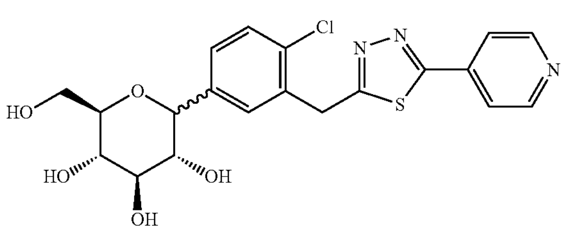 [SMILES: OC[C@H]1OC(c2ccc(Cl)c(Cc3nnc(-c4ccncc4)s3)c2)[C@H](O)[C@@H](O)[C@@H]1O] | (3R,4R,5S,6R)-2-(4-Chloro-3-((5-(pyridin-4-yl)-1,3,4-thiadiazol-2-yl)methyl)phenyl)-6-(hydroxymethyl)-tetrahydro-2H-pyran-3,4,5-triol | 53.0 |

TABLE 1-continued hSGLT2 Inhibitory Activity

| Exam. No. | Structure | Name | IC$_{50}$ (nM) |
|---|---|---|---|
| 21 | 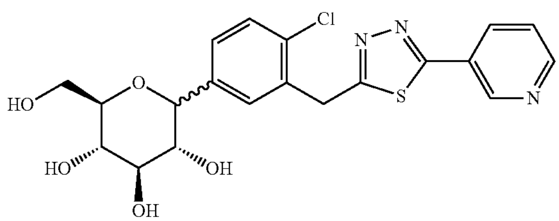 [SMILES: OC[C@H]1OC(c2ccc(Cl)c(Cc3nnc(-c4cccnc4)s3)c2)[C@H](O)[C@@H](O)[C@@H]1O] | (3R,4R,5S,6R)-2-(4-Chloro-3-((5-(pyridin-3-yl)-1,3,4-thiadiazol-2-yl)methyl)phenyl)-6-(hydroxymethyl)-tetrahydro-2H-pyran-3,4,5-triol | 45.3 |
| 22 | 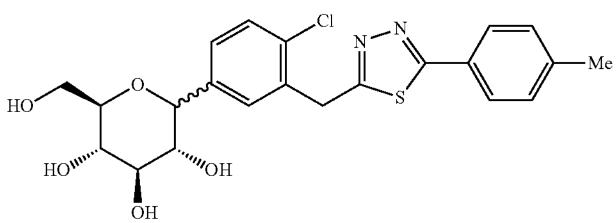 [SMILES: Cc1ccc(-c2nnc(Cc3cc(C4O[C@H](CO)[C@@H](O)[C@H](O)[C@H]4O)ccc3Cl)s2)cc1] | (3R,4R,5S,6R)-2-(4-chloro-3-((5-p-tolyl-1,3,4-thiadiazol-2-yl)methyl)phenyl)-6-(hydroxymethyl)-tetrahydro-2H-pyran-3,4,5-triol | 103 |
| 23 | 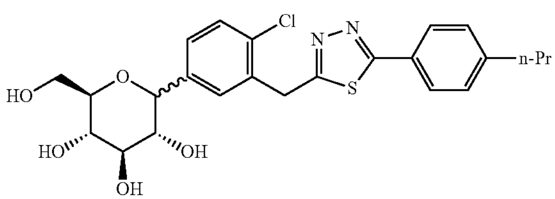 | (3R,4R,5S,6R)-2-(4-Chloro-3-((5-(4-propylphenyl)-1,3,4-thiadiazol-2-yl)methyl)phenyl)-6-(hydroxymethyl)-tetrahydro-2H-pyran-3,4,5-triol | 24.9 |
| 24 | 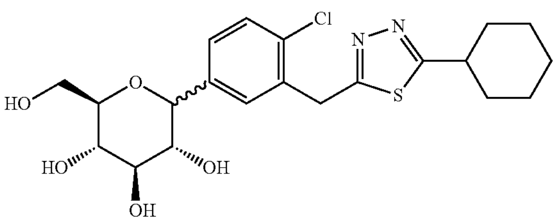 [SMILES: OC[C@H]1OC(c2ccc(Cl)c(Cc3nnc(C4CCCCC4)s3)c2)[C@H](O)[C@@H](O)[C@@H]1O] | (3R,4R,5S,6R)-2-(4-Chloro-3-((5-cyclohexyl-1,3,4-thiadiazol-2-yl)methyl)phenyl)-6-(hydroxymethyl)-tetrahydro-2H-pyran-3,4,5-triol | 542 |
| 25 | 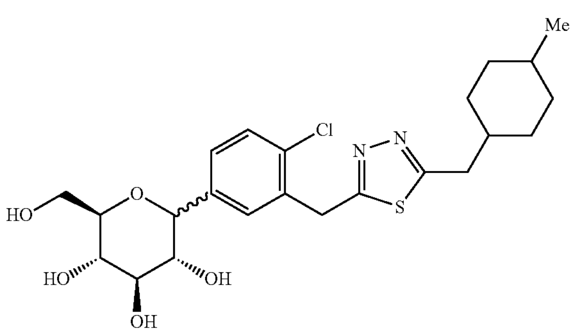 [SMILES: CC1CCC(Cc2nnc(Cc3cc(C4O[C@H](CO)[C@@H](O)[C@H](O)[C@H]4O)ccc3Cl)s2)CC1] | (3R,4R,5S,6R)-2-(4-Chloro-3-((5-((4-methylcyclohexyl)methyl)-1,3,4-thiadiazol-2-yl)methyl)phenyl)-6-(hydroxymethyl)-tetrahydro-2H-pyran-3,4,5-triol | 460 |
| 26 | 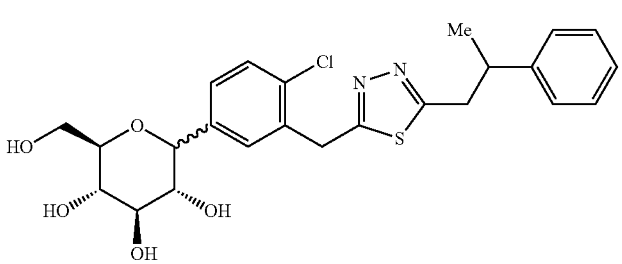 [SMILES: CC(Cc1nnc(Cc2cc(C3O[C@H](CO)[C@@H](O)[C@H](O)[C@H]3O)ccc2Cl)s1)c1ccccc1] | (3R,4R,5S,6R)-2-(4-Chloro-3-((5-(2-phenylpropyl)-1,3,4-thiadiazol-2-yl)methyl)phenyl)-6-(hydroxymethyl)-tetrahydro-2H-pyran-3,4,5-triol | 548 |

TABLE 1-continued hSGLT2 Inhibitory Activity

| Exam. No. | Structure | Name | IC$_{50}$ (nM) |
|---|---|---|---|
| 27 | 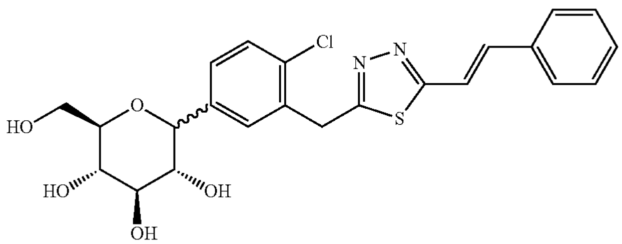 [SMILES: OC[C@H]1OC(c2ccc(Cl)c(Cc3nnc(/C=C/c4ccccc4)s3)c2)[C@H](O)[C@@H](O)[C@@H]1O] | (3R,4R,5S,6R,E)-2-(4-Chloro-3-((5-styryl-1,3,4-thiadiazol-2-yl)methyl)phenyl)-6-(hydroxymethyl)-tetrahydro-2H-pyran-3,4,5-triol | 730 |
| 28 | 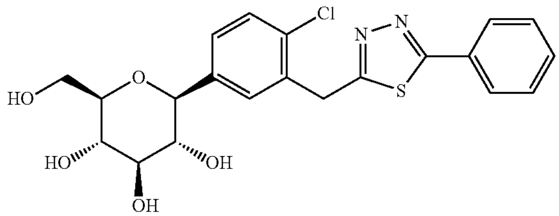 [SMILES: OC[C@H]1O[C@@H](c2ccc(Cl)c(Cc3nnc(-c4ccccc4)s3)c2)[C@H](O)[C@@H](O)[C@@H]1O] | (2S,3R,4R,5S,6R)-2-(4-Chloro-3-((5-phenyl-1,3,4-thiadiazol-2-yl)methyl)phenyl)-6-(hydroxymethyl)-tetrahydro-2H-pyran-3,4,5-triol | 16.6 |
| 29 | 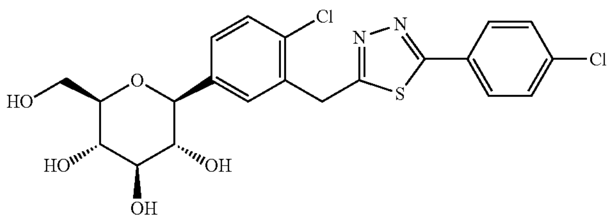 [SMILES: OC[C@H]1O[C@@H](c2ccc(Cl)c(Cc3nnc(-c4ccc(Cl)cc4)s3)c2)[C@H](O)[C@@H](O)[C@@H]1O] | (2S,3R,4R,5S,6R)-2-(4-chloro-3-((5-(4-Chlorophenyl)-1,3,4-thiadiazol-2-yl)methyl)phenyl)-6-(hydroxymethyl)-tetrahydro-2H-pyran-3,4,5-triol | 126 |
| 30 | 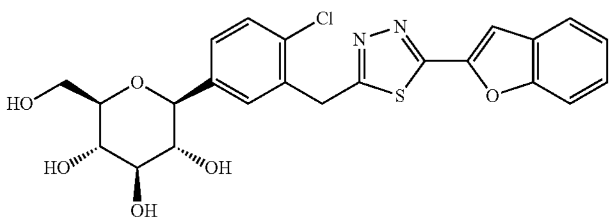 [SMILES: OC[C@H]1O[C@@H](c2ccc(Cl)c(Cc3nnc(-c4cc5ccccc5o4)s3)c2)[C@H](O)[C@@H](O)[C@@H]1O] | (2S,3R,4R,5S,6R)-2-(3-((5-(Benzofuran-2-yl)-1,3,4-thiadiazol-2-yl)methyl)-4-chlorophenyl)-6-(hydroxymethyl)-tetrahydro-2H-pyran-3,4,5-triol | 249 |
| 31 | 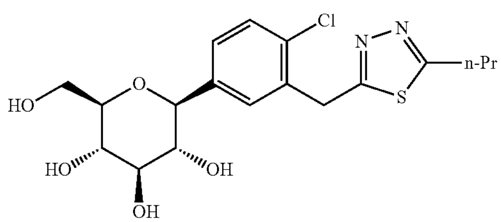 | (2S,3R,4R,5S,6R)-2-(4-Chloro-3-((5-propyl-1,3,4-thiadiazol-2-yl)methyl)phenyl)-6-(hydroxymethyl)-tetrahydro-2H-pyran-3,4,5-triol | 214 |
| 32 | 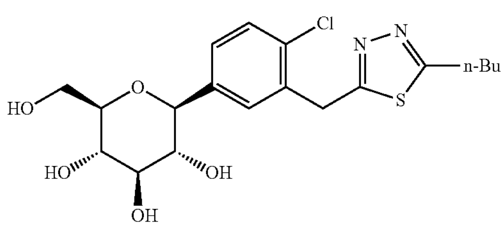 | (2S,3R,4R,5S,6R)-2-(3-((5-Butyl-1,3,4-thiadiazol-2-yl)methyl)-4-chlorophenyl)-6-(hydroxymethyl)-tetrahydro-2H-pyran-3,4,5-triol | 379 |

TABLE 1-continued hSGLT2 Inhibitory Activity

| Exam. No. | Structure | Name | IC$_{50}$ (nM) |
|---|---|---|---|
| 33 | 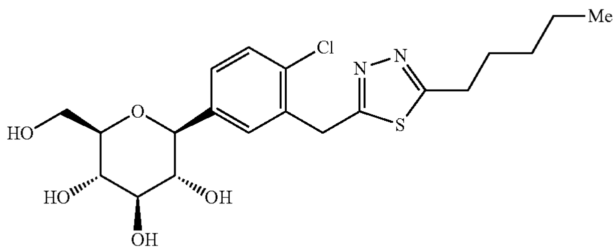 [SMILES: CCCCCc1nnc(Cc2cc([C@@H]3O[C@H](CO)[C@@H](O)[C@H](O)[C@H]3O)ccc2Cl)s1] | (2S,3R,4R,5S,6R)-2-(4-Chloro-3-((5-pentyl-1,3,4-thiadiazol-2-yl)methyl)phenyl)-6-(hydroxymethyl)-tetrahydro-2H-pyran-3,4,5-triol | 353 |
| 34 | 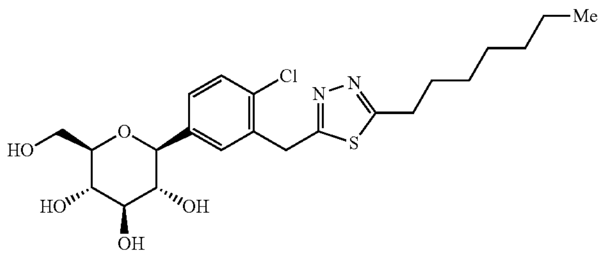 [SMILES: CCCCCCCc1nnc(Cc2cc([C@@H]3O[C@H](CO)[C@@H](O)[C@H](O)[C@H]3O)ccc2Cl)s1] | (2S,3R,4R,5S,6R)-2-(4-Chloro-3-((5-heptyl-1,3,4-thiadiazol-2-yl)methyl)phenyl)-6-(hydroxymethyl)-tetrahydro-2H-pyran-3,4,5-triol | 122 |
| 35 | 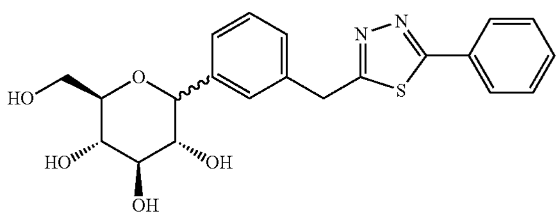 [SMILES: OC[C@H]1OC(c2cccc(Cc3nnc(-c4ccccc4)s3)c2)[C@H](O)[C@@H](O)[C@@H]1O] | (2R,3S,4R,5R)-2-(Hydroxymethyl)-6-(3-((5-phenyl-1,3,4-thiadiazol-2-yl)methyl)phenyl)-tetrahydro-2H-pyran-3,4,5-triol | 1420 |
| 36 | 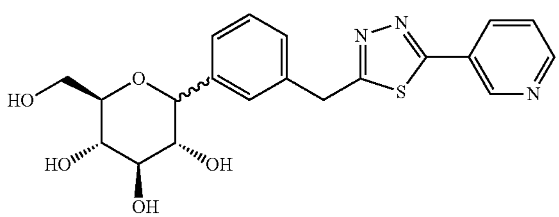 [SMILES: OC[C@H]1OC(c2cccc(Cc3nnc(-c4cccnc4)s3)c2)[C@H](O)[C@@H](O)[C@@H]1O] | (2R,3S,4R,5R)-2-(Hydroxymethyl)-6-(3-((5-(pyridin-3-yl)-1,3,4-thiadiazol-2-yl)methyl)phenyl)-tetrahydro-2H-pyran-3,4,5-triol | 1230 |
| 37 | 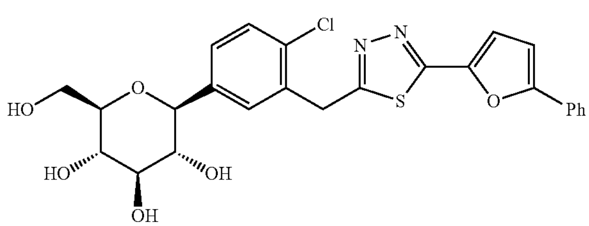 [SMILES: OC[C@H]1O[C@@H](c2ccc(Cl)c(Cc3nnc(-c4ccc(-c5ccccc5)o4)s3)c2)[C@H](O)[C@@H](O)[C@@H]1O] | (2S,3R,4R,5S,6R)-2-(4-Chloro-3-((5-(5-phenylfuran-2-yl)-1,3,4-thiadiazol-2-yl)methyl)phenyl)-6-(hydroxymethyl)-tetrahydro-2H-pyran-3,4,5-triol | 10.6 |
| 38 | 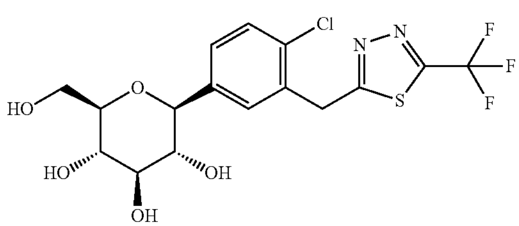 [SMILES: OC[C@H]1O[C@@H](c2ccc(Cl)c(Cc3nnc(C(F)(F)F)s3)c2)[C@H](O)[C@@H](O)[C@@H]1O] | (2S,3R,4R,5S,6R)-2-(4-Chloro-3-((5-(trifluoromethyl)-1,3,4-thiadiazol-2-yl)methyl)phenyl)-6-(hydroxymethyl)tetrahydro-2H-pyran-3,4,5-triol | 155 |

TABLE 1-continued hSGLT2 Inhibitory Activity

| Exam. No. | Structure | Name | IC$_{50}$ (nM) |
|---|---|---|---|
| 39 | 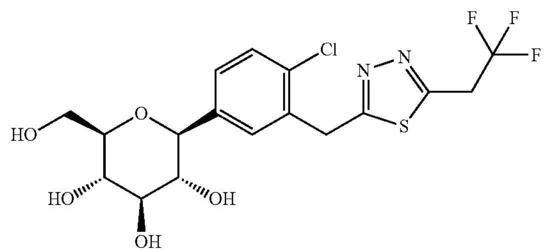 [SMILES: OC[C@H]1O[C@@H](c2ccc(Cl)c(Cc3nnc(CC(F)(F)F)s3)c2)[C@H](O)[C@@H](O)[C@@H]1O] | (2S,3R,4R,5S,6R)-2-(4-Chloro-3-((5-(2,2,2-trifluoroethyl)-1,3,4-thiadiazol-2-yl)methyl)phenyl)-6-(hydroxymethyl)tetrahydro-2H-pyran-3,4,5-triol | 758 |
| 40 | 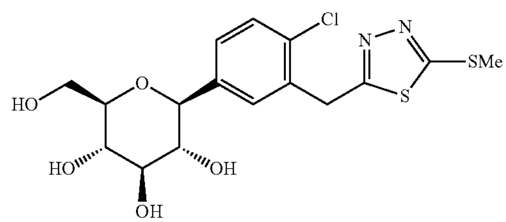 | (2S,3R,4R,5S,6R)-2-(4-Chloro-3-((5-(methylthio)-1,3,4-thiadiazol-2-yl)methyl)phenyl)-6-(hydroxymethyl)-tetrahydro-2H-pyran-3,4,5-triol | 10.9 |
| 41 | 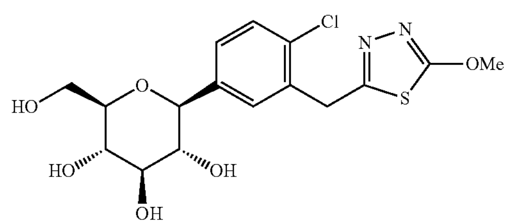 | (2S,3R,4R,5S,6R)-2-(4-Chloro-3-((5-methoxy-1,3,4-thiadiazol-2-yl)methyl)phenyl)-6-(hydroxymethyl)-tetrahydro-2H-pyran-3,4,5-triol | 146 |
| 42 | 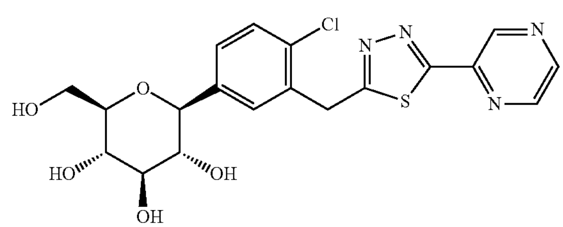 [SMILES: OC[C@H]1O[C@@H](c2ccc(Cl)c(Cc3nnc(-c4cnccn4)s3)c2)[C@H](O)[C@@H](O)[C@@H]1O] | (2S,3R,4R,5S,6R)-2-(4-Chloro-3-((5-(pyrazin-2-yl)-1,3,4-thiadiazol-2-yl)methyl)phenyl)-6-(hydroxymethyl)-tetrahydro-2H-pyran-3,4,5-triol | 4.06 |
| 43 | 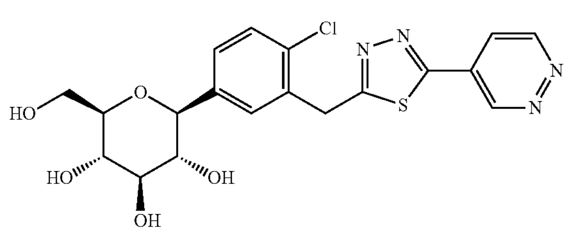 [SMILES: OC[C@H]1O[C@@H](c2ccc(Cl)c(Cc3nnc(-c4ccnnc4)s3)c2)[C@H](O)[C@@H](O)[C@@H]1O] | (2S,3R,4R,5S,6R)-2-(4-Chloro-3-((5-(pyridazin-4-yl)-1,3,4-thiadiazol-2-yl)methyl)phenyl)-6-(hydroxymethyl)-tetrahydro-2H-pyran-3,4,5-triol | 190 |
| 44 | 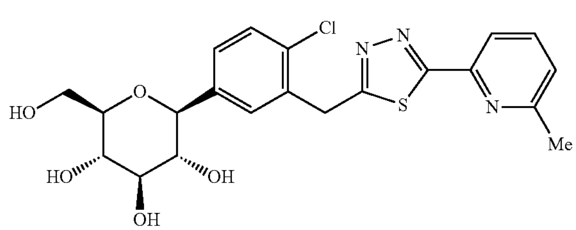 [SMILES: Cc1cccc(-c2nnc(Cc3cc([C@@H]4O[C@H](CO)[C@@H](O)[C@H](O)[C@H]4O)ccc3Cl)s2)n1] | (2S,3R,4R,5S,6R)-2-(4-Chloro-3-((5-(6-methylpyridin-2-yl)-1,3,4-thiadiazol-2-yl)methyl)phenyl)-6-(hydroxymethyl)-tetrahydro-2H-pyran-3,4,5-triol | 638 |

TABLE 1-continued hSGLT2 Inhibitory Activity

| Exam. No. | Structure | Name | IC$_{50}$ (nM) |
|---|---|---|---|
| 45 | 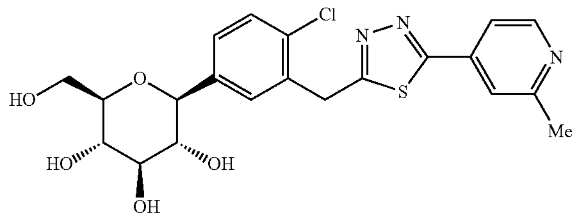 [SMILES: Cc1cc(-c2nnc(Cc3cc([C@@H]4O[C@H](CO)[C@@H](O)[C@H](O)[C@H]4O)ccc3Cl)s2)ccn1] | (2S,3R,4R,5S,6R)-2-(4-Chloro-3-((5-(2-methylpyridin-4-yl)-1,3,4-thiadiazol-2-yl)methyl)phenyl)-6-(hydroxymethyl)-tetrahydro-2H-pyran-3,4,5-triol | 36.4 |
| 46 | 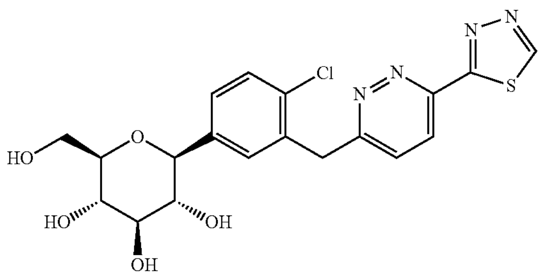 [SMILES: OC[C@H]1O[C@@H](c2ccc(Cl)c(Cc3ccc(-c4nncs4)nn3)c2)[C@H](O)[C@@H](O)[C@@H]1O] | (2S,3R,4R,5S,6R)-2-(3-((6-(1,3,4-Thiadiazol-2-yl)pyridazin-3-yl)methyl)-4-chlorophenyl)-6-(hydroxymethyl)-tetrahydro-2H-pyran-3,4,5-triol | 11.4 |
| 47 | 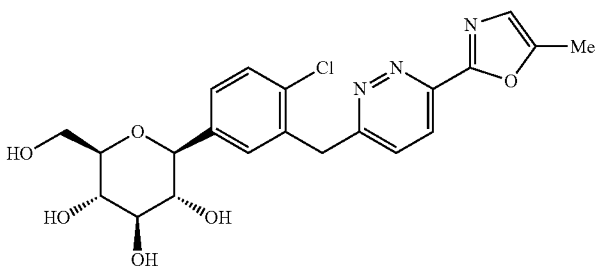 [SMILES: Cc1cnc(-c2ccc(Cc3cc([C@@H]4O[C@H](CO)[C@@H](O)[C@H](O)[C@H]4O)ccc3Cl)nn2)o1] | (2S,3R,4R,5S,6R)-2-(4-Chloro-3-((6-(5-methyloxazol-2-yl)pyridazin-3-yl)methyl)phenyl)-6-(hydroxymethyl)-tetrahydro-2H-pyran-3,4,5-triol | 1710 |
| 48 | 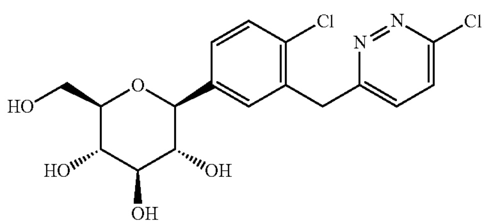 [SMILES: OC[C@H]1O[C@@H](c2ccc(Cl)c(Cc3ccc(Cl)nn3)c2)[C@H](O)[C@@H](O)[C@@H]1O] | (2S,3R,4R,5S,6R)-2-(4-Chloro-3-((6-chloropyridazin-3-yl)methyl)phenyl)-6-(hydroxymethyl)-tetrahydro-2H-pyran-3,4,5-triol | 202 |
| 49 | 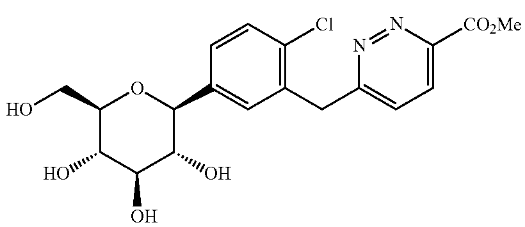 [SMILES: COC(=O)c1ccc(Cc2cc([C@@H]3O[C@H](CO)[C@@H](O)[C@H](O)[C@H]3O)ccc2Cl)nn1] | Methyl 6-(2-chloro-5-(((2S,3R,4R,5S,6R)-3,4,5-trihydroxy-6-(hydroxymethyl)-tetrahydro-2H-pyran-2-yl)benzyl)pyridazine-3-carboxylate | 201 |
| 50 | 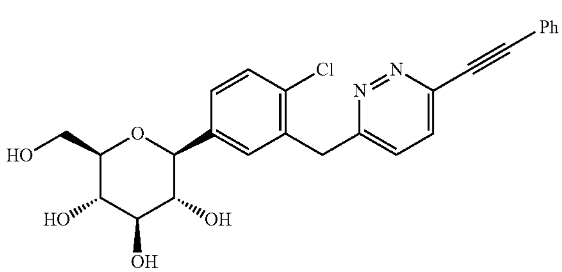 [SMILES: OC[C@H]1O[C@@H](c2ccc(Cl)c(Cc3ccc(C#Cc4ccccc4)nn3)c2)[C@H](O)[C@@H](O)[C@@H]1O] | (2S,3R,4R,5S,6R)-2-(4-Chloro-3-((6-(phenylethynyl)pyridazin-3-yl)methyl)phenyl)-6-(hydroxymethyl)-tetrahydro-2H-pyran-3,4,5-triol | 176 |

TABLE 1-continued hSGLT2 Inhibitory Activity

| Exam. No. | Structure | Name | IC$_{50}$ (nM) |
|---|---|---|---|
| 51 | 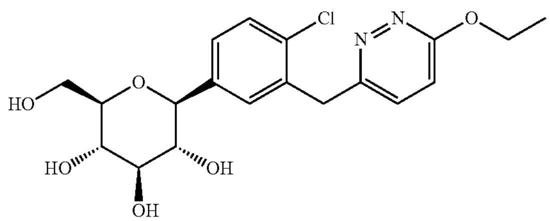 | (2S,3R,4R,5S,6R)-2-(4-Chloro-3-((6-ethoxypyridazin-3-yl)methyl)phenyl)-6-(hydroxymethyl)-tetrahydro-2H-pyran-3,4,5-triol | 43 |
| 52 | 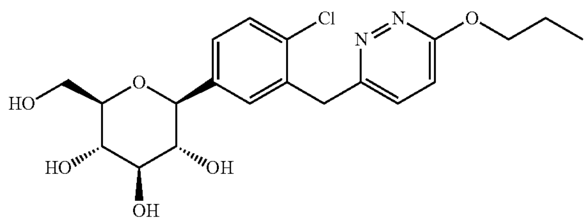 | (2S,3R,4R,5S,6R)-2-(4-Chloro-3-((6-propoxypyridazin-3-yl)methyl)phenyl)-6-(hydroxymethyl)-tetrahydro-2H-pyran-3,4,5-triol | 70.8 |
| 53 | 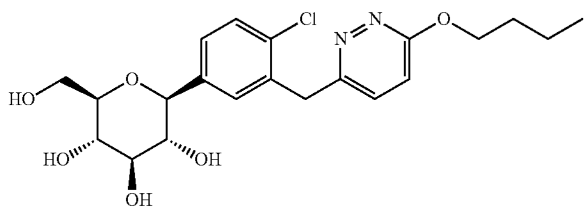 | (2S,3R,4R,5S,6R)-2-(3-((6-Butoxypyridazin-3-yl)methyl)-4-chlorophenyl)-6-(hydroxymethyl)-tetrahydro-2H-pyran-3,4,5-triol | 109 |
| 54 | 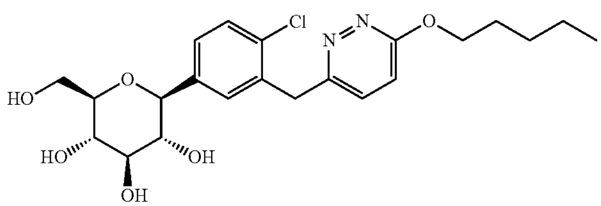 [SMILES: CCCCCOc1ccc(Cc2cc([C@@H]3O[C@H](CO)[C@@H](O)[C@H](O)[C@H]3O)ccc2Cl)nn1] | (2S,3R,4R,5S,6R)-2-(4-Chloro-3-((6-(pentyloxy)pyridazin-3-yl)methyl)phenyl)-6-(hydroxymethyl)-tetrahydro-2H-pyran-3,4,5-triol | 17.0 |
| 55 | 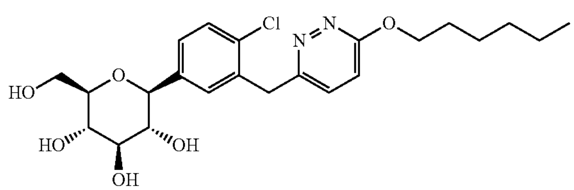 [SMILES: CCCCCCOc1ccc(Cc2cc([C@@H]3O[C@H](CO)[C@@H](O)[C@H](O)[C@H]3O)ccc2Cl)nn1] | (2S,3R,4R,5S,6R)-2-(4-Chloro-3-((6-(hexyloxy)pyridazin-3-yl)methyl)phenyl)-6-(hydroxymethyl)-tetrahydro-2H-pyran-3,4,5-triol | 17.3 |
| 56 | 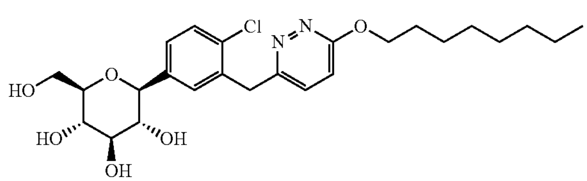 [SMILES: CCCCCCCCOc1ccc(Cc2cc([C@@H]3O[C@H](CO)[C@@H](O)[C@H](O)[C@H]3O)ccc2Cl)nn1] | (2S,3R,4R,5S,6R)-2-(4-Chloro-3-((6-(octyloxy)pyridazin-3-yl)methyl)phenyl)-6-(hydroxymethyl)-tetrahydro-2H-pyran-3,4,5-triol | 50.5 |
| 57 | 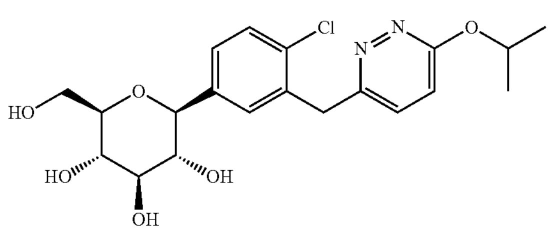 | (2S,3R,4R,5S,6R)-2-(4-Chloro-3-((6-isopropoxypyridazin-3-yl)methyl)phenyl)-6-(hydroxymethyl)-tetrahydro-2H-pyran-3,4,5-triol | 110 |

TABLE 1-continued hSGLT2 Inhibitory Activity

| Exam. No. | Structure | Name | IC$_{50}$ (nM) |
|---|---|---|---|
| 58 | | (2S,3R,4R,5S,6R)-2-(4-Chloro-3-((6-isobutoxypyridazin-3-yl)methyl)phenyl)-6-(hydroxymethyl)-tetrahydro-2H-pyran-3,4,5-triol | 435 |
| 59 | | (2S,3R,4R,5S,6R)-2-(4-Chloro-3-((6-(cyclohexyloxy)pyridazin-3-yl)methyl)phenyl)-6-(hydroxymethyl)-tetrahydro-2H-pyran-3,4,5-triol | 111 |
| 60 | | (2S,3R,4R,5S,6R)-2-(4-Chloro-3-((6-(tetrahydro-2H-pyran-4-yloxy)pyridazin-3-yl)methyl)phenyl)-6-(hydroxymethyl)-tetrahydro-2H-pyran-3,4,5-triol | 77.6 |
| 61 | | (2S,3R,4R,5S,6R)-2-(4-chloro-3-((6-phenylpyridazin-3-yl)methyl)phenyl)-6-(hydroxymethyl)-tetrahydro-2H-pyran-3,4,5-triol | 222 |
| 62 | | (2S,3R,4R,5S,6R)-2-(4-chloro-3-((6-(furan-2-yl)pyridazin-3-yl)methyl)phenyl)-6-(hydroxymethyl)-tetrahydro-2H-pyran-3,4,5-triol | 64.3 |
| 63 | | (2S,3R,4R,5S,6R)-2-(4-Chloro-3-((6-(furan-3-yl)pyridazin-3-yl)methyl)phenyl)-6-(hydroxymethyl)-tetrahydro-2H-pyran-3,4,5-triol | 61.3 |

TABLE 1-continued hSGLT2 Inhibitory Activity

| Exam. No. | Structure | Name | IC$_{50}$ (nM) |
|---|---|---|---|
| 64 | 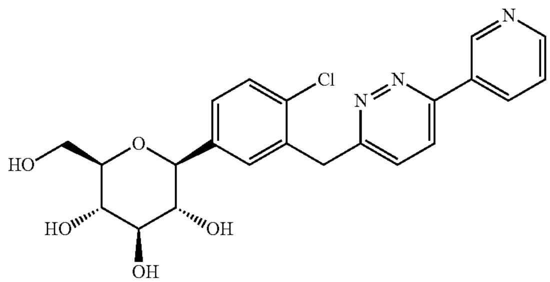 | (2S,3R,4R,5S,6R)-2-(4-Chloro-3-((6-(pyridin-3-yl)pyridazin-3-yl)methyl)phenyl)-6-(hydroxymethyl)-tetrahydro-2H-pyran-3,4,5-triol | 64.9 |
| 65 | 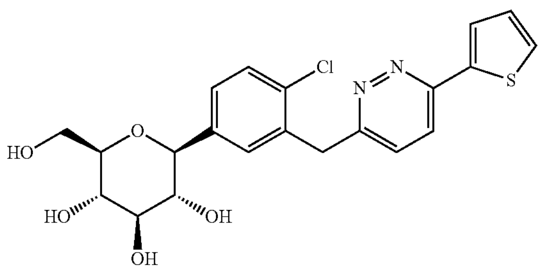 [SMILES: OC[C@H]1O[C@@H](c2ccc(Cl)c(Cc3ccc(-c4ccco4)nn3)c2)[C@H](O)[C@@H](O)[C@@H]1O] | (2S,3R,4R,5S,6R)-2-(4-Chloro-3-((6-(thiophen-2-yl)pyridazin-3-yl)methyl)phenyl)-6-(hydroxymethyl)-tetrahydro-2H-pyran-3,4,5-triol | 71.4 |
| 66 | 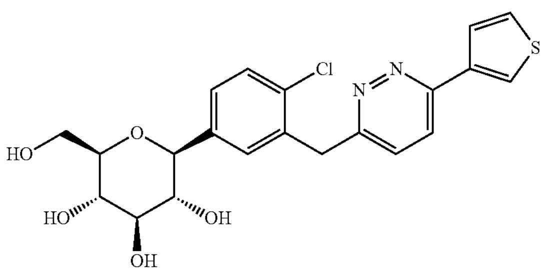 [SMILES: OC[C@H]1O[C@@H](c2ccc(Cl)c(Cc3ccc(-c4ccoc4)nn3)c2)[C@H](O)[C@@H](O)[C@@H]1O] | (2S,3R,4R,5S,6R)-2-(4-chloro-3-((6-(thiophen-3-yl)pyridazin-3-yl)methyl)phenyl)-6-(hydroxymethyl)-tetrahydro-2H-pyran-3,4,5-triol | 75.4 |
| 67 | 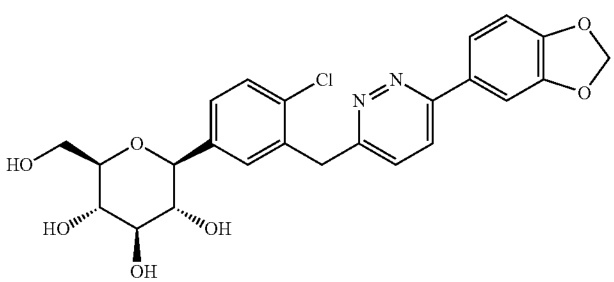 [SMILES: OC[C@H]1O[C@@H](c2ccc(Cl)c(Cc3ccc(-c4ccc5c(c4)OCO5)nn3)c2)[C@H](O)[C@@H](O)[C@@H]1O] | (2S,3R,4R,5S,6R)-2-(3-((6-(Benzo[d][1,3]dioxol-5-yl)pyridazin-3-yl)methyl)-4-chlorophenyl)-6-(hydroxymethyl)-tetrahydro-2H-pyran-3,4,5-triol | 82.7 |
| 68 | 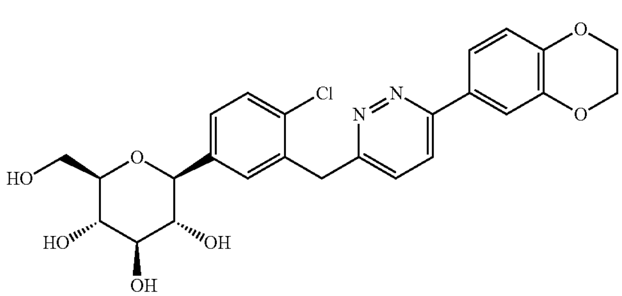 [SMILES: OC[C@H]1O[C@@H](c2ccc(Cl)c(Cc3ccc(-c4ccc5c(c4)OCCO5)nn3)c2)[C@H](O)[C@@H](O)[C@@H]1O] | (2S,3R,4R,5S,6R)-2-(4-Chloro-3-((6-(2,3-dihydrobenzo[b][1,4]dioxin-6-yl)pyridazin-3-yl)methyl)phenyl)-6-(hydroxymethyl)-tetrahydro-2H-pyran-3,4,5-triol | 103 |

TABLE 1-continued hSGLT2 Inhibitory Activity

| Exam. No. | Structure | Name | IC$_{50}$ (nM) |
|---|---|---|---|
| 69 | 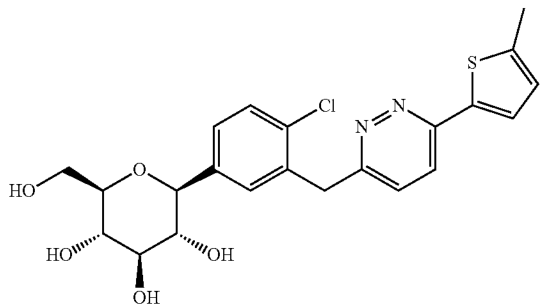 [SMILES: Cc1ccc(-c2ccc(Cc3cc([C@@H]4O[C@H](CO)[C@@H](O)[C@H](O)[C@H]4O)ccc3Cl)nn2)s1] | (2S,3R,4R,5S,6R)-2-(4-Chloro-3-((6-(5-methylthiophen-2-yl)pyridazin-3-yl)methyl)phenyl)-6-(hydroxymethyl)-tetrahydro-2H-pyran-3,4,5-triol | 168 |
| 70 | 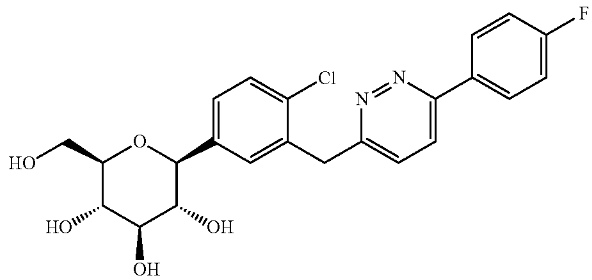 [SMILES: OC[C@H]1O[C@@H](c2ccc(Cl)c(Cc3ccc(-c4ccc(F)cc4)nn3)c2)[C@H](O)[C@@H](O)[C@@H]1O] | (2S,3R,4R,5S,6R)-2-(4-Chloro-3-((6-(4-fluorophenyl)pyridazin-3-yl)methyl)phenyl)-6-(hydroxymethyl)-tetrahydro-2H-pyran-3,4,5-triol | 272 |
| 71 | 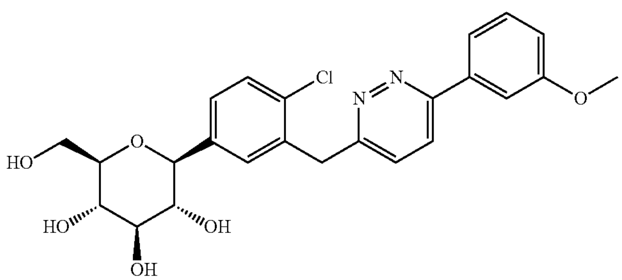 [SMILES: COc1cccc(-c2ccc(Cc3cc([C@@H]4O[C@H](CO)[C@@H](O)[C@H](O)[C@H]4O)ccc3Cl)nn2)c1] | (2S,3R,4R,5S,6R)-2-(4-Chloro-3-((6-(3-methoxyphenyl)pyridazin-3-yl)methyl)phenyl)-6-(hydroxymethyl)-tetrahydro-2H-pyran-3,4,5-triol | 351 |
| 72 | 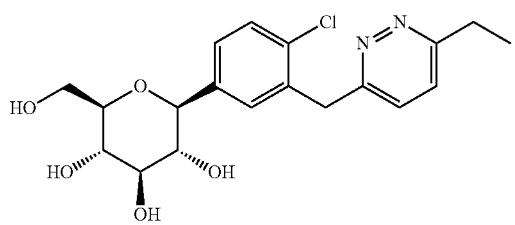 | (2S,3R,4R,5S,6R)-2-(4-Chloro-3-((6-ethylpyridazin-3-yl)methyl)phenyl)-6-(hydroxymethyl)-tetrahydro-2H-pyran-3,4,5-triol | 131 |
| 73 | 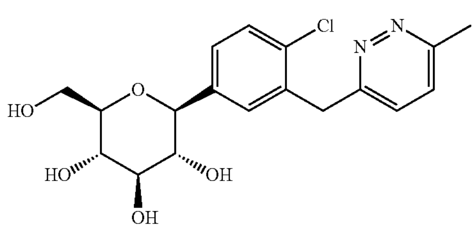 [SMILES: Cc1ccc(Cc2cc([C@@H]3O[C@H](CO)[C@@H](O)[C@H](O)[C@H]3O)ccc2Cl)nn1] | (2S,3R,4R,5S,6R)-2-(4-Chloro-3-((6-methylpyridazin-3-yl)methyl)phenyl)-6-(hydroxymethyl)-tetrahydro-2H-pyran-3,4,5-triol | 293 |
| 74 | 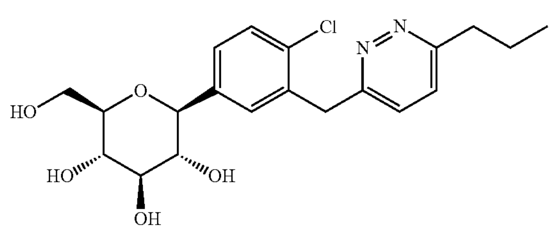 [SMILES: CCCc1ccc(Cc2cc([C@@H]3O[C@H](CO)[C@@H](O)[C@H](O)[C@H]3O)ccc2Cl)nn1] | (2S,3R,4R,5S,6R)-2-(4-Chloro-3-((6-propylpyridazin-3-yl)methyl)phenyl)-6-(hydroxymethyl)-tetrahydro-2H-pyran-3,4,5-triol | 237 |

TABLE 1-continued hSGLT2 Inhibitory Activity

| Exam. No. | Structure | Name | IC$_{50}$ (nM) |
|---|---|---|---|
| 75 | 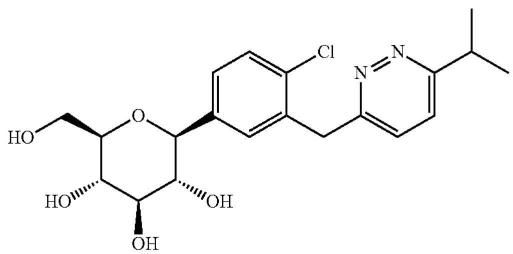 [SMILES: CC(C)c1ccc(Cc2cc([C@@H]3O[C@H](CO)[C@@H](O)[C@H](O)[C@H]3O)ccc2Cl)nn1] | (2S,3R,4R,5S,6R)-2-(4-Chloro-3-((6-isopropylpyridazin-3-yl)methyl)phenyl)-6-(hydroxymethyl)-tetrahydro-2H-pyran-3,4,5-triol | 259 |
| 76 | 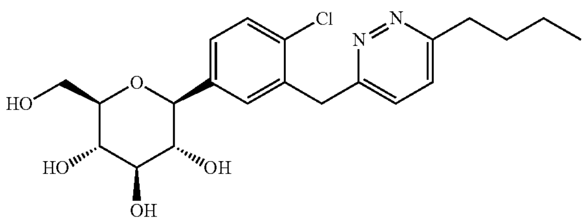 [SMILES: CCCCc1ccc(Cc2cc([C@@H]3O[C@H](CO)[C@@H](O)[C@H](O)[C@H]3O)ccc2Cl)nn1] | (2S,3R,4R,5S,6R)-2-(3-((6-Butylpyridazin-3-yl)methyl)-4-chlorophenyl)-6-(hydroxymethyl)-tetrahydro-2H-pyran-3,4,5-triol | 356 |
| 77 | 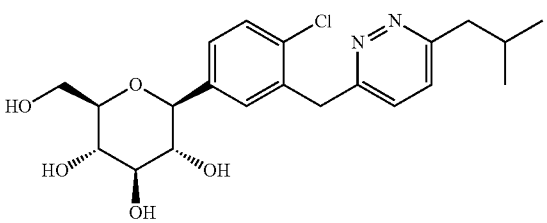 [SMILES: CC(C)Cc1ccc(Cc2cc([C@@H]3O[C@H](CO)[C@@H](O)[C@H](O)[C@H]3O)ccc2Cl)nn1] | (2S,3R,4R,5S,6R)-2-(4-Chloro-3-((6-isobutylpyridazin-3-yl)methyl)phenyl)-6-(hydroxymethyl)-tetrahydro-2H-pyran-3,4,5-triol | 811 |
| 78 | 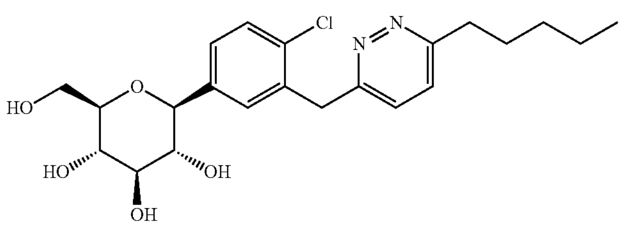 [SMILES: CCCCCc1ccc(Cc2cc([C@@H]3O[C@H](CO)[C@@H](O)[C@H](O)[C@H]3O)ccc2Cl)nn1] | (2S,3R,4R,5S,6R)-2-(4-Chloro-3-((6-pentylpyridazin-3-yl)methyl)phenyl)-6-(hydroxymethyl)-tetrahydro-2H-pyran-3,4,5-triol | 134 |
| 79 | 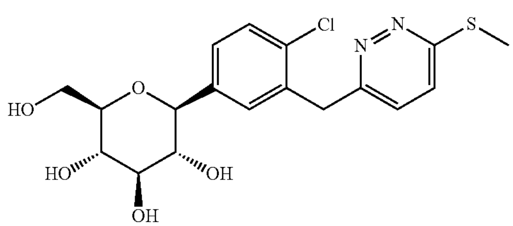 [SMILES: CSc1ccc(Cc2cc([C@@H]3O[C@H](CO)[C@@H](O)[C@H](O)[C@H]3O)ccc2Cl)nn1] | (2S,3R,4R,5S,6R)-2-(4-Chloro-3-((6-(methylthio)pyridazin-3-yl)methyl)phenyl)-6-(hydroxymethyl)-tetrahydro-2H-pyran-3,4,5-triol | 13.4 |
| 80 | 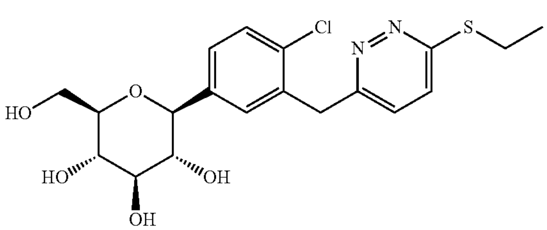 | (2S,3R,4R,5S,6R)-2-(4-Chloro-3-((6-(ethylthio)pyridazin-3-yl)methyl)phenyl)-6-(hydroxymethyl)-tetrahydro-2H-pyran-3,4,5-triol | 71.3 |

TABLE 1-continued hSGLT2 Inhibitory Activity

| Exam. No. | Structure | Name | IC$_{50}$ (nM) |
|---|---|---|---|
| 81 | 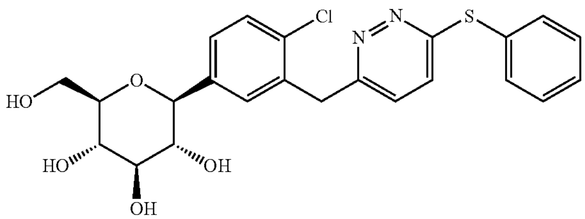 [SMILES: OC[C@H]1O[C@@H](c2ccc(Cl)c(Cc3ccc(Sc4ccccc4)nn3)c2)[C@H](O)[C@@H](O)[C@@H]1O] | (2S,3R,4R,5S,6R)-2-(4-Chloro-3-((6-(phenylthio)pyridazin-3-yl)methyl)phenyl)-6-(hydroxymethyl)-tetrahydro-2H-pyran-3,4,5-triol | 1870 |
| 82 | 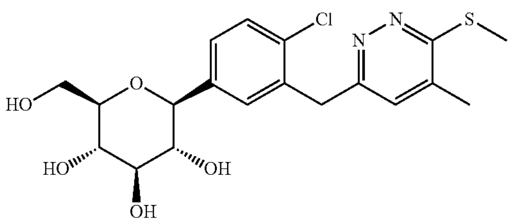 [SMILES: CSc1nnc(Cc2cc([C@@H]3O[C@H](CO)[C@@H](O)[C@H](O)[C@H]3O)ccc2Cl)cc1C] | (2S,3R,4R,5S,6R)-2-(4-Chloro-3-((5-methyl-6-(methylthio)pyridazin-3-yl)methyl)phenyl)-6-(hydroxymethyl)tetrahydro-2H-pyran-3,4,5-triol | 1520 |
| 83 | 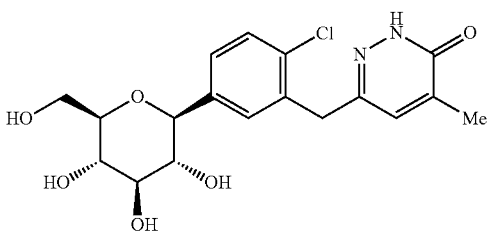 [SMILES: Cc1cc(Cc2cc([C@@H]3O[C@H](CO)[C@@H](O)[C@H](O)[C@H]3O)ccc2Cl)n[nH]c1=O] | 6-(2-Chloro-5-((2S,3R,4R,5S,6R)-3,4,5-trihydroxy-6-(hydroxymethyl)-tetrahydro-2H-pyran-2-yl)benzyl)-4-methylpyridazin-3(2H)-one | 618 |
| 84 | 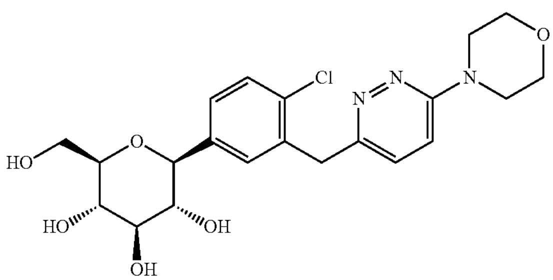 [SMILES: OC[C@H]1O[C@@H](c2ccc(Cl)c(Cc3ccc(N4CCOCC4)nn3)c2)[C@H](O)[C@@H](O)[C@@H]1O] | (2S,3R,4R,5S,6R)-2-(4-Chloro-3-((6-morpholinopyridazin-3-yl)methyl)phenyl)-6-(hydroxymethyl)-tetrahydro-2H-pyran-3,4,5-triol | 700 |
| 85 | 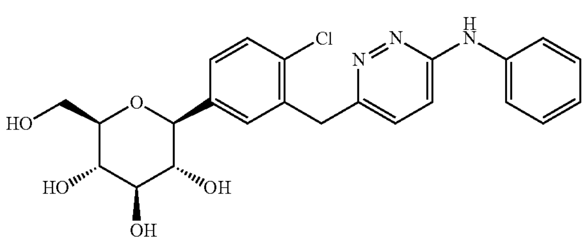 [SMILES: OC[C@H]1O[C@@H](c2ccc(Cl)c(Cc3ccc(Nc4ccccc4)nn3)c2)[C@H](O)[C@@H](O)[C@@H]1O] | (2S,3R,4R,5S,6R)-2-(4-Chloro-3-((6-(phenylamino)pyridazin-3-yl)methyl)phenyl)-6-(hydroxymethyl)-tetrahydro-2H-pyran-3,4,5-triol | 1140 |
| 86 | 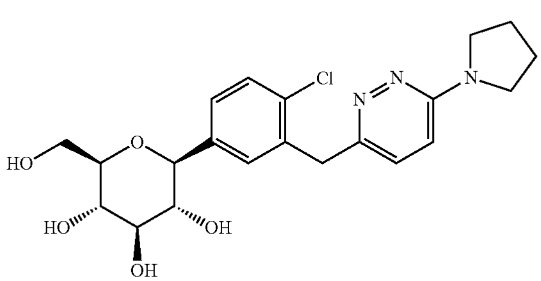 [SMILES: OC[C@H]1O[C@@H](c2ccc(Cl)c(Cc3ccc(N4CCCC4)nn3)c2)[C@H](O)[C@@H](O)[C@@H]1O] | (2S,3R,4R,5S,6R)-2-(4-Chloro-3-((6-(pyrrolidin-1-yl)pyridazin-3-yl)methyl)phenyl)-6-(hydroxymethyl)-tetrahydro-2H-pyran-3,4,5-triol | 1040 |

TABLE 1-continued hSGLT2 Inhibitory Activity

| Exam. No. | Structure | Name | IC$_{50}$ (nM) |
|---|---|---|---|
| 87 | 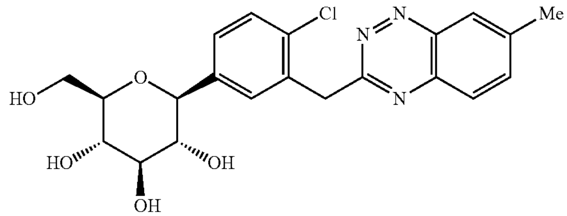 [SMILES: Cc1ccc2nc(Cc3cc([C@@H]4O[C@H](CO)[C@@H](O)[C@H](O)[C@H]4O)ccc3Cl)nnc2c1] | (2S,3R,4R,5S,6R)-2-(4-Chloro-3-((7-methylbenzo[e][1,2,4]triazin-3-yl)methyl)phenyl)-6-(hydroxymethyl)tetrahydro-2H-pyran-3,4,5-triol | 532 |
| 88 | 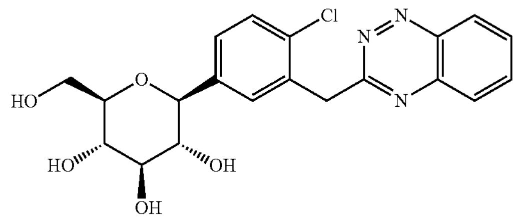 [SMILES: OC[C@H]1O[C@@H](c2ccc(Cl)c(Cc3nnc4ccccc4n3)c2)[C@H](O)[C@@H](O)[C@@H]1O] | (2S,3R,4R,5S,6R)-2-(3-(Benzo[e][1,2,4]triazin-3-ylmethyl)-4-chlorophenyl)-6-(hydroxymethyl)tetrahydro-2H-pyran-3,4,5-triol | 491 |
| 89 | 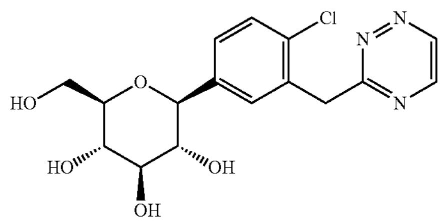 [SMILES: OC[C@H]1O[C@@H](c2ccc(Cl)c(Cc3nccnn3)c2)[C@H](O)[C@@H](O)[C@@H]1O] | (2S,3R,4R,5S,6R)-2-(3-((1,2,4-triazin-3-yl)methyl)-4-chlorophenyl)-6-(hydroxymethyl)tetrahydro-2H-pyran-3,4,5-triol | 261 |
| 90 | 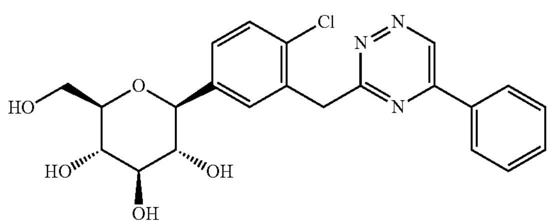 [SMILES: OC[C@H]1O[C@@H](c2ccc(Cl)c(Cc3nncc(-c4ccccc4)n3)c2)[C@H](O)[C@@H](O)[C@@H]1O] | (2S,3R,4R,5S,6R)-2-(4-chloro-3-((5-phenyl-1,2,4-triazin-3-yl)methyl)phenyl)-6-(hydroxymethyl)tetrahydro-2H-pyran-3,4,5-triol | 402 |
| 91 | 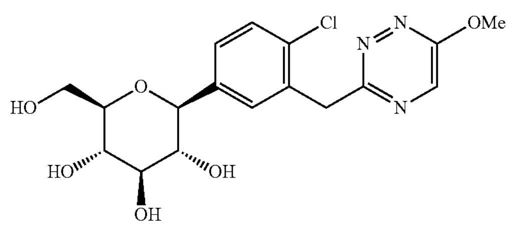 [SMILES: COc1cnc(Cc2cc([C@@H]3O[C@H](CO)[C@@H](O)[C@H](O)[C@H]3O)ccc2Cl)nn1] | (2S,3R,4R,5S,6R)-2-(4-Chloro-3-((6-methoxy-1,2,4-triazin-3-yl)methyl)phenyl)-6-(hydroxymethyl)tetrahydro-2H-pyran-3,4,5-triol | 24.9 |
| 92 | 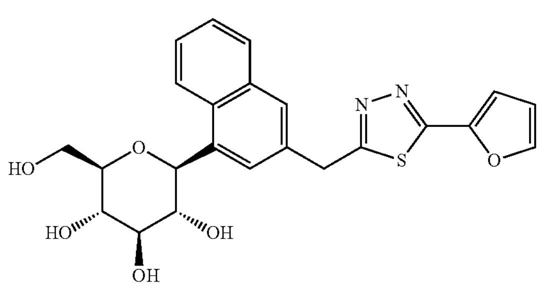 [SMILES: OC[C@H]1O[C@@H](c2cc(Cc3nnc(-c4ccco4)s3)cc3ccccc23)[C@H](O)[C@@H](O)[C@@H]1O] | (2S,3R,4R,5S,6R)-2-(3-((5-(Furan-2-yl)-1,3,4-thiadiazol-2-yl)methyl)naphthalene-1-yl)-6-(hydroxymethyl)-tetrahydro-2H-pyran-3,4,5-triol | 88.9 |

TABLE 1-continued hSGLT2 Inhibitory Activity

| Exam. No. | Structure | Name | IC$_{50}$ (nM) |
|---|---|---|---|
| 93 | 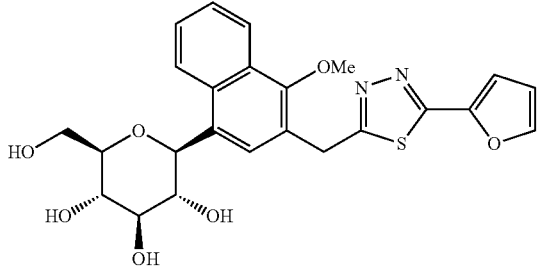 [SMILES: COc1c(Cc2nnc(-c3ccco3)s2)cc([C@@H]2O[C@H](CO)[C@@H](O)[C@H](O)[C@H]2O)c2ccccc12] | (2S,3R,4R,5S,6R)-2-(3-((5-(Furan-2-yl)-1,3,4-thiadiazol-2-yl)methyl)-4-methoxynaphthalen-1-yl)-6-(hydroxymethyl)-tetrahydro-2H-pyran-3,4,5-triol | 10.7 |
| 94 | 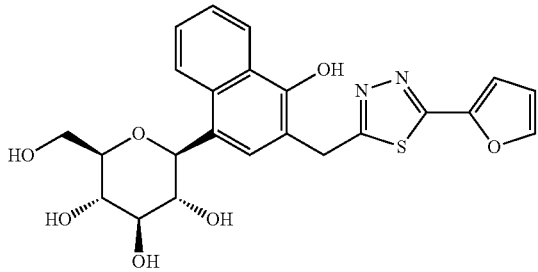 [SMILES: OC[C@H]1O[C@@H](c2cc(Cc3nnc(-c4ccco4)s3)c(O)c3ccccc23)[C@H](O)[C@@H](O)[C@@H]1O] | (2S,3R,4R,5S,6R)-2-(3-((5-(Furan-2-yl)-1,3,4-thiadiazol-2-yl)methyl)-4-hydroxynaphthalen-1-yl)-6-(hydroxymethyl)-tetrahydro-2H-pyran-3,4,5-triol | 24.8 |
| 95 | 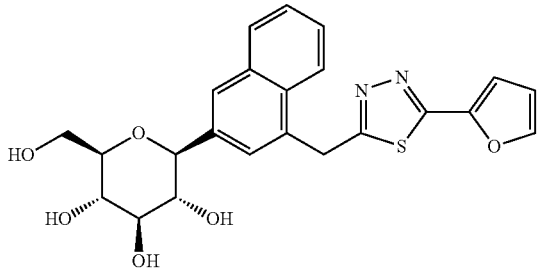 [SMILES: OC[C@H]1O[C@@H](c2cc(Cc3nnc(-c4ccco4)s3)c3ccccc3c2)[C@H](O)[C@@H](O)[C@@H]1O] | (2S,3R,4R,5S,6R)-2-(4-((5-(Furan-2-yl)-1,3,4-thiadiazol-2-yl)methyl)naphthalen-2-yl)-6-(hydroxymethyl)-tetrahydro-2H-pyran-3,4,5-triol | 323 |
| 96 | 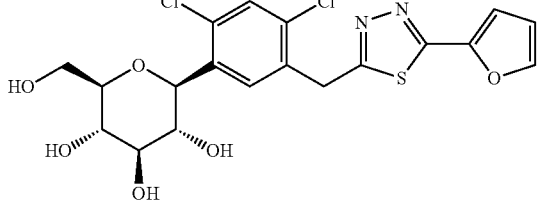 | (2S,3R,4R,5S,6R)-2-(2,4-Dichloro-5-((5-(furan-2-yl)-1,3,4-thiadiazol-2-yl)methyl)phenyl)-6-(hydroxymethyl)-tetrahydro-2H-pyran-3,4,5-triol | 17.6 |
| 97 | 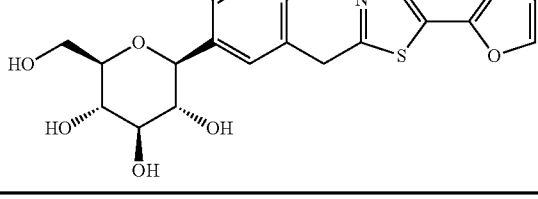 | (2S,3R,4R,5S,6R)-2-(4-Chloro-5-((5-(furan-2-yl)-1,3,4-thiadiazol-2-yl )methyl)-2-methoxyphenyl)-6-(hydroxymethyl)-tetrahydro-2H-pyran-3,4,5-triol | 5.55 |

*Reference compound sergliflozin active form (non-prodrug form) IC$_{50}$ = 6.25 ± 0.62 nM Experimental Example 3

Urinary Glucose Excretion in Normal Animals 3-1. Animals

Male Sprague-Dawley (SD) rats were purchased from Charles River Laboratory. All animals were housed at 23±2° C. under a 12-h light/dark cycle (light on 7:00) and were fed a standard chow and water ad libitum.

3-2. Urinary Glucose Excretion in Normal Animal

For glucosuria assessment, overnight-fasted SD rats (5 weeks of ages) were placed into metabolism cages for baseline urine collection over 24 h. Rats were weighted, randomized into experimental groups (n=4) and orally administered with 50% aqueous glucose solution (2 g/kg) and drugs. Rats were returned to metabolism cages for 24 h urine collection. After the urine volume had been measured, the glucose concentration in the urine was determined using a LabAssay™ (Wako Pure Chemicals). These data were normalized per 200 g body weight.

Figure 1B:
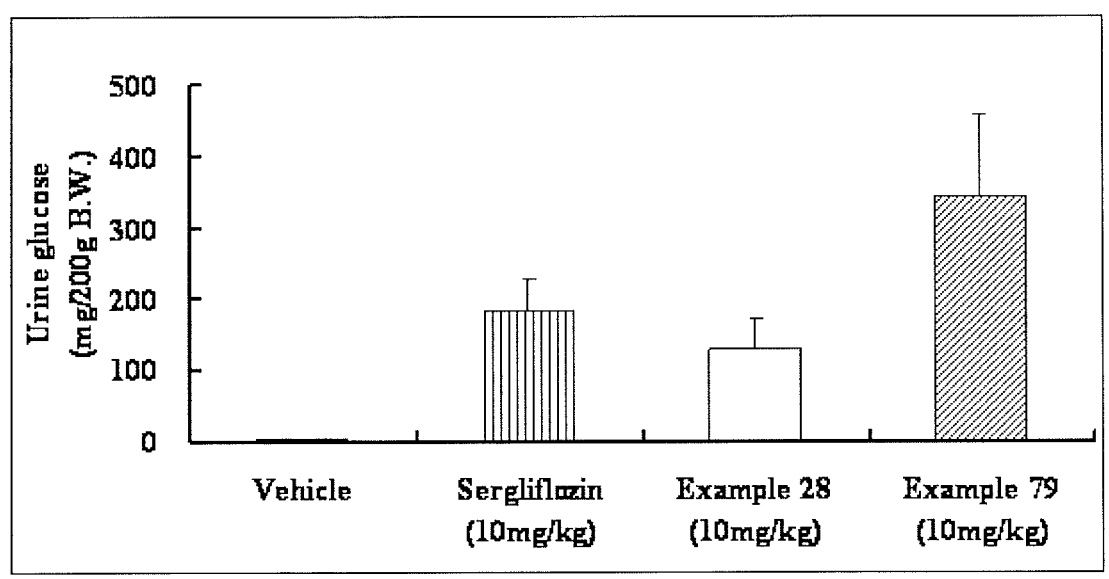
FIG. 1b: a graph showing effect of single oral administration of Sergliflozin, the compound of Example 28 and the compound of Example 79 respectively on urine glucose excretion in normal SD rats.

FIG. 1a is a graph showing effects of single oral administration of Sergliflozin, Example 28 and Example 79 on Urine volume in Normal SD ratsm and FIG. 1b is a graph showing effects of single oral administration of Sergliflozin, Example 28 and Example 79 on Urine glucose excretion in Normal SD rats.

As shown in FIGS. 1a and 1b, the inventive C-aryl glucoside compound of formula (I) is effective as an inhibitor against sodium-dependent glucose cotransporter (SGLT2), thereby preventing or treating diabetes.

Accordingly, the present invention provides a pharmaceutical composition for preventing or treating diabetes, which comprises the compound of formula (I), or a pharmaceutically acceptable salt or a prodrug thereof as an active ingredient and a pharmaceutically acceptable carrier.

While the invention has been described with respect to the above specific embodiments, it should be recognized that various modifications and changes may be made to the invention by those skilled in the art which also fall within the scope of the invention as defined by the appended claims.

What is claimed is:

1. A compound of formula (I), or a pharmaceutically acceptable salt or a prodrug thereof:

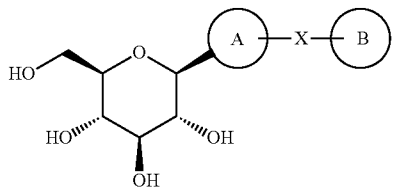
(I)

wherein,

Ring A is selected from the group consisting of benzene ring, substituted benzene ring, naphthalene ring and substituted naphthalene ring;

Ring B is selected from the group consisting of pyridazine ring, substituted pyridazine ring, pyridazinone ring, substituted pyridazinone ring, thiadiazole ring, substituted thiadiazole ring, triazine ring, substituted triazine ring, benzotriazine ring and substituted benzotriazine ring; and X is —CH$_2$—.

2. The compound of claim 1, wherein Ring A is

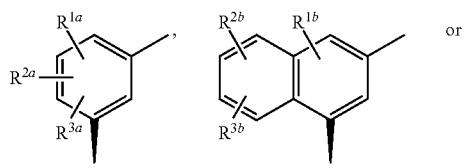 or

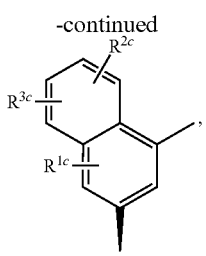

$R^{1a}$, $R^{2a}$, $R^{3a}$, $R^{1b}$, $R^{2b}$, $R^{3b}$, $R^{1c}$, $R^{2c}$, and $R^{3c}$ being each independently hydrogen, halogen, hydroxy, $C_{1-4}$ alkyl, substituted $C_{1-4}$ alkyl, $C_{2-4}$ alkenyl, substituted $C_{2-4}$ alkenyl, $C_{2-4}$ alkynyl, substituted $C_{2-4}$ alkynyl, hydroxyl ($C_{1-4}$ alkyl), ($C_{1-8}$ alkoxy)($C_{1-4}$ alkyl), $C_{1-8}$ alkoxy, $C_{3-7}$ cycloalkyl, $C_{3-7}$ cycloalkenyl, $C_{3-7}$ cycloalkyloxy, phenyl($C_{1-8}$ alkoxy), cyano, nitro, amino, mono- or di-($C_{1-4}$ alkyl)amino, alkanoylamino, carboxy, ($C_{1-8}$ alkoxy)carbonyl, carbamoyl, mono- or di-($C_{1-4}$ alkyl)carbamoyl, alkanoyl, ($C_{1-4}$ alkyl)sulfonylamino, phenylsulfonylamino, ($C_{1-4}$ alkyl)sulfinyl, ($C_{1-4}$ alkyl) sulfonyl, phenylsulfonyl, aryl, substituted aryl, heteroaryl, substituted heteroaryl heterocycle, or substituted heterocycle, and

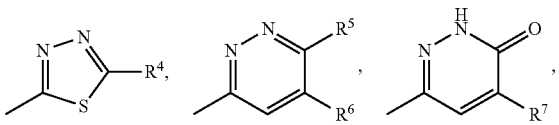

Ring B is

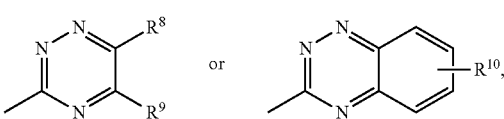

in which, $R^4$ is $C_{1-2}$ alkoxy, $C_{1-4}$ alkylthio, $C_{1-7}$ alkyl, substituted $C_{1-7}$ alkyl, $C_{2-7}$ alkenyl, substituted $C_{2-7}$ alkenyl, $C_{2-7}$ alkynyl, substituted $C_{2-7}$ alkynyl, $C_{3-7}$ cycloalkyl, substituted $C_{3-7}$ cycloalkyl, aryl, substituted aryl, heteroaryl, substituted heteroaryl, heterocycloalkyl or substituted heterocycloalkyl;

$R^5$ is hydrogen, halogen, cyano, amino, mono- or di-($C_{1-4}$ alkyl)amino, $C_{1-8}$ alkoxy, substituted $C_{1-8}$ alkoxy, cycloalkyloxy, heterocyclooxy, $C_{1-4}$ alkylthio, —S-aryl, $C_{1-8}$ alkoxycarbonyl, $C_{1-7}$ alkyl, substituted $C_{1-7}$ alkyl, $C_{2-7}$ alkenyl, substituted $C_{2-7}$ alkenyl, $C_{2-7}$ alkynyl, substituted $C_{2-7}$ alkynyl, $C_{3-7}$ cycloalkyl, substituted $C_{3-7}$ cycloalkyl, $C_{3-7}$ cycloalkenyl, substituted $C_{3-7}$ cycloalkenyl, aryl, substituted aryl, heteroaryl, substituted heteroaryl, heterocycloalkyl, or substituted heterocycloalkyl;

$R^6$ and $R^7$ are each independently hydrogen or methyl;

$R^8$ is hydrogen, halogen, cyano, amino, mono- or di-($C_{1-4}$ alkyl)amino, $C_{1-8}$ alkoxy, substituted ($C_{1-8}$ alkoxy, cycloalkyloxy, heterocyclooxy, $C_{1-4}$ alkylthio, —S-aryl, $C_{1-8}$ alkoxycarbonyl, $C_{1-7}$alkyl, substituted $C_{1-7}$ alkyl, $C_{2-7}$ alkenyl, substituted $C_{2-7}$ alkenyl, $C_{2-7}$ alkynyl, substituted $C_{2-7}$ alkynyl, $C_{3-7}$ cycloalkyl, substituted $C_{3-7}$ cycloalkyl, $C_{3-7}$ cycloalkenyl, substituted $C_{3-7}$ cycloalkenyl, aryl, substituted aryl, heteroaryl, substituted heteroaryl, heterocyclic, or substituted heterocyclic;

R⁹ is hydrogen, $C_{1-7}$ alkyl, substituted $C_{1-7}$ alkyl, $C_{2-7}$ alkenyl, substituted $C_{2-7}$ alkenyl, $C_{2-7}$ alkynyl, substituted $C_{2-7}$ alkynyl, $C_{3-7}$ cycloalkyl, substituted $C_{3-7}$ cycloalkyl, aryl, substituted aryl, heteroaryl, substituted heteroaryl, heterocyclic, or substituted heterocyclic; and R¹⁰ is hydrogen, halogen, cyano, $C_{1-4}$ alkoxy, substituted $C_{1-4}$ alkoxy, $C_{1-4}$ alkyl, substituted $C_{1-4}$ alkyl, aryl, substituted aryl, heteroaryl, substituted heteroaryl, heterocyclic, or substituted heterocyclic.

3. The compound of claim 2, which is selected from the group consisting of the compounds of formulae (Ia) to (Id):

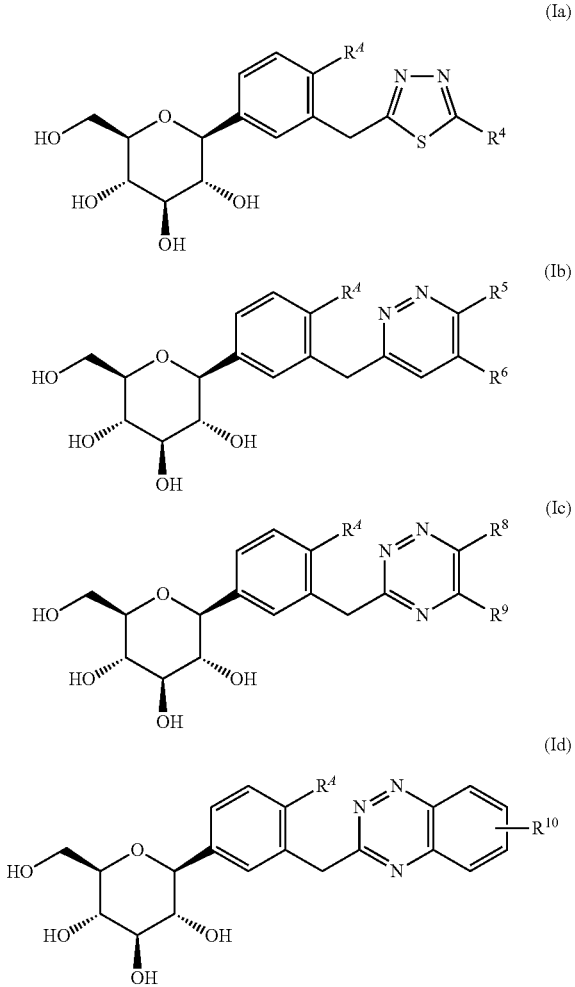

wherein, $R^A$ is halogen, $C_{1-4}$ alkyl or $C_{1-4}$ alkoxy; and $R^4$ to $R^{10}$ have the same meanings as defined in claim 2.

4. The compound of claim 1, which is selected from the group consisting of:

(2S,3R,4R,5S,6R)-2-(4-Chloro-3-((5-(furan-2-yl)-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-(5-methylfuran-2-yl)-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-(3-methylfuran-2-yl)-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-(furan-3-yl)-1,3,4-thiadiazol-2-yl)methyl)phenyl)-6-(hydroxymethyl)tetrahydro-2H-pyran-3,4,5-triol;

(2S,3R,4R,5S,6R)-2-(4-Chloro-3-((5-(thiophen-2-yl)-1,3,4-thiadiazol-2-yl)methyl)phenyl)-6-(hydroxymethyl)tetrahydro-2H-pyran-3,4,5-triol;

(2S,3R,4R,5S,6R)-2-(3-((5-(Benzo[b]thiophen-2-yl)-1,3,4-thiadiazol-2-yl)methyl)-4-chlorophenyl)-6-(hydroxymethyl)-tetrahydro-2H-pyran-3,4,5-triol;

(2S,3R,4R,5S,6R)-2-(4-chloro-3-((5-(3-methylthiophen-2-yl)-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-(5-chlorothiophen-2-yl)-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-(3-chlorothiophen-2-yl)-1,3,4-thiadiazol-2-yl)methyl)phenyl)-6-(hydroxymethyl)tetrahydro-2H-pyran-3,4,5-triol;

(2S,3R,4R,5S,6R)-2-(4-Chloro-3-((5-(thiophen-3-yl)-1,3,4-thiadiazol-2-yl)methyl)phenyl)-6-(hydroxymethyl)tetrahydro-2H-pyran-3,4,5-triol;

(2S,3R,4R,5S,6R)-2-(4-Chloro-3-((5-(1-methyl-1H-pyrrol-2-yl)-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-(5-methylisoxazol-3-yl)-1,3,4-thiadiazol-2-yl)methyl)phenyl)-6-(hydroxymethyl)tetrahydro-2H-pyran-3,4,5-triol;

(2S,3R,4R,5S,6R)-2-(4-Chloro-3-((5-(thiazol-4-yl)-1,3,4-thiadiazol-2-yl)methyl)phenyl)-6-(hydroxymethyl)tetrahydro-2H-pyran-3,4,5-triol;

(2S,3R,4R,5S,6R)-2-(4-Chloro-3-((5-(2-(pyridin-4-yl)thiazol-5-yl)-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-(pyridin-2-yl)-1,3,4-thiadiazol-2-yl)methyl)phenyl)-6-(hydroxymethyl)tetrahydro-2H-pyran-3,4,5-triol;

(2S,3R,4R,5S,6R)-2-(4-Chloro-3-((5-(6-methylpyridin-3-yl)-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-(quinolin-2-yl)-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-(isoquinolin-3-yl)-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-cyclopentyl-1,3,4-thiadiazol-2-yl)methyl)phenyl)-6-(hydroxymethyl)tetrahydro-2H-pyran-3,4,5-triol;

(3R,4R,5S,6R)-2-(4-Chloro-3-((5-(pyridin-4-yl)-1,3,4-thiadiazol-2-yl)methyl)phenyl)-6-(hydroxymethyl)-tetrahydro-2H-pyran-3,4,5-triol;

(3R,4R,5S,6R)-2-(4-Chloro-3-((5-(pyridin-3-yl)-1,3,4-thiadiazol-2-yl)methyl)phenyl)-6-(hydroxymethyl)-tetrahydro-2H-pyran-3,4,5-triol;

(3R,4R,5S,6R)-2-(4-chloro-3-((5-p-tolyl-1,3,4-thiadiazol-2-yl)methyl)phenyl)-6-(hydroxymethyl)-tetrahydro-2H-pyran-3,4,5-triol;

(3R,4R,5S,6R)-2-(4-Chloro-3-((5-(4-propylphenyl)-1,3,4-thiadiazol-2-yl)methyl)phenyl)-6-(hydroxymethyl)-tetrahydro-2H-pyran-3,4,5-triol;

(3R,4R,5S,6R)-2-(4-Chloro-3-((5-cyclohexyl-1,3,4-thiadiazol-2-yl)methyl)phenyl)-6-(hydroxymethyl)-tetrahydro-2H-pyran-3,4,5-triol;

(3R,4R,5S,6R)-2-(4-Chloro-3-((5-((4-methylcyclohexyl)methyl)-1,3,4-thiadiazol-2-yl)methyl)phenyl)-6-(hydroxymethyl)-tetrahydro-2H-pyran-3,4,5-triol;

(3R,4R,5S,6R)-2-(4-Chloro-3-((5-(2-phenylpropyl)-1,3,4-thiadiazol-2-yl)methyl)phenyl)-6-(hydroxymethyl)-tetrahydro-2H-pyran-3,4,5-triol;

(3R,4R,5S,6R,E)-2-(4-Chloro-3-((5-styryl-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-phenyl-1,3,4-thiadiazol-2-yl)methyl)phenyl)-6-(hydroxymethyl)-tetrahydro-2H-pyran-3,4,5-triol;

(2S,3R,4R,5S,6R)-2-(4-chloro-3-((5-(4-Chlorophenyl)-1,3,4-thiadiazol-2-yl)methyl)phenyl)-6-(hydroxymethyl)-tetrahydro-2H-pyran-3,4,5-triol;

(2S,3R,4R,5S,6R)-2-(3-((5-(Benzofuran-2-yl)-1,3,4-thiadiazol-2-yl)methyl)-4-chlorophenyl)-6-(hydroxymethyl)-tetrahydro-2H-pyran-3,4,5-triol;

(2S,3R,4R,5S,6R)-2-(4-Chloro-3-((5-propyl-1,3,4-thiadiazol-2-yl)methyl)phenyl)-6-(hydroxymethyl)-tetrahydro-2H-pyran-3,4,5-triol;

(2S,3R,4R,5S,6R)-2-(3-((5-Butyl-1,3,4-thiadiazol-2-yl)methyl)-4-chlorophenyl)-6-(hydroxymethyl)-tetrahydro-2H-pyran-3,4,5-triol;

(2S,3R,4R,5S,6R)-2-(4-Chloro-3-((5-pentyl-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-heptyl-1,3,4-thiadiazol-2-yl)methyl)phenyl)-6-(hydroxymethyl)-tetrahydro-2H-pyran-3,4,5-triol;

(2S,3S,4R,5R)-2-(Hydroxymethyl)-6-(3-((5-phenyl-1,3,4-thiadiazol-2-yl)methyl)phenyl)-tetrahydro-2H-pyran-3,4,5-triol;

(2S,3S,4R,5R)-2-(Hydroxymethyl)-6-(3-((5-(pyridin-3-yl)-1,3,4-thiadiazol-2-yl)methyl)phenyl)-tetrahydro-2H-pyran-3,4,5-triol;

(2S,3R,4R,5S,6R)-2-(4-Chloro-3-((5-(5-phenylfuran-2-yl)-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-(trifluoromethyl)-1,3,4-thiadiazol-2-yl)methyl)phenyl)-6-(hydroxymethyl)tetrahydro-2H-pyran-3,4,5-triol;

(2S,3R,4R,5S,6R)-2-(4-Chloro-3-((5-(2,2,2-trifluoroethyl)-1,3,4-thiadiazol-2-yl)methyl)phenyl)-6-(hydroxymethyl)tetrahydro-2H-pyran-3,4,5-triol;

(2S,3R,4R,5S,6R)-2-(4-Chloro-3-((5-(methylthio)-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-methoxy-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-(pyrazin-2-yl)-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-(pyridazin-4-yl)-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-(6-methylpyridin-2-yl)-1,3,4-thiadiazol-2-yl)methyl)phenyl)-6-(hydroxymethyl)-tetrahydro-2H-pyran-3,4,5-triol;

(2S,3R,4R,5S,6R)-2-(4-Chloro-3-((5-(2-methylpyridin-4-yl)-1,3,4-thiadiazol-2-yl)methyl)phenyl)-6-(hydroxymethyl)-tetrahydro-2H-pyran-3,4,5-triol;

(2S,3R,4R,5S,6R)-2-(3-((6-(1,3,4-Thiadiazol-2-yl)pyridazin-3-yl)methyl)-4-chlorophenyl)-6-(hydroxymethyl)-tetrahydro-2H-pyran-3,4,5-triol;

(2S,3R,4R,5S,6R)-2-(4-Chloro-3-((6-(5-methyloxazol-2-yl)pyridazin-3-yl)methyl)phenyl)-6-(hydroxymethyl)-tetrahydro-2H-pyran-3,4,5-triol;

(2S,3R,4R,5S,6R)-2-(4-Chloro-3-((6-chloropyridazin-3-yl)methyl)phenyl)-6-(hydroxymethyl)-tetrahydro-2H-pyran-3,4,5-triol;

Methyl 6-(2-chloro-5-((2S,3R,4R,5S,6R)-3,4,5-trihydroxy-6-(hydroxymethyl)-tetrahydro-2H-pyran-2-yl)benzyl)pyridazine-3-carboxylate;

(2S,3R,4R,5S,6R)-2-(4-Chloro-3-((6-(phenylethynyl)pyridazin-3-yl)methyl)phenyl)-6-(hydroxymethyl)-tetrahydro-2H-pyran-3,4,5-triol;

(2S,3R,4R,5S,6R)-2-(4-Chloro-3-((6-ethoxypyridazin-3-yl)methyl)phenyl)-6-(hydroxymethyl)-tetrahydro-2H-pyran-3,4,5-triol;

(2S,3R,4R,5S,6R)-2-(4-Chloro-3-((6-propoxypyridazin-3-yl)methyl)phenyl)-6-(hydroxymethyl)-tetrahydro-2H-pyran-3,4,5-triol (2S,3R,4R,5S,6R)-2-(3-((6-Butoxypyridazin-3-yl)methyl)-4-chlorophenyl)-6-(hydroxymethyl)-tetrahydro-2H-pyran-3,4,5-triol;

(2S,3R,4R,5S,6R)-2-(4-Chloro-3-((6-(pentyloxy)pyridazin-3-yl)methyl)phenyl)-6-(hydroxymethyl)-tetrahydro-2H-pyran-3,4,5-triol;

(2S,3R,4R,5S,6R)-2-(4-Chloro-3-((6-(hexyloxy)pyridazin-3-yl)methyl)phenyl)-6-(hydroxymethyl)-tetrahydro-2H-pyran-3,4,5-triol;

(2S,3R,4R,5S,6R)-2-(4-Chloro-3-((6-(octyloxy)pyridazin-3-yl)methyl)phenyl)-6-(hydroxymethyl)-tetrahydro-2H-pyran-3,4,5-triol;

(2S,3R,4R,5S,6R)-2-(4-Chloro-3-((6-isopropoxypyridazin-3-yl)methyl)phenyl)-6-(hydroxymethyl)-tetrahydro-2H-pyran-3,4,5-triol;

(2S,3R,4R,5S,6R)-2-(4-Chloro-3-((6-isobutoxypyridazin-3-yl)methyl)phenyl)-6-(hydroxymethyl)-tetrahydro-2H-pyran-3,4,5-triol;

(2S,3R,4R,5S,6R)-2-(4-Chloro-3-((6-(cyclohexyloxy)pyridazin-3-yl)methyl)phenyl)-6-(hydroxymethyl)-tetrahydro-2H-pyran-3,4,5-triol;

(2S,3R,4R,5S,6R)-2-(4-Chloro-3-((6-(tetrahydro-2H-pyran-4-yloxy)pyridazin-3-yl)methyl)phenyl)-6-(hydroxymethyl)-tetrahydro-2H-pyran-3,4,5-triol;

(2S,3R,4R,5S,6R)-2-(4-chloro-3-((6-phenylpyridazin-3-yl)methyl)phenyl)-6-(hydroxymethyl)-tetrahydro-2H-pyran-3,4,5-triol;

(2S,3R,4R,5S,6R)-2-(4-chloro-3-((6-(furan-2-yl)pyridazin-3-yl)methyl)phenyl)-6-(hydroxymethyl)-tetrahydro-2H-pyran-3,4,5-triol;

(2S,3R,4R,5S,6R)-2-(4-Chloro-3-((6-(furan-3-yl)pyridazin-3-yl)methyl)phenyl)-6-(hydroxymethyl)-tetrahydro-2H-pyran-3,4,5-triol;

(2S,3R,4R,5S,6R)-2-(4-Chloro-3-((6-(pyridin-3-yl)pyridazin-3-yl)methyl)phenyl)-6-(hydroxymethyl)-tetrahydro-2H-pyran-3,4,5-triol;

(2S,3R,4R,5S,6R)-2-(4-Chloro-3-((6-(thiophen-2-yl)pyridazin-3-yl)methyl)phenyl)-6-(hydroxymethyl)-tetrahydro-2H-pyran-3,4,5-triol;

(2S,3R,4R,5S,6R)-2-(4-chloro-3-((6-(thiophen-3-yl)pyridazin-3-yl)methyl)phenyl)-6-(hydroxymethyl)-tetrahydro-2H-pyran-3,4,5-triol;

(2S,3R,4R,5S,6R)-2-(3-((6-(Benzo[d][1,3]dioxol-5-yl)pyridazin-3-yl)methyl)-4-chlorophenyl)-6-(hydroxymethyl)-tetrahydro-2H-pyran-3,4,5-triol;

(2S,3R,4R,5S,6R)-2-(4-Chloro-3-((6-(2,3-dihydrobenzo[b][1,4]dioxin-6-yl)pyridazin-3-yl)methyl)phenyl)-6-(hydroxymethyl)-tetrahydro-2H-pyran-3,4,5-triol;

(2S,3R,4R,5S,6R)-2-(4-Chloro-3-((6-(5-methylthiophen-2-yl)pyridazin-3-yl)methyl)phenyl)-6-(hydroxymethyl)-tetrahydro-2H-pyran-3,4,5-triol;

(2S,3R,4R,5S,6R)-2-(4-Chloro-3-((6-(4-fluorophenyl)pyridazin-3-yl)methyl)phenyl)-6-(hydroxymethyl)-tetrahydro-2H-pyran-3,4,5-triol;

(2S,3R,4R,5S,6R)-2-(4-Chloro-3-((6-(3-methoxyphenyl)pyridazin-3-yl)methyl)phenyl)-6-(hydroxymethyl)-tetrahydro-2H-pyran-3,4,5-triol;

(2S,3R,4R,5S,6R)-2-(4-Chloro-3-((6-ethylpyridazin-3-yl)methyl)phenyl)-6-(hydroxymethyl)-tetrahydro-2H-pyran-3,4,5-triol;

(2S,3R,4R,5S,6R)-2-(4-Chloro-3-((6-methylpyridazin-3-yl)methyl)phenyl)-6-(hydroxymethyl)-tetrahydro-2H-pyran-3,4,5-triol (2S,3R,4R,5S,6R)-2-(4-Chloro-3-((6-propylpyridazin-3-yl)methyl)phenyl)-6-(hydroxymethyl)-tetrahydro-2H-pyran-3,4,5-triol;

(2S,3R,4R,5S,6R)-2-(4-Chloro-3-((6-isopropylpyridazin-3-yl)methyl)phenyl)-6-(hydroxymethyl)-tetrahydro-2H-pyran-3,4,5-triol;

(2S,3R,4R,5S,6R)-2-(3-[((6-Butylpyridazin-3-yl)methyl)-4-chlorophenyl)-6-(hydroxymethyl)-tetrahydro-2H-pyran-3,4,5-triol;

(2S,3R,4R,5S,6R)-2-(4-Chloro-3-((6-isobutylpyridazin-3-yl)methyl)phenyl)-6-(hydroxymethyl)-tetrahydro-2H-pyran-3,4,5-triol;

(2S,3R,4R,5S,6R)-2-(4-Chloro-3-((6-pentylpyridazin-3-yl)methyl)phenyl)-6-(hydroxymethyl)-tetrahydro-2H-pyran-3,4,5-triol;

(2S,3R,4R,5S,6R)-2-(4-Chloro-3-((6-(methylthio)pyridazin-3-yl)methyl)phenyl)-6-(hydroxymethyl)-tetrahydro-2H-pyran-3,4,5-triol;

(2S,3R,4R,5S,6R)-2-(4-Chloro-3-((6-(ethylthio)pyridazin-3-yl)methyl)phenyl)-6-(hydroxymethyl)-tetrahydro-2H-pyran-3,4,5-triol;

(2S,3R,4R,5S,6R)-2-(4-Chloro-3-((6-(phenylthio)pyridazin-3-yl)methyl)phenyl)-6-(hydroxymethyl)-tetrahydro-2H-pyran-3,4,5-triol;

(2S,3R,4R,5S,6R)-2-(4-Chloro-3-((5-methyl-6-(methylthio)pyridazin-3-yl)methyl)phenyl)-6-(hydroxymethyl)tetrahydro-2H-pyran-3,4,5-triol;

6-(2-Chloro-5-((2S,3R,4R,5S,6R)-3,4,5-trihydroxy-6-(hydroxymethyl)-tetrahydro-2H-pyran-2-yl)benzyl)-4-methylpyridazin-3(2H)-one;

(2S,3R,4R,5S,6R)-2-(4-Chloro-3-((6-morpholinopyridazin-3-yl)methyl)phenyl)-6-(hydroxymethyl)-tetrahydro-2H-pyran-3,4,5-triol;

(2S,3R,4R,5S,6R)-2-(4-Chloro-3-((6-(phenylamino)pyridazin-3-yl)methyl)phenyl)-6-(hydroxymethyl)-tetrahydro-2H-pyran-3,4,5-triol;

(2S,3R,4R,5S,6R)-2-(4-Chloro-3-((6-(pyrrolidin-1-yl)pyridazin-3-yl)methyl)phenyl)-6-(hydroxymethyl)-tetrahydro-2H-pyran-3,4,5-triol;

(2S,3R,4R,5S,6R)-2-(4-Chloro-3-((7-methylbenzo[e][1,2,4]triazin-3-yl)methyl)phenyl)-6-(hydroxymethyl)tetrahydro-2H-pyran-3,4,5-triol;

(2S,3R,4R,5S,6R)-2-(3-(Benzo[e][1,2,4] triazin-3-ylmethyl)-4-chlorophenyl)-6-(hydroxymethyl)tetrahydro-2H-pyran-3,4,5-triol;

(2S,3R,4R,5S,6R)-2-(3-((1,2,4-triazin-3-yl)methyl)-4-chlorophenyl)-6-(hydroxymethyl)tetrahydro-2H-pyran-3,4,5-triol;

(2S,3R,4R,5S,6R)-2-(4-chloro-3-((5-phenyl-1,2,4-triazin-3-yl)methyl)phenyl)-6-(hydroxymethyl)tetrahydro-2H-pyran-3,4,5-triol;

(2S,3R,4R,5S,6R)-2-(4-Chloro-3-((6-methoxy-1,2,4-triazin-3-yl)methyl)phenyl)-6-(hydroxymethyl)tetrahydro-2H-pyran-3,4,5-triol;

(2S,3R,4R,5S,6R)-2-(3-((5-(Furan-2-yl)-1,3,4-thiadiazol-2-yl)methyl)naphthalene-1-yl)-6-(hydroxymethyl)-tetrahydro-2H-pyran-3,4,5-triol;

(2S,3R,4R,5S,6R)-2-(3-((5-(Furan-2-yl)-1,3,4-thiadiazol-2-yl)methyl)-4-methoxynaphthalen-1-yl)-6-(hydroxymethyl)-tetrahydro-2H-pyran-3,4,5-triol;

(2S,3R,4R,5S,6R)-2-(3-((5-(Furan-2-yl)-1,3,4-thiadiazol-2-yl)methyl)-4-hydroxynaphthalen-1-yl)-6-(hydroxymethyl)-tetrahydro-2H-pyran-3,4,5-triol;

(2S,3R,4R,5S,6R)-2-(4-((5-(Furan-2-yl)-1,3,4-thiadiazol-2-yl)methyl)naphthalen-2-yl)-6-(hydroxymethyl)-tetrahydro-2H-pyran-3,4,5-triol;

(2S,3R,4R,5S,6R)-2-(2,4-Dichloro-5-((5-(furan-2-yl)-1,3,4-thiadiazol-2-yl)methyl)phenyl)-6-(hydroxymethyl)-tetrahydro-2H-pyran-3,4,5-triol; and (2S,3R,4R,5S,6R)-2-(4-Chloro-5-((5-(furan-2-yl)-1,3,4-thiadiazol-2-yl)methyl)-2-methoxyphenyl)-6-(hydroxymethyl)-tetrahydro-2H-pyran-3,4,5-triol.

5. A method for preparing a compound of formula (Ie) comprising the steps of:

subjecting a compound of formula (II) to a coupling reaction with a hydrazide of formula (III) to obtain an acylhydrazide of formula (IV), or converting the compound of formula (II) to a hydrazide of formula (V) using hydrazine, followed by a coupling reaction of the hydrazide of formula (V) with a carboxylic acid of formula (VI) to obtain an acylhydrazide of formula (IV);

conducting a cyclization of the acylhydrazide of formula (IV) using Lawesson's reagent to obtain a thiadiazole of formula (VII); and carrying out deprotection of the benzyl groups of the thiadiazole of formula (VII), followed by peracylation and hydrolysis of the resulting compound,

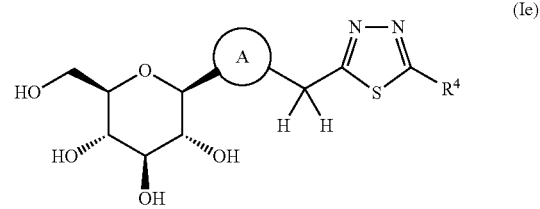

(Ie)

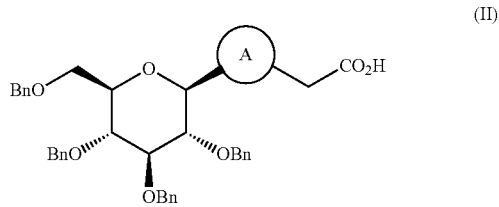

(II)

(III)

R$^4$CONHNH$_2$

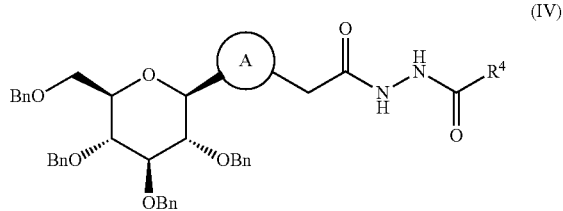

(IV)

-continued

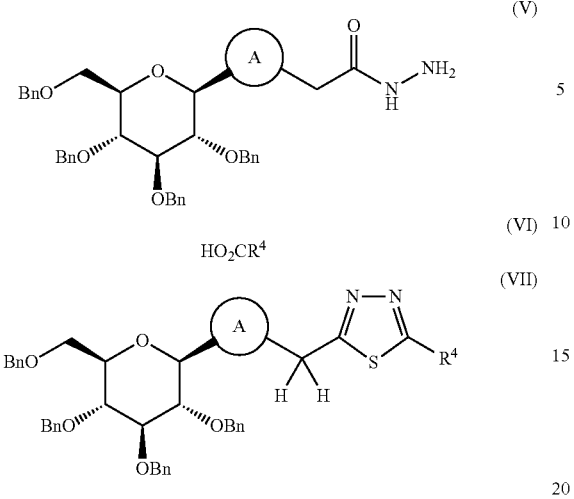

wherein,
Ring A is selected from the group consisting of benzene ring, substituted benzene ring, naphthalene ring and substituted naphthalene ring; and
$R^4$ has the same meaning as defined in claim 2.

6. A method for preparing a compound of formula (If), comprising the steps of:
subjecting a compound of formula (II) to a coupling reaction and cyclization with thiosemicarbazide using phosphorus(V) oxychloride to obtain an aminothiadiazole;
converting the aminothiadiazole to a thiadiazole of formula (VIII) using sodium nitrite and copper under an acidic condition; and
treating the thiadiazole of formula (VIII) with $NaR^4$ (in which $R^4$ has the same meaning as defined claim 2), followed by deprotection of benzyl groups,

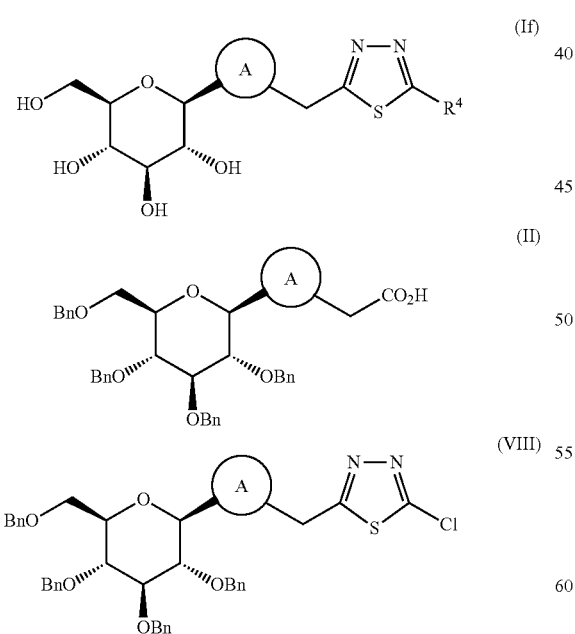

wherein,
Ring A is selected from the group consisting of benzene ring, substituted benzene ring, naphthalene ring and substituted naphthalene ring.

7. A method for preparing the compound of formula (Ig) comprising the steps of:
subjecting a compound of formula (IX) to a reaction with 3,6-dichloropyridazine or 3-(methylsulfonyl)-5-phenyl-1,2,4-triazine under a basic condition to obtain an ester of formula (X);
conducting a hydrolyzation and decarboxylation of the ester of formula (X) using lithium hydroxide to obtain a compound of formula (XI); and
removing the benzyl groups of the compound of formula (XI),

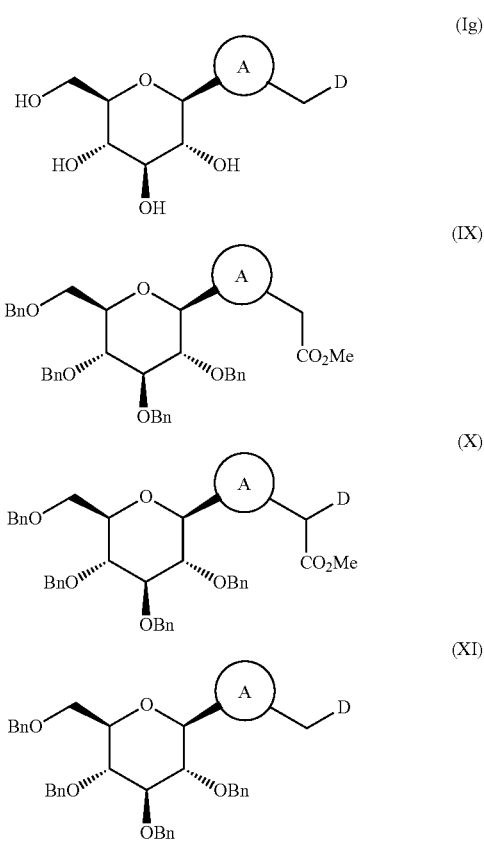

wherein,
Ring A is selected from the group consisting of benzene ring, substituted benzene ring, naphthalene ring and substituted naphthalene ring, and

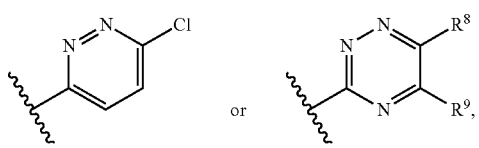

in which $R^8$ and $R^9$ have the same meanings as defined claim 1.

8. A method for preparing the compound of formula (Ih) comprising the steps of:
subjecting a compound of formula (XII) to a reaction with $NaOR^{11}$, NaSMe or $HNR^{12}R^{13}$ ($R^{11}$, $R^{12}R^{13}$ are each independently H or $C_{1-4}$ alkyl); a Fe(III)-mediated alkylation using Grignard reagent; a Sonogashira reaction with ethynylbenzene; a Palladium(0)-catalyzed cyanation under microwave irradiation; or a Suzuki-Miyaura coupling with boronic acid, to obtain a compound of formula (XIII); and removing the benzyl groups of the compound of formula (XIII),

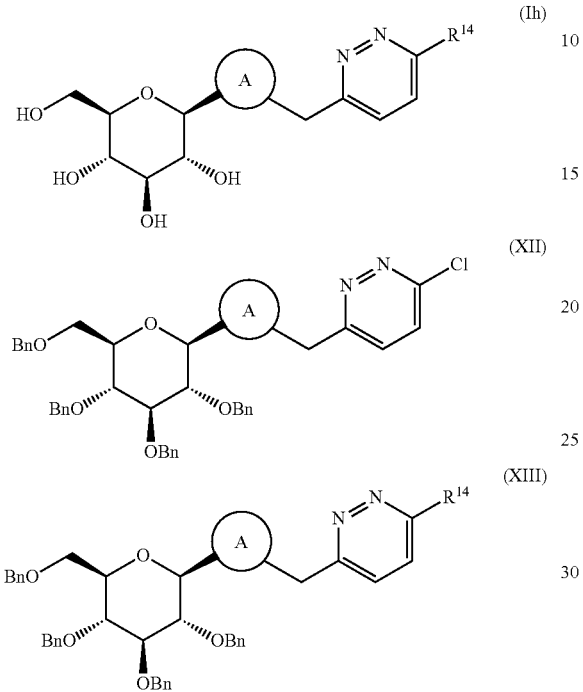

wherein,

Ring A is selected from the group consisting of benzene ring, substituted benzene ring, naphthalene ring and substituted naphthalene ring, and $R^{14}$ is $C_{1-4}$ alkyl, $C_{1-4}$ alkoxy, —$SCH_3$, phenylethynyl, cyano, amino or aryl.

9. A method for preparing the compound of formula (II) comprising the steps of:

subjecting a compound of formula (IX) to a reaction with a chlorobenzotriazine compound to obtaine a triazine oxide;

conducting a reduction of the triazine oxide to obtain a compound of formula (XIV);

hydrolyzing the compound of formula (XIV) using metal hydroxide to obtain a compound of formula (XV); and removing benzyl groups of the compound of formula (XV),

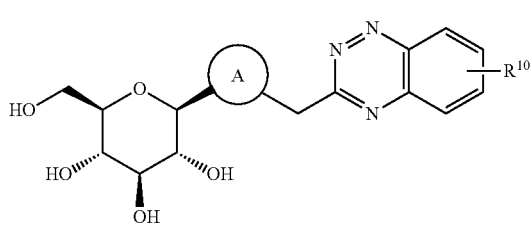

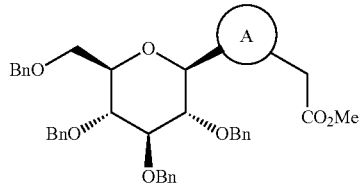

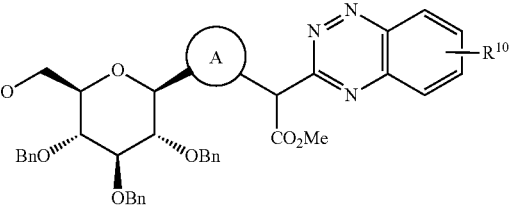

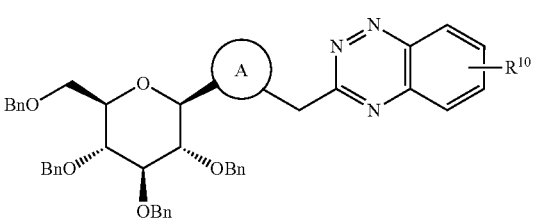

wherein,

Ring A is selected from the group consisting of benzene ring, substituted benzene ring, naphthalene ring and substituted naphthalene ring, and $R^{10}$ has the same meaning as defined in claim 2.

10. A pharmaceutical composition comprising the compound of claim 1 as an active ingredient, and a pharmaceutically acceptable carrier.

11. The pharmaceutical composition according to claim 10, which is for treating diabetes.

12. A method for treating a metabolic disorder, which comprises administering the compound of claim 1 to a mammal in need thereof, wherein the metabolic disorder is selected from the group consisting of diabetes, hyperglycemia and disorders arising from hyperglycemia.

13. A method for inhibiting sodium-dependent glucose cotransporter 2 in a mammal, which comprises administering the compound of claim 1 to the mammal.

14. A pharmaceutical composition comprising the compound of claim 2 as an active ingredient, and a pharmaceutically acceptable carrier.

15. A pharmaceutical composition comprising the compound of claim 3 as an active ingredient, and a pharmaceutically acceptable carrier.

16. A pharmaceutical composition comprising the compound of claim 4 as an active ingredient, and a pharmaceutically acceptable carrier.

* * * * *